US007250262B2

(12) United States Patent
Carroll et al.

(10) Patent No.: US 7,250,262 B2
(45) Date of Patent: Jul. 31, 2007

(54) METHODS FOR IDENTIFYING COMPOUNDS WHICH MODULATE HEMATOPOIESTS

(75) Inventors: Joseph M. Carroll, Cambridge, MA (US); Aileen Healy, Medford, MA (US); Nadine S. Weich, Brookline, MA (US); Louise M. Kelly, Brookline, MA (US)

(73) Assignee: Bayerhealth Care AG, Leverkusen (DE)

( * ) Notice: Subject to any disclaimer, the term of this patent is extended or adjusted under 35 U.S.C. 154(b) by 488 days.

(21) Appl. No.: 10/352,684

(22) Filed: Jan. 28, 2003

(65) Prior Publication Data

US 2003/0215452 A1   Nov. 20, 2003

Related U.S. Application Data

(60) Provisional application No. 60/429,048, filed on Nov. 25, 2002, provisional application No. 60/407,045, filed on Aug. 30, 2002, provisional application No. 60/403,221, filed on Aug. 13, 2002, provisional application No. 60/399,783, filed on Jul. 31, 2002, provisional application No. 60/394,128, filed on Jul. 3, 2002, provisional application No. 60/392,480, filed on Jun. 28, 2002, provisional application No. 60/390,965, filed on Jun. 24, 2002, provisional application No. 60/386,494, filed on Jun. 6, 2002, provisional application No. 60/375,626, filed on Apr. 26, 2002, provisional application No. 60/364,476, filed on Mar. 15, 2002, provisional application No. 60/360,258, filed on Feb. 28, 2002, provisional application No. 60/354,333, filed on Feb. 4, 2002.

(51) Int. Cl.
*G01N 33/53* (2006.01)
(52) U.S. Cl. .......................... 435/7.1; 435/7.1; 514/2; 514/12; 530/350; 530/387.1; 530/300
(58) Field of Classification Search ..................... None
See application file for complete search history.

(56) References Cited

U.S. PATENT DOCUMENTS

| 6,342,360 B1 | 1/2002 | Civelli et al. |
| 2003/0039995 A1 | 2/2003 | Taga et al. |

FOREIGN PATENT DOCUMENTS

| CA | 2 368 823 | 11/2000 |
| JP | 2002000279 | 8/2002 |
| WO | WO 02/059612 A2 | 8/2002 |
| WO | WO 02/079425 A2 | 10/2002 |
| WO | WO 2003016475 A2 | 2/2003 |

OTHER PUBLICATIONS

Wells, Biochemistry, vol. 29, pp. 8509-8517, 1990.*
Seffernick et al., J. Bacteriology, vol. 183, pp. 2405-2410, 2001.*
Van Slegtenhorst, et al., "A Gene from the Xp22.3 Region Shares Homology with Voltage-gated Chloride Channels," *Human Molecular Genetics*, (1994), vol. 3, No. 4, pp. 547-552.
Kawasaki, et al., "Identification of an Acid-activated C1 Channel from Human Skeletal Muscles," *Am. J. Physiol.* 277, (1999), pp. C-948-C954.
Rugarli, et al., "Different Chromosomal Localization of the Clcn4 Gene in *Mus spretus* and C57BL/6J Mice," *Nature Genetics*, (Aug. 1995), vol. 10, pp. 466-471.
Jentsch, et al., "Properties of Voltage-gated Chloride Channels of the C1C Gene Family," *Journal of Physiology*, (1995), 482P, pp. 19S-25S.
Rae, J. L., "Chloride Channel Protein 4 (C1C-4)," submitted Jul. 1999 (sequence) GenPept [online] Bethesda, MD, USA: National Center for Biotechnology Information [retrieved on Oct. 31, 2005]. Retrieved from the Internet: URL www.ncbi.nlm.nih.gov/>. Swiss Prot Accession No. P51793.
Kawasaki, et al., "Homo Sapiens mRNA for Chloride Channel Protein 4, Complete CDS," No. 2, 1998 (sequence) GenBank [online] Bethesda, MD, USA: National Center for Biotechnology Information [retrieved on Oct. 31, 2005], Retrieved from the Internet: URL www.ncbi.nlm.nih.gov/>. GenBank Accession No. AB019432.
Borsani, G., "H. Sapiens mRNA for Chloride Channel," Jan. 22, 1994 (sequence) GenBank [online] Bethesda, MD, USA: National Center for Biotechnology Information [retrieved on Oct. 31, 2005 ]. Retrieved from the Internet: URL www.ncbi.nlm.nih.gov/>. GenBank Accession No. X77197.
Rae, J.L., "Homo Sapiens Chloride Channel CLC4 (C1C4) mRNA, Complete CDS," Jul. 20, 1999 (sequence) GenBank [online] Bethesda, MD, USA: National Center for Biotechnology Information [retrieved on Oct. 31, 2005]. Retrieved from the Internet: URL www.ncbi.nlm.nih.gov/>. GenBank Accession No. AF170492.

(Continued)

*Primary Examiner*—Hope Robinson
(74) *Attorney, Agent, or Firm*—Banner & Witcoff, Ltd.

(57) ABSTRACT

The present invention relates to methods for the diagnosis and treatment of hematological disorders. Specifically, the present invention identifies the differential expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 and 13249 genes in tissues relating to hematological disorders sensation, relative to their expression in normal, or non-hematological disorders disease states, and/or in response to manipulations relevant to hematological disorders. The present invention describes methods for the diagnostic evaluation and prognosis of various hematological disorders, and for the identification of subjects exhibiting a predisposition to such conditions. The invention also provides methods for identifying a compound capable of modulating hematological disorders. The present invention also provides methods for the identification and therapeutic use of compounds as treatments of hematological disorders.

6 Claims, No Drawings

OTHER PUBLICATIONS

Rugarli, et al., "Chloride Channel Protein 4 (C1C-4)," created Jul. 15, 1998 (sequence) GenPept [online] Bethesda, MD, USA: National Center for Biotechnology Information [retrieved on Oct. 31, 2005]. Retrieved from the Internet: URL www.ncbi.nlm.nih.gov/>. Swiss Prot Accession No. Q61418.

Jentsch, et al., "Chloride Channel Protein 4 (C1C-4)," created Oct. 1, 1996 (sequence) GenPept [online] Bethesda, MD, USA: National Center for Biotechnology Information [retrieved on Oct. 31, 2005]. Retrieved from the Internet: URL www.ncbi.nlm.nih.gov/>. Swiss Prot Accession No. P51794.

Bulger et al., "Towards More Specific Therapy for Leukemia: Terminal Transferase As a Therapeutic Target," *Leukemia Research 15*, 285-88, 1991.

* cited by examiner

SEQUENCE LISTING

```
<160> NUMBER OF SEQ ID NOS: 62

<210> SEQ ID NO 1
<211> LENGTH: 1332
<212> TYPE: DNA
<213> ORGANISM: Homo Sapiens
<220> FEATURE:
<221> NAME/KEY: CDS
<222> LOCATION: (1)...(1332)

<400> SEQUENCE: 1 atg gat cca ctg aat ctg tcc tgg tat gat gat gat ctg gag agg cag      48
Met Asp Pro Leu Asn Leu Ser Trp Tyr Asp Asp Asp Leu Glu Arg Gln
  1               5                  10                  15 aac tgg agc cgg ccc ttc aac ggg tca gac ggg aag gcg gac aga ccc      96
Asn Trp Ser Arg Pro Phe Asn Gly Ser Asp Gly Lys Ala Asp Arg Pro
             20                  25                  30 cac tac aac tac tat gcc aca ctg ctc acc ctg ctc atc gct gtc atc     144
His Tyr Asn Tyr Tyr Ala Thr Leu Leu Thr Leu Leu Ile Ala Val Ile
         35                  40                  45 gtc ttc ggc aac gtg ctg gtg tgc atg gct gtg tcc cgc gag aag gcg     192
Val Phe Gly Asn Val Leu Val Cys Met Ala Val Ser Arg Glu Lys Ala
     50                  55                  60 ctg cag acc acc aac tac ctg atc gtc agc ctc gca gtg gcc gac         240
Leu Gln Thr Thr Thr Asn Tyr Leu Ile Val Ser Leu Ala Val Ala Asp
 65                  70                  75                  80 ctc ctc gtc gcc aca ctg gtc atg cca tgg gtt gtc tac ctg gag gtg     288
Leu Leu Val Ala Thr Leu Val Met Pro Trp Val Val Tyr Leu Glu Val
                 85                  90                  95 gta ggt gag tgg aaa ttc agc agg att cac tgt gac atc ttc gtc act     336
Val Gly Glu Trp Lys Phe Ser Arg Ile His Cys Asp Ile Phe Val Thr
            100                 105                 110
```

-continued

| | |
|---|---|
| ctg gac gtc atg atg tgc acg gcg agc atc ctg aac ttg tgt gcc atc<br>Leu Asp Val Met Met Cys Thr Ala Ser Ile Leu Asn Leu Cys Ala Ile<br>115                       120                    125 | 384 |
| agc atc gac agg tac aca gct gtg gcc atg ccc atg ctg tac aat acg<br>Ser Ile Asp Arg Tyr Thr Ala Val Ala Met Pro Met Leu Tyr Asn Thr<br>   130                     135                    140 | 432 |
| cgc tac agc tcc aag cgc cgg gtc acc gtc atg atc tcc atc gtc tgg<br>Arg Tyr Ser Ser Lys Arg Arg Val Thr Val Met Ile Ser Ile Val Trp<br>145                       150                    155                    160 | 480 |
| gtc ctg tcc ttc acc atc tcc tgc cca ctc ctc ttc gga ctc aat aac<br>Val Leu Ser Phe Thr Ile Ser Cys Pro Leu Leu Phe Gly Leu Asn Asn<br>                    165                    170                    175 | 528 |
| gca gac cag aac gag tgc atc att gcc aac ccg gcc ttc gtg gtc tac<br>Ala Asp Gln Asn Glu Cys Ile Ile Ala Asn Pro Ala Phe Val Val Tyr<br>              180                     185                    190 | 576 |
| tcc tcc atc gtc tcc ttc tac gtg ccc ttc att gtc acc ctg ctg gtc<br>Ser Ser Ile Val Ser Phe Tyr Val Pro Phe Ile Val Thr Leu Leu Val<br>                    195                    200                    205 | 624 |
| tac atc aag atc tac att gtc ctc cgc aga cgc cgc aag cga gtc aac<br>Tyr Ile Lys Ile Tyr Ile Val Leu Arg Arg Arg Arg Lys Arg Val Asn<br>210                       215                    220 | 672 |
| acc aaa cgc agc agc cga gct ttc agg gcc cac ctg agg gct cca cta<br>Thr Lys Arg Ser Ser Arg Ala Phe Arg Ala His Leu Arg Ala Pro Leu<br>225                       230                    235                    240 | 720 |
| aag ggc aac tgt act cac ccc gag gac atg aaa ctc tgc acc gtt atc<br>Lys Gly Asn Cys Thr His Pro Glu Asp Met Lys Leu Cys Thr Val Ile<br>                    245                    250                    255 | 768 |
| atg aag tct aat ggg agt ttc cca gtg aac agg cgg aga gtg gag gct<br>Met Lys Ser Asn Gly Ser Phe Pro Val Asn Arg Arg Arg Val Glu Ala<br>                      260                    265                    270 | 816 |
| gcc cgg cga gcc cag gag ctg gag atg gag atg ctc tcc agc acc agc<br>Ala Arg Arg Ala Gln Glu Leu Glu Met Glu Met Leu Ser Ser Thr Ser<br>275                       280                    285 | 864 |
| cca ccc gag agg acc cgg tac agc ccc atc cca ccc agc cac cac cag<br>Pro Pro Glu Arg Thr Arg Tyr Ser Pro Ile Pro Pro Ser His His Gln<br>   290                     295                    300 | 912 |
| ctg act ctc ccc gac ccg tcc cac cac ggt ctc cac agc act cct gac<br>Leu Thr Leu Pro Asp Pro Ser His His Gly Leu His Ser Thr Pro Asp<br>305                       310                    315                    320 | 960 |
| agc ccc gcc aaa cca gag aag aat ggg cat gcc aaa gac cac ccc aag<br>Ser Pro Ala Lys Pro Glu Lys Asn Gly His Ala Lys Asp His Pro Lys<br>                    325                    330                    335 | 1008 |
| att gcc aag atc ttt gag atc cag acc atg ccc aat ggc aaa acc cgg<br>Ile Ala Lys Ile Phe Glu Ile Gln Thr Met Pro Asn Gly Lys Thr Arg<br>              340                     345                    350 | 1056 |
| acc tcc ctc aag acc atg agc cgt aga aag ctc tcc cag cag aag gag<br>Thr Ser Leu Lys Thr Met Ser Arg Arg Lys Leu Ser Gln Gln Lys Glu<br>355                       360                    365 | 1104 |
| aag aaa gcc act cag atg ctc gcc att gtt ctc ggc gtg ttc atc atc<br>Lys Lys Ala Thr Gln Met Leu Ala Ile Val Leu Gly Val Phe Ile Ile<br>   370                     375                    380 | 1152 |
| tgc tgg ctg ccc ttc ttc atc aca cac atc ctg aac ata cac tgt gac<br>Cys Trp Leu Pro Phe Phe Ile Thr His Ile Leu Asn Ile His Cys Asp<br>385                       390                    395                    400 | 1200 |
| tgc aac atc ccg cct gtc ctg tac agc gcc ttc acg tgg ctg ggc tat<br>Cys Asn Ile Pro Pro Val Leu Tyr Ser Ala Phe Thr Trp Leu Gly Tyr<br>                    405                    410                    415 | 1248 |
| gtc aac agc gcc gtg aac ccc atc atc tac acc acc ttc aac att gag<br>Val Asn Ser Ala Val Asn Pro Ile Ile Tyr Thr Thr Phe Asn Ile Glu<br>                      420                    425                    430 | 1296 |

```
ttc cgc aag gcc ttc ctg aag atc ctt cac tgc tga                      1332
Phe Arg Lys Ala Phe Leu Lys Ile Leu His Cys  *
    435                 440
```

<210> SEQ ID NO 2
<211> LENGTH: 443
<212> TYPE: PRT
<213> ORGANISM: Homo Sapiens

<400> SEQUENCE: 2

```
Met Asp Pro Leu Asn Leu Ser Trp Tyr Asp Asp Leu Glu Arg Gln
  1               5                  10                  15

Asn Trp Ser Arg Pro Phe Asn Gly Ser Asp Gly Lys Ala Asp Arg Pro
             20                  25                  30

His Tyr Asn Tyr Tyr Ala Thr Leu Leu Thr Leu Leu Ile Ala Val Ile
         35                  40                  45

Val Phe Gly Asn Val Leu Val Cys Met Ala Val Ser Arg Glu Lys Ala
     50                  55                  60

Leu Gln Thr Thr Thr Asn Tyr Leu Ile Val Ser Leu Ala Val Ala Asp
 65                  70                  75                  80

Leu Leu Val Ala Thr Leu Val Met Pro Trp Val Val Tyr Leu Glu Val
                 85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
        115                 120                 125

Ser Ile Asp Arg Tyr Thr Ala Val Ala Met Pro Met Leu Tyr Asn Thr
    130                 135                 140

Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Arg Arg Arg Lys Arg Val Asn
    210                 215                 220

Thr Lys Arg Ser Ser Arg Ala Phe Arg Ala His Leu Arg Ala Pro Leu
225                 230                 235                 240

Lys Gly Asn Cys Thr His Pro Glu Asp Met Lys Leu Cys Thr Val Ile
                245                 250                 255

Met Lys Ser Asn Gly Ser Phe Pro Val Asn Arg Arg Arg Val Glu Ala
            260                 265                 270

Ala Arg Arg Ala Gln Glu Leu Glu Met Glu Met Leu Ser Ser Thr Ser
        275                 280                 285

Pro Pro Glu Arg Thr Arg Tyr Ser Pro Ile Pro Pro Ser His His Gln
    290                 295                 300

Leu Thr Leu Pro Asp Pro Ser His His Gly Leu His Ser Thr Pro Asp
305                 310                 315                 320

Ser Pro Ala Lys Pro Glu Lys Asn Gly His Ala Lys Asp His Pro Lys
                325                 330                 335

Ile Ala Lys Ile Phe Glu Ile Gln Thr Met Pro Asn Gly Lys Thr Arg
            340                 345                 350
```

```
Thr Ser Leu Lys Thr Met Ser Arg Arg Lys Leu Ser Gln Gln Lys Glu
        355                 360                 365

Lys Lys Ala Thr Gln Met Leu Ala Ile Val Leu Gly Val Phe Ile Ile
    370                 375                 380

Cys Trp Leu Pro Phe Phe Ile Thr His Ile Leu Asn Ile His Cys Asp
385                 390                 395                 400

Cys Asn Ile Pro Pro Val Leu Tyr Ser Ala Phe Thr Trp Leu Gly Tyr
                405                 410                 415

Val Asn Ser Ala Val Asn Pro Ile Ile Tyr Thr Thr Phe Asn Ile Glu
            420                 425                 430

Phe Arg Lys Ala Phe Leu Lys Ile Leu His Cys
        435                 440
```

```
<210> SEQ ID NO 3
<211> LENGTH: 1434
<212> TYPE: DNA
<213> ORGANISM: Homo Sapiens
<220> FEATURE:
<221> NAME/KEY: CDS
<222> LOCATION: (1)...(1434)

<400> SEQUENCE: 3
```

| | | |
|---|---|---|
| atg ctg ccg cca ggc agc aac ggc acc gcg tac ccg ggg cag ttc gct<br>Met Leu Pro Pro Gly Ser Asn Gly Thr Ala Tyr Pro Gly Gln Phe Ala<br>1               5               10              15 | 48 |
| cta tac cag cag ctg gcg cag ggg aac gcc gtg ggg ggc tcg gcg ggg<br>Leu Tyr Gln Gln Leu Ala Gln Gly Asn Ala Val Gly Gly Ser Ala Gly<br>              20               25              30 | 96 |
| gca ccg cca ctg ggg ccc tca cag gtg gtc acc gcc tgc ctg ctg acc<br>Ala Pro Pro Leu Gly Pro Ser Gln Val Val Thr Ala Cys Leu Leu Thr<br>        35               40              45 | 144 |
| cta ctc atc atc tgg acc ctg ctg ggc aac gtg ctg gtg tgc gca gcc<br>Leu Leu Ile Ile Trp Thr Leu Leu Gly Asn Val Leu Val Cys Ala Ala<br>50              55              60 | 192 |
| atc gtg cgg agc cgc cac ctg cgc gcc aac atg acc aac gtc ttc atc<br>Ile Val Arg Ser Arg His Leu Arg Ala Asn Met Thr Asn Val Phe Ile<br>65               70              75              80 | 240 |
| gtg tct ctg gcc gtg tca gac ctt ttc gtg gcg ctg ctg gtc atg ccc<br>Val Ser Leu Ala Val Ser Asp Leu Phe Val Ala Leu Leu Val Met Pro<br>                 85              90              95 | 288 |
| tgg aag gca gtc gcc gag gtg gcc ggt tac tgg ccc ttt gga gcg ttc<br>Trp Lys Ala Val Ala Glu Val Ala Gly Tyr Trp Pro Phe Gly Ala Phe<br>             100             105           110 | 336 |
| tgc gac gtc tgg gtg gcc ttc gac atc atg tgc tcc act gcc tcc atc<br>Cys Asp Val Trp Val Ala Phe Asp Ile Met Cys Ser Thr Ala Ser Ile<br>           115             120            125 | 384 |
| ctg aac ctg tgc gtc atc agc gtg gac cgc tac tgg gcc atc tcc agg<br>Leu Asn Leu Cys Val Ile Ser Val Asp Arg Tyr Trp Ala Ile Ser Arg<br>      130              135            140 | 432 |
| ccc ttc cgc tac aag cgc aag atg act cag cgc atg gcc ttg gtc atg<br>Pro Phe Arg Tyr Lys Arg Lys Met Thr Gln Arg Met Ala Leu Val Met<br>145             150             155           160 | 480 |
| gtc ggc ctg gca tgg acc ttg tcc atc ctc atc tcc ttc att ccg gtc<br>Val Gly Leu Ala Trp Thr Leu Ser Ile Leu Ile Ser Phe Ile Pro Val<br>           165             170            175 | 528 |
| cag ctc aac tgg cac agg gac cag gcg gcc tct tgg ggc ggg ctg gac<br>Gln Leu Asn Trp His Arg Asp Gln Ala Ala Ser Trp Gly Gly Leu Asp<br>        180              185           190 | 576 |
| ctg cca aac aac ctg gcc aac tgg acg ccc tgg gag gag gac ttt tgg<br>Leu Pro Asn Asn Leu Ala Asn Trp Thr Pro Trp Glu Glu Asp Phe Trp | 624 |

```
                195                 200                 205
gag ccc gac gtg aat gca gag aac tgt gac tcc agc ctg aat cga acc        672
Glu Pro Asp Val Asn Ala Glu Asn Cys Asp Ser Ser Leu Asn Arg Thr
        210                 215                 220 tac gcc atc tct tcc tcg ctc atc agc ttc tac atc ccc gtt gcc atc        720
Tyr Ala Ile Ser Ser Ser Leu Ile Ser Phe Tyr Ile Pro Val Ala Ile
225                 230                 235                 240 atg atc gtg acc tac acg cgc atc tac cgc atc gcc cag gtg cag atc        768
Met Ile Val Thr Tyr Thr Arg Ile Tyr Arg Ile Ala Gln Val Gln Ile
                245                 250                 255 cgc agg att tcc tcc ctg gag agg gcc gca gag cac gcg cag agc tgc        816
Arg Arg Ile Ser Ser Leu Glu Arg Ala Ala Glu His Ala Gln Ser Cys
        260                 265                 270 cgg agc agc gca gcc tgc gcg ccc gac acc agc ctg cgc gct tcc atc        864
Arg Ser Ser Ala Ala Cys Ala Pro Asp Thr Ser Leu Arg Ala Ser Ile
    275                 280                 285 aag aag gag acc aag gtt ctc aag acc ctg tcg gtg atc atg ggg gtc        912
Lys Lys Glu Thr Lys Val Leu Lys Thr Leu Ser Val Ile Met Gly Val
290                 295                 300 ttc gtg tgt tgc tgg ctg ccc ttc ttc atc ctt aac tgc atg gtc cct        960
Phe Val Cys Cys Trp Leu Pro Phe Phe Ile Leu Asn Cys Met Val Pro
305                 310                 315                 320 ttc tgc agt gga cac ccc gaa ggc cct ccg gcc ggc ttc ccc tgc gtc       1008
Phe Cys Ser Gly His Pro Glu Gly Pro Pro Ala Gly Phe Pro Cys Val
                325                 330                 335 agt gag acc acc ttc gac gtc ttc gtc tgg ttc ggc tgg gct aac tcc       1056
Ser Glu Thr Thr Phe Asp Val Phe Val Trp Phe Gly Trp Ala Asn Ser
        340                 345                 350 tca ctc aac ccc gtc atc tat gcc ttc aac gcc gac ttt cag aag gtg       1104
Ser Leu Asn Pro Val Ile Tyr Ala Phe Asn Ala Asp Phe Gln Lys Val
    355                 360                 365 ttt gcc cag ctg ctg ggg tgc agc cac ttc tgc tcc cgc acg ccg gtg       1152
Phe Ala Gln Leu Leu Gly Cys Ser His Phe Cys Ser Arg Thr Pro Val
370                 375                 380 gag acg gtg aac atc agc aat gag ctc atc tcc tac aac caa gac atc       1200
Glu Thr Val Asn Ile Ser Asn Glu Leu Ile Ser Tyr Asn Gln Asp Ile
385                 390                 395                 400 gtc ttc cac aag gaa atc gca gct gcc tac atc cac atg atg ccc aac       1248
Val Phe His Lys Glu Ile Ala Ala Ala Tyr Ile His Met Met Pro Asn
                405                 410                 415 gcc gtt acc ccc ggc aac cgg gag gtg gac aac gac gag gag gag ggt       1296
Ala Val Thr Pro Gly Asn Arg Glu Val Asp Asn Asp Glu Glu Glu Gly
        420                 425                 430 cct ttc gat cgc atg ttc cag atc tat cag acg tcc cca gat ggt gac       1344
Pro Phe Asp Arg Met Phe Gln Ile Tyr Gln Thr Ser Pro Asp Gly Asp
    435                 440                 445 cct gtt gct gag tct gtc tgg gag ctg gac tgc gag ggg gag att tct       1392
Pro Val Ala Glu Ser Val Trp Glu Leu Asp Cys Glu Gly Glu Ile Ser
450                 455                 460 tta gac aaa ata aca cct ttc acc ccg aat gga ttc cat taa               1434
Leu Asp Lys Ile Thr Pro Phe Thr Pro Asn Gly Phe His *
465                 470                 475

<210> SEQ ID NO 4
<211> LENGTH: 477
<212> TYPE: PRT
<213> ORGANISM: Homo Sapiens

<400> SEQUENCE: 4

Met Leu Pro Pro Gly Ser Asn Gly Thr Ala Tyr Pro Gly Gln Phe Ala
```

-continued

```
  1               5                   10                  15
Leu Tyr Gln Gln Leu Ala Gln Gly Asn Ala Val Gly Gly Ser Ala Gly
                20                  25                  30

Ala Pro Pro Leu Gly Pro Ser Gln Val Val Thr Ala Cys Leu Leu Thr
                35                  40              45

Leu Leu Ile Ile Trp Thr Leu Leu Gly Asn Val Leu Val Cys Ala Ala
50                      55                  60

Ile Val Arg Ser Arg His Leu Arg Ala Asn Met Thr Asn Val Phe Ile
65                  70                  75                  80

Val Ser Leu Ala Val Ser Asp Leu Phe Val Ala Leu Leu Val Met Pro
                85                  90                  95

Trp Lys Ala Val Ala Glu Val Ala Gly Tyr Trp Pro Phe Gly Ala Phe
                100                 105                 110

Cys Asp Val Trp Val Ala Phe Asp Ile Met Cys Ser Thr Ala Ser Ile
                115                 120             125

Leu Asn Leu Cys Val Ile Ser Val Asp Arg Tyr Trp Ala Ile Ser Arg
            130                 135                 140

Pro Phe Arg Tyr Lys Arg Lys Met Thr Gln Arg Met Ala Leu Val Met
145                 150                 155                 160

Val Gly Leu Ala Trp Thr Leu Ser Ile Leu Ile Ser Phe Ile Pro Val
                165                 170                 175

Gln Leu Asn Trp His Arg Asp Gln Ala Ala Ser Trp Gly Gly Leu Asp
                180             185                 190

Leu Pro Asn Asn Leu Ala Asn Trp Thr Pro Trp Glu Glu Asp Phe Trp
            195                 200                 205

Glu Pro Asp Val Asn Ala Glu Asn Cys Asp Ser Ser Leu Asn Arg Thr
            210                 215                 220

Tyr Ala Ile Ser Ser Leu Ile Ser Phe Tyr Ile Pro Val Ala Ile
225                 230                 235                 240

Met Ile Val Thr Tyr Thr Arg Ile Tyr Arg Ile Ala Gln Val Gln Ile
                245                 250                 255

Arg Arg Ile Ser Ser Leu Glu Arg Ala Ala Glu His Ala Gln Ser Cys
            260                 265                 270

Arg Ser Ser Ala Ala Cys Ala Pro Asp Thr Ser Leu Arg Ala Ser Ile
        275                 280                 285

Lys Lys Glu Thr Lys Val Leu Lys Thr Leu Ser Val Ile Met Gly Val
        290                 295                 300

Phe Val Cys Cys Trp Leu Pro Phe Phe Ile Leu Asn Cys Met Val Pro
305                 310                 315                 320

Phe Cys Ser Gly His Pro Glu Gly Pro Pro Ala Gly Phe Pro Cys Val
                325                 330                 335

Ser Glu Thr Thr Phe Asp Val Phe Val Trp Phe Gly Trp Ala Asn Ser
                340                 345                 350

Ser Leu Asn Pro Val Ile Tyr Ala Phe Asn Ala Asp Phe Gln Lys Val
            355                 360                 365

Phe Ala Gln Leu Leu Gly Cys Ser His Phe Cys Ser Arg Thr Pro Val
        370                 375                 380

Glu Thr Val Asn Ile Ser Asn Glu Leu Ile Ser Tyr Asn Gln Asp Ile
385                 390                 395                 400

Val Phe His Lys Glu Ile Ala Ala Ala Tyr Ile His Met Met Pro Asn
                405                 410                 415

Ala Val Thr Pro Gly Asn Arg Glu Val Asp Asn Asp Glu Glu Glu Gly
                420                 425                 430
```

```
Pro Phe Asp Arg Met Phe Gln Ile Tyr Gln Thr Ser Pro Asp Gly Asp
    435                 440                 445

Pro Val Ala Glu Ser Val Trp Glu Leu Asp Cys Glu Gly Glu Ile Ser
450                 455                 460

Leu Asp Lys Ile Thr Pro Phe Thr Pro Asn Gly Phe His
465                 470                 475

<210> SEQ ID NO 5
<211> LENGTH: 1141
<212> TYPE: DNA
<213> ORGANISM: Homo Sapiens
<220> FEATURE:
<221> NAME/KEY: CDS
<222> LOCATION: (27)...(1127)

<400> SEQUENCE: 5
```

| | |
|---|---|
| tatattaatc ttttaaaaca aagaaa atg gat ttc tta aat tca tct gat caa<br>              Met Asp Phe Leu Asn Ser Ser Asp Gln<br>               1      5 | 53 |
| aac ttg acc tca gag gaa ctg tta aac aga atg cca tcc aaa att ctg<br>Asn Leu Thr Ser Glu Glu Leu Leu Asn Arg Met Pro Ser Lys Ile Leu<br> 10        15       20       25 | 101 |
| gtg tcc ctc act ctg tct ggg ctg gca ctg atg aca aca act atc aac<br>Val Ser Leu Thr Leu Ser Gly Leu Ala Leu Met Thr Thr Thr Ile Asn<br>        30         35        40 | 149 |
| tcc ctt gtg atc gct gca att att gtg acc cgg aag ctg cac cat cca<br>Ser Leu Val Ile Ala Ala Ile Ile Val Thr Arg Lys Leu His His Pro<br>        45         50        55 | 197 |
| gcc aat tat tta att tgt tcc ctt gca gtc aca gat ttt ctt gtg gct<br>Ala Asn Tyr Leu Ile Cys Ser Leu Ala Val Thr Asp Phe Leu Val Ala<br>    60         65        70 | 245 |
| gtc ctg gtg atg ccc ttc agc att gtg tat att gtg aga gag agc tgg<br>Val Leu Val Met Pro Phe Ser Ile Val Tyr Ile Val Arg Glu Ser Trp<br> 75         80        85 | 293 |
| att atg ggg caa gtg gtc tgt gac att tgg ctg agt gtt gac att acc<br>Ile Met Gly Gln Val Val Cys Asp Ile Trp Leu Ser Val Asp Ile Thr<br> 90         95       100       105 | 341 |
| tgc tgc acg tgc tcc atc ttg cat ctc tca gct ata gct ttg gat cgg<br>Cys Cys Thr Cys Ser Ile Leu His Leu Ser Ala Ile Ala Leu Asp Arg<br>        110        115       120 | 389 |
| tat cga gca atc aca gat gct gtt gag tat gcc agg aaa agg act cca<br>Tyr Arg Ala Ile Thr Asp Ala Val Glu Tyr Ala Arg Lys Arg Thr Pro<br>        125        130       135 | 437 |
| aag cat gct ggc att atg att aca ata gtt tgg att ata tct gtt ttt<br>Lys His Ala Gly Ile Met Ile Thr Ile Val Trp Ile Ile Ser Val Phe<br>    140        145        150 | 485 |
| atc tct atg cct cct cta ttc tgg agg cac caa gga act agc aga gat<br>Ile Ser Met Pro Pro Leu Phe Trp Arg His Gln Gly Thr Ser Arg Asp<br> 155        160       165 | 533 |
| gat gaa tgc atc atc aag cac gac cac att gtt tcc acc att tac tca<br>Asp Glu Cys Ile Ile Lys His Asp His Ile Val Ser Thr Ile Tyr Ser<br>170        175       180       185 | 581 |
| aca ttt gga gct ttc tac atc cca ctg gca ttg att tgt atc ctt tac<br>Thr Phe Gly Ala Phe Tyr Ile Pro Leu Ala Leu Ile Leu Ile Leu Tyr<br>        190        195       200 | 629 |
| tac aaa ata tat aga gca gca aag aca tta tac cac aag aga caa gca<br>Tyr Lys Ile Tyr Arg Ala Ala Lys Thr Leu Tyr His Lys Arg Gln Ala<br>        205        210       215 | 677 |
| agt agg att gca aag gag gag gtg aat ggc caa gtc ctt ttg gag agt<br>Ser Arg Ile Ala Lys Glu Glu Val Asn Gly Gln Val Leu Leu Glu Ser | 725 |

-continued

```
                    220                 225                 230
ggt gag aaa agc act aaa tca gtt tcc aca tcc tat gta cta gaa aag      773
Gly Glu Lys Ser Thr Lys Ser Val Ser Thr Ser Tyr Val Leu Glu Lys
        235                 240                 245 tct tta tct gac cca tca aca gac ttt gat aaa att cat agc aca gtg      821
Ser Leu Ser Asp Pro Ser Thr Asp Phe Asp Lys Ile His Ser Thr Val
250                 255                 260                 265 aga agt ctc agg tct gaa ttc aag cat gag aaa tct tgg aga agg caa      869
Arg Ser Leu Arg Ser Glu Phe Lys His Glu Lys Ser Trp Arg Arg Gln
                270                 275                 280 aag atc tca ggt aca aga gaa cgg aaa gca gcc act acc ctg gga tta      917
Lys Ile Ser Gly Thr Arg Glu Arg Lys Ala Ala Thr Thr Leu Gly Leu
            285                 290                 295 atc ttg ggt gca ttt gta ata tgt tgg ctt cct ttt ttt gta aaa gaa      965
Ile Leu Gly Ala Phe Val Ile Cys Trp Leu Pro Phe Phe Val Lys Glu
        300                 305                 310 tta gtt gtt aat gtc tgt gac aaa tgt aaa att tct gaa gaa atg tcc     1013
Leu Val Val Asn Val Cys Asp Lys Cys Lys Ile Ser Glu Glu Met Ser
315                 320                 325 aat ttt ttg gca tgg ctt ggg tat ctc aat tcc ctt ata aat cca ctg     1061
Asn Phe Leu Ala Trp Leu Gly Tyr Leu Asn Ser Leu Ile Asn Pro Leu
330                 335                 340                 345 att tac aca atc ttt aat gaa gac ttc aag aaa gca ttc caa aag ctt     1109
Ile Tyr Thr Ile Phe Asn Glu Asp Phe Lys Lys Ala Phe Gln Lys Leu
                350                 355                 360 gtg cga tgt cga tgt tag ttttaaaaat gttt                             1141
Val Arg Cys Arg Cys *
            365

<210> SEQ ID NO 6
<211> LENGTH: 366
<212> TYPE: PRT
<213> ORGANISM: Homo Sapiens

<400> SEQUENCE: 6

Met Asp Phe Leu Asn Ser Ser Asp Gln Asn Leu Thr Ser Glu Glu Leu
1               5                   10                  15

Leu Asn Arg Met Pro Ser Lys Ile Leu Val Ser Leu Thr Leu Ser Gly
            20                  25                  30

Leu Ala Leu Met Thr Thr Thr Ile Asn Ser Leu Val Ile Ala Ala Ile
        35                  40                  45

Ile Val Thr Arg Lys Leu His His Pro Ala Asn Tyr Leu Ile Cys Ser
    50                  55                  60

Leu Ala Val Thr Asp Phe Leu Val Ala Val Leu Val Met Pro Phe Ser
65                  70                  75                  80

Ile Val Tyr Ile Val Arg Glu Ser Trp Ile Met Gly Gln Val Val Cys
                85                  90                  95

Asp Ile Trp Leu Ser Val Asp Ile Thr Cys Cys Thr Cys Ser Ile Leu
            100                 105                 110

His Leu Ser Ala Ile Ala Leu Asp Arg Tyr Arg Ala Ile Thr Asp Ala
        115                 120                 125

Val Glu Tyr Ala Arg Lys Arg Thr Pro Lys His Ala Gly Ile Met Ile
    130                 135                 140

Thr Ile Val Trp Ile Ile Ser Val Phe Ile Ser Met Pro Pro Leu Phe
145                 150                 155                 160

Trp Arg His Gln Gly Thr Ser Arg Asp Asp Glu Cys Ile Ile Lys His
                165                 170                 175
```

-continued

```
Asp His Ile Val Ser Thr Ile Tyr Ser Thr Phe Gly Ala Phe Tyr Ile
            180                 185                 190

Pro Leu Ala Leu Ile Leu Ile Leu Tyr Tyr Lys Ile Tyr Arg Ala Ala
            195                 200                 205

Lys Thr Leu Tyr His Lys Arg Gln Ala Ser Arg Ile Ala Lys Glu Glu
            210                 215                 220

Val Asn Gly Gln Val Leu Leu Glu Ser Gly Glu Lys Ser Thr Lys Ser
225                 230                 235                 240

Val Ser Thr Ser Tyr Val Leu Glu Lys Ser Leu Ser Asp Pro Ser Thr
                245                 250                 255

Asp Phe Asp Lys Ile His Ser Thr Val Arg Ser Leu Arg Ser Glu Phe
            260                 265                 270

Lys His Glu Lys Ser Trp Arg Arg Gln Lys Ile Ser Gly Thr Arg Glu
            275                 280                 285

Arg Lys Ala Ala Thr Thr Leu Gly Leu Ile Leu Gly Ala Phe Val Ile
            290                 295                 300

Cys Trp Leu Pro Phe Phe Val Lys Glu Leu Val Val Asn Val Cys Asp
305                 310                 315                 320

Lys Cys Lys Ile Ser Glu Glu Met Ser Asn Phe Leu Ala Trp Leu Gly
                325                 330                 335

Tyr Leu Asn Ser Leu Ile Asn Pro Leu Ile Tyr Thr Ile Phe Asn Glu
            340                 345                 350

Asp Phe Lys Lys Ala Phe Gln Lys Leu Val Arg Cys Arg Cys
            355                 360                 365

<210> SEQ ID NO 7
<211> LENGTH: 1408
<212> TYPE: DNA
<213> ORGANISM: Homo Sapiens
<220> FEATURE:
<221> NAME/KEY: CDS
<222> LOCATION: (84)...(1343)

<400> SEQUENCE: 7
ccacgcgtcc gcggacgcgt gggtcggcac cggcgaggcc gtgctggaac ccgggcctca      60
gccgcagccg cagcggggcc gac atg acg aca gct ccc cag gag ccc ccc gcc    113
                         Met Thr Thr Ala Pro Gln Glu Pro Pro Ala
                           1               5                  10 cgg ccc ctc cag gcg ggc agt gga gct ggc ccg gcg cct ggg cgc gcc      161
Arg Pro Leu Gln Ala Gly Ser Gly Ala Gly Pro Ala Pro Gly Arg Ala
                15                  20                  25 atg cgc agc acc acg ctc ctg gcc ctg ctg gcg ctg gtc ttg ctt tac      209
Met Arg Ser Thr Thr Leu Leu Ala Leu Leu Ala Leu Val Leu Leu Tyr
        30                  35                  40 ttg gtg tct ggt gcc ctg gtg ttc cgg gcc ctg gag cag ccc cac gag      257
Leu Val Ser Gly Ala Leu Val Phe Arg Ala Leu Glu Gln Pro His Glu
    45                  50                  55 cag cag gcc cag agg gag ctg ggg gag gtc cga gag aag ttc ctg agg      305
Gln Gln Ala Gln Arg Glu Leu Gly Glu Val Arg Glu Lys Phe Leu Arg
60                  65                  70 gcc cat ccg tgt gtg agc gac cag gag ctg ggc ctc ctc atc aag gag      353
Ala His Pro Cys Val Ser Asp Gln Glu Leu Gly Leu Leu Ile Lys Glu
75                  80                  85                  90 gtg gct gat gcc ctg gga ggg ggt gcg gac cca gaa acc aac tcg acc      401
Val Ala Asp Ala Leu Gly Gly Gly Ala Asp Pro Glu Thr Asn Ser Thr
                95                  100                 105 agc aac agc agc cac tca gcc tgg gac ctg ggc agc gcc ttc ttt ttc      449
Ser Asn Ser Ser His Ser Ala Trp Asp Leu Gly Ser Ala Phe Phe Phe
            110                 115                 120
```

-continued

```
                    110                 115                 120
tca ggg acc atc atc acc acc atc ggc tat ggc aat gtg gcc ctg cgc        497
Ser Gly Thr Ile Ile Thr Thr Ile Gly Tyr Gly Asn Val Ala Leu Arg
        125                 130                 135 aca gat gcc ggg cgc ctc ttc tgc atc ttt tat gcg ctg gtg ggg att        545
Thr Asp Ala Gly Arg Leu Phe Cys Ile Phe Tyr Ala Leu Val Gly Ile
    140                 145                 150 ccg ctg ttt ggg atc cta ctg gca ggg gtc ggg gac cgg ctg ggc tcc        593
Pro Leu Phe Gly Ile Leu Leu Ala Gly Val Gly Asp Arg Leu Gly Ser
155                 160                 165                 170 tcc ctg cgc cat ggc atc ggt cac att gaa gcc atc ttc ttg aag tgg        641
Ser Leu Arg His Gly Ile Gly His Ile Glu Ala Ile Phe Leu Lys Trp
                175                 180                 185 cac gtg cca ccg gag cta gta aga gtg ctg tcg gcg atg ctt ttc ctg        689
His Val Pro Pro Glu Leu Val Arg Val Leu Ser Ala Met Leu Phe Leu
            190                 195                 200 ctg atc ggc tgc ctg ctc ttt gtc ctc acg ccc acg ttc gtg ttc tgc        737
Leu Ile Gly Cys Leu Leu Phe Val Leu Thr Pro Thr Phe Val Phe Cys
        205                 210                 215 tat atg gag gac tgg agc aag ctg gag gcc atc tac ttt gtc ata gtg        785
Tyr Met Glu Asp Trp Ser Lys Leu Glu Ala Ile Tyr Phe Val Ile Val
    220                 225                 230 acg ctt acc acc gtg ggc ttt ggc gac tat gtg gcc ggc gcg gac ccc        833
Thr Leu Thr Thr Val Gly Phe Gly Asp Tyr Val Ala Gly Ala Asp Pro
235                 240                 245                 250 agg cag gac tcc ccg gcc tat cag ccg ctg gtg tgg ttc tgg atc ctg        881
Arg Gln Asp Ser Pro Ala Tyr Gln Pro Leu Val Trp Phe Trp Ile Leu
                255                 260                 265 ctc ggc ctg gct tac ttc gcc tca gtg ctc acc acc atc ggg aac tgg        929
Leu Gly Leu Ala Tyr Phe Ala Ser Val Leu Thr Thr Ile Gly Asn Trp
            270                 275                 280 ctg cga gta gtg tcc cgc cgc act cgg gca gag atg ggc ggc ctc acg        977
Leu Arg Val Val Ser Arg Arg Thr Arg Ala Glu Met Gly Gly Leu Thr
        285                 290                 295 gct cag gct gcc agc tgg act ggc aca gtg aca gcg cgc gtg acc cag       1025
Ala Gln Ala Ala Ser Trp Thr Gly Thr Val Thr Ala Arg Val Thr Gln
    300                 305                 310 cga gcc ggg ccc gcc gcc ccg ccg gag aag gag cag cca ctg ctg            1073
Arg Ala Gly Pro Ala Ala Pro Pro Glu Lys Glu Gln Pro Leu Leu
315                 320                 325                 330 cct cca ccg ccc tgt cca gcg cag ccg ctg ggc agg ccc cga tcc cct       1121
Pro Pro Pro Pro Cys Pro Ala Gln Pro Leu Gly Arg Pro Arg Ser Pro
                335                 340                 345 tcg ccc ccc gag aag gct cag ccg cct tcc ccg ccc acg gcc tcg gcc       1169
Ser Pro Pro Glu Lys Ala Gln Pro Pro Ser Pro Pro Thr Ala Ser Ala
            350                 355                 360 ctg gat tat ccc agc gag aac ctg gcc ttc atc gac gag tcc tcg gat       1217
Leu Asp Tyr Pro Ser Glu Asn Leu Ala Phe Ile Asp Glu Ser Ser Asp
        365                 370                 375 acg cag agc gag cgc ggc tgc ccg ctg ccc cgc gcg ccg aga ggt cgc       1265
Thr Gln Ser Glu Arg Gly Cys Pro Leu Pro Arg Ala Pro Arg Gly Arg
    380                 385                 390 cgc cgc cca aat ccc ccc agg aag ccc gtg cgg ccc cgc ggc ccc ggg       1313
Arg Arg Pro Asn Pro Pro Arg Lys Pro Val Arg Pro Arg Gly Pro Gly
395                 400                 405                 410 cgt ccc cga gac aaa ggc gtg ccg gtg tag gggcaggatc cctggccggg         1363
Arg Pro Arg Asp Lys Gly Val Pro Val  *
                415 cctctcaagg gcttcgtttc tgctctcccc ggcatgcctg gcttc                    1408
```

<210> SEQ ID NO 8
<211> LENGTH: 419
<212> TYPE: PRT
<213> ORGANISM: Homo Sapiens

<400> SEQUENCE: 8

```
Met Thr Thr Ala Pro Gln Glu Pro Pro Ala Arg Pro Leu Gln Ala Gly
 1               5                  10                  15

Ser Gly Ala Gly Pro Ala Pro Gly Arg Ala Met Arg Ser Thr Thr Leu
            20                  25                  30

Leu Ala Leu Leu Ala Leu Val Leu Leu Tyr Leu Val Ser Gly Ala Leu
        35                  40                  45

Val Phe Arg Ala Leu Glu Gln Pro His Glu Gln Gln Ala Gln Arg Glu
50                  55                  60

Leu Gly Glu Val Arg Glu Lys Phe Leu Arg Ala His Pro Cys Val Ser
65                  70                  75                  80

Asp Gln Glu Leu Gly Leu Leu Ile Lys Glu Val Ala Asp Ala Leu Gly
                85                  90                  95

Gly Gly Ala Asp Pro Glu Thr Asn Ser Thr Ser Asn Ser Ser His Ser
            100                 105                 110

Ala Trp Asp Leu Gly Ser Ala Phe Phe Phe Ser Gly Thr Ile Ile Thr
        115                 120                 125

Thr Ile Gly Tyr Gly Asn Val Ala Leu Arg Thr Asp Ala Gly Arg Leu
130                 135                 140

Phe Cys Ile Phe Tyr Ala Leu Val Gly Ile Pro Leu Phe Gly Ile Leu
145                 150                 155                 160

Leu Ala Gly Val Gly Asp Arg Leu Gly Ser Ser Leu Arg His Gly Ile
                165                 170                 175

Gly His Ile Glu Ala Ile Phe Leu Lys Trp His Val Pro Pro Glu Leu
            180                 185                 190

Val Arg Val Leu Ser Ala Met Leu Phe Leu Leu Ile Gly Cys Leu Leu
        195                 200                 205

Phe Val Leu Thr Pro Thr Phe Val Phe Cys Tyr Met Glu Asp Trp Ser
210                 215                 220

Lys Leu Glu Ala Ile Tyr Phe Val Ile Val Thr Leu Thr Thr Val Gly
225                 230                 235                 240

Phe Gly Asp Tyr Val Ala Gly Ala Asp Pro Arg Gln Asp Ser Pro Ala
                245                 250                 255

Tyr Gln Pro Leu Val Trp Phe Trp Ile Leu Leu Gly Leu Ala Tyr Phe
            260                 265                 270

Ala Ser Val Leu Thr Thr Ile Gly Asn Trp Leu Arg Val Val Ser Arg
        275                 280                 285

Arg Thr Arg Ala Glu Met Gly Gly Leu Thr Ala Gln Ala Ala Ser Trp
290                 295                 300

Thr Gly Thr Val Thr Ala Arg Val Thr Gln Arg Ala Gly Pro Ala Ala
305                 310                 315                 320

Pro Pro Pro Glu Lys Glu Gln Pro Leu Leu Pro Pro Pro Cys Pro
                325                 330                 335

Ala Gln Pro Leu Gly Arg Pro Arg Ser Pro Ser Pro Glu Lys Ala
            340                 345                 350

Gln Pro Pro Ser Pro Pro Thr Ala Ser Ala Leu Asp Tyr Pro Ser Glu
        355                 360                 365

Asn Leu Ala Phe Ile Asp Glu Ser Ser Asp Thr Gln Ser Glu Arg Gly
```

-continued

```
                  370                 375                 380
Cys Pro Leu Pro Arg Ala Pro Arg Gly Arg Arg Pro Asn Pro Pro
385                 390                 395                 400

Arg Lys Pro Val Arg Pro Arg Gly Pro Gly Arg Pro Arg Asp Lys Gly
                405                 410                 415

Val Pro Val

<210> SEQ ID NO 9
<211> LENGTH: 1597
<212> TYPE: DNA
<213> ORGANISM: Homo Sapiens
<220> FEATURE:
<221> NAME/KEY: CDS
<222> LOCATION: (18)...(1394)

<400> SEQUENCE: 9
cagccaaggc ggagctg atg gct gcg ccg agg gcg ggg cgg ggt gca ggc        50
                   Met Ala Ala Pro Arg Ala Gly Arg Gly Ala Gly
                    1               5                   10 tgg agc ctt cgg gca tgg cgg gct ttg ggg ggc att cgc tgg ggg agg       98
Trp Ser Leu Arg Ala Trp Arg Ala Leu Gly Gly Ile Arg Trp Gly Arg
                15                  20                  25 aga ccc cgt ttg acc cct gac ctc cgg gcc ctg ctg acg tca gga act      146
Arg Pro Arg Leu Thr Pro Asp Leu Arg Ala Leu Leu Thr Ser Gly Thr
            30                  35                  40 tct gac ccc cgg gcc cga gtg act tat ggg acc ccc agt ctc tgg gcc      194
Ser Asp Pro Arg Ala Arg Val Thr Tyr Gly Thr Pro Ser Leu Trp Ala
        45                  50                  55 cgg ttg tct gtt ggg gtc act gaa ccc cga gca tgc ctg acg tct ggg      242
Arg Leu Ser Val Gly Val Thr Glu Pro Arg Ala Cys Leu Thr Ser Gly
    60                  65                  70                  75 acc ccg ggt ccc cgg gca caa ctg act gcg gtg acc cca gat acc agg      290
Thr Pro Gly Pro Arg Ala Gln Leu Thr Ala Val Thr Pro Asp Thr Arg
                80                  85                  90 acc cgg gag gcc tca gag aac tct gga acc cgt tcg cgc gcg tgg ctg      338
Thr Arg Glu Ala Ser Glu Asn Ser Gly Thr Arg Ser Arg Ala Trp Leu
            95                 100                 105 gcg gtg gcg ctg ggc gct ggg ggg gca gtg ctg ttg ttg tgg ggc          386
Ala Val Ala Leu Gly Ala Gly Gly Ala Val Leu Leu Leu Leu Trp Gly
        110                 115                 120 ggg ggt cgg ggt cct ccg gcc gtc ctc gcc gcc gtc cct agc ccg ccg      434
Gly Gly Arg Gly Pro Pro Ala Val Leu Ala Ala Val Pro Ser Pro Pro
    125                 130                 135 ccc gct tct ccc cgg agt cag tac aac ttc atc gca gat gtg gtg gag      482
Pro Ala Ser Pro Arg Ser Gln Tyr Asn Phe Ile Ala Asp Val Val Glu
140                 145                 150                 155 aag aca gca cct gcc gtg gtc tat atc gag atc ctg gac cgg cac cct      530
Lys Thr Ala Pro Ala Val Val Tyr Ile Glu Ile Leu Asp Arg His Pro
                160                 165                 170 ttc ttg ggc cgc gag gtc cct atc tcg aac ggc tca gga ttc gtg gtg      578
Phe Leu Gly Arg Glu Val Pro Ile Ser Asn Gly Ser Gly Phe Val Val
            175                 180                 185 gct gcc gat ggg ctc att gtc acc aac gcc cat gtg gtg gct gat cgg      626
Ala Ala Asp Gly Leu Ile Val Thr Asn Ala His Val Val Ala Asp Arg
        190                 195                 200 cgc aga gtc cgt gtg aga ctg cta agc ggc gac acg tat gag gcc gtg      674
Arg Arg Val Arg Val Arg Leu Leu Ser Gly Asp Thr Tyr Glu Ala Val
    205                 210                 215 gtc aca gct gtg gat ccc gtg gca gac atc gca acg ctg agg att cag      722
Val Thr Ala Val Asp Pro Val Ala Asp Ile Ala Thr Leu Arg Ile Gln
```

```
                    220              225              230              235
act aag gag cct ctc ccc acg ctg cct ctg gga cgc tca gct gat gtc        770
Thr Lys Glu Pro Leu Pro Thr Leu Pro Leu Gly Arg Ser Ala Asp Val
                    240              245              250 cgg caa ggg gag ttt gtt gtt gcc atg gga agt ccc ttt gca ctg cag        818
Arg Gln Gly Glu Phe Val Val Ala Met Gly Ser Pro Phe Ala Leu Gln
            255              260              265 aac acg atc aca tcc ggc att gtt agc tct gct cag cgt cca gcc aga        866
Asn Thr Ile Thr Ser Gly Ile Val Ser Ser Ala Gln Arg Pro Ala Arg
        270              275              280 gac ctg gga ctc ccc caa acc aat gtg gaa tac att caa act gat gca        914
Asp Leu Gly Leu Pro Gln Thr Asn Val Glu Tyr Ile Gln Thr Asp Ala
    285              290              295 gct att gat ttt gga aac tct gga ggt ccc ctg gtt aac ctg gat ggg        962
Ala Ile Asp Phe Gly Asn Ser Gly Gly Pro Leu Val Asn Leu Asp Gly
300              305              310              315 gag gtg att gga gtg aac acc atg aag gtc aca gct gga atc tcc ttt       1010
Glu Val Ile Gly Val Asn Thr Met Lys Val Thr Ala Gly Ile Ser Phe
                320              325              330 gcc atc cct tct gat cgt ctt cga gag ttt ctg cat cgt ggg gaa aag       1058
Ala Ile Pro Ser Asp Arg Leu Arg Glu Phe Leu His Arg Gly Glu Lys
            335              340              345 aag aat tcc tcc tcc gga atc agt ggg tcc cag cgg cgc tac att ggg       1106
Lys Asn Ser Ser Ser Gly Ile Ser Gly Ser Gln Arg Arg Tyr Ile Gly
        350              355              360 gtg atg atg ctg acc ctg agt ccc agc atc ctt gct gaa cta cag ctt       1154
Val Met Met Leu Thr Leu Ser Pro Ser Ile Leu Ala Glu Leu Gln Leu
    365              370              375 cga gaa cca agc ttt ccc gat gtt cag cat ggt gta ctc atc cat aaa       1202
Arg Glu Pro Ser Phe Pro Asp Val Gln His Gly Val Leu Ile His Lys
380              385              390              395 gtc atc ctg ggc tcc cct gca cac cgg gct ggt ctg cgg cct ggt gat       1250
Val Ile Leu Gly Ser Pro Ala His Arg Ala Gly Leu Arg Pro Gly Asp
                400              405              410 gtg att ttg gcc att ggg gag cag atg gta caa aat gct gaa gat gtt       1298
Val Ile Leu Ala Ile Gly Glu Gln Met Val Gln Asn Ala Glu Asp Val
            415              420              425 tat gaa gct gtt cga acc caa tcc cag ttg gca gtg cag atc cgg cgg       1346
Tyr Glu Ala Val Arg Thr Gln Ser Gln Leu Ala Val Gln Ile Arg Arg
        430              435              440 gga cga gaa aca ctg acc tta tat gtg acc cct gag gtc aca gaa tga       1394
Gly Arg Glu Thr Leu Thr Leu Tyr Val Thr Pro Glu Val Thr Glu *
    445              450              455 atagatcacc aagagtatga ggctcctgct ctgatttcct cctttccttt ctggctgagg     1454
ttctgagggc accgagacag agggttaaat gaaccagtgg gggcaggtcc ctccaaccac     1514
cagcactgac tcctaggctt ctgaacaatc acagaaacac tttttatata aaataaaatt     1574
atacctagca aaaaaaaaaa aaa                                            1597

<210> SEQ ID NO 10
<211> LENGTH: 458
<212> TYPE: PRT
<213> ORGANISM: Homo Sapiens

<400> SEQUENCE: 10

Met Ala Ala Pro Arg Ala Gly Arg Gly Ala Gly Trp Ser Leu Arg Ala
1               5                   10                  15

Trp Arg Ala Leu Gly Gly Ile Arg Trp Gly Arg Arg Pro Arg Leu Thr
            20                  25                  30
```

```
Pro Asp Leu Arg Ala Leu Leu Thr Ser Gly Thr Ser Asp Pro Arg Ala
         35                  40                  45

Arg Val Thr Tyr Gly Thr Pro Ser Leu Trp Ala Arg Leu Ser Val Gly
 50                  55                  60

Val Thr Glu Pro Arg Ala Cys Leu Thr Ser Gly Thr Pro Gly Pro Arg
 65                  70                  75                  80

Ala Gln Leu Thr Ala Val Thr Pro Asp Thr Arg Thr Arg Glu Ala Ser
                 85                  90                  95

Glu Asn Ser Gly Thr Arg Ser Arg Ala Trp Leu Ala Val Ala Leu Gly
            100                 105                 110

Ala Gly Gly Ala Val Leu Leu Leu Trp Gly Gly Arg Gly Pro
        115                 120                 125

Pro Ala Val Leu Ala Ala Val Pro Ser Pro Pro Ala Ser Pro Arg
        130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Leu Gly Arg Glu
                165                 170                 175

Val Pro Ile Ser Asn Gly Ser Gly Phe Val Val Ala Ala Asp Gly Leu
            180                 185                 190

Ile Val Thr Asn Ala His Val Val Ala Asp Arg Arg Arg Val Arg Val
        195                 200                 205

Arg Leu Leu Ser Gly Asp Thr Tyr Glu Ala Val Thr Ala Val Asp
210                 215                 220

Pro Val Ala Asp Ile Ala Thr Leu Arg Ile Gln Thr Lys Glu Pro Leu
225                 230                 235                 240

Pro Thr Leu Pro Leu Gly Arg Ser Ala Asp Val Arg Gln Gly Glu Phe
                245                 250                 255

Val Val Ala Met Gly Ser Pro Phe Ala Leu Gln Asn Thr Ile Thr Ser
            260                 265                 270

Gly Ile Val Ser Ser Ala Gln Arg Pro Ala Arg Asp Leu Gly Leu Pro
        275                 280                 285

Gln Thr Asn Val Glu Tyr Ile Gln Thr Asp Ala Ala Ile Asp Phe Gly
290                 295                 300

Asn Ser Gly Gly Pro Leu Val Asn Leu Asp Gly Glu Val Ile Gly Val
305                 310                 315                 320

Asn Thr Met Lys Val Thr Ala Gly Ile Ser Phe Ala Ile Pro Ser Asp
                325                 330                 335

Arg Leu Arg Glu Phe Leu His Arg Gly Glu Lys Lys Asn Ser Ser Ser
            340                 345                 350

Gly Ile Ser Gly Ser Gln Arg Arg Tyr Ile Gly Val Met Met Leu Thr
        355                 360                 365

Leu Ser Pro Ser Ile Leu Ala Glu Leu Gln Leu Arg Glu Pro Ser Phe
370                 375                 380

Pro Asp Val Gln His Gly Val Leu Ile His Lys Val Ile Leu Gly Ser
385                 390                 395                 400

Pro Ala His Arg Ala Gly Leu Arg Pro Gly Asp Val Ile Leu Ala Ile
                405                 410                 415

Gly Glu Gln Met Val Gln Asn Ala Glu Asp Val Tyr Glu Ala Val Arg
            420                 425                 430

Thr Gln Ser Gln Leu Ala Val Gln Ile Arg Arg Gly Arg Glu Thr Leu
        435                 440                 445
```

```
        Thr Leu Tyr Val Thr Pro Glu Val Thr Glu
            450                 455

<210> SEQ ID NO 11
<211> LENGTH: 1881
<212> TYPE: DNA
<213> ORGANISM: Homo Sapiens
<220> FEATURE:
<221> NAME/KEY: CDS
<222> LOCATION: (214)...(1713)

<400> SEQUENCE: 11
gatatcgaat tccggaattc cccgggaaag gtggccagca gatgtgtcgg gcctggtgag    60
agggtgaggc gagacggccc gatcgcccag ggccccggaa gctgcggagg tcaccccgc   120 ctggccttag ctcagggaca ccctggattc acgtgggagc ccctgctcct gcctcccccg   180
tcccaccact gaggctgttg ggccaggcca gtc atg cta gaa cgg cct cct gca   234
                                   Met Leu Glu Arg Pro Pro Ala
                                     1               5 ctg gcc atg ccc atg ccc acg gag ggc acc ccg cca cct ctg agt ggc   282
Leu Ala Met Pro Met Pro Thr Glu Gly Thr Pro Pro Pro Leu Ser Gly
         10                  15                  20 acc ccc atc cca gtc cca gcc tac ttc cgc cac gca gaa cct gga ttc   330
Thr Pro Ile Pro Val Pro Ala Tyr Phe Arg His Ala Glu Pro Gly Phe
 25                  30                  35 tcc ctc aag agg ccc agg ggg ctc agc cgg agc ctc cca cct ccg ccc   378
Ser Leu Lys Arg Pro Arg Gly Leu Ser Arg Ser Leu Pro Pro Pro Pro
 40                  45                  50                  55 cct gcc aag ggc agc att ccc atc agc cgc ctc ttc cct cct cgg acc   426
Pro Ala Lys Gly Ser Ile Pro Ile Ser Arg Leu Phe Pro Pro Arg Thr
                 60                  65                  70 cca ggc tgg cac cag ctg cag ccc cgg cgg gtg tca ttc cgg ggc gag   474
Pro Gly Trp His Gln Leu Gln Pro Arg Arg Val Ser Phe Arg Gly Glu
     75                  80                  85 gcc tca gag act ctg cag agc cct ggg tat gac cca agc cgg cca gag   522
Ala Ser Glu Thr Leu Gln Ser Pro Gly Tyr Asp Pro Ser Arg Pro Glu
 90                  95                 100 tcc ttc ttc cag cag agc ttc cag agg ctc agc cgc ctg ggc cat ggc   570
Ser Phe Phe Gln Gln Ser Phe Gln Arg Leu Ser Arg Leu Gly His Gly
105                 110                 115 tcc tac gga gag gtc ttc aag gtg cgc tcc aag gag gac ggc cgg ctc   618
Ser Tyr Gly Glu Val Phe Lys Val Arg Ser Lys Glu Asp Gly Arg Leu
120                 125                 130                 135 tat gcg gta aag cgt tcc atg tca cca ttc cgg ggc ccc aag gac cgg   666
Tyr Ala Val Lys Arg Ser Met Ser Pro Phe Arg Gly Pro Lys Asp Arg
                140                 145                 150 gcc cgc aag ttg gcc gag gtg ggc agc cac gag aag gtg ggg cag cac   714
Ala Arg Lys Leu Ala Glu Val Gly Ser His Glu Lys Val Gly Gln His
            155                 160                 165 cca tgc tgc gtg cgg ctg gag cag gcc tgg gag gag ggc ggc atc ctg   762
Pro Cys Cys Val Arg Leu Glu Gln Ala Trp Glu Glu Gly Gly Ile Leu
        170                 175                 180 tac ctg cag acg gag ctg tgc ggg ccc agc ctg cag caa cac tgt gag   810
Tyr Leu Gln Thr Glu Leu Cys Gly Pro Ser Leu Gln Gln His Cys Glu
    185                 190                 195 gcc tgg ggt gcc agc ctg cct gag gcc cag gtc tgg ggc tac ctg cgg   858
Ala Trp Gly Ala Ser Leu Pro Glu Ala Gln Val Trp Gly Tyr Leu Arg
200                 205                 210                 215 gac acg ctg ctt gcc ctg gcc cat ctg cac agc cag ggc ctg gtg cac   906
Asp Thr Leu Leu Ala Leu Ala His Leu His Ser Gln Gly Leu Val His
                220                 225                 230
```

```
ctt gat gtc aag cct gcc aac atc ttc ctg ggg ccc cgg ggc cgc tgc     954
Leu Asp Val Lys Pro Ala Asn Ile Phe Leu Gly Pro Arg Gly Arg Cys
        235                 240                 245 aag ctg ggt gac ttc gga ctg ctg gtg gag ctg ggt aca gca gga gct    1002
Lys Leu Gly Asp Phe Gly Leu Leu Val Glu Leu Gly Thr Ala Gly Ala
    250                 255                 260 ggt gag gtc cag gag gga gac ccc cgc tac atg gcc ccc gag ctg ctg    1050
Gly Glu Val Gln Glu Gly Asp Pro Arg Tyr Met Ala Pro Glu Leu Leu
265                 270                 275 cag ggc tcc tat ggg aca gca gcg gat gtg ttc agt ctg ggc ctc acc    1098
Gln Gly Ser Tyr Gly Thr Ala Ala Asp Val Phe Ser Leu Gly Leu Thr
280                 285                 290                 295 atc ctg gaa gtg gca tgc aac atg gag ctg ccc cac ggt ggg gag ggc    1146
Ile Leu Glu Val Ala Cys Asn Met Glu Leu Pro His Gly Gly Glu Gly
            300                 305                 310 tgg cag cag ctg cgc cag ggc tac ctg ccc cct gag ttc act gcc ggt    1194
Trp Gln Gln Leu Arg Gln Gly Tyr Leu Pro Pro Glu Phe Thr Ala Gly
        315                 320                 325 ctg tct tcc gag ctg cgt tct gtc ctt gtc atg atg ctg gag cca gac    1242
Leu Ser Ser Glu Leu Arg Ser Val Leu Val Met Met Leu Glu Pro Asp
    330                 335                 340 ccc aag ctg cgg gcc acg gcc gag gcc ctg ctg gca ctg cct gtg ttg    1290
Pro Lys Leu Arg Ala Thr Ala Glu Ala Leu Leu Ala Leu Pro Val Leu
345                 350                 355 agg cag ccg cgg gcc tgg ggt gtg ctg tgg tgc atg gca gcg gag gcc    1338
Arg Gln Pro Arg Ala Trp Gly Val Leu Trp Cys Met Ala Ala Glu Ala
360                 365                 370                 375 ctg agc cga ggg tgg gcc ctg tgg cag gcc ctg ctt gcc ctg ctc tgc    1386
Leu Ser Arg Gly Trp Ala Leu Trp Gln Ala Leu Leu Ala Leu Leu Cys
            380                 385                 390 tgg ctc tgg cat ggg ctg gct cac cct gcc agc tgg cta cag ccc ctg    1434
Trp Leu Trp His Gly Leu Ala His Pro Ala Ser Trp Leu Gln Pro Leu
        395                 400                 405 ggc ccg cca gcc acc ccg cct ggc tca cca ccc tgc agt ttg ctc ctg    1482
Gly Pro Pro Ala Thr Pro Pro Gly Ser Pro Pro Cys Ser Leu Leu Leu
    410                 415                 420 gac agc agc ctc tcc agc aac tgg gat gac gac agc cta ggg cct tca    1530
Asp Ser Ser Leu Ser Ser Asn Trp Asp Asp Asp Ser Leu Gly Pro Ser
425                 430                 435 ctc tcc cct gag gct gtc ctg gcc cgg act gtg ggg agc acc tcc acc    1578
Leu Ser Pro Glu Ala Val Leu Ala Arg Thr Val Gly Ser Thr Ser Thr
440                 445                 450                 455 ccc cgg agc agg tgc aca ccc agg gat gcc ctg gac tta agt gac atc    1626
Pro Arg Ser Arg Cys Thr Pro Arg Asp Ala Leu Asp Leu Ser Asp Ile
            460                 465                 470 aac tca gag cct cct cgg ggc tcc ttc ccc tcc ttt gag cct cgg aac    1674
Asn Ser Glu Pro Pro Arg Gly Ser Phe Pro Ser Phe Glu Pro Arg Asn
        475                 480                 485 ctc ctc agc ctg ttt gag gac acc cta gac cca acc tga gccccagact    1723
Leu Leu Ser Leu Phe Glu Asp Thr Leu Asp Pro Thr *
    490                 495 ctgcctctgc acttttaacc ttttatcctg tgtctctccc gtcgcccttg aaagctgggg    1783
cccctcggga actcccatgg tcttctctgc ctggccgtgt ctaataaaaa gtatttgaac    1843
cttgggagca cccaagcttg ctcatgtggc ggaattcc                            1881

<210> SEQ ID NO 12
<211> LENGTH: 499
<212> TYPE: PRT
```

<213> ORGANISM: Homo Sapiens

<400> SEQUENCE: 12

```
Met Leu Glu Arg Pro Pro Ala Leu Ala Met Pro Met Pro Thr Glu Gly
1               5                   10                  15

Thr Pro Pro Pro Leu Ser Gly Thr Pro Ile Pro Val Pro Ala Tyr Phe
            20                  25                  30

Arg His Ala Glu Pro Gly Phe Ser Leu Lys Arg Pro Arg Gly Leu Ser
        35                  40                  45

Arg Ser Leu Pro Pro Pro Pro Ala Lys Gly Ser Ile Pro Ile Ser
50                  55                  60

Arg Leu Phe Pro Pro Arg Thr Pro Gly Trp His Gln Leu Gln Pro Arg
65                  70                  75                  80

Arg Val Ser Phe Arg Gly Glu Ala Ser Glu Thr Leu Gln Ser Pro Gly
                85                  90                  95

Tyr Asp Pro Ser Arg Pro Glu Ser Phe Phe Gln Gln Ser Phe Gln Arg
            100                 105                 110

Leu Ser Arg Leu Gly His Gly Ser Tyr Gly Glu Val Phe Lys Val Arg
        115                 120                 125

Ser Lys Glu Asp Gly Arg Leu Tyr Ala Val Lys Arg Ser Met Ser Pro
130                 135                 140

Phe Arg Gly Pro Lys Asp Arg Ala Arg Lys Leu Ala Glu Val Gly Ser
145                 150                 155                 160

His Glu Lys Val Gly Gln His Pro Cys Cys Val Arg Leu Glu Gln Ala
                165                 170                 175

Trp Glu Glu Gly Gly Ile Leu Tyr Leu Gln Thr Glu Leu Cys Gly Pro
            180                 185                 190

Ser Leu Gln Gln His Cys Glu Ala Trp Gly Ala Ser Leu Pro Glu Ala
        195                 200                 205

Gln Val Trp Gly Tyr Leu Arg Asp Thr Leu Leu Ala Leu Ala His Leu
210                 215                 220

His Ser Gln Gly Leu Val His Leu Asp Val Lys Pro Ala Asn Ile Phe
225                 230                 235                 240

Leu Gly Pro Arg Gly Arg Cys Lys Leu Gly Asp Phe Gly Leu Leu Val
                245                 250                 255

Glu Leu Gly Thr Ala Gly Ala Gly Glu Val Gln Glu Gly Asp Pro Arg
            260                 265                 270

Tyr Met Ala Pro Glu Leu Leu Gln Gly Ser Tyr Gly Thr Ala Ala Asp
        275                 280                 285

Val Phe Ser Leu Gly Leu Thr Ile Leu Glu Val Ala Cys Asn Met Glu
290                 295                 300

Leu Pro His Gly Gly Glu Gly Trp Gln Gln Leu Arg Gln Gly Tyr Leu
305                 310                 315                 320

Pro Pro Glu Phe Thr Ala Gly Leu Ser Ser Glu Leu Arg Ser Val Leu
                325                 330                 335

Val Met Met Leu Glu Pro Asp Pro Lys Leu Arg Ala Thr Ala Glu Ala
            340                 345                 350

Leu Leu Ala Leu Pro Val Leu Arg Gln Pro Arg Ala Trp Gly Val Leu
        355                 360                 365

Trp Cys Met Ala Ala Glu Leu Ser Arg Gly Trp Ala Leu Trp Gln
370                 375                 380

Ala Leu Leu Ala Leu Leu Cys Trp Leu Trp His Gly Leu Ala His Pro
385                 390                 395                 400
```

```
Ala Ser Trp Leu Gln Pro Leu Gly Pro Pro Ala Thr Pro Pro Gly Ser
                405                 410                 415

Pro Pro Cys Ser Leu Leu Asp Ser Ser Leu Ser Ser Asn Trp Asp
            420                 425                 430

Asp Asp Ser Leu Gly Pro Ser Leu Ser Pro Glu Ala Val Leu Ala Arg
            435                 440                 445

Thr Val Gly Ser Thr Ser Thr Pro Arg Ser Arg Cys Thr Pro Arg Asp
        450                 455                 460

Ala Leu Asp Leu Ser Asp Ile Asn Ser Glu Pro Pro Arg Gly Ser Phe
465                 470                 475                 480

Pro Ser Phe Glu Pro Arg Asn Leu Leu Ser Leu Phe Glu Asp Thr Leu
                485                 490                 495

Asp Pro Thr

<210> SEQ ID NO 13
<211> LENGTH: 1700
<212> TYPE: DNA
<213> ORGANISM: Homo Sapiens
<220> FEATURE:
<221> NAME/KEY: CDS
<222> LOCATION: (125)...(1585)

<400> SEQUENCE: 13
cggaattggt gggttcttgg tctcactgag ttctagaatg aagctgcaga ccctcgcagt        60
gagtgttaca gctcttaagg ctctctgact gccaccctg cctgcctgcc cggccctgca       120 caac atg cag ccc tcc ggc ctc gag ggt ccc ggc acg ttt ggt cgg tgg       169
     Met Gln Pro Ser Gly Leu Glu Gly Pro Gly Thr Phe Gly Arg Trp
     1               5                   10                  15 cct ctg ctg agt ctg ctg ctc ctg ctg ctg ctc cag cct gta acc           217
Pro Leu Leu Ser Leu Leu Leu Leu Leu Leu Leu Gln Pro Val Thr
                20                  25                  30 tgt gcc tac acc acg cca ggc ccc ccc aga gcc ctc acc acg ctg ggc       265
Cys Ala Tyr Thr Thr Pro Gly Pro Pro Arg Ala Leu Thr Thr Leu Gly
                35                  40                  45 gcc ccc aga gcc cac acc atg ccg ggc acc tac gct ccc tcg acc aca       313
Ala Pro Arg Ala His Thr Met Pro Gly Thr Tyr Ala Pro Ser Thr Thr
        50                  55                  60 ctc agt agt ccc agc acc cag ggc ctg caa gag cag gca cgg gcc ctg       361
Leu Ser Ser Pro Ser Thr Gln Gly Leu Gln Glu Gln Ala Arg Ala Leu
65                  70                  75 atg cgg gac ttc ccg ctc gtg gac ggc cac aac gac ctg ccc ctg gtc       409
Met Arg Asp Phe Pro Leu Val Asp Gly His Asn Asp Leu Pro Leu Val
80                  85                  90                  95 cta agg cag gtt tac cag aaa ggg cta cag gat gtt aac ctg cgc aat       457
Leu Arg Gln Val Tyr Gln Lys Gly Leu Gln Asp Val Asn Leu Arg Asn
                100                 105                 110 ttc agc tac ggc cag acc agc ctg gac agg ctt aga gat ggc ctc gtg       505
Phe Ser Tyr Gly Gln Thr Ser Leu Asp Arg Leu Arg Asp Gly Leu Val
            115                 120                 125 ggc gcc cag ttc tgg tca gcc tat gtg cca tgc cag acc cag gac cgg       553
Gly Ala Gln Phe Trp Ser Ala Tyr Val Pro Cys Gln Thr Gln Asp Arg
        130                 135                 140 gat gcc ctg cgc ctc acc ctg gag cag att gac ctc ata cgc cgc atg       601
Asp Ala Leu Arg Leu Thr Leu Glu Gln Ile Asp Leu Ile Arg Arg Met
145                 150                 155 tgt gcc tcc tat tct gag ctg gag ctt gtg acc tcg gct aaa gct ctg       649
Cys Ala Ser Tyr Ser Glu Leu Glu Leu Val Thr Ser Ala Lys Ala Leu
160                 165                 170                 175
```

```
aac gac act cag aaa ttg gcc tgc ctc atc ggt gta gag ggt ggc cac       697
Asn Asp Thr Gln Lys Leu Ala Cys Leu Ile Gly Val Glu Gly Gly His
                180             185             190 tcg ctg gac aat agc ctc tcc atc tta cgt acc ttc tac atg ctg gga       745
Ser Leu Asp Asn Ser Leu Ser Ile Leu Arg Thr Phe Tyr Met Leu Gly
            195             200             205 gtg cgc tac ctg acg ctc acc cac acc tgc aac aca ccc tgg gca gag       793
Val Arg Tyr Leu Thr Leu Thr His Thr Cys Asn Thr Pro Trp Ala Glu
        210             215             220 agc tcc gct aag ggc gtc cac tcc ttc tac aac aac atc agc ggg ctg       841
Ser Ser Ala Lys Gly Val His Ser Phe Tyr Asn Asn Ile Ser Gly Leu
    225             230             235 act gac ttt ggt gag aag gtg gtg gca gaa atg aac cgc ctg ggc atg       889
Thr Asp Phe Gly Glu Lys Val Val Ala Glu Met Asn Arg Leu Gly Met
240             245             250             255 atg gta gac tta tcc cat gtc tca gat gct gtg gca cgg cgg gcc ctg       937
Met Val Asp Leu Ser His Val Ser Asp Ala Val Ala Arg Arg Ala Leu
            260             265             270 gaa gtg tca cag gca cct gtg atc ttc tcc cac tcg gct gcc cgg ggt       985
Glu Val Ser Gln Ala Pro Val Ile Phe Ser His Ser Ala Ala Arg Gly
        275             280             285 gtg tgc aac agt gct cgg aat gtt cct gat gac atc ctg cag ctt ctg      1033
Val Cys Asn Ser Ala Arg Asn Val Pro Asp Asp Ile Leu Gln Leu Leu
    290             295             300 aag aag aac ggt ggc gtc gtg atg gtg tct ttg tcc atg gga gta ata      1081
Lys Lys Asn Gly Gly Val Val Met Val Ser Leu Ser Met Gly Val Ile
305             310             315 cag tgc aac cca tca gcc aat gtg tcc act gtg gca gat cac ttc gac      1129
Gln Cys Asn Pro Ser Ala Asn Val Ser Thr Val Ala Asp His Phe Asp
320             325             330             335 cac atc aag gct gtc att gga tcc aag ttc atc ggg att ggt gga gat      1177
His Ile Lys Ala Val Ile Gly Ser Lys Phe Ile Gly Ile Gly Gly Asp
            340             345             350 tat gat ggg gcc ggc aaa ttc cct cag ggg ctg gaa gac gtg tcc aca      1225
Tyr Asp Gly Ala Gly Lys Phe Pro Gln Gly Leu Glu Asp Val Ser Thr
        355             360             365 tac ccg gtc ctg ata gag gag ttg ctg agt cgt ggc tgg agt gag gaa      1273
Tyr Pro Val Leu Ile Glu Glu Leu Leu Ser Arg Gly Trp Ser Glu Glu
    370             375             380 gag ctt cag ggt gtc ctt cgt gga aac ctg ctg cgg gtc ttc aga caa      1321
Glu Leu Gln Gly Val Leu Arg Gly Asn Leu Leu Arg Val Phe Arg Gln
385             390             395 gtg gaa aag gta cag gaa gaa aac aaa tgg caa agc ccc ttg gag gac      1369
Val Glu Lys Val Gln Glu Glu Asn Lys Trp Gln Ser Pro Leu Glu Asp
400             405             410             415 aag ttc ccg gat gag cag ctg agc agt tcc tgc cac tcc gac ctc tca      1417
Lys Phe Pro Asp Glu Gln Leu Ser Ser Ser Cys His Ser Asp Leu Ser
            420             425             430 cgt ctg cgt cag aga cag agt ctg act tca ggc cag gaa ctc act gag      1465
Arg Leu Arg Gln Arg Gln Ser Leu Thr Ser Gly Gln Glu Leu Thr Glu
        435             440             445 att ccc ata cac tgg aca gcc aag tta cca gcc aag tgg tca gtc tca      1513
Ile Pro Ile His Trp Thr Ala Lys Leu Pro Ala Lys Trp Ser Val Ser
    450             455             460 gag tcc tcc ccc cac atg gcc cca gtc ctt gca gtt gtg gcc acc ttc      1561
Glu Ser Ser Pro His Met Ala Pro Val Leu Ala Val Val Ala Thr Phe
465             470             475 cca gtc ctt att ctg tgg ctc tga tgacccagtt agtcctgcca gatgtcactg     1615
Pro Val Leu Ile Leu Trp Leu *
480             485
```

```
tagcaagcca cagacacccc acaaagttcc cctgttgtgc aggcacaaat atttcttgaa    1675
ataaatgttt tggacataga aaaaa                                          1700
```

<210> SEQ ID NO 14
<211> LENGTH: 486
<212> TYPE: PRT
<213> ORGANISM: Homo Sapiens

<400> SEQUENCE: 14

```
Met Gln Pro Ser Gly Leu Glu Gly Pro Gly Thr Phe Gly Arg Trp Pro
  1               5                  10                  15

Leu Leu Ser Leu Leu Leu Leu Leu Leu Gln Pro Val Thr Cys
             20                  25                  30

Ala Tyr Thr Thr Pro Gly Pro Pro Arg Ala Leu Thr Thr Leu Gly Ala
             35                  40                  45

Pro Arg Ala His Thr Met Pro Gly Thr Tyr Ala Pro Ser Thr Thr Leu
 50                  55                  60

Ser Ser Pro Ser Thr Gln Gly Leu Gln Glu Gln Ala Arg Ala Leu Met
 65                  70                  75                  80

Arg Asp Phe Pro Leu Val Asp Gly His Asn Asp Leu Pro Leu Val Leu
                 85                  90                  95

Arg Gln Val Tyr Gln Lys Gly Leu Gln Asp Val Asn Leu Arg Asn Phe
            100                 105                 110

Ser Tyr Gly Gln Thr Ser Leu Asp Arg Leu Arg Asp Gly Leu Val Gly
            115                 120                 125

Ala Gln Phe Trp Ser Ala Tyr Val Pro Cys Gln Thr Gln Asp Arg Asp
130                 135                 140

Ala Leu Arg Leu Thr Leu Glu Gln Ile Asp Leu Ile Arg Arg Met Cys
145                 150                 155                 160

Ala Ser Tyr Ser Glu Leu Glu Leu Val Thr Ser Ala Lys Ala Leu Asn
                165                 170                 175

Asp Thr Gln Lys Leu Ala Cys Leu Ile Gly Val Glu Gly Gly His Ser
            180                 185                 190

Leu Asp Asn Ser Leu Ser Ile Leu Arg Thr Phe Tyr Met Leu Gly Val
            195                 200                 205

Arg Tyr Leu Thr Leu Thr His Thr Cys Asn Thr Pro Trp Ala Glu Ser
        210                 215                 220

Ser Ala Lys Gly Val His Ser Phe Tyr Asn Asn Ile Ser Gly Leu Thr
225                 230                 235                 240

Asp Phe Gly Glu Lys Val Val Ala Glu Met Asn Arg Leu Gly Met Met
                245                 250                 255

Val Asp Leu Ser His Val Ser Asp Ala Val Ala Arg Arg Ala Leu Glu
            260                 265                 270

Val Ser Gln Ala Pro Val Ile Phe Ser His Ser Ala Ala Arg Gly Val
            275                 280                 285

Cys Asn Ser Ala Arg Asn Val Pro Asp Asp Ile Leu Gln Leu Leu Lys
290                 295                 300

Lys Asn Gly Gly Val Val Met Val Ser Leu Ser Met Gly Val Ile Gln
305                 310                 315                 320

Cys Asn Pro Ser Ala Asn Val Ser Thr Val Ala Asp His Phe Asp His
                325                 330                 335

Ile Lys Ala Val Ile Gly Ser Lys Phe Ile Gly Ile Gly Gly Asp Tyr
            340                 345                 350
```

-continued

```
Asp Gly Ala Gly Lys Phe Pro Gln Gly Leu Glu Asp Val Ser Thr Tyr
        355                 360                 365
Pro Val Leu Ile Glu Glu Leu Leu Ser Arg Gly Trp Ser Glu Glu Glu
370                 375                 380
Leu Gln Gly Val Leu Arg Gly Asn Leu Leu Arg Val Phe Arg Gln Val
385                 390                 395                 400
Glu Lys Val Gln Glu Asn Lys Trp Gln Ser Pro Leu Glu Asp Lys
                405                 410                 415
Phe Pro Asp Glu Gln Leu Ser Ser Cys His Ser Asp Leu Ser Arg
            420                 425                 430
Leu Arg Gln Arg Gln Ser Leu Thr Ser Gly Gln Glu Leu Thr Glu Ile
        435                 440                 445
Pro Ile His Trp Thr Ala Lys Leu Pro Ala Lys Trp Ser Val Ser Glu
    450                 455                 460
Ser Ser Pro His Met Ala Pro Val Leu Ala Val Val Ala Thr Phe Pro
465                 470                 475                 480
Val Leu Ile Leu Trp Leu
                485
```

<210> SEQ ID NO 15
<211> LENGTH: 1159
<212> TYPE: DNA
<213> ORGANISM: Homo Sapiens
<220> FEATURE:
<221> NAME/KEY: CDS
<222> LOCATION: (64)...(1137)

<400> SEQUENCE: 15

```
cccccttaag tcctcttgaa caccccttct gcaagtaccc cagggcggtc tcctgaccca       60 gag atg gat tta cca gtg aac cta acc tcc ttt tcc ctc tcc acc ccc      108
    Met Asp Leu Pro Val Asn Leu Thr Ser Phe Ser Leu Ser Thr Pro
    1               5                   10                  15 tcc cct ttg gag acc aac cac agc ctc ggc aaa gac gac ctg cgc ccc      156
Ser Pro Leu Glu Thr Asn His Ser Leu Gly Lys Asp Asp Leu Arg Pro
                20                  25                  30 agc tcg ccc ctg ctc tcg gtc ttc gga gtg ctt att ctc acc ttg ctg      204
Ser Ser Pro Leu Leu Ser Val Phe Gly Val Leu Ile Leu Thr Leu Leu
            35                  40                  45 ggc ttt ctg gtg gcg gcg acg ttc gcc tgg aac ctg ctg gtg ctg gcg      252
Gly Phe Leu Val Ala Ala Thr Phe Ala Trp Asn Leu Leu Val Leu Ala
        50                  55                  60 acc atc ctc cgt gta cgc acc ttc cac cgc gtg ccc cac aac ctg gtg      300
Thr Ile Leu Arg Val Arg Thr Phe His Arg Val Pro His Asn Leu Val
    65                  70                  75 gca tcc atg gcc gtc tcg gat gtc ctg gtg gcc gcg ctg gtc atg ccg      348
Ala Ser Met Ala Val Ser Asp Val Leu Val Ala Ala Leu Val Met Pro
80                  85                  90                  95 ctg agc ctg gtg cat gag ctg tcc ggg cgc cgc tgg cag cta ggt cgg      396
Leu Ser Leu Val His Glu Leu Ser Gly Arg Arg Trp Gln Leu Gly Arg
                100                 105                 110 agg ctg tgc cag ctt tgg atc gcg tgc gac gtg ctt tgc tgc acg gcc      444
Arg Leu Cys Gln Leu Trp Ile Ala Cys Asp Val Leu Cys Cys Thr Ala
            115                 120                 125 agc atc tgg aac gtg acg gcc ata gcc ctg gac cgc tac tgg tcc atc      492
Ser Ile Trp Asn Val Thr Ala Ile Ala Leu Asp Arg Tyr Trp Ser Ile
        130                 135                 140 acg cgc cac atg gaa tac acg ctc cgc acc cgc aag tgc gtc tcc aac      540
Thr Arg His Met Glu Tyr Thr Leu Arg Thr Arg Lys Cys Val Ser Asn
    145                 150                 155
```

```
gtc atg atc gcg ctc acc tgg gca ctc tcc gct gtc atc tct ctg gcc         588
Val Met Ile Ala Leu Thr Trp Ala Leu Ser Ala Val Ile Ser Leu Ala
160                 165                 170                 175 ccg ctg ctt ttt ggc tgg gga gag acg tac tct gag ggc agc gag gag         636
Pro Leu Leu Phe Gly Trp Gly Glu Thr Tyr Ser Glu Gly Ser Glu Glu
                180                 185                 190 tgc cag gta agc cgc gag cct tcc tac gcc gtg ttc tcc acc gta ggc         684
Cys Gln Val Ser Arg Glu Pro Ser Tyr Ala Val Phe Ser Thr Val Gly
            195                 200                 205 gcc ttc tac ctg ccg ctc tgt gtg gtg ctc ttc gtg tac tgg aag atc         732
Ala Phe Tyr Leu Pro Leu Cys Val Val Leu Phe Val Tyr Trp Lys Ile
        210                 215                 220 tac aag gct gcc aag ttc cgc gtg ggc tcc agg aag acc aat agc gtc         780
Tyr Lys Ala Ala Lys Phe Arg Val Gly Ser Arg Lys Thr Asn Ser Val
    225                 230                 235 tca ccc ata tcc gaa gct gtg gag gtg aag gac tct gcc aaa cag ccc         828
Ser Pro Ile Ser Glu Ala Val Glu Val Lys Asp Ser Ala Lys Gln Pro
240                 245                 250                 255 cag atg gtg ttc acg gtc cgc cac gcc acc gtc acc ttc cag cca gaa         876
Gln Met Val Phe Thr Val Arg His Ala Thr Val Thr Phe Gln Pro Glu
                260                 265                 270 ggg gac acg tgg cgg gag cag aag gag cag cgg gcc gcc ctc atg gtg         924
Gly Asp Thr Trp Arg Glu Gln Lys Glu Gln Arg Ala Ala Leu Met Val
            275                 280                 285 ggc atc ctc att ggc gtg ttc gtg ctc tgc tgg atc ccc ttc ttt ctc         972
Gly Ile Leu Ile Gly Val Phe Val Leu Cys Trp Ile Pro Phe Phe Leu
        290                 295                 300 acc gag ctc atc agt ccc ctc tgc tcc tgt gac atc ccc gcc atc tgg        1020
Thr Glu Leu Ile Ser Pro Leu Cys Ser Cys Asp Ile Pro Ala Ile Trp
    305                 310                 315 aaa agc atc ttc ctg tgg ctt ggc tac tcc aac tcc ttc ttt aac ccc        1068
Lys Ser Ile Phe Leu Trp Leu Gly Tyr Ser Asn Ser Phe Phe Asn Pro
320                 325                 330                 335 ctg atc tat acg gct ttc aac aag aac tac aac agc gcc ttc aag aac        1116
Leu Ile Tyr Thr Ala Phe Asn Lys Asn Tyr Asn Ser Ala Phe Lys Asn
                340                 345                 350 ttc ttt tct agg caa cac tga gggagaggga ttgatggaat tc                   1159
Phe Phe Ser Arg Gln His *
            355

<210> SEQ ID NO 16
<211> LENGTH: 357
<212> TYPE: PRT
<213> ORGANISM: Homo Sapiens

<400> SEQUENCE: 16

Met Asp Leu Pro Val Asn Leu Thr Ser Phe Ser Leu Ser Thr Pro Ser
1               5                   10                  15

Pro Leu Glu Thr Asn His Ser Leu Gly Lys Asp Asp Leu Arg Pro Ser
            20                  25                  30

Ser Pro Leu Leu Ser Val Phe Gly Val Leu Ile Leu Thr Leu Leu Gly
        35                  40                  45

Phe Leu Val Ala Ala Thr Phe Ala Trp Asn Leu Leu Val Leu Ala Thr
    50                  55                  60

Ile Leu Arg Val Arg Thr Phe His Arg Val Pro His Asn Leu Val Ala
65                  70                  75                  80

Ser Met Ala Val Ser Asp Val Leu Val Ala Ala Leu Val Met Pro Leu
                85                  90                  95
```

-continued

```
Ser Leu Val His Glu Leu Ser Gly Arg Arg Trp Gln Leu Gly Arg Arg
        100                 105                 110

Leu Cys Gln Leu Trp Ile Ala Cys Asp Val Leu Cys Thr Ala Ser
        115                 120                 125

Ile Trp Asn Val Thr Ala Ile Ala Leu Asp Arg Tyr Trp Ser Ile Thr
        130                 135                 140

Arg His Met Glu Tyr Thr Leu Arg Thr Arg Lys Cys Val Ser Asn Val
145                 150                 155                 160

Met Ile Ala Leu Thr Trp Ala Leu Ser Ala Val Ile Ser Leu Ala Pro
                165                 170                 175

Leu Leu Phe Gly Trp Gly Glu Thr Tyr Ser Glu Gly Ser Glu Glu Cys
                180                 185                 190

Gln Val Ser Arg Glu Pro Ser Tyr Ala Val Phe Ser Thr Val Gly Ala
        195                 200                 205

Phe Tyr Leu Pro Leu Cys Val Val Leu Phe Val Tyr Trp Lys Ile Tyr
        210                 215                 220

Lys Ala Ala Lys Phe Arg Val Gly Ser Arg Lys Thr Asn Ser Val Ser
225                 230                 235                 240

Pro Ile Ser Glu Ala Val Glu Val Lys Asp Ser Ala Lys Gln Pro Gln
                245                 250                 255

Met Val Phe Thr Val Arg His Ala Thr Val Thr Phe Gln Pro Glu Gly
                260                 265                 270

Asp Thr Trp Arg Glu Gln Lys Glu Gln Arg Ala Ala Leu Met Val Gly
        275                 280                 285

Ile Leu Ile Gly Val Phe Val Leu Cys Trp Ile Pro Phe Phe Leu Thr
        290                 295                 300

Glu Leu Ile Ser Pro Leu Cys Ser Cys Asp Ile Pro Ala Ile Trp Lys
305                 310                 315                 320

Ser Ile Phe Leu Trp Leu Gly Tyr Ser Asn Ser Phe Phe Asn Pro Leu
                325                 330                 335

Ile Tyr Thr Ala Phe Asn Lys Asn Tyr Asn Ser Ala Phe Lys Asn Phe
                340                 345                 350

Phe Ser Arg Gln His
        355

<210> SEQ ID NO 17
<211> LENGTH: 1077
<212> TYPE: DNA
<213> ORGANISM: Homo Sapiens
<220> FEATURE:
<221> NAME/KEY: CDS
<222> LOCATION: (1)...(1077)

<400> SEQUENCE: 17 atg tcg gtc tgc tac cgt ccc cca ggg aac gag aca ctg ctg agc tgg      48
Met Ser Val Cys Tyr Arg Pro Pro Gly Asn Glu Thr Leu Leu Ser Trp
1               5                   10                  15 aag act tcg cgg gcc aca ggc aca gcc ttc ctg ctg ctg gcg gcg ctg      96
Lys Thr Ser Arg Ala Thr Gly Thr Ala Phe Leu Leu Leu Ala Ala Leu
                20                  25                  30 ctg ggg ctg cct ggc aac ggc ttc gtg gtg tgg agc ttg gcg ggc tgg     144
Leu Gly Leu Pro Gly Asn Gly Phe Val Val Trp Ser Leu Ala Gly Trp
        35                  40                  45 cgg cct gca cgg ggg cga ccg ctg gcg gcc acg ctt gtg ctg cac ctg     192
Arg Pro Ala Arg Gly Arg Pro Leu Ala Ala Thr Leu Val Leu His Leu
        50                  55                  60 gcg ctg gcc gac ggc gcg gtg ctg ctg ctc acg ccg ctc ttt gtg gcc     240
```

|   |   |   |   |   |   |   |   |   |   |   |   |   |   |   |   |   |
|---|---|---|---|---|---|---|---|---|---|---|---|---|---|---|---|---|
| Ala | Leu | Ala | Asp | Gly | Ala | Val | Leu | Leu | Leu | Thr | Pro | Leu | Phe | Val | Ala | |
| 65 | | | | 70 | | | | | 75 | | | | | 80 | | |

```
ttc ctg acc cgg cag gcc tgg ccg ctg ggc cag gcg ggc tgc aag gcg      288
Phe Leu Thr Arg Gln Ala Trp Pro Leu Gly Gln Ala Gly Cys Lys Ala
                85                  90                  95 gtg tac tac gtg tgc gcg ctc agc atg tac gcc agc gtg ctc ctc acc      336
Val Tyr Tyr Val Cys Ala Leu Ser Met Tyr Ala Ser Val Leu Leu Thr
            100                 105                 110 ggc ctg ctc agc ctg cag cgc tgc ctc gca gtc acc cgc ccc ttc ctg      384
Gly Leu Leu Ser Leu Gln Arg Cys Leu Ala Val Thr Arg Pro Phe Leu
        115                 120                 125 gcg cct cgg ctg cgc agc ccg gcc ctg gcc cgc cgc ctg ctg ctg gcg      432
Ala Pro Arg Leu Arg Ser Pro Ala Leu Ala Arg Arg Leu Leu Leu Ala
    130                 135                 140 gtc tgg ctg gcc gcc ctg ttg ctc gcc gtc ccg gcc gcc gtc tac cgc      480
Val Trp Leu Ala Ala Leu Leu Leu Ala Val Pro Ala Ala Val Tyr Arg
145                 150                 155                 160 cac ctg tgg agg gac cgc gta tgc cag ctg tgc cac ccg tcg ccg gtc      528
His Leu Trp Arg Asp Arg Val Cys Gln Leu Cys His Pro Ser Pro Val
                165                 170                 175 cac gcc gcc gcc cac ctg agc ctg gag act ctg acc gct ttc gtg ctt      576
His Ala Ala Ala His Leu Ser Leu Glu Thr Leu Thr Ala Phe Val Leu
            180                 185                 190 cct ttc ggg ctg atg ctc ggc tgc tac agc gtg acg ctg gca cgg ctg      624
Pro Phe Gly Leu Met Leu Gly Cys Tyr Ser Val Thr Leu Ala Arg Leu
        195                 200                 205 cgg ggc gcc cgc tgg ggc tcc ggg cgc cac ggg gcg cgg gtg ggc cgg      672
Arg Gly Ala Arg Trp Gly Ser Gly Arg His Gly Ala Arg Val Gly Arg
    210                 215                 220 ctg gtg agc gcc atc gtg ctt gcc ttc ggc ttg ctc tgg gcc ccc tac      720
Leu Val Ser Ala Ile Val Leu Ala Phe Gly Leu Leu Trp Ala Pro Tyr
225                 230                 235                 240 cac gca gtc aac ctt ctg cag gcg gtc gca gcg ctg gct cca ccg gaa      768
His Ala Val Asn Leu Leu Gln Ala Val Ala Ala Leu Ala Pro Pro Glu
                245                 250                 255 ggg gcc ttg gcg aag ctg ggc gga gcc ggc cag gcg gcg cga gcg gga      816
Gly Ala Leu Ala Lys Leu Gly Gly Ala Gly Gln Ala Ala Arg Ala Gly
            260                 265                 270 act acg gcc ttg gcc ttc ttc agt tct agc gtc aac ccg gtg ctc tac      864
Thr Thr Ala Leu Ala Phe Phe Ser Ser Ser Val Asn Pro Val Leu Tyr
        275                 280                 285 gtc ttc acc gct gga gat ctg ctg ccc cgg gca ggt ccc cgt ttc ctc      912
Val Phe Thr Ala Gly Asp Leu Leu Pro Arg Ala Gly Pro Arg Phe Leu
    290                 295                 300 acg cgg ctc ttc gaa ggc tct ggg gag gcc cga ggg ggc ggc cgc tct      960
Thr Arg Leu Phe Glu Gly Ser Gly Glu Ala Arg Gly Gly Gly Arg Ser
305                 310                 315                 320 agg gaa ggg acc atg gag ctc cga act acc cct cag ctg aaa gtg gtg     1008
Arg Glu Gly Thr Met Glu Leu Arg Thr Thr Pro Gln Leu Lys Val Val
                325                 330                 335 ggg cag ggc cgc ggc aat gga gac ccg ggg ggt ggg atg gag aag gac     1056
Gly Gln Gly Arg Gly Asn Gly Asp Pro Gly Gly Gly Met Glu Lys Asp
            340                 345                 350 ggt ccg gaa tgg gac ctt tga                                         1077
Gly Pro Glu Trp Asp Leu  *
        355
```

<210> SEQ ID NO 18
<211> LENGTH: 358
<212> TYPE: PRT

<213> ORGANISM: Homo Sapiens

<400> SEQUENCE: 18

```
Met Ser Val Cys Tyr Arg Pro Pro Gly Asn Glu Thr Leu Leu Ser Trp
 1               5                  10                  15
Lys Thr Ser Arg Ala Thr Gly Thr Ala Phe Leu Leu Leu Ala Ala Leu
             20                  25                  30
Leu Gly Leu Pro Gly Asn Gly Phe Val Val Trp Ser Leu Ala Gly Trp
         35                  40                  45
Arg Pro Ala Arg Gly Arg Pro Leu Ala Ala Thr Leu Val Leu His Leu
 50                  55                  60
Ala Leu Ala Asp Gly Ala Val Leu Leu Leu Thr Pro Leu Phe Val Ala
 65                  70                  75                  80
Phe Leu Thr Arg Gln Ala Trp Pro Leu Gly Gln Ala Gly Cys Lys Ala
                 85                  90                  95
Val Tyr Tyr Val Cys Ala Leu Ser Met Tyr Ala Ser Val Leu Leu Thr
             100                 105                 110
Gly Leu Leu Ser Leu Gln Arg Cys Leu Ala Val Thr Arg Pro Phe Leu
         115                 120                 125
Ala Pro Arg Leu Arg Ser Pro Ala Leu Ala Arg Arg Leu Leu Leu Ala
130                 135                 140
Val Trp Leu Ala Ala Leu Leu Ala Val Pro Ala Ala Val Tyr Arg
145                 150                 155                 160
His Leu Trp Arg Asp Arg Val Cys Gln Leu Cys His Pro Ser Pro Val
                 165                 170                 175
His Ala Ala His Leu Ser Leu Glu Thr Leu Thr Ala Phe Val Leu
             180                 185                 190
Pro Phe Gly Leu Met Leu Gly Cys Tyr Ser Val Thr Leu Ala Arg Leu
         195                 200                 205
Arg Gly Ala Arg Trp Gly Ser Gly Arg His Gly Ala Arg Val Gly Arg
210                 215                 220
Leu Val Ser Ala Ile Val Leu Ala Phe Gly Leu Leu Trp Ala Pro Tyr
225                 230                 235                 240
His Ala Val Asn Leu Leu Gln Ala Val Ala Ala Leu Ala Pro Pro Glu
                 245                 250                 255
Gly Ala Leu Ala Lys Leu Gly Gly Ala Gly Gln Ala Ala Arg Ala Gly
             260                 265                 270
Thr Thr Ala Leu Ala Phe Phe Ser Ser Ser Val Asn Pro Val Leu Tyr
         275                 280                 285
Val Phe Thr Ala Gly Asp Leu Leu Pro Arg Ala Gly Pro Arg Phe Leu
290                 295                 300
Thr Arg Leu Phe Glu Gly Ser Gly Glu Ala Arg Gly Gly Arg Ser
305                 310                 315                 320
Arg Glu Gly Thr Met Glu Leu Arg Thr Thr Pro Gln Leu Lys Val Val
                 325                 330                 335
Gly Gln Gly Arg Gly Asn Gly Asp Pro Gly Gly Met Glu Lys Asp
             340                 345                 350
Gly Pro Glu Trp Asp Leu
         355
```

<210> SEQ ID NO 19
<211> LENGTH: 1634
<212> TYPE: DNA
<213> ORGANISM: Homo Sapiens
<220> FEATURE:

-continued

```
<221> NAME/KEY: CDS
<222> LOCATION: (100)...(1275)

<400> SEQUENCE: 19
ctgcaggcaa gcggtcgggt ggggagggag ggcgcaggcg gcgggtgcgc gaggagaaag      60
ccccagccct ggcagcccca ctggcccccc tcagctggg atg ttc ccc aat ggc       114
                                            Met Phe Pro Asn Gly
                                            1               5 acc gcc tcc tct cct tcc tcc tct cct agc ccc agc ccg ggc agc tgc      162
Thr Ala Ser Ser Pro Ser Ser Ser Pro Ser Pro Ser Pro Gly Ser Cys
            10                  15                  20 ggc gaa ggc ggc ggc agc agg ggc ccc ggg gcc ggc gct gcg gac ggc      210
Gly Glu Gly Gly Gly Ser Arg Gly Pro Gly Ala Gly Ala Ala Asp Gly
        25                  30                  35 atg gag gag cca ggg cga aat gcg tcc cag aac ggg acc ttg agc gag      258
Met Glu Glu Pro Gly Arg Asn Ala Ser Gln Asn Gly Thr Leu Ser Glu
    40                  45                  50 ggc cag ggc agc gcc atc ctg atc tct ttc atc tac tcc gtg gtg tgc      306
Gly Gln Gly Ser Ala Ile Leu Ile Ser Phe Ile Tyr Ser Val Val Cys
55                  60                  65 ctg gtg ggg ctg tgt ggg aac tct atg gtc atc tac gtg atc ctg cgc      354
Leu Val Gly Leu Cys Gly Asn Ser Met Val Ile Tyr Val Ile Leu Arg
70                  75                  80                  85 tat gcc aag atg aag acg gcc acc aac atc tac atc cta aat ctg gcc      402
Tyr Ala Lys Met Lys Thr Ala Thr Asn Ile Tyr Ile Leu Asn Leu Ala
                90                  95                  100 att gct gat gag ctg ctc atg ctc agc gtg ccc ttc cta gtc acc tcc      450
Ile Ala Asp Glu Leu Leu Met Leu Ser Val Pro Phe Leu Val Thr Ser
            105                 110                 115 acg ttg ttg cgc cac tgg ccc ttc ggt gcg ctg ctc tgc cgc ctc gtg      498
Thr Leu Leu Arg His Trp Pro Phe Gly Ala Leu Leu Cys Arg Leu Val
        120                 125                 130 ctc agc gtg gac gcg gtc aac atg ttc acc agc atc tac tgt ctg act      546
Leu Ser Val Asp Ala Val Asn Met Phe Thr Ser Ile Tyr Cys Leu Thr
    135                 140                 145 gtg ctc agc gtg gac cgc tac gtg gcc gtg gtg cat ccc atc aag gcg      594
Val Leu Ser Val Asp Arg Tyr Val Ala Val Val His Pro Ile Lys Ala
150                 155                 160                 165 gcc cgc tac cgc cgg ccc acc gtg gcc aag gta gta aac ctg ggc gtg      642
Ala Arg Tyr Arg Arg Pro Thr Val Ala Lys Val Val Asn Leu Gly Val
                170                 175                 180 tgg gtg cta tcg ctg ctc gtc atc ctg ccc atc gtg gtc ttc tct cgc      690
Trp Val Leu Ser Leu Leu Val Ile Leu Pro Ile Val Val Phe Ser Arg
            185                 190                 195 acc gcg gcc aac agc gac ggc acg gtg gct tgc aac atg ctc atg cca      738
Thr Ala Ala Asn Ser Asp Gly Thr Val Ala Cys Asn Met Leu Met Pro
        200                 205                 210 gag ccc gct caa cgc tgg ctg gtg ggc ttc gtg ttg tac aca ttt ctc      786
Glu Pro Ala Gln Arg Trp Leu Val Gly Phe Val Leu Tyr Thr Phe Leu
    215                 220                 225 atg ggc ttc ctg ctg ccc gtg ggg gct atc tgc ctg tgc tac gtg ctc      834
Met Gly Phe Leu Leu Pro Val Gly Ala Ile Cys Leu Cys Tyr Val Leu
230                 235                 240                 245 atc att gct aag atg cgc atg gtg gcc ctc aag gcc ggc tgg cag cag      882
Ile Ile Ala Lys Met Arg Met Val Ala Leu Lys Ala Gly Trp Gln Gln
                250                 255                 260 cgc aag cgc tcg gag cgc aag atc acc tta atg gtg atg atg gtg gtg      930
Arg Lys Arg Ser Glu Arg Lys Ile Thr Leu Met Val Met Met Val Val
            265                 270                 275
```

-continued

```
atg gtg ttt gtc atc tgc tgg atg cct ttc tac gtg gtg cag ctg gtt      978
Met Val Phe Val Ile Cys Trp Met Pro Phe Tyr Val Val Gln Leu Val
        280                 285                 290 aac gtg ttt gct gag cag gac gac gcc acg gtg agt cag ctg tcg gtc     1026
Asn Val Phe Ala Glu Gln Asp Asp Ala Thr Val Ser Gln Leu Ser Val
    295                 300                 305 atc ctc ggc tat gcc aac agc tgc gcc aac ccc atc ctc tat ggc ttt     1074
Ile Leu Gly Tyr Ala Asn Ser Cys Ala Asn Pro Ile Leu Tyr Gly Phe
310                 315                 320                 325 ctc tca gac aac ttc aag cgc tct ttc caa cgc atc cta tgc ctc agc     1122
Leu Ser Asp Asn Phe Lys Arg Ser Phe Gln Arg Ile Leu Cys Leu Ser
                330                 335                 340 tgg atg gac aac gcc gcg gag gag ccg gtt gac tat tac gcc acc gcg     1170
Trp Met Asp Asn Ala Ala Glu Glu Pro Val Asp Tyr Tyr Ala Thr Ala
            345                 350                 355 ctc aag agc cgt gcc tac agt gtg gaa gac ttc caa cct gag aac ctg     1218
Leu Lys Ser Arg Ala Tyr Ser Val Glu Asp Phe Gln Pro Glu Asn Leu
        360                 365                 370 gag tcc ggc ggc gtc ttc cgt aat ggc acc tgc acg tcc cgg atc acg     1266
Glu Ser Gly Gly Val Phe Arg Asn Gly Thr Cys Thr Ser Arg Ile Thr
    375                 380                 385 acg ctc tga gcccgggcca cgcaggggct ctgagcccgg gccacgcagg             1315
Thr Leu *
390 ggccctgagc caaagagggg ggagaatgag aagggaaggc cgggtgcgaa agggacggta   1375 tccagggcgc cagggtgctg tcgggataac gtggggctag acactgaca gcctttgatg    1435 gaggaaccca agaaaggcgc gcgacaatgg tagaagtgag agctttgctt ataaactggg   1495 aaggctttca ggctaccttt ttctgggtct cccactttct gttccttcct ccactgcgct   1555 tgctcctctg accctccttc tatttccccc accctgcaac ttctatcctt tcttccgcac   1615 cgtcccgcca gtgcagatc                                               1634
```

<210> SEQ ID NO 20
<211> LENGTH: 391
<212> TYPE: PRT
<213> ORGANISM: Homo Sapiens

<400> SEQUENCE: 20

```
Met Phe Pro Asn Gly Thr Ala Ser Ser Pro Ser Ser Pro Ser Pro
  1               5                  10                  15

Ser Pro Gly Ser Cys Gly Glu Gly Gly Ser Arg Gly Pro Gly Ala
            20                  25                  30

Gly Ala Ala Asp Gly Met Glu Glu Pro Gly Arg Asn Ala Ser Gln Asn
            35                  40                  45

Gly Thr Leu Ser Glu Gly Gln Gly Ser Ala Ile Leu Ile Ser Phe Ile
50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140
```

-continued

```
Ile Tyr Cys Leu Thr Val Leu Ser Val Asp Arg Tyr Val Ala Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Thr Ser Arg Ile Thr Thr Leu
385                 390

<210> SEQ ID NO 21
<211> LENGTH: 1564
<212> TYPE: DNA
<213> ORGANISM: Homo Sapiens
<220> FEATURE:
<221> NAME/KEY: CDS
<222> LOCATION: (154)...(1431)

<400> SEQUENCE: 21
cctcccttca ggaagtttga ggctgagacc cgaaaagacc tgggtgcaag cctccaggca      60
ccctgaaggg agtgggctga ggctggccc  aagctccctc ctctccctct gtagagccta     120
ggatgcccct ctgctgcagc ggctcctgag ctc atg gag ccc tca gcc acc cca     174
                                    Met Glu Pro Ser Ala Thr Pro
                                     1               5 ggg gcc cag atg ggg gtc ccc cct ggc agc aga gag ccg tcc cct gtg     222
Gly Ala Gln Met Gly Val Pro Pro Gly Ser Arg Glu Pro Ser Pro Val
            10                  15                  20 cct cca gac tat gaa gat gag ttt ctc cgc tat ctg tgg cgt gat tat     270
Pro Pro Asp Tyr Glu Asp Glu Phe Leu Arg Tyr Leu Trp Arg Asp Tyr
         25                  30                  35 ctg tac cca aaa cag tat gag tgg gtc ctc atc gca gcc tat gtg gct     318
Leu Tyr Pro Lys Gln Tyr Glu Trp Val Leu Ile Ala Ala Tyr Val Ala
 40                  45                  50                  55
```

-continued

| | |
|---|---|
| gtg ttc gtc gtg gcc ctg gtg ggc aac acg ctg gtc tgc ctg gcc gtg<br>Val Phe Val Val Ala Leu Val Gly Asn Thr Leu Val Cys Leu Ala Val<br>                            60                         65                      70 | 366 |
| tgg cgg aac cac cac atg agg aca gtc acc aac tac ttc att gtc aac<br>Trp Arg Asn His His Met Arg Thr Val Thr Asn Tyr Phe Ile Val Asn<br>              75                       80                      85 | 414 |
| ctg tcc ctg gct gac gtt ctg gtg act gct atc tgc ctg ccg gcc agc<br>Leu Ser Leu Ala Asp Val Leu Val Thr Ala Ile Cys Leu Pro Ala Ser<br>              90                       95                    100 | 462 |
| ctg ctg gtg gac atc act gag tcc tgg ctg ttc ggc cat gcc ctc tgc<br>Leu Leu Val Asp Ile Thr Glu Ser Trp Leu Phe Gly His Ala Leu Cys<br>105                     110                    115 | 510 |
| aag gtc atc ccc tat cta cag gct gtg tcc gtg tca gtg gca gtg cta<br>Lys Val Ile Pro Tyr Leu Gln Ala Val Ser Val Ser Val Ala Val Leu<br>120                     125                    130                    135 | 558 |
| act ctc agc ttc atc gcc ctg gac cgc tgg tat gcc atc tgc cac cca<br>Thr Leu Ser Phe Ile Ala Leu Asp Arg Trp Tyr Ala Ile Cys His Pro<br>                     140                    145                    150 | 606 |
| cta ttg ttc aag agc aca gcc cgg cgg gcc cgt ggc tcc atc ctg ggc<br>Leu Leu Phe Lys Ser Thr Ala Arg Arg Ala Arg Gly Ser Ile Leu Gly<br>               155                    160                    165 | 654 |
| atc tgg gct gtg tcg ctg gcc atc atg gtg ccc cag gct gca gtc atg<br>Ile Trp Ala Val Ser Leu Ala Ile Met Val Pro Gln Ala Ala Val Met<br>              170                    175                    180 | 702 |
| gaa tgc agc agt gtg ctg cct gag cta gcc aac cgc aca cgg ctc ttc<br>Glu Cys Ser Ser Val Leu Pro Glu Leu Ala Asn Arg Thr Arg Leu Phe<br>185                     190                    195 | 750 |
| tca gtc tgt gat gaa cgc tgg gca gat gac ctc tat ccc aag atc tac<br>Ser Val Cys Asp Glu Arg Trp Ala Asp Asp Leu Tyr Pro Lys Ile Tyr<br>200                     205                    210                    215 | 798 |
| cac agt tgc ttc ttt att gtc acc tac ctg gcc cca ctg ggc ctc atg<br>His Ser Cys Phe Phe Ile Val Thr Tyr Leu Ala Pro Leu Gly Leu Met<br>              220                    225                    230 | 846 |
| gcc atg gcc tat ttc cag ata ttc cgc aag ctc tgg ggc cgc cag atc<br>Ala Met Ala Tyr Phe Gln Ile Phe Arg Lys Leu Trp Gly Arg Gln Ile<br>              235                    240                    245 | 894 |
| ccc ggc acc acc tca gca ctg gtg cgg aac tgg aag cgc ccc tca gac<br>Pro Gly Thr Thr Ser Ala Leu Val Arg Asn Trp Lys Arg Pro Ser Asp<br>250                     255                    260 | 942 |
| cag ctg ggg gac ctg gag cag ggc ctg agt gga gag ccc cag ccc cgg<br>Gln Leu Gly Asp Leu Glu Gln Gly Leu Ser Gly Glu Pro Gln Pro Arg<br>            265                    270                    275 | 990 |
| ggc cgc gcc ttc ctg gct gaa gtg aag cag atg cgt gca cgg agg aag<br>Gly Arg Ala Phe Leu Ala Glu Val Lys Gln Met Arg Ala Arg Arg Lys<br>280                     285                    290                    295 | 1038 |
| aca gcc aag atg ctg atg gtg gtg ctg ctg gtc ttc gcc ctc tgc tac<br>Thr Ala Lys Met Leu Met Val Val Leu Leu Val Phe Ala Leu Cys Tyr<br>                    300                    305                    310 | 1086 |
| ctg ccc atc agc gtc ctc aat gtc ctt aag agg gtg ttc ggg atg ttc<br>Leu Pro Ile Ser Val Leu Asn Val Leu Lys Arg Val Phe Gly Met Phe<br>              315                    320                    325 | 1134 |
| cgc caa gcc agt gac cgc gaa gct gtc tac gcc tgc ttc acc ttc tcc<br>Arg Gln Ala Ser Asp Arg Glu Ala Val Tyr Ala Cys Phe Thr Phe Ser<br>                     330                    335                    340 | 1182 |
| cac tgg ctg gtg tac gcc aac agc gct gcc aac ccc atc atc tac aac<br>His Trp Leu Val Tyr Ala Asn Ser Ala Ala Asn Pro Ile Ile Tyr Asn<br>              345                    350                    355 | 1230 |
| ttc ctc agt ggg aaa ttc cgg gag cag ttt aag gct gcc ttc tcc tgc<br>Phe Leu Ser Gly Lys Phe Arg Glu Gln Phe Lys Ala Ala Phe Ser Cys<br>360                     365                    370                    375 | 1278 |

```
tgc ctg cct ggc ctg ggt ccc tgc ggc tct ctg aag gcc cct agt ccc       1326
Cys Leu Pro Gly Leu Gly Pro Cys Gly Ser Leu Lys Ala Pro Ser Pro
            380                 385                 390 cgc tcc tct gcc agc cac aag tcc ttg tcc ttg cag agc cga tgc tcc       1374
Arg Ser Ser Ala Ser His Lys Ser Leu Ser Leu Gln Ser Arg Cys Ser
            395                 400                 405 atc tcc aaa atc tct gag cat gtg gtg ctc acc agc gtc acc aca gtg       1422
Ile Ser Lys Ile Ser Glu His Val Val Leu Thr Ser Val Thr Thr Val
            410                 415                 420 ctg ccc tga gcgagggctg ccctggaggc tccggctcgg gggatctgcc               1471
Leu Pro *
    425 cctaccctc atggaaagac agctggatgt ggtgaaaggc tgtggcttca gtcctgggtt      1531
tctgcctgtg tgactctgga taagtcactt cct                                   1564

<210> SEQ ID NO 22
<211> LENGTH: 425
<212> TYPE: PRT
<213> ORGANISM: Homo Sapiens

<400> SEQUENCE: 22

Met Glu Pro Ser Ala Thr Pro Gly Ala Gln Met Gly Val Pro Pro Gly
1               5                   10                  15

Ser Arg Glu Pro Ser Pro Val Pro Pro Asp Tyr Glu Asp Glu Phe Leu
            20                  25                  30

Arg Tyr Leu Trp Arg Asp Tyr Leu Tyr Pro Lys Gln Tyr Glu Trp Val
        35                  40                  45

Leu Ile Ala Ala Tyr Val Ala Val Phe Val Val Ala Leu Val Gly Asn
    50                  55                  60

Thr Leu Val Cys Leu Ala Val Trp Arg Asn His His Met Arg Thr Val
65                  70                  75                  80

Thr Asn Tyr Phe Ile Val Asn Leu Ser Leu Ala Asp Val Leu Val Thr
                85                  90                  95

Ala Ile Cys Leu Pro Ala Ser Leu Leu Val Asp Ile Thr Glu Ser Trp
            100                 105                 110

Leu Phe Gly His Ala Leu Cys Lys Val Ile Pro Tyr Leu Gln Ala Val
        115                 120                 125

Ser Val Ser Val Ala Val Leu Thr Leu Ser Phe Ile Ala Leu Asp Arg
    130                 135                 140

Trp Tyr Ala Ile Cys His Pro Leu Leu Phe Lys Ser Thr Ala Arg Arg
145                 150                 155                 160

Ala Arg Gly Ser Ile Leu Gly Ile Trp Ala Val Ser Leu Ala Ile Met
                165                 170                 175

Val Pro Gln Ala Ala Val Met Glu Cys Ser Ser Val Leu Pro Glu Leu
            180                 185                 190

Ala Asn Arg Thr Arg Leu Phe Ser Val Cys Asp Glu Arg Trp Ala Asp
        195                 200                 205

Asp Leu Tyr Pro Lys Ile Tyr His Ser Cys Phe Phe Ile Val Thr Tyr
    210                 215                 220

Leu Ala Pro Leu Gly Leu Met Ala Met Ala Tyr Phe Gln Ile Phe Arg
225                 230                 235                 240

Lys Leu Trp Gly Arg Gln Ile Pro Gly Thr Thr Ser Ala Leu Val Arg
                245                 250                 255

Asn Trp Lys Arg Pro Ser Asp Gln Leu Gly Asp Leu Glu Gln Gly Leu
            260                 265                 270
```

-continued

```
Ser Gly Glu Pro Gln Pro Arg Gly Arg Ala Phe Leu Ala Glu Val Lys
        275                 280                 285

Gln Met Arg Ala Arg Arg Lys Thr Ala Lys Met Leu Met Val Val Leu
        290                 295                 300

Leu Val Phe Ala Leu Cys Tyr Leu Pro Ile Ser Val Leu Asn Val Leu
305                 310                 315                 320

Lys Arg Val Phe Gly Met Phe Arg Gln Ala Ser Asp Arg Glu Ala Val
                325                 330                 335

Tyr Ala Cys Phe Thr Phe Ser His Trp Leu Val Tyr Ala Asn Ser Ala
                340                 345                 350

Ala Asn Pro Ile Ile Tyr Asn Phe Leu Ser Gly Lys Phe Arg Glu Gln
        355                 360                 365

Phe Lys Ala Ala Phe Ser Cys Cys Leu Pro Gly Leu Gly Pro Cys Gly
        370                 375                 380

Ser Leu Lys Ala Pro Ser Pro Arg Ser Ser Ala Ser His Lys Ser Leu
385                 390                 395                 400

Ser Leu Gln Ser Arg Cys Ser Ile Ser Lys Ile Ser Glu His Val Val
                405                 410                 415

Leu Thr Ser Val Thr Thr Val Leu Pro
                420                 425

<210> SEQ ID NO 23
<211> LENGTH: 4632
<212> TYPE: DNA
<213> ORGANISM: Homo Sapiens
<220> FEATURE:
<221> NAME/KEY: CDS
<222> LOCATION: (225)...(3581)
<220> FEATURE:
<221> NAME/KEY: misc_feature
<222> LOCATION: (1)...(4632)
<223> OTHER INFORMATION: n = A,T,C or G

<400> SEQUENCE: 23
cacgcgtccg cccacgcgtc cgcccacgcg tccgagcccc ctttcaagcc ttagcttccg      60
gctccaagcc gaccccctcc ccctccctgt ccccttcccc ttctcccatc cctctctcgg     120
ccacagcgtc ttgttagtcc tctccctcta ctccgcaata ttttctttct ttctccctcc     180
tctcctccat tgttgtttg atgtttccca ctctttgagg aagg atg gtt gat ttg      236
                                              Met Val Asp Leu
                                                1 gag agc gaa gtg ccc cct ctg cct ccc agg tac agg ttt cga gat ttg       284
Glu Ser Glu Val Pro Pro Leu Pro Pro Arg Tyr Arg Phe Arg Asp Leu
  5                  10                  15                  20 ctg cta ggg gac caa gga tgg caa aac gat gac aga gta caa gtt gaa       332
Leu Leu Gly Asp Gln Gly Trp Gln Asn Asp Asp Arg Val Gln Val Glu
                 25                  30                  35 ttc tat atg aat gaa aat aca ttt aaa gaa aga cta aaa tta ttt ttc       380
Phe Tyr Met Asn Glu Asn Thr Phe Lys Glu Arg Leu Lys Leu Phe Phe
             40                  45                  50 ata aaa aac cag aga tca agt cta agg ata cgc ctg ttc aat ttt tct       428
Ile Lys Asn Gln Arg Ser Ser Leu Arg Ile Arg Leu Phe Asn Phe Ser
         55                  60                  65 ctc aaa tta cta agc tgc tta tta tac ata atc cga gta cta cta gaa       476
Leu Lys Leu Leu Ser Cys Leu Leu Tyr Ile Ile Arg Val Leu Leu Glu
 70                  75                  80 aac cct tca caa gga aat gaa tgg tct cat atc ttt tgg gtg aac aga       524
Asn Pro Ser Gln Gly Asn Glu Trp Ser His Ile Phe Trp Val Asn Arg
 85                  90                  95                 100
```

| | |
|---|---|
| agt cta cct ttg tgg ggc tta cag gtt tca gtg gca ttg ata agt ctg<br>Ser Leu Pro Leu Trp Gly Leu Gln Val Ser Val Ala Leu Ile Ser Leu<br>105                    110                    115 | 572 |
| ttt gaa aca ata tta ctt ggt tat ctt agt tat aag gga aac atc tgg<br>Phe Glu Thr Ile Leu Leu Gly Tyr Leu Ser Tyr Lys Gly Asn Ile Trp<br>    120                    125                    130 | 620 |
| gaa cag att tta cga ata ccc ttc atc ttg gaa ata att aat gca gtt<br>Glu Gln Ile Leu Arg Ile Pro Phe Ile Leu Glu Ile Ile Asn Ala Val<br>        135                    140                    145 | 668 |
| ccc ttc att atc tca ata ttc tgg cct tcc tta agg aat cta ttt gtc<br>Pro Phe Ile Ile Ser Ile Phe Trp Pro Ser Leu Arg Asn Leu Phe Val<br>150                    155                    160 | 716 |
| cca gtc ttt ctg aac tgt tgg ctt gcc aaa cat gcc ttg gaa aat atg<br>Pro Val Phe Leu Asn Cys Trp Leu Ala Lys His Ala Leu Glu Asn Met<br>165                    170                    175                    180 | 764 |
| att aat gat cta cac aga gcc att cag cgt aca cag tct gca atg ttt<br>Ile Asn Asp Leu His Arg Ala Ile Gln Arg Thr Gln Ser Ala Met Phe<br>                  185                    190                    195 | 812 |
| aat caa gtt ttg att tta ata tct aca tta cta tgc ctt atc ttc acc<br>Asn Gln Val Leu Ile Leu Ile Ser Thr Leu Leu Cys Leu Ile Phe Thr<br>            200                    205                    210 | 860 |
| tgc att tgt ggg atc caa cat ctg gaa cga ata gga aag agg ctg aat<br>Cys Ile Cys Gly Ile Gln His Leu Glu Arg Ile Gly Lys Arg Leu Asn<br>        215                    220                    225 | 908 |
| ctc ttt gac tcc ctt tat ttc tgc att gtg acg ttt tct act gtg ggc<br>Leu Phe Asp Ser Leu Tyr Phe Cys Ile Val Thr Phe Ser Thr Val Gly<br>230                    235                    240 | 956 |
| ttc ggg gat gtc act cct gaa aca tgg tcc tcc aag ctt ttt gta gtt<br>Phe Gly Asp Val Thr Pro Glu Thr Trp Ser Ser Lys Leu Phe Val Val<br>245                    250                    255                    260 | 1004 |
| gct atg att tgt gtt gct ctt gtg gtt cta ccc ata cag ttt gaa cag<br>Ala Met Ile Cys Val Ala Leu Val Val Leu Pro Ile Gln Phe Glu Gln<br>                  265                    270                    275 | 1052 |
| ctg gct tat ttg tgg atg gag aga caa aag tca gga gga aac tat agt<br>Leu Ala Tyr Leu Trp Met Glu Arg Gln Lys Ser Gly Gly Asn Tyr Ser<br>            280                    285                    290 | 1100 |
| cga cat aga gct caa act gaa aag cat gtc gtc ctg tgt gtc agc tca<br>Arg His Arg Ala Gln Thr Glu Lys His Val Val Leu Cys Val Ser Ser<br>        295                    300                    305 | 1148 |
| ctg aag att gat tta ctt atg gat ttt tta aat gaa ttc tat gct cat<br>Leu Lys Ile Asp Leu Leu Met Asp Phe Leu Asn Glu Phe Tyr Ala His<br>310                    315                    320 | 1196 |
| cct agg ctc cag gat tat tat gtg gtg att ttg tgt cct act gaa atg<br>Pro Arg Leu Gln Asp Tyr Tyr Val Val Ile Leu Cys Pro Thr Glu Met<br>325                    330                    335                    340 | 1244 |
| gat gta cag gtt cga agg gta ctg cag att cca atg tgg tcc caa cga<br>Asp Val Gln Val Arg Arg Val Leu Gln Ile Pro Met Trp Ser Gln Arg<br>                  345                    350                    355 | 1292 |
| gtt atc tac ctt caa ggt tca gcc ctt aaa gat caa gac cta ttg aga<br>Val Ile Tyr Leu Gln Gly Ser Ala Leu Lys Asp Gln Asp Leu Leu Arg<br>            360                    365                    370 | 1340 |
| gca aag atg gat gac gct gag gcc tgt ttt att ctc agt agc cgt tgt<br>Ala Lys Met Asp Asp Ala Glu Ala Cys Phe Ile Leu Ser Ser Arg Cys<br>        375                    380                    385 | 1388 |
| gaa gtg gat agg aca tca tct gat cac caa aca att ttg aga gca tgg<br>Glu Val Asp Arg Thr Ser Ser Asp His Gln Thr Ile Leu Arg Ala Trp<br>390                    395                    400 | 1436 |
| gct gtg aaa gat ttt gct cca aat tgt cct ttg tat gtc cag ata tta<br>Ala Val Lys Asp Phe Ala Pro Asn Cys Pro Leu Tyr Val Gln Ile Leu | 1484 |

```
                405                 410                 415                 420
aag cct gaa aat aaa ttt cac atc aaa ttt gct gat cat gtt gtt tgt         1532
Lys Pro Glu Asn Lys Phe His Ile Lys Phe Ala Asp His Val Val Cys
                425                 430                 435 gaa gaa gag ttt aaa tac gcc atg tta gct tta aac tgt ata tgc cca         1580
Glu Glu Glu Phe Lys Tyr Ala Met Leu Ala Leu Asn Cys Ile Cys Pro
            440                 445                 450 gca aca tct aca ctt att aca cta ctg gtt cat acc tct aga ggg caa         1628
Ala Thr Ser Thr Leu Ile Thr Leu Leu Val His Thr Ser Arg Gly Gln
                455                 460                 465 gaa ggc cag caa tcg cca gaa caa tgg cag aag atg tac ggt aga tgc         1676
Glu Gly Gln Gln Ser Pro Glu Gln Trp Gln Lys Met Tyr Gly Arg Cys
        470                 475                 480 tcc ggg aat gaa gtc tac cac att gtt ttg gaa gaa agt aca ttt ttt         1724
Ser Gly Asn Glu Val Tyr His Ile Val Leu Glu Glu Ser Thr Phe Phe
485                 490                 495                 500 gct gaa tat gaa gga aag agt ttt aca tat gcc tct ttc cat gca cac         1772
Ala Glu Tyr Glu Gly Lys Ser Phe Thr Tyr Ala Ser Phe His Ala His
                505                 510                 515 aaa aag ttt ggc gtc tgc ttg att ggt gtt agg agg gag gat aat aaa         1820
Lys Lys Phe Gly Val Cys Leu Ile Gly Val Arg Arg Glu Asp Asn Lys
            520                 525                 530 aac att ttg ctg aat cca ggt cct cga tac att atg aat tct acg gac         1868
Asn Ile Leu Leu Asn Pro Gly Pro Arg Tyr Ile Met Asn Ser Thr Asp
                535                 540                 545 ata tgc ttt tat att aat att acc aaa gaa gag aat tca gca ttt aaa         1916
Ile Cys Phe Tyr Ile Asn Ile Thr Lys Glu Glu Asn Ser Ala Phe Lys
        550                 555                 560 aac caa gac cag cag aga aaa agc aat gtg tcc agg tcg ttt tat cat         1964
Asn Gln Asp Gln Gln Arg Lys Ser Asn Val Ser Arg Ser Phe Tyr His
565                 570                 575                 580 gga cct tcc aga tta cct gta cat agc ata att gcc agc atg ggt act         2012
Gly Pro Ser Arg Leu Pro Val His Ser Ile Ile Ala Ser Met Gly Thr
                585                 590                 595 gtg gct ata gac ctg caa gat aca agc tgt aga tca gca agt ggc cct         2060
Val Ala Ile Asp Leu Gln Asp Thr Ser Cys Arg Ser Ala Ser Gly Pro
            600                 605                 610 acc ctg tct ctt cct aca gag gga agc aaa gaa ata aga aga cct agc         2108
Thr Leu Ser Leu Pro Thr Glu Gly Ser Lys Glu Ile Arg Arg Pro Ser
                615                 620                 625 att gct cct gtt tta gag gtt gca gat aca tca tcg att caa aca tgt         2156
Ile Ala Pro Val Leu Glu Val Ala Asp Thr Ser Ser Ile Gln Thr Cys
        630                 635                 640 gat ctt cta agt gac caa tca gaa gat gaa act aca cca gat gaa gaa         2204
Asp Leu Leu Ser Asp Gln Ser Glu Asp Glu Thr Thr Pro Asp Glu Glu
645                 650                 655                 660 atg tct tca aac tta gag tat gct aaa ggt tac cca cct tat tct cca         2252
Met Ser Ser Asn Leu Glu Tyr Ala Lys Gly Tyr Pro Pro Tyr Ser Pro
                665                 670                 675 tat ata gga agt tca ccc act ttt tgt cat ctc ctt cat gaa aaa gta         2300
Tyr Ile Gly Ser Ser Pro Thr Phe Cys His Leu Leu His Glu Lys Val
            680                 685                 690 cca ttt tgc tgc tta aga tta gac aag agt tgc caa cat aac tac tat         2348
Pro Phe Cys Cys Leu Arg Leu Asp Lys Ser Cys Gln His Asn Tyr Tyr
                695                 700                 705 gag gat gca aaa gcc tat gga ttc aaa aat aaa cta att ata gtt gca         2396
Glu Asp Ala Lys Ala Tyr Gly Phe Lys Asn Lys Leu Ile Ile Val Ala
        710                 715                 720 gct gaa aca gct gga aat gga tta tat aac ttt att gtt cct ctc agg         2444
```

```
Ala Glu Thr Ala Gly Asn Gly Leu Tyr Asn Phe Ile Val Pro Leu Arg
725                 730                 735                 740 gca tat tat aga cca aag aaa gaa ctt aat ccc ata gta ctg cta ttg      2492
Ala Tyr Tyr Arg Pro Lys Lys Glu Leu Asn Pro Ile Val Leu Leu Leu
            745                 750                 755 gat aac ccc cta gat gac tta ctc agg tgt gga gtg act ttt gct gct      2540
Asp Asn Pro Leu Asp Asp Leu Leu Arg Cys Gly Val Thr Phe Ala Ala
        760                 765                 770 aat atg gtg gtt gtg gat aaa gag agc acc atg agt gcc gag gaa gac      2588
Asn Met Val Val Val Asp Lys Glu Ser Thr Met Ser Ala Glu Glu Asp
            775                 780                 785 tac atg gca gat gcc aaa acc att gtg aac gtg cag aca ctc ttc agg      2636
Tyr Met Ala Asp Ala Lys Thr Ile Val Asn Val Gln Thr Leu Phe Arg
    790                 795                 800 ttg ttt tcc agt ctc agt att atc aca gag cta act cac ccc gcc aac      2684
Leu Phe Ser Ser Leu Ser Ile Ile Thr Glu Leu Thr His Pro Ala Asn
805                 810                 815                 820 atg aga ttc atg caa ttc aga gcc aaa gac tgt tac tct ctt gct ctt      2732
Met Arg Phe Met Gln Phe Arg Ala Lys Asp Cys Tyr Ser Leu Ala Leu
            825                 830                 835 tca aaa ctg gaa aag aaa gaa cgg gag aga ggc tct aac ttg gcc ttt      2780
Ser Lys Leu Glu Lys Lys Glu Arg Glu Arg Gly Ser Asn Leu Ala Phe
        840                 845                 850 atg ttt cga ctg cct ttt gct gct ggg agg gtg ttt agc atc agt atg      2828
Met Phe Arg Leu Pro Phe Ala Ala Gly Arg Val Phe Ser Ile Ser Met
            855                 860                 865 ttg gac act ctg ctg tat cag tca ttt gtg aag gat tat atg att tct      2876
Leu Asp Thr Leu Leu Tyr Gln Ser Phe Val Lys Asp Tyr Met Ile Ser
870                 875                 880 atc acg aga ctt ctg ttg gga ctg gac act aca cca gga tct ggg ttt      2924
Ile Thr Arg Leu Leu Leu Gly Leu Asp Thr Thr Pro Gly Ser Gly Phe
885                 890                 895                 900 ctt tgt tct atg aaa atc act gca gat gac tta tgg atc aga act tat      2972
Leu Cys Ser Met Lys Ile Thr Ala Asp Asp Leu Trp Ile Arg Thr Tyr
            905                 910                 915 gcc aga ctt tat cag aag ttg tgt tct tct act gga gat gtt ccc att      3020
Ala Arg Leu Tyr Gln Lys Leu Cys Ser Ser Thr Gly Asp Val Pro Ile
        920                 925                 930 gga atc tac agg act gag tct cag aaa ctt act aca tct gag tct cga      3068
Gly Ile Tyr Arg Thr Glu Ser Gln Lys Leu Thr Thr Ser Glu Ser Arg
            935                 940                 945 aaa ata gca tca caa tct caa ata tct atc agt gta gaa gag tgg gaa      3116
Lys Ile Ala Ser Gln Ser Gln Ile Ser Ile Ser Val Glu Glu Trp Glu
950                 955                 960 gac acc aaa gac tcc aaa gaa caa ggg cac cac cgc agc aac cac cgc      3164
Asp Thr Lys Asp Ser Lys Glu Gln Gly His His Arg Ser Asn His Arg
965                 970                 975                 980 aac tca aca tcc agt gac cag tcg gac cat ccc ttg ctg cgg aga aaa      3212
Asn Ser Thr Ser Ser Asp Gln Ser Asp His Pro Leu Leu Arg Arg Lys
            985                 990                 995 agc atg cag tgg gcc cga aga ctg agc aga aaa ggc cca aaa cac tct      3260
Ser Met Gln Trp Ala Arg Arg Leu Ser Arg Lys Gly Pro Lys His Ser
        1000                1005                1010 ggt aaa aca gct gaa aaa ata acc cag cag cga ctg aac ctc tac agg      3308
Gly Lys Thr Ala Glu Lys Ile Thr Gln Gln Arg Leu Asn Leu Tyr Arg
            1015                1020                1025 agg tca gaa aga caa gag ctt gct gaa ctt gtg aaa aat aga atg aaa      3356
Arg Ser Glu Arg Gln Glu Leu Ala Glu Leu Val Lys Asn Arg Met Lys
    1030                1035                1040
```

-continued

| | | | | | | | | | | | | | | |
|---|---|---|---|---|---|---|---|---|---|---|---|---|---|---|
| cac | ttg | ggt | ctt | tct | aca | gtg | gga | tat | gat | gaa | atg | aat | gat cat caa | 3404 |
| His | Leu | Gly | Leu | Ser | Thr | Val | Gly | Tyr | Asp | Glu | Met | Asn | Asp His Gln | |
| | 1045 | | | | 1050 | | | | 1055 | | | | 1060 | |
| agt | acc | ctc | tcc | tac | atc | ctg | att | aac | cca | tct | cca | gat | acc aga ata | 3452 |
| Ser | Thr | Leu | Ser | Tyr | Ile | Leu | Ile | Asn | Pro | Ser | Pro | Asp | Thr Arg Ile | |
| | | | | 1065 | | | | | 1070 | | | | 1075 | |
| gag | ctg | aat | gat | gtt | gta | tac | tta | att | cga | cca | gat | cca | ctg gcc tac | 3500 |
| Glu | Leu | Asn | Asp | Val | Val | Tyr | Leu | Ile | Arg | Pro | Asp | Pro | Leu Ala Tyr | |
| | | | 1080 | | | | | 1085 | | | | | 1090 | |
| ctt | cca | aac | agt | gag | ccc | agt | cga | aga | aac | agc | atc | tgc | aat gtc act | 3548 |
| Leu | Pro | Asn | Ser | Glu | Pro | Ser | Arg | Arg | Asn | Ser | Ile | Cys | Asn Val Thr | |
| | | | 1095 | | | | | 1100 | | | | | 1105 | |
| ggt | caa | gat | tct | cgg | gag | gaa | act | caa | ctt | tga | taaaaataaa | | atgagaaact | 3601 |
| Gly | Gln | Asp | Ser | Arg | Glu | Glu | Thr | Gln | Leu | * | | | | |
| | 1110 | | | | | 1115 | | | | | | | | |

| | |
|---|---|
| ttttccctac aaagaccttg cttgaaacca caaaagttttt gctggcacga aagaaactag | 3661 |
| atggaaatat atgtaattct ctcatattta aaaacgtaat ctcttctctt agaagtatag | 3721 |
| atcattttga aacttaatgt actacttact ggtactctcc ctattaatat ttgaaggacc | 3781 |
| tcaatggaat aaatttgaaa agctaaatta aaatacaaaa atttaaatct gacatttaat | 3841 |
| tgttttataa taatccaaac tctatgaaag caatttttaaa aattattaag gttttatgaa | 3901 |
| gttgacaaaa tctaactata tttggtgcat cacaatggac acagaatgct gctgctcctc | 3961 |
| ttaaaaatta aatgtgtcat attatattct ttaaacttac tgttttacaa aattgagctc | 4021 |
| atcgtaaatg tctagtcttc tcacatagag attaaccaac aaacttgtgt ggctgacttt | 4081 |
| tgtgtaagaa tcatagtttg ctttagaata caaatcttta agtcatttta acttttttttt | 4141 |
| ctgccttacg atataaaaat atttatctta gaatttgaga tgttcatagc atgttttatt | 4201 |
| acattgaaga aactaaaaca taaatgaaaa gaaacactag gttcctgcac tttttggtaa | 4261 |
| ctttatgtct agcaaatatt ttatgccaag aaaagcatac tataaagcaa atatctatta | 4321 |
| ttctcctaaa cgaatgccta gcatagagaa aatacttaat acacatttgt tgacttaaat | 4381 |
| ttaattcaag gattgaaaaa ttaactggat atcttgaaat atacagtaat gattgtcctt | 4441 |
| agactcttga actttaccat ctttcctatt catatatcta tatagtaaat ttcactagaa | 4501 |
| aaattctttt aaaattgaca gaagataatt tatacctttt atggactctg aagcacttc | 4561 |
| aaaacattaa aagtccttat gtctttggta atgaaacata cactcaatga ngatgtatta | 4621 |
| aattttgact t | 4632 |

<210> SEQ ID NO 24
<211> LENGTH: 1118
<212> TYPE: PRT
<213> ORGANISM: Homo Sapiens

<400> SEQUENCE: 24

Met Val Asp Leu Glu Ser Glu Val Pro Pro Leu Pro Pro Arg Tyr Arg
1               5                   10                  15

Phe Arg Asp Leu Leu Leu Gly Asp Gln Gly Trp Gln Asn Asp Asp Arg
            20                  25                  30

Val Gln Val Glu Phe Tyr Met Asn Glu Asn Thr Phe Lys Glu Arg Leu
        35                  40                  45

Lys Leu Phe Phe Ile Lys Asn Gln Arg Ser Ser Leu Arg Ile Arg Leu
    50                  55                  60

Phe Asn Phe Ser Leu Lys Leu Leu Ser Cys Leu Leu Tyr Ile Ile Arg
65                  70                  75                  80

-continued

```
Val Leu Leu Glu Asn Pro Ser Gln Gly Asn Glu Trp Ser His Ile Phe
             85                  90                  95

Trp Val Asn Arg Ser Leu Pro Leu Trp Gly Leu Gln Val Ser Val Ala
            100                 105                 110

Leu Ile Ser Leu Phe Glu Thr Ile Leu Leu Gly Tyr Leu Ser Tyr Lys
            115                 120                 125

Gly Asn Ile Trp Glu Gln Ile Leu Arg Ile Pro Phe Ile Leu Glu Ile
            130                 135                 140

Ile Asn Ala Val Pro Phe Ile Ser Ile Phe Trp Pro Ser Leu Arg
145                 150                 155                 160

Asn Leu Phe Val Pro Val Phe Leu Asn Cys Trp Leu Ala Lys His Ala
                165                 170                 175

Leu Glu Asn Met Ile Asn Asp Leu His Arg Ala Ile Gln Arg Thr Gln
            180                 185                 190

Ser Ala Met Phe Asn Gln Val Leu Ile Leu Ile Ser Thr Leu Leu Cys
            195                 200                 205

Leu Ile Phe Thr Cys Ile Cys Gly Ile Gln His Leu Glu Arg Ile Gly
        210                 215                 220

Lys Arg Leu Asn Leu Phe Asp Ser Leu Tyr Phe Cys Ile Val Thr Phe
225                 230                 235                 240

Ser Thr Val Gly Phe Gly Asp Val Thr Pro Glu Thr Trp Ser Ser Lys
                245                 250                 255

Leu Phe Val Val Ala Met Ile Cys Val Ala Leu Val Val Leu Pro Ile
            260                 265                 270

Gln Phe Glu Gln Leu Ala Tyr Leu Trp Met Glu Arg Gln Lys Ser Gly
        275                 280                 285

Gly Asn Tyr Ser Arg His Arg Ala Gln Thr Glu Lys His Val Val Leu
        290                 295                 300

Cys Val Ser Ser Leu Lys Ile Asp Leu Leu Met Asp Phe Leu Asn Glu
305                 310                 315                 320

Phe Tyr Ala His Pro Arg Leu Gln Asp Tyr Tyr Val Val Ile Leu Cys
                325                 330                 335

Pro Thr Glu Met Asp Val Gln Val Arg Arg Val Leu Gln Ile Pro Met
            340                 345                 350

Trp Ser Gln Arg Val Ile Tyr Leu Gln Gly Ser Ala Leu Lys Asp Gln
        355                 360                 365

Asp Leu Leu Arg Ala Lys Met Asp Asp Ala Glu Ala Cys Phe Ile Leu
370                 375                 380

Ser Ser Arg Cys Glu Val Asp Arg Thr Ser Ser Asp His Gln Thr Ile
385                 390                 395                 400

Leu Arg Ala Trp Ala Val Lys Asp Phe Ala Pro Asn Cys Pro Leu Tyr
                405                 410                 415

Val Gln Ile Leu Lys Pro Glu Asn Lys Phe His Ile Lys Phe Ala Asp
            420                 425                 430

His Val Val Cys Glu Glu Glu Phe Lys Tyr Ala Met Leu Ala Leu Asn
            435                 440                 445

Cys Ile Cys Pro Ala Thr Ser Thr Leu Ile Thr Leu Leu Val His Thr
450                 455                 460

Ser Arg Gly Gln Glu Gly Gln Gln Ser Pro Glu Gln Trp Gln Lys Met
465                 470                 475                 480

Tyr Gly Arg Cys Ser Gly Asn Glu Val Tyr His Ile Val Leu Glu Glu
                485                 490                 495

Ser Thr Phe Phe Ala Glu Tyr Glu Gly Lys Ser Phe Thr Tyr Ala Ser
```

```
                500             505             510
Phe His Ala His Lys Phe Gly Val Cys Leu Ile Gly Val Arg Arg
        515                 520                 525

Glu Asp Asn Lys Asn Ile Leu Leu Asn Pro Gly Pro Arg Tyr Ile Met
    530                 535                 540

Asn Ser Thr Asp Ile Cys Phe Tyr Ile Asn Ile Thr Lys Glu Glu Asn
545                 550                 555                 560

Ser Ala Phe Lys Asn Gln Asp Gln Gln Arg Lys Ser Asn Val Ser Arg
                565                 570                 575

Ser Phe Tyr His Gly Pro Ser Arg Leu Pro Val His Ser Ile Ile Ala
            580                 585                 590

Ser Met Gly Thr Val Ala Ile Asp Leu Gln Asp Thr Ser Cys Arg Ser
            595                 600                 605

Ala Ser Gly Pro Thr Leu Ser Leu Pro Thr Glu Gly Ser Lys Glu Ile
        610                 615                 620

Arg Arg Pro Ser Ile Ala Pro Val Leu Glu Val Ala Asp Thr Ser Ser
625                 630                 635                 640

Ile Gln Thr Cys Asp Leu Leu Ser Asp Gln Ser Glu Asp Glu Thr Thr
                645                 650                 655

Pro Asp Glu Glu Met Ser Ser Asn Leu Glu Tyr Ala Lys Gly Tyr Pro
            660                 665                 670

Pro Tyr Ser Pro Tyr Ile Gly Ser Ser Pro Thr Phe Cys His Leu Leu
            675                 680                 685

His Glu Lys Val Pro Phe Cys Cys Leu Arg Leu Asp Lys Ser Cys Gln
        690                 695                 700

His Asn Tyr Tyr Glu Asp Ala Lys Ala Tyr Gly Phe Lys Asn Lys Leu
705                 710                 715                 720

Ile Ile Val Ala Ala Glu Thr Ala Gly Asn Gly Leu Tyr Asn Phe Ile
                725                 730                 735

Val Pro Leu Arg Ala Tyr Tyr Arg Pro Lys Lys Glu Leu Asn Pro Ile
            740                 745                 750

Val Leu Leu Leu Asp Asn Pro Leu Asp Asp Leu Leu Arg Cys Gly Val
            755                 760                 765

Thr Phe Ala Ala Asn Met Val Val Asp Lys Glu Ser Thr Met Ser
770                 775                 780

Ala Glu Glu Asp Tyr Met Ala Asp Ala Lys Thr Ile Val Asn Val Gln
785                 790                 795                 800

Thr Leu Phe Arg Leu Phe Ser Ser Leu Ser Ile Ile Thr Glu Leu Thr
            805                 810                 815

His Pro Ala Asn Met Arg Phe Met Gln Phe Arg Ala Lys Asp Cys Tyr
            820                 825                 830

Ser Leu Ala Leu Ser Lys Leu Glu Lys Lys Glu Arg Glu Arg Gly Ser
            835                 840                 845

Asn Leu Ala Phe Met Phe Arg Leu Pro Phe Ala Ala Gly Arg Val Phe
            850                 855                 860

Ser Ile Ser Met Leu Asp Thr Leu Leu Tyr Gln Ser Phe Val Lys Asp
865                 870                 875                 880

Tyr Met Ile Ser Ile Thr Arg Leu Leu Leu Gly Leu Asp Thr Thr Pro
                885                 890                 895

Gly Ser Gly Phe Leu Cys Ser Met Lys Ile Thr Ala Asp Asp Leu Trp
            900                 905                 910

Ile Arg Thr Tyr Ala Arg Leu Tyr Gln Lys Leu Cys Ser Ser Thr Gly
            915                 920                 925
```

```
Asp Val Pro Ile Gly Ile Tyr Arg Thr Glu Ser Gln Lys Leu Thr Thr
    930             935                 940

Ser Glu Ser Arg Lys Ile Ala Ser Gln Ser Gln Ile Ser Ile Ser Val
945                 950                 955                 960

Glu Glu Trp Glu Asp Thr Lys Asp Ser Lys Glu Gln Gly His His Arg
                965                 970                 975

Ser Asn His Arg Asn Ser Thr Ser Ser Asp Gln Ser Asp His Pro Leu
            980                 985                 990

Leu Arg Arg Lys Ser Met Gln Trp Ala Arg Arg Leu Ser Arg Lys Gly
        995                 1000                1005

Pro Lys His Ser Gly Lys Thr Ala Glu Lys Ile Thr Gln Gln Arg Leu
    1010                1015                1020

Asn Leu Tyr Arg Arg Ser Glu Arg Gln Glu Leu Ala Glu Leu Val Lys
1025                1030                1035                1040

Asn Arg Met Lys His Leu Gly Leu Ser Thr Val Gly Tyr Asp Glu Met
                1045                1050                1055

Asn Asp His Gln Ser Thr Leu Ser Tyr Ile Leu Ile Asn Pro Ser Pro
            1060                1065                1070

Asp Thr Arg Ile Glu Leu Asn Asp Val Val Tyr Leu Ile Arg Pro Asp
        1075                1080                1085

Pro Leu Ala Tyr Leu Pro Asn Ser Glu Pro Ser Arg Arg Asn Ser Ile
    1090                1095                1100

Cys Asn Val Thr Gly Gln Asp Ser Arg Glu Glu Thr Gln Leu
1105                1110                1115

<210> SEQ ID NO 25
<211> LENGTH: 4454
<212> TYPE: DNA
<213> ORGANISM: Homo Sapiens
<220> FEATURE:
<221> NAME/KEY: CDS
<222> LOCATION: (276)...(2558)

<400> SEQUENCE: 25
ggccaggcaa gctgcacaca tcaagcgaaa cgcctgaggg gcggccagcg cgagggtttc      60
tggccatcga ccctcacctc ccgggacttc cagggtcttc cccccacccc gcgcacacct    120
ccctgcctcg ccccgagggc gtcacgtggc agcgtggggc ccgcctcctg gtgatgtcac    180
ggcgctcgca gccgtcgcgc tgaagaaagg atgctcgagg atgctgtcca ggtgggcggc    240
cgcgggcgcg atgcggcact gcaggtgtaa ttagc atg gtc aat gcg gga gcg      293
                                      Met Val Asn Ala Gly Ala
                                        1               5 atg agt ggc tct gga aac ctg atg gat ttc ctc gat gag ccg ttc cct      341
Met Ser Gly Ser Gly Asn Leu Met Asp Phe Leu Asp Glu Pro Phe Pro
            10                  15                  20 gat gtg ggg acg tat gag gac ttc cac acc atc gac tgg cta agg gaa      389
Asp Val Gly Thr Tyr Glu Asp Phe His Thr Ile Asp Trp Leu Arg Glu
        25                  30                  35 aag tca cgg gac acc gac aga cac agg aag atc acc agc aag agc aag      437
Lys Ser Arg Asp Thr Asp Arg His Arg Lys Ile Thr Ser Lys Ser Lys
    40                  45                  50 gag tcc ata tgg gag ttc atc aag agc ctg ctg gat gcc tgg tcg gga      485
Glu Ser Ile Trp Glu Phe Ile Lys Ser Leu Leu Asp Ala Trp Ser Gly
55                  60                  65                  70 tgg gtg gtg atg ctg ctc atc ggc ctg ctg gcg ggc acc ttg gct ggg      533
Trp Val Val Met Leu Leu Ile Gly Leu Leu Ala Gly Thr Leu Ala Gly
                75                  80                  85
```

-continued

| | |
|---|---|
| gtc atc gat ctc gcc gtg gac tgg atg acg gac ctg aag gag ggg gtc<br>Val Ile Asp Leu Ala Val Asp Trp Met Thr Asp Leu Lys Glu Gly Val<br>          90                      95                        100 | 581 |
| tgc ctg tct gcc ttc tgg tat agc cat gag cag tgt tgc tgg act tct<br>Cys Leu Ser Ala Phe Trp Tyr Ser His Glu Gln Cys Cys Trp Thr Ser<br>          105                    110                    115 | 629 |
| aac gag acc act ttt gag gac aga gac aag tgt ccc ctg tgg cag aaa<br>Asn Glu Thr Thr Phe Glu Asp Arg Asp Lys Cys Pro Leu Trp Gln Lys<br>120                        125                    130 | 677 |
| tgg tcg gag ctg ctg gtg aat cag tca gag ggt gcc agt gct tac att<br>Trp Ser Glu Leu Leu Val Asn Gln Ser Glu Gly Ala Ser Ala Tyr Ile<br>135                        140                    145                    150 | 725 |
| ctg aat tac tta atg tac atc cta tgg gcg ctg ctg ttt gca ttt ttg<br>Leu Asn Tyr Leu Met Tyr Ile Leu Trp Ala Leu Leu Phe Ala Phe Leu<br>                        155                    160                    165 | 773 |
| gct gtc tcc ctg gtg cgt gta ttt gca cca tat gcc tgt ggc tct ggc<br>Ala Val Ser Leu Val Arg Val Phe Ala Pro Tyr Ala Cys Gly Ser Gly<br>          170                    175                    180 | 821 |
| ata cca gag ata aag acc att ttg agc ggc ttt atc atc agg ggc tac<br>Ile Pro Glu Ile Lys Thr Ile Leu Ser Gly Phe Ile Ile Arg Gly Tyr<br>                    185                    190                    195 | 869 |
| ttg ggg aag tgg acc ctg cta atc aag aca gtc acg ctg gtg ctg gta<br>Leu Gly Lys Trp Thr Leu Leu Ile Lys Thr Val Thr Leu Val Leu Val<br>200                        205                    210 | 917 |
| gtg tcc tcc ggt ctg agc ctt ggg aag gaa ggg ccg cta gtg cac gtg<br>Val Ser Ser Gly Leu Ser Leu Gly Lys Glu Gly Pro Leu Val His Val<br>215                        220                    225                    230 | 965 |
| gct tgt tgc tgt ggc aac ttc ttc agc agc ctt ttc tcc aag tac agc<br>Ala Cys Cys Cys Gly Asn Phe Phe Ser Ser Leu Phe Ser Lys Tyr Ser<br>                        235                    240                    245 | 1013 |
| aag aat gag ggc aag agg cgg gag gtg ctt tca gct gca gcg gct gct<br>Lys Asn Glu Gly Lys Arg Arg Glu Val Leu Ser Ala Ala Ala Ala Ala<br>                    250                    255                    260 | 1061 |
| gga gtc tct gtt gcc ttt ggt gca cca att gga ggc gtg ctt ttc agt<br>Gly Val Ser Val Ala Phe Gly Ala Pro Ile Gly Gly Val Leu Phe Ser<br>          265                    270                    275 | 1109 |
| cta gaa gag gtc agt tac tac ttt ccc ctg aag acc ttg tgg agg tca<br>Leu Glu Glu Val Ser Tyr Tyr Phe Pro Leu Lys Thr Leu Trp Arg Ser<br>280                        285                    290 | 1157 |
| ttt ttc gca gcc ctg gtg gcg gcc ttt acg ctg aga tcc atc aat ccc<br>Phe Phe Ala Ala Leu Val Ala Ala Phe Thr Leu Arg Ser Ile Asn Pro<br>295                        300                    305                    310 | 1205 |
| ttt ggg aat agc cgt ctc gtt ctc ttt tat gtg gaa tac cac acg ccc<br>Phe Gly Asn Ser Arg Leu Val Leu Phe Tyr Val Glu Tyr His Thr Pro<br>                    315                    320                    325 | 1253 |
| tgg tac atg gct gaa ctc ttc ccc ttc atc ctg ctt ggg gtc ttc ggg<br>Trp Tyr Met Ala Glu Leu Phe Pro Phe Ile Leu Leu Gly Val Phe Gly<br>                    330                    335                    340 | 1301 |
| ggc ttg tgg gga acc ctc ttc atc cgc tgc aac atc gcc tgg tgc agg<br>Gly Leu Trp Gly Thr Leu Phe Ile Arg Cys Asn Ile Ala Trp Cys Arg<br>          345                    350                    355 | 1349 |
| agg cgc aag acc acc agg ctg ggg aag tac ccg gtg ctg gag gtc att<br>Arg Arg Lys Thr Thr Arg Leu Gly Lys Tyr Pro Val Leu Glu Val Ile<br>360                        365                    370 | 1397 |
| gtg gtg act gcc atc act gcc atc att gcc tac ccc aat ccc tac aca<br>Val Val Thr Ala Ile Thr Ala Ile Ile Ala Tyr Pro Asn Pro Tyr Thr<br>375                        380                    385                    390 | 1445 |
| cgc cag agc acc agc gag ctc att tct gag ctg ttc aat gac tgt gga<br>Arg Gln Ser Thr Ser Glu Leu Ile Ser Glu Leu Phe Asn Asp Cys Gly | 1493 |

-continued

```
                395                 400                 405
gcc ctt gag tct tcc cag ctc tgt gac tac atc aat gac ccc aac atg    1541
Ala Leu Glu Ser Ser Gln Leu Cys Asp Tyr Ile Asn Asp Pro Asn Met
            410                 415                 420 act cgg cct gtg gat gac att cca gac cgg ccg gct ggt gtc ggt gtt    1589
Thr Arg Pro Val Asp Asp Ile Pro Asp Arg Pro Ala Gly Val Gly Val
        425                 430                 435 tac acg gcc atg tgg cag ctg gcc ctg gca ctg atc ttc aaa atc gtc    1637
Tyr Thr Ala Met Trp Gln Leu Ala Leu Ala Leu Ile Phe Lys Ile Val
    440                 445                 450 gtt acc ata ttt acc ttt ggc atg aag atc ccg tcg ggc ctc ttc atc    1685
Val Thr Ile Phe Thr Phe Gly Met Lys Ile Pro Ser Gly Leu Phe Ile
455                 460                 465                 470 ccc agc atg gct gtg ggc gcg ata gcg ggc agg atg gtg gga att ggc    1733
Pro Ser Met Ala Val Gly Ala Ile Ala Gly Arg Met Val Gly Ile Gly
                475                 480                 485 gtg gag cag ctg gcc tac cat cac cat gac tgg atc atc ttc agg aac    1781
Val Glu Gln Leu Ala Tyr His His His Asp Trp Ile Ile Phe Arg Asn
            490                 495                 500 tgg tgc aga ccc ggt gca gac tgt gtc acg cca ggg ctg tac gca atg    1829
Trp Cys Arg Pro Gly Ala Asp Cys Val Thr Pro Gly Leu Tyr Ala Met
        505                 510                 515 gtg gga gct gcg gcc tgc ctc ggt gga gtt acc agg atg acg gtg tca    1877
Val Gly Ala Ala Ala Cys Leu Gly Gly Val Thr Arg Met Thr Val Ser
    520                 525                 530 ttg gtg gtc atc atg ttt gaa tta acc ggg ggt ctg gag tac atc gtg    1925
Leu Val Val Ile Met Phe Glu Leu Thr Gly Gly Leu Glu Tyr Ile Val
535                 540                 545                 550 ccc ctg atg gcg gcg gct gtg acc agc aag tgg gta gct gat gca ttt    1973
Pro Leu Met Ala Ala Ala Val Thr Ser Lys Trp Val Ala Asp Ala Phe
                555                 560                 565 ggg aaa gaa ggc atc tac gag gcc cac atc cac tta aat ggg tac cct    2021
Gly Lys Glu Gly Ile Tyr Glu Ala His Ile His Leu Asn Gly Tyr Pro
            570                 575                 580 ttc ctt gac gtg aag gac gag ttt act cac cgc aca ctg gcc acc gac    2069
Phe Leu Asp Val Lys Asp Glu Phe Thr His Arg Thr Leu Ala Thr Asp
        585                 590                 595 gtc atg cgg ccc cgg cgg gga gag ccg cca ctg tcg gtg ctc acc cag    2117
Val Met Arg Pro Arg Arg Gly Glu Pro Pro Leu Ser Val Leu Thr Gln
    600                 605                 610 gac agc atg act gtc gag gac gtg gag acg ctc atc aag gag acc gac    2165
Asp Ser Met Thr Val Glu Asp Val Glu Thr Leu Ile Lys Glu Thr Asp
615                 620                 625                 630 tac aac ggc ttc ccc gtg gtg gtc tcc aga gac tcc gag cgc ctc att    2213
Tyr Asn Gly Phe Pro Val Val Val Ser Arg Asp Ser Glu Arg Leu Ile
                635                 640                 645 gga ttt gcc cag agg agg gaa ctg att ctc gca ata aag aac gcc aga    2261
Gly Phe Ala Gln Arg Arg Glu Leu Ile Leu Ala Ile Lys Asn Ala Arg
            650                 655                 660 cag agg cag gag ggc att gtg agc aat tcc atc atg tac ttc acg gag    2309
Gln Arg Gln Glu Gly Ile Val Ser Asn Ser Ile Met Tyr Phe Thr Glu
        665                 670                 675 gaa ccc ccc gag ctg ccg gcc aac agc cca cat ccc ctg aag ctg cgg    2357
Glu Pro Pro Glu Leu Pro Ala Asn Ser Pro His Pro Leu Lys Leu Arg
    680                 685                 690 cgc atc ctg aac ctc agc ccg ttt aca gtg aca gac cac act ccg atg    2405
Arg Ile Leu Asn Leu Ser Pro Phe Thr Val Thr Asp His Thr Pro Met
695                 700                 705                 710 gaa acg gtg gtg gat atc ttc cgg aaa ctg ggg ctt cgg cag tgc ctg    2453
```

| | | |
|---|---|---|
| Glu Thr Val Val Asp Ile Phe Arg Lys Leu Gly Leu Arg Gln Cys Leu<br>715                 720                 725 | | |
| gtg acg cgg agc ggg aga ctt ctt ggc atc atc aca aaa aag gat gtt<br>Val Thr Arg Ser Gly Arg Leu Leu Gly Ile Ile Thr Lys Lys Asp Val<br>          730                 735                 740 | | 2501 |
| ctg aga cat atg gcc cag atg gca aac cag gac ccc gaa tcc atc atg<br>Leu Arg His Met Ala Gln Met Ala Asn Gln Asp Pro Glu Ser Ile Met<br>     745                 750                 755 | | 2549 |
| ttt aat tag caacaaggtg gcaattattt tcagaaaaac actgactgtg<br>Phe Asn *<br>     760 | | 2598 |
| tcatttaaaa agaaataaat gatatgttat tatcccaatg aaagatcatg cattggggac | | 2658 |
| agcagaaaca aaagcttttt tggaaaggcg gggaagaagg atgaaacctt taaaaacaaa | | 2718 |
| aacaaaaaca tcaatgagta ggcattttat agctttaacc ccgtatgagt ttcaagctgt | | 2778 |
| gtttcctaat gagtttgcta ctgctgtggg ggcatgtggg tgggtaaatg atgtaaatga | | 2838 |
| tgtgatctgt acaagtatgt ggagcatgaa tgctgactca agaaactttt actccttctg | | 2898 |
| ctcaaggctg atgtttgtaa cttatgaaca cacgtgaagt gttgagtcca aaagacaaag | | 2958 |
| gggcatcggc atgtcagcgt ccttatttat tggttcttga agttttgctg ctatgttact | | 3018 |
| gaatcatact aaagacattt gcgcttactt tgttgaaaaa gaaaaagaaa ttaaatttga | | 3078 |
| acacagtgaa agctgcaagt atgccagtgg gtccgctcac gaccgtcctg tttcttgctc | | 3138 |
| ctgttctcag cctgttatct ggcttatcca tcagtttctg aaccaacatc aggggcacct | | 3198 |
| gccatgatga gtgtgaagaa atcatttctc tatgcaagac tggcatcctg ggactgcacg | | 3258 |
| atgaactatt ggagcataca gtactgcggt gtgtctcctc ccatacaaag ggacacatcc | | 3318 |
| ttattttgag ggtatactca cccgatcatt gatttgcatc cccatggcat ttgcttcatt | | 3378 |
| tatttattgc ttttgcccat gcattcaata ttgatcagct cagcacttcc atgggccata | | 3438 |
| gccggtatgc ccccagcctg ccataagcgt gctttcattt tcaagtagca tatgcaagag | | 3498 |
| tccaaacagg ctacccaatg ttactactta ttttttcctct caggtcttat cagatacggc | | 3558 |
| tgtggagagg atgaggcata tgcgttgtca gttggaatcc ctccaaatgg attgcaagag | | 3618 |
| aaatactaaa ttgattctaa atctgttcca ttatcttctc tgtaggatgc aaaacatcca | | 3678 |
| gttgtaatgt ataagcatgc acttcatact agcaatcaca gcacaggagg acagcattaa | | 3738 |
| attttatata gccaatttgg gcactgggca tctttgtatt tgaacttaac gacacattta | | 3798 |
| ctcttttagt caggatttcg gtcttttctg cgggaaggaa ttaagctatg tattaggtcc | | 3858 |
| accatacgat ctgtgtaagt aagattatcc cacttgccct ttctctttag tctttgtccc | | 3918 |
| ttccttttca ctaagtgccc ctcatccttt tcaatctcat tgtcactgga tagtgctgta | | 3978 |
| tcacttaggt gtgcattcgg ctgcaaataa cagaaaaccc agcaaacact gaagggctgg | | 4038 |
| ataagaaccc tgagaggggg tactccagga ctgtctccat aacatcattg ggatccccat | | 4098 |
| cccgttgcta tttctttttc accgttttta ccttttgtcc tctggcttat tgcctcagag | | 4158 |
| ttgcaagatg gttcctgaac tgtcaggtat catgtctgct ttctaagtgg aagaggaag | | 4218 |
| ggagaggcaa gcaactaggt acaatgtcta tcaggaaagc aaagcttccc cagagacgct | | 4278 |
| cagcttgtat ccattgactg gaagtctgtc acgtggctcc ccctagccgc acactagtgt | | 4338 |
| gggaaggaaa atattgagct aggcacatta ctctctgaac gaaattcata ttatcttatt | | 4398 |
| aaggaagagt gttggtcttc aggaggggaa gtttgctgta ttggatgcca tcatcg | | 4454 |

<210> SEQ ID NO 26

-continued

```
<211> LENGTH: 760
<212> TYPE: PRT
<213> ORGANISM: Homo Sapiens

<400> SEQUENCE: 26

Met Val Asn Ala Gly Ala Met Ser Gly Ser Gly Asn Leu Met Asp Phe
1               5                   10                  15

Leu Asp Glu Pro Phe Pro Asp Val Gly Thr Tyr Glu Asp Phe His Thr
            20                  25                  30

Ile Asp Trp Leu Arg Glu Lys Ser Arg Asp Thr Asp Arg His Arg Lys
        35                  40                  45

Ile Thr Ser Lys Ser Lys Glu Ser Ile Trp Glu Phe Ile Lys Ser Leu
    50                  55                  60

Leu Asp Ala Trp Ser Gly Trp Val Val Met Leu Leu Ile Gly Leu Leu
65                  70                  75                  80

Ala Gly Thr Leu Ala Gly Val Ile Asp Leu Ala Val Asp Trp Met Thr
                85                  90                  95

Asp Leu Lys Glu Gly Val Cys Leu Ser Ala Phe Trp Tyr Ser His Glu
            100                 105                 110

Gln Cys Cys Trp Thr Ser Asn Glu Thr Thr Phe Glu Asp Arg Asp Lys
        115                 120                 125

Cys Pro Leu Trp Gln Lys Trp Ser Glu Leu Leu Val Asn Gln Ser Glu
    130                 135                 140

Gly Ala Ser Ala Tyr Ile Leu Asn Tyr Leu Met Tyr Ile Leu Trp Ala
145                 150                 155                 160

Leu Leu Phe Ala Phe Leu Ala Val Ser Leu Val Arg Val Phe Ala Pro
                165                 170                 175

Tyr Ala Cys Gly Ser Gly Ile Pro Glu Ile Lys Thr Ile Leu Ser Gly
            180                 185                 190

Phe Ile Ile Arg Gly Tyr Leu Gly Lys Trp Thr Leu Leu Ile Lys Thr
        195                 200                 205

Val Thr Leu Val Leu Val Val Ser Ser Gly Leu Ser Leu Gly Lys Glu
    210                 215                 220

Gly Pro Leu Val His Val Ala Cys Cys Cys Gly Asn Phe Phe Ser Ser
225                 230                 235                 240

Leu Phe Ser Lys Tyr Ser Lys Asn Glu Gly Lys Arg Arg Glu Val Leu
                245                 250                 255

Ser Ala Ala Ala Ala Gly Val Ser Val Ala Phe Gly Ala Pro Ile
            260                 265                 270

Gly Gly Val Leu Phe Ser Leu Glu Glu Val Ser Tyr Tyr Phe Pro Leu
        275                 280                 285

Lys Thr Leu Trp Arg Ser Phe Phe Ala Ala Leu Val Ala Ala Phe Thr
    290                 295                 300

Leu Arg Ser Ile Asn Pro Phe Gly Asn Ser Arg Leu Val Leu Phe Tyr
305                 310                 315                 320

Val Glu Tyr His Thr Pro Trp Tyr Met Ala Glu Leu Phe Pro Phe Ile
                325                 330                 335

Leu Leu Gly Val Phe Gly Gly Leu Trp Gly Thr Leu Phe Ile Arg Cys
            340                 345                 350

Asn Ile Ala Trp Cys Arg Arg Arg Lys Thr Thr Arg Leu Gly Lys Tyr
        355                 360                 365

Pro Val Leu Glu Val Ile Val Val Thr Ala Ile Thr Ala Ile Ile Ala
    370                 375                 380

Tyr Pro Asn Pro Tyr Thr Arg Gln Ser Thr Ser Glu Leu Ile Ser Glu
```

```
            385                 390                 395                 400
Leu Phe Asn Asp Cys Gly Ala Leu Glu Ser Ser Gln Leu Cys Asp Tyr
                405                 410                 415
Ile Asn Asp Pro Asn Met Thr Arg Pro Val Asp Ile Pro Asp Arg
            420                 425                 430
Pro Ala Gly Val Gly Val Tyr Thr Ala Met Trp Gln Leu Ala Leu Ala
            435                 440                 445
Leu Ile Phe Lys Ile Val Val Thr Ile Phe Thr Phe Gly Met Lys Ile
        450                 455                 460
Pro Ser Gly Leu Phe Ile Pro Ser Met Ala Val Gly Ala Ile Ala Gly
465                 470                 475                 480
Arg Met Val Gly Ile Gly Val Glu Gln Leu Ala Tyr His His His Asp
                485                 490                 495
Trp Ile Ile Phe Arg Asn Trp Cys Arg Pro Gly Ala Asp Cys Val Thr
            500                 505                 510
Pro Gly Leu Tyr Ala Met Val Gly Ala Ala Ala Cys Leu Gly Gly Val
            515                 520                 525
Thr Arg Met Thr Val Ser Leu Val Val Ile Met Phe Glu Leu Thr Gly
        530                 535                 540
Gly Leu Glu Tyr Ile Val Pro Leu Met Ala Ala Ala Val Thr Ser Lys
545                 550                 555                 560
Trp Val Ala Asp Ala Phe Gly Lys Glu Gly Ile Tyr Glu Ala His Ile
                565                 570                 575
His Leu Asn Gly Tyr Pro Phe Leu Asp Val Lys Asp Glu Phe Thr His
            580                 585                 590
Arg Thr Leu Ala Thr Asp Val Met Arg Pro Arg Arg Gly Glu Pro Pro
            595                 600                 605
Leu Ser Val Leu Thr Gln Asp Ser Met Thr Val Glu Asp Val Glu Thr
        610                 615                 620
Leu Ile Lys Glu Thr Asp Tyr Asn Gly Phe Pro Val Val Val Ser Arg
625                 630                 635                 640
Asp Ser Glu Arg Leu Ile Gly Phe Ala Gln Arg Arg Glu Leu Ile Leu
                645                 650                 655
Ala Ile Lys Asn Ala Arg Gln Arg Gln Glu Gly Ile Val Ser Asn Ser
            660                 665                 670
Ile Met Tyr Phe Thr Glu Glu Pro Glu Leu Pro Ala Asn Ser Pro
            675                 680                 685
His Pro Leu Lys Leu Arg Arg Ile Leu Asn Leu Ser Pro Phe Thr Val
        690                 695                 700
Thr Asp His Thr Pro Met Glu Thr Val Val Asp Ile Phe Arg Lys Leu
705                 710                 715                 720
Gly Leu Arg Gln Cys Leu Val Thr Arg Ser Gly Arg Leu Leu Gly Ile
                725                 730                 735
Ile Thr Lys Lys Asp Val Leu Arg His Met Ala Gln Met Ala Asn Gln
            740                 745                 750
Asp Pro Glu Ser Ile Met Phe Asn
            755                 760

<210> SEQ ID NO 27
<211> LENGTH: 1284
<212> TYPE: DNA
<213> ORGANISM: Homo Sapiens
<220> FEATURE:
<221> NAME/KEY: CDS
<222> LOCATION: (1)...(1284)
```

<400> SEQUENCE: 27

```
atg ggc ggg gat ctg gtg ctt ggc ctg ggg gcc ttg aga cgc cga aag        48
Met Gly Gly Asp Leu Val Leu Gly Leu Gly Ala Leu Arg Arg Arg Lys
 1               5                  10                  15 cgc ttg ctg gag cag gag aag tct ctg gcc ggc tgg gca ctg gtg ctg        96
Arg Leu Leu Glu Gln Glu Lys Ser Leu Ala Gly Trp Ala Leu Val Leu
                20                  25                  30 gca gga act ggc att gga ctc atg gtg ctg cat gca gag atg ctg tgg       144
Ala Gly Thr Gly Ile Gly Leu Met Val Leu His Ala Glu Met Leu Trp
            35                  40                  45 ttc ggg ggg tgc tcg tgg gcg ctc tac ctg ttc ctg gtt aaa tgc acg       192
Phe Gly Gly Cys Ser Trp Ala Leu Tyr Leu Phe Leu Val Lys Cys Thr
        50                  55                  60 atc agc att tcc acc ttc tta ctc ctc tgc ctc atc gtg gcc ttt cat       240
Ile Ser Ile Ser Thr Phe Leu Leu Leu Cys Leu Ile Val Ala Phe His
 65                  70                  75                  80 gcc aaa gag gtc cag ctg ttc atg acc gac aac ggg ctg cgg gac tgg       288
Ala Lys Glu Val Gln Leu Phe Met Thr Asp Asn Gly Leu Arg Asp Trp
                85                  90                  95 cgc gtg gcg ctg acc ggg cgg cag gcg gcg cag atc gtg ctg gag ctg       336
Arg Val Ala Leu Thr Gly Arg Gln Ala Ala Gln Ile Val Leu Glu Leu
               100                 105                 110 gtg gtg tgt ggg ctg cac ccg gcg ccc gtg cgg ggc ccg ccg tgc gtg       384
Val Val Cys Gly Leu His Pro Ala Pro Val Arg Gly Pro Pro Cys Val
            115                 120                 125 cag gat tta ggg gcg ccg ctg acc tcc ccg cag ccc tgg ccg gga ttc       432
Gln Asp Leu Gly Ala Pro Leu Thr Ser Pro Gln Pro Trp Pro Gly Phe
        130                 135                 140 ctg ggc caa ggg gaa gcg ctg ctg tcc ctg gcc atg ctg ctg cgt ctc       480
Leu Gly Gln Gly Glu Ala Leu Leu Ser Leu Ala Met Leu Leu Arg Leu
145                 150                 155                 160 tac ctg gtg ccc cgc gcc gtg ctc ctg cgc agc ggc gtc ctg ctc aac       528
Tyr Leu Val Pro Arg Ala Val Leu Leu Arg Ser Gly Val Leu Leu Asn
                165                 170                 175 gct tcc tac cgc agc atc ggc gct ctc aat caa gtc cgc ttc cgc cac       576
Ala Ser Tyr Arg Ser Ile Gly Ala Leu Asn Gln Val Arg Phe Arg His
            180                 185                 190 tgg ttc gtg gcc aag ctt tac atg aac acg cac cct ggc cgc ctg ctg       624
Trp Phe Val Ala Lys Leu Tyr Met Asn Thr His Pro Gly Arg Leu Leu
        195                 200                 205 ctc ggc ctc acg ctt ggc ctc tgg ctg acc acc gcc tgg gtg ctg tcc       672
Leu Gly Leu Thr Leu Gly Leu Trp Leu Thr Thr Ala Trp Val Leu Ser
210                 215                 220 gtg gcc gag agg cag gct gtt aat gcc act ggg cac ctt tca gac aca       720
Val Ala Glu Arg Gln Ala Val Asn Ala Thr Gly His Leu Ser Asp Thr
225                 230                 235                 240 ctt tgg ctg atc ccc atc aca ttc ctg acc atc ggc tat ggt gac gtg       768
Leu Trp Leu Ile Pro Ile Thr Phe Leu Thr Ile Gly Tyr Gly Asp Val
                245                 250                 255 gtg ccg ggc acc atg tgg ggc aag atc gtc tgc ctg tgc act gga gtc       816
Val Pro Gly Thr Met Trp Gly Lys Ile Val Cys Leu Cys Thr Gly Val
            260                 265                 270 atg ggt gtc tgc tgc aca gcc ctg ctg gtg gcc gtg gtg gcc cgg aag       864
Met Gly Val Cys Cys Thr Ala Leu Leu Val Ala Val Val Ala Arg Lys
        275                 280                 285 ctg gag ttt aac aag gca gag aag cac gtg cac aac ttc atg atg gat       912
Leu Glu Phe Asn Lys Ala Glu Lys His Val His Asn Phe Met Met Asp
    290                 295                 300
```

-continued

```
atc cag tat acc aaa gag atg aag gag tcc gct gcc cga gtg cta caa    960
Ile Gln Tyr Thr Lys Glu Met Lys Glu Ser Ala Ala Arg Val Leu Gln
305                 310                 315                 320 gaa gcc tgg atg ttc tac aaa cat act cgc agg aag gag tct cat gct   1008
Glu Ala Trp Met Phe Tyr Lys His Thr Arg Arg Lys Glu Ser His Ala
            325                 330                 335 gcc cgc agg cat cag cgc aag ctg ctg gcc gcc atc aac gcg ttc cgc   1056
Ala Arg Arg His Gln Arg Lys Leu Leu Ala Ala Ile Asn Ala Phe Arg
        340                 345                 350 cag gtg cgg ctg aaa cac cgg aag ctc cgg gaa caa gtg aac tcc atg   1104
Gln Val Arg Leu Lys His Arg Lys Leu Arg Glu Gln Val Asn Ser Met
    355                 360                 365 gtg gac atc tcc aag atg cac atg atc ctg tat gac ctg cag cag aat   1152
Val Asp Ile Ser Lys Met His Met Ile Leu Tyr Asp Leu Gln Gln Asn
370                 375                 380 ctg agc agc tca cac cgg gcc ctg gag aaa cag att gac acg ctg gcg   1200
Leu Ser Ser Ser His Arg Ala Leu Glu Lys Gln Ile Asp Thr Leu Ala
385                 390                 395                 400 ggg aag ctg gat gcc ctg act gag ctg ctt agc act gcc ctg ggg ccg   1248
Gly Lys Leu Asp Ala Leu Thr Glu Leu Leu Ser Thr Ala Leu Gly Pro
            405                 410                 415 agg cag ctt cca gaa ccc agc cag cag tcc aag tag                    1284
Arg Gln Leu Pro Glu Pro Ser Gln Gln Ser Lys  *
        420                 425
```

<210> SEQ ID NO 28
<211> LENGTH: 427
<212> TYPE: PRT
<213> ORGANISM: Homo Sapiens

<400> SEQUENCE: 28

```
Met Gly Gly Asp Leu Val Gly Leu Gly Ala Leu Arg Arg Arg Lys
 1               5                  10                  15

Arg Leu Leu Glu Gln Glu Lys Ser Leu Ala Gly Trp Ala Leu Val Leu
            20                  25                  30

Ala Gly Thr Gly Ile Gly Leu Met Val Leu His Ala Glu Met Leu Trp
        35                  40                  45

Phe Gly Gly Cys Ser Trp Ala Leu Tyr Leu Phe Leu Val Lys Cys Thr
    50                  55                  60

Ile Ser Ile Ser Thr Phe Leu Leu Leu Cys Leu Ile Val Ala Phe His
65                  70                  75                  80

Ala Lys Glu Val Gln Leu Phe Met Thr Asp Asn Gly Leu Arg Asp Trp
                85                  90                  95

Arg Val Ala Leu Thr Gly Arg Gln Ala Ala Gln Ile Val Leu Glu Leu
            100                 105                 110

Val Val Cys Gly Leu His Pro Ala Pro Val Arg Gly Pro Cys Val
        115                 120                 125

Gln Asp Leu Gly Ala Pro Leu Thr Ser Pro Gln Pro Trp Pro Gly Phe
    130                 135                 140

Leu Gly Gln Gly Glu Ala Leu Leu Ser Leu Ala Met Leu Leu Arg Leu
145                 150                 155                 160

Tyr Leu Val Pro Arg Ala Val Leu Leu Arg Ser Gly Val Leu Leu Asn
                165                 170                 175

Ala Ser Tyr Arg Ser Ile Gly Ala Leu Asn Gln Val Arg Phe Arg His
            180                 185                 190

Trp Phe Val Ala Lys Leu Tyr Met Asn Thr His Pro Gly Arg Leu Leu
        195                 200                 205
```

```
Leu Gly Leu Thr Leu Gly Leu Trp Leu Thr Thr Ala Trp Val Leu Ser
    210                 215                 220

Val Ala Glu Arg Gln Ala Val Asn Ala Thr Gly His Leu Ser Asp Thr
225                 230                 235                 240

Leu Trp Leu Ile Pro Ile Thr Phe Leu Thr Ile Gly Tyr Gly Asp Val
                245                 250                 255

Val Pro Gly Thr Met Trp Gly Lys Ile Val Cys Leu Cys Thr Gly Val
            260                 265                 270

Met Gly Val Cys Cys Thr Ala Leu Leu Val Ala Val Ala Arg Lys
        275                 280                 285

Leu Glu Phe Asn Lys Ala Glu Lys His Val His Asn Phe Met Met Asp
    290                 295                 300

Ile Gln Tyr Thr Lys Glu Met Lys Glu Ser Ala Ala Arg Val Leu Gln
305                 310                 315                 320

Glu Ala Trp Met Phe Tyr Lys His Thr Arg Arg Lys Glu Ser His Ala
                325                 330                 335

Ala Arg Arg His Gln Arg Lys Leu Leu Ala Ala Ile Asn Ala Phe Arg
            340                 345                 350

Gln Val Arg Leu Lys His Arg Lys Leu Arg Glu Gln Val Asn Ser Met
        355                 360                 365

Val Asp Ile Ser Lys Met His Met Ile Leu Tyr Asp Leu Gln Gln Asn
370                 375                 380

Leu Ser Ser Ser His Arg Ala Leu Glu Lys Gln Ile Asp Thr Leu Ala
385                 390                 395                 400

Gly Lys Leu Asp Ala Leu Thr Glu Leu Leu Ser Thr Ala Leu Gly Pro
                405                 410                 415

Arg Gln Leu Pro Glu Pro Ser Gln Gln Ser Lys
            420                 425

<210> SEQ ID NO 29
<211> LENGTH: 2871
<212> TYPE: DNA
<213> ORGANISM: Homo Sapiens
<220> FEATURE:
<221> NAME/KEY: CDS
<222> LOCATION: (1)...(2871)

<400> SEQUENCE: 29 atg ccc cgc gtc tcg gcg cct ttg gtg ctg ctt cct gcg tgg ctc gtg      48
Met Pro Arg Val Ser Ala Pro Leu Val Leu Leu Pro Ala Trp Leu Val
1               5                   10                  15 atg gtc gcc tgc agc ccg cac tcc ttg agg atc gct gct atc ttg gac      96
Met Val Ala Cys Ser Pro His Ser Leu Arg Ile Ala Ala Ile Leu Asp
            20                  25                  30 gac ccc atg gag tgc agc aga ggg gag cgg ctc tcc atc acc ctg gcc     144
Asp Pro Met Glu Cys Ser Arg Gly Glu Arg Leu Ser Ile Thr Leu Ala
        35                  40                  45 aag aac cgc atc aac cgc gct cct gag agg ctg ggc aag gcc aag gtc     192
Lys Asn Arg Ile Asn Arg Ala Pro Glu Arg Leu Gly Lys Ala Lys Val
    50                  55                  60 gaa gtg gac atc ttt gag ctt ctc aga gac agc gag tac gag act gca     240
Glu Val Asp Ile Phe Glu Leu Leu Arg Asp Ser Glu Tyr Glu Thr Ala
65                  70                  75                  80 gaa acc atg tgt cag atc ctc ccc aag ggg gtg gtc gct gtc ctc gga     288
Glu Thr Met Cys Gln Ile Leu Pro Lys Gly Val Val Ala Val Leu Gly
                85                  90                  95 cca tcg tcc agc cca gcc tcc agc tcc atc atc agc aac atc tgt gga     336
Pro Ser Ser Ser Pro Ala Ser Ser Ser Ile Ile Ser Asn Ile Cys Gly
            100                 105                 110
```

-continued

```
            100                 105                 110
gag aag gag gtc cct cac ttc aaa gtg gcc cca gag gag ttc gtc aag     384
Glu Lys Glu Val Pro His Phe Lys Val Ala Pro Glu Glu Phe Val Lys
            115                 120                 125 ttc cag ttc cag aga ttc aca acc ctg aac ctc cac ccc agc aac act     432
Phe Gln Phe Gln Arg Phe Thr Thr Leu Asn Leu His Pro Ser Asn Thr
130                 135                 140 gac atc agc gtg gct gta gct ggg atc ctg aac ttc ttc aac tgc acc     480
Asp Ile Ser Val Ala Val Ala Gly Ile Leu Asn Phe Phe Asn Cys Thr
145                 150                 155                 160 acc gcc tgc ctc atc tgt gcc aaa gca gaa tgc ctt tta aac cta gag     528
Thr Ala Cys Leu Ile Cys Ala Lys Ala Glu Cys Leu Leu Asn Leu Glu
                165                 170                 175 aag ctg ctc cgg caa ttc ctt atc tcc aag gac acg ctg tcc gtc cgc     576
Lys Leu Leu Arg Gln Phe Leu Ile Ser Lys Asp Thr Leu Ser Val Arg
            180                 185                 190 atg ctg gat gac acc cgg gac ccc acc ccg ctc ctc aag gag atc cgg     624
Met Leu Asp Asp Thr Arg Asp Pro Thr Pro Leu Leu Lys Glu Ile Arg
        195                 200                 205 gac gac aag acc gcc acc atc atc atc cac gcc aac gcc tcc atg tcc     672
Asp Asp Lys Thr Ala Thr Ile Ile Ile His Ala Asn Ala Ser Met Ser
210                 215                 220 cac acc atc ctc ctg aag gca gcc gaa ctt ggg atg gtg tca gcc tat     720
His Thr Ile Leu Leu Lys Ala Ala Glu Leu Gly Met Val Ser Ala Tyr
225                 230                 235                 240 tac aca tac atc ttc act aat ctg gag ttc tca ctc cag aga acg gac     768
Tyr Thr Tyr Ile Phe Thr Asn Leu Glu Phe Ser Leu Gln Arg Thr Asp
                245                 250                 255 agc ctt gtg gat gat cgt gtc aac atc ctg gga ttt tcc att ttc aac     816
Ser Leu Val Asp Asp Arg Val Asn Ile Leu Gly Phe Ser Ile Phe Asn
            260                 265                 270 caa tcc cat gct ttc ttc caa gag ttt gcc cag agc ctc aac cag tcc     864
Gln Ser His Ala Phe Phe Gln Glu Phe Ala Gln Ser Leu Asn Gln Ser
        275                 280                 285 tgg cag gag aac tgt gac cat gtg ccc ttc act ggg cct gcg ctc tcc     912
Trp Gln Glu Asn Cys Asp His Val Pro Phe Thr Gly Pro Ala Leu Ser
290                 295                 300 tcg gcc ctg ctg ttt gat gct gtc tat gct gtg gtg act gcg gtg cag     960
Ser Ala Leu Leu Phe Asp Ala Val Tyr Ala Val Val Thr Ala Val Gln
305                 310                 315                 320 gaa ctg aac cgg agc caa gag atc ggc gtg aag ccc ttg tcc tgc ggc     1008
Glu Leu Asn Arg Ser Gln Glu Ile Gly Val Lys Pro Leu Ser Cys Gly
                325                 330                 335 tcg gcc cag atc tgg cag cac ggc acc agc ctc atg aac tac ctg cgc     1056
Ser Ala Gln Ile Trp Gln His Gly Thr Ser Leu Met Asn Tyr Leu Arg
            340                 345                 350 atg gta gaa ttg gaa ggt ctt acc ggc cac att gaa ttc aac agc aaa     1104
Met Val Glu Leu Glu Gly Leu Thr Gly His Ile Glu Phe Asn Ser Lys
        355                 360                 365 ggc cag agg tcc aac tac gct ttg aaa atc tta cag ttc aca agg aat     1152
Gly Gln Arg Ser Asn Tyr Ala Leu Lys Ile Leu Gln Phe Thr Arg Asn
370                 375                 380 ggt ttt cgg cag atc ggc cag tgg cac gtg gca gag ggc ctc agc atg     1200
Gly Phe Arg Gln Ile Gly Gln Trp His Val Ala Glu Gly Leu Ser Met
385                 390                 395                 400 gac agc cac ctc tat gcc tcc aac atc tcg gac act ctc ttc aac acc     1248
Asp Ser His Leu Tyr Ala Ser Asn Ile Ser Asp Thr Leu Phe Asn Thr
                405                 410                 415 acc ctg gtc gtc acc acc atc ctg gaa aac cca tat tta atg ctg aag     1296
```

-continued

| | | |
|---|---|---|
| Thr Leu Val Val Thr Thr Ile Leu Glu Asn Pro Tyr Leu Met Leu Lys<br>420                        425                     430 | | |
| ggg aac cac cag gag atg gaa ggc aat gac cgc tac gag ggc ttc tgt<br>Gly Asn His Gln Glu Met Glu Gly Asn Asp Arg Tyr Glu Gly Phe Cys<br>           435                    440                    445 | 1344 |
| gtg gac atg ctc aag gag ctg gca gag atc ctc cga ttc aac tac aag<br>Val Asp Met Leu Lys Glu Leu Ala Glu Ile Leu Arg Phe Asn Tyr Lys<br>450                        455                    460 | 1392 |
| atc cgc ctg gtt ggg gat ggc gtg tac ggc gtt ccc gag gcc aac ggc<br>Ile Arg Leu Val Gly Asp Gly Val Tyr Gly Val Pro Glu Ala Asn Gly<br>465                      470                    475                    480 | 1440 |
| acc tgg acg gga atg gtc ggg gag ctg atc gct agg aaa gca gat ctg<br>Thr Trp Thr Gly Met Val Gly Glu Leu Ile Ala Arg Lys Ala Asp Leu<br>                     485                    490                    495 | 1488 |
| gct gtg gca ggc ctc acc att aca gct gaa cgg gag aag gtg att gat<br>Ala Val Ala Gly Leu Thr Ile Thr Ala Glu Arg Glu Lys Val Ile Asp<br>500                        505                    510 | 1536 |
| ttc tct aag cca ttc atg act ctg gga att agc att ctt tac cgc att<br>Phe Ser Lys Pro Phe Met Thr Leu Gly Ile Ser Ile Leu Tyr Arg Ile<br>           515                    520                    525 | 1584 |
| cat atg gga cgc aaa ccc ggc tat ttc tcc ttc ctg gac cca ttt tct<br>His Met Gly Arg Lys Pro Gly Tyr Phe Ser Phe Leu Asp Pro Phe Ser<br>530                        535                    540 | 1632 |
| ccg ggc gtc tgg ctc ttc atg ctt cta gcc tat ctg gcc gtc agc tgt<br>Pro Gly Val Trp Leu Phe Met Leu Leu Ala Tyr Leu Ala Val Ser Cys<br>545                      550                    555                    560 | 1680 |
| gtc ctc ttc ctg gtg gct cgg ttg acg ccc tac gag tgg tac agc cca<br>Val Leu Phe Leu Val Ala Arg Leu Thr Pro Tyr Glu Trp Tyr Ser Pro<br>                   565                    570                    575 | 1728 |
| cac cca tgt gcc cag ggc cgg tgc aac ctc ctg gtg aac cag tac tcc<br>His Pro Cys Ala Gln Gly Arg Cys Asn Leu Leu Val Asn Gln Tyr Ser<br>               580                    585                    590 | 1776 |
| ctg ggc aac agc ctc tgg ttt ccg gtc ggg ggg ttc atg cag cag ggc<br>Leu Gly Asn Ser Leu Trp Phe Pro Val Gly Gly Phe Met Gln Gln Gly<br>           595                    600                    605 | 1824 |
| tcc acc atc gcc cct cgc gcc tta tcc acc cgc tgt gtc agt ggc gtc<br>Ser Thr Ile Ala Pro Arg Ala Leu Ser Thr Arg Cys Val Ser Gly Val<br>610                        615                    620 | 1872 |
| tgg tgg gca ttc acg ctg atc atc atc tca tcc tac acg gcc aac ctg<br>Trp Trp Ala Phe Thr Leu Ile Ile Ile Ser Ser Tyr Thr Ala Asn Leu<br>625                      630                    635                    640 | 1920 |
| gca gcc ttc ctg acc gtg cag cgc atg gat gtg ccc att gag tca gtg<br>Ala Ala Phe Leu Thr Val Gln Arg Met Asp Val Pro Ile Glu Ser Val<br>                   645                    650                    655 | 1968 |
| gat gac ctg gct gac cag acc gcc att gaa tat ggc aca att cac gga<br>Asp Asp Leu Ala Asp Gln Thr Ala Ile Glu Tyr Gly Thr Ile His Gly<br>               660                    665                    670 | 2016 |
| ggc tcc agc atg acc ttc ttc caa aat tcc cgc tac cag acc tac caa<br>Gly Ser Ser Met Thr Phe Phe Gln Asn Ser Arg Tyr Gln Thr Tyr Gln<br>           675                    680                    685 | 2064 |
| cgc atg tgg aat tac atg tat tcc aag cag ccc agc gtg ttc gtg aag<br>Arg Met Trp Asn Tyr Met Tyr Ser Lys Gln Pro Ser Val Phe Val Lys<br>690                        695                    700 | 2112 |
| agc aca gag gag gga atc gcc agg gtg ttg aat tcc aac tac gcc ttc<br>Ser Thr Glu Glu Gly Ile Ala Arg Val Leu Asn Ser Asn Tyr Ala Phe<br>705                        710                    715                    720 | 2160 |
| ctc ctg gaa tcc acc atg aac gag tac tat cgg cag cga aac tgc aac<br>Leu Leu Glu Ser Thr Met Asn Glu Tyr Tyr Arg Gln Arg Asn Cys Asn<br>                     725                    730                    735 | 2208 |

-continued

```
ctc act cag att ggg ggc ctg ctg gac acc aag ggc tat ggg att ggc    2256
Leu Thr Gln Ile Gly Gly Leu Leu Asp Thr Lys Gly Tyr Gly Ile Gly
        740                 745                 750 atg cca gtc ggc tcg gtt ttc cgg gac gag ttt gat ctg gcc att ctc    2304
Met Pro Val Gly Ser Val Phe Arg Asp Glu Phe Asp Leu Ala Ile Leu
    755                 760                 765 cag ctg cag gag aac aac cgc ctg gag atc ctg aag cgc aaa tgg tgg    2352
Gln Leu Gln Glu Asn Asn Arg Leu Glu Ile Leu Lys Arg Lys Trp Trp
770                 775                 780 gaa gga ggg aag tgc ccc aag gag gaa gat cac aga gct aaa ggc ctg    2400
Glu Gly Gly Lys Cys Pro Lys Glu Glu Asp His Arg Ala Lys Gly Leu
785                 790                 795                 800 gga atg gag aat att ggt gga atc ttt gtg gtt ctt att tgt ggc tta    2448
Gly Met Glu Asn Ile Gly Gly Ile Phe Val Val Leu Ile Cys Gly Leu
                805                 810                 815 atc gtg gcc att ttt atg gct atg ttg gag ttt tta tgg act ctc aga    2496
Ile Val Ala Ile Phe Met Ala Met Leu Glu Phe Leu Trp Thr Leu Arg
        820                 825                 830 cac tca gaa gca act gag gtg tcc gtc tgc cag gag atg gtg acc gag    2544
His Ser Glu Ala Thr Glu Val Ser Val Cys Gln Glu Met Val Thr Glu
    835                 840                 845 ctg cgc agc att atc ctg tgt cag gac agt atc cac ccc cgc cgg cgg    2592
Leu Arg Ser Ile Ile Leu Cys Gln Asp Ser Ile His Pro Arg Arg Arg
850                 855                 860 cgc gcc gca gtc ccg ccg ccc cgg ccc ccc atc ccc gag gag cgc cga    2640
Arg Ala Ala Val Pro Pro Pro Arg Pro Pro Ile Pro Glu Glu Arg Arg
865                 870                 875                 880 ccg cgg ggc acg gcg acg ctc agc aac ggg aag ctg tgc ggg gca ggg    2688
Pro Arg Gly Thr Ala Thr Leu Ser Asn Gly Lys Leu Cys Gly Ala Gly
                885                 890                 895 gag ccc gac cag ctc gcg cag aga ctg gcg cag gag gcc gcc ctg gtg    2736
Glu Pro Asp Gln Leu Ala Gln Arg Leu Ala Gln Glu Ala Ala Leu Val
        900                 905                 910 gcc cgc ggc tgc acg cac atc cgc gtc tgc ccc gag tgc cgc cgc ttc    2784
Ala Arg Gly Cys Thr His Ile Arg Val Cys Pro Glu Cys Arg Arg Phe
    915                 920                 925 cag ggc ctg cgg gca cgg ccg tcg ccc gcc cgc agc gag gag agc ctg    2832
Gln Gly Leu Arg Ala Arg Pro Ser Pro Ala Arg Ser Glu Glu Ser Leu
930                 935                 940 gag tgg gag aaa acc acc aac agc agc gag ccc gag tag               2871
Glu Trp Glu Lys Thr Thr Asn Ser Ser Glu Pro Glu *
945                 950                 955

<210> SEQ ID NO 30
<211> LENGTH: 956
<212> TYPE: PRT
<213> ORGANISM: Homo Sapiens

<400> SEQUENCE: 30

Met Pro Arg Val Ser Ala Pro Leu Val Leu Leu Pro Ala Trp Leu Val
 1               5                  10                  15

Met Val Ala Cys Ser Pro His Ser Leu Arg Ile Ala Ala Ile Leu Asp
                20                  25                  30

Asp Pro Met Glu Cys Ser Arg Gly Glu Arg Leu Ser Ile Thr Leu Ala
            35                  40                  45

Lys Asn Arg Ile Asn Arg Ala Pro Glu Arg Leu Gly Lys Ala Lys Val
        50                  55                  60

Glu Val Asp Ile Phe Glu Leu Leu Arg Asp Ser Glu Tyr Glu Thr Ala
65                  70                  75                  80
```

-continued

```
Glu Thr Met Cys Gln Ile Leu Pro Lys Gly Val Ala Val Leu Gly
                85                  90                  95
Pro Ser Ser Ser Pro Ala Ser Ser Ile Ile Ser Asn Ile Cys Gly
            100                 105                 110
Glu Lys Glu Val Pro His Phe Lys Val Ala Pro Glu Glu Phe Val Lys
        115                 120                 125
Phe Gln Phe Gln Arg Phe Thr Thr Leu Asn Leu His Pro Ser Asn Thr
130                 135                 140
Asp Ile Ser Val Ala Val Ala Gly Ile Leu Asn Phe Phe Asn Cys Thr
145                 150                 155                 160
Thr Ala Cys Leu Ile Cys Ala Lys Ala Glu Cys Leu Leu Asn Leu Glu
                165                 170                 175
Lys Leu Leu Arg Gln Phe Leu Ile Ser Lys Asp Thr Leu Ser Val Arg
            180                 185                 190
Met Leu Asp Asp Thr Arg Asp Pro Thr Pro Leu Leu Lys Glu Ile Arg
        195                 200                 205
Asp Asp Lys Thr Ala Thr Ile Ile His Ala Asn Ala Ser Met Ser
210                 215                 220
His Thr Ile Leu Leu Lys Ala Ala Glu Leu Gly Met Val Ser Ala Tyr
225                 230                 235                 240
Tyr Thr Tyr Ile Phe Thr Asn Leu Glu Phe Ser Leu Gln Arg Thr Asp
                245                 250                 255
Ser Leu Val Asp Asp Arg Val Asn Ile Leu Gly Phe Ser Ile Phe Asn
            260                 265                 270
Gln Ser His Ala Phe Phe Gln Glu Phe Ala Gln Ser Leu Asn Gln Ser
        275                 280                 285
Trp Gln Glu Asn Cys Asp His Val Pro Phe Thr Gly Pro Ala Leu Ser
290                 295                 300
Ser Ala Leu Leu Phe Asp Ala Val Tyr Ala Val Val Thr Ala Val Gln
305                 310                 315                 320
Glu Leu Asn Arg Ser Gln Glu Ile Gly Val Lys Pro Leu Ser Cys Gly
                325                 330                 335
Ser Ala Gln Ile Trp Gln His Gly Thr Ser Leu Met Asn Tyr Leu Arg
            340                 345                 350
Met Val Glu Leu Glu Gly Leu Thr Gly His Ile Glu Phe Asn Ser Lys
        355                 360                 365
Gly Gln Arg Ser Asn Tyr Ala Leu Lys Ile Leu Gln Phe Thr Arg Asn
370                 375                 380
Gly Phe Arg Gln Ile Gly Gln Trp His Val Ala Glu Gly Leu Ser Met
385                 390                 395                 400
Asp Ser His Leu Tyr Ala Ser Asn Ile Ser Asp Thr Leu Phe Asn Thr
                405                 410                 415
Thr Leu Val Val Thr Thr Ile Leu Glu Asn Pro Tyr Leu Met Leu Lys
            420                 425                 430
Gly Asn His Gln Glu Met Glu Gly Asn Asp Arg Tyr Glu Gly Phe Cys
        435                 440                 445
Val Asp Met Leu Lys Glu Leu Ala Glu Ile Leu Arg Phe Asn Tyr Lys
450                 455                 460
Ile Arg Leu Val Gly Asp Gly Val Tyr Gly Val Pro Glu Ala Asn Gly
465                 470                 475                 480
Thr Trp Thr Gly Met Val Gly Glu Leu Ile Ala Arg Lys Ala Asp Leu
                485                 490                 495
Ala Val Ala Gly Leu Thr Ile Thr Ala Glu Arg Glu Lys Val Ile Asp
```

-continued

```
              500                 505                 510
Phe Ser Lys Pro Phe Met Thr Leu Gly Ile Ser Ile Leu Tyr Arg Ile
        515                 520                 525
His Met Gly Arg Lys Pro Gly Tyr Phe Ser Phe Leu Asp Pro Phe Ser
        530                 535                 540
Pro Gly Val Trp Leu Phe Met Leu Leu Ala Tyr Leu Ala Val Ser Cys
545                 550                 555                 560
Val Leu Phe Leu Val Ala Arg Leu Thr Pro Tyr Glu Trp Tyr Ser Pro
                565                 570                 575
His Pro Cys Ala Gln Gly Arg Cys Asn Leu Leu Val Asn Gln Tyr Ser
            580                 585                 590
Leu Gly Asn Ser Leu Trp Phe Pro Val Gly Phe Met Gln Gln Gly
        595                 600                 605
Ser Thr Ile Ala Pro Arg Ala Leu Ser Thr Arg Cys Val Ser Gly Val
        610                 615                 620
Trp Trp Ala Phe Thr Leu Ile Ile Ile Ser Ser Tyr Thr Ala Asn Leu
625                 630                 635                 640
Ala Ala Phe Leu Thr Val Gln Arg Met Asp Val Pro Ile Glu Ser Val
                645                 650                 655
Asp Asp Leu Ala Asp Gln Thr Ala Ile Glu Tyr Gly Thr Ile His Gly
            660                 665                 670
Gly Ser Ser Met Thr Phe Phe Gln Asn Ser Arg Tyr Gln Thr Tyr Gln
            675                 680                 685
Arg Met Trp Asn Tyr Met Tyr Ser Lys Gln Pro Ser Val Phe Val Lys
        690                 695                 700
Ser Thr Glu Glu Gly Ile Ala Arg Val Leu Asn Ser Asn Tyr Ala Phe
705                 710                 715                 720
Leu Leu Glu Ser Thr Met Asn Glu Tyr Tyr Arg Gln Arg Asn Cys Asn
                725                 730                 735
Leu Thr Gln Ile Gly Gly Leu Leu Asp Thr Lys Gly Tyr Gly Ile Gly
            740                 745                 750
Met Pro Val Gly Ser Val Phe Arg Asp Glu Phe Asp Leu Ala Ile Leu
        755                 760                 765
Gln Leu Gln Glu Asn Asn Arg Leu Glu Ile Leu Lys Arg Lys Trp Trp
        770                 775                 780
Glu Gly Gly Lys Cys Pro Lys Glu Glu Asp His Arg Ala Lys Gly Leu
785                 790                 795                 800
Gly Met Glu Asn Ile Gly Gly Ile Phe Val Val Leu Ile Cys Gly Leu
                805                 810                 815
Ile Val Ala Ile Phe Met Ala Met Leu Glu Phe Leu Trp Thr Leu Arg
            820                 825                 830
His Ser Glu Ala Thr Glu Val Ser Val Cys Gln Glu Met Val Thr Glu
        835                 840                 845
Leu Arg Ser Ile Ile Leu Cys Gln Asp Ser Ile His Pro Arg Arg Arg
        850                 855                 860
Arg Ala Ala Val Pro Pro Pro Arg Pro Ile Pro Glu Glu Arg Arg
865                 870                 875                 880
Pro Arg Gly Thr Ala Thr Leu Ser Asn Gly Lys Leu Cys Gly Ala Gly
                885                 890                 895
Glu Pro Asp Gln Leu Ala Gln Arg Leu Ala Gln Glu Ala Ala Leu Val
            900                 905                 910
Ala Arg Gly Cys Thr His Ile Arg Val Cys Pro Glu Cys Arg Arg Phe
            915                 920                 925
```

```
Gln Gly Leu Arg Ala Arg Pro Ser Pro Ala Arg Ser Glu Glu Ser Leu
        930                 935                 940

Glu Trp Glu Lys Thr Thr Asn Ser Ser Glu Pro Glu
945                 950                 955

<210> SEQ ID NO 31
<211> LENGTH: 2534
<212> TYPE: DNA
<213> ORGANISM: Homo Sapiens
<220> FEATURE:
<221> NAME/KEY: CDS
<222> LOCATION: (118)...(1230)

<400> SEQUENCE: 31
cctgctctgc acctgtcgtc gactgccagc cggctgaggg cgggggtctc cacggtggtc      60
ccagctccca aggaggttgc agaagtaccg tacagagtgg atttgcaggg cagtggc atg    120
                                                                Met
                                                                  1 gag ccc ctc ttc ccc gcg ccg ttc tgg gag gtt atc tac ggc agc cac       168
Glu Pro Leu Phe Pro Ala Pro Phe Trp Glu Val Ile Tyr Gly Ser His
            5                  10                  15 ctt cag ggc aac ctg tcc ctg ctg agc ccc aac cac agt ctg ctg ccc       216
Leu Gln Gly Asn Leu Ser Leu Leu Ser Pro Asn His Ser Leu Leu Pro
        20                  25                  30 ccg cat ctg ctg ctc aat gcc agc cac ggc gcc ttc ctg ccc ctc ggg       264
Pro His Leu Leu Leu Asn Ala Ser His Gly Ala Phe Leu Pro Leu Gly
    35                  40                  45 ctc aag gtc acc atc gtg ggg ctc tac ctg gcc gtg tgt gtc gga ggg       312
Leu Lys Val Thr Ile Val Gly Leu Tyr Leu Ala Val Cys Val Gly Gly
50                  55                  60                  65 ctc ctg ggg aac tgc ctt gtc atg tac gtc atc ctc agg cac acc aaa       360
Leu Leu Gly Asn Cys Leu Val Met Tyr Val Ile Leu Arg His Thr Lys
                70                  75                  80 atg aag aca gcc acc aat att tac atc ttt aac ctg gcc ctg gcc gac       408
Met Lys Thr Ala Thr Asn Ile Tyr Ile Phe Asn Leu Ala Leu Ala Asp
            85                  90                  95 act ctg gtc ctg ctg acg ctg ccc ttc cag ggc acg gac atc ctc ctg       456
Thr Leu Val Leu Leu Thr Leu Pro Phe Gln Gly Thr Asp Ile Leu Leu
        100                 105                 110 ggc ttc tgg ccg ttt ggg aat gcg ctg tgc aag aca gtc att gcc att       504
Gly Phe Trp Pro Phe Gly Asn Ala Leu Cys Lys Thr Val Ile Ala Ile
    115                 120                 125 gac tac tac aac atg ttc acc agc acc ttc acc cta act gcc atg agt       552
Asp Tyr Tyr Asn Met Phe Thr Ser Thr Phe Thr Leu Thr Ala Met Ser
130                 135                 140                 145 gtg gat cgc tat gta gcc atc tgc cac ccc atc cgt gcc ctc gac gtc       600
Val Asp Arg Tyr Val Ala Ile Cys His Pro Ile Arg Ala Leu Asp Val
                150                 155                 160 cgc acg tcc agc aaa gcc cag gct gtc aat gtg gcc atc tgg gcc ctg       648
Arg Thr Ser Ser Lys Ala Gln Ala Val Asn Val Ala Ile Trp Ala Leu
            165                 170                 175 gcc tct gtt gtc ggt gtt ccc gtt gcc atc atg ggc tcg gca cag gtc       696
Ala Ser Val Val Gly Val Pro Val Ala Ile Met Gly Ser Ala Gln Val
        180                 185                 190 gag gat gaa gag atc gag tgc ctg gtg gag atc cct acc cct cag gat       744
Glu Asp Glu Glu Ile Glu Cys Leu Val Glu Ile Pro Thr Pro Gln Asp
    195                 200                 205 tac tgg ggc ccg gtg ttt gcc atc tgc atc ttc ctc ttc tcc ttc atc       792
Tyr Trp Gly Pro Val Phe Ala Ile Cys Ile Phe Leu Phe Ser Phe Ile
210                 215                 220                 225
```

-continued

| | | |
|---|---|---|
| gtc ccc gtg ctc gtc atc tct gtc tgc tac agc ctc atg atc cgg cgg<br>Val Pro Val Leu Val Ile Ser Val Cys Tyr Ser Leu Met Ile Arg Arg<br>       230       235       240 | | 840 |
| ctc cgt gga gtc cgc ctg ctc tcg ggc tcc cga gag aag gac cgg aac<br>Leu Arg Gly Val Arg Leu Leu Ser Gly Ser Arg Glu Lys Asp Arg Asn<br>     245       250       255 | | 888 |
| ctg cgg cgc atc act cgg ctg gtg ctg gtg gta gtg gct gtg ttc gtg<br>Leu Arg Arg Ile Thr Arg Leu Val Leu Val Val Val Ala Val Phe Val<br>    260       265       270 | | 936 |
| ggc tgc tgg acg cct gtc cag gtc ttc gtg ctg gcc caa ggg ctg ggg<br>Gly Cys Trp Thr Pro Val Gln Val Phe Val Leu Ala Gln Gly Leu Gly<br>275        280       285 | | 984 |
| gtt cag ccg agc agc gag act gcc gtg gcc att ctg cgc ttc tgc acg<br>Val Gln Pro Ser Ser Glu Thr Ala Val Ala Ile Leu Arg Phe Cys Thr<br>290        295       300       305 | | 1032 |
| gcc ctg ggc tac gtc aac agc tgc ctc aac ccc atc ctc tac gcc ttc<br>Ala Leu Gly Tyr Val Asn Ser Cys Leu Asn Pro Ile Leu Tyr Ala Phe<br>       310       315       320 | | 1080 |
| ctg gat gag aac ttc aag gcc tgc ttc cgc aag ttc tgc tgt gca tct<br>Leu Asp Glu Asn Phe Lys Ala Cys Phe Arg Lys Phe Cys Cys Ala Ser<br>     325       330       335 | | 1128 |
| gcc ctg cgc cgg gac gtg cag gtg tct gac cgc gtg cgc agc att gcc<br>Ala Leu Arg Arg Asp Val Gln Val Ser Asp Arg Val Arg Ser Ile Ala<br>    340       345       350 | | 1176 |
| aag gac gtg gcc ctg gcc tgc aag acc tct gag acg gta ccg cgg ccc<br>Lys Asp Val Ala Leu Ala Cys Lys Thr Ser Glu Thr Val Pro Arg Pro<br>355        360       365 | | 1224 |
| gca tga ctaggcgtgg acctgcccat ggtgcctgtc agcccgcaga gcccatctac<br>Ala *<br>370 | | 1280 |
| gcccaacaca gagctcacac aggtcactgc tctctaggcg acacaccct gggccctgag | | 1340 |
| catccagagc ctgggatggg cttttccctg tgggccaggg atgctcggtc ccagaggagg | | 1400 |
| acctagtgac atcatgggac aggtcaaagc attagggcca cctccatggc cccagacaga | | 1460 |
| ctaaagctgc cctcctggtg cagggccgag gggacacaag gacctacctg gaagcagctg | | 1520 |
| acatgctggt ggacggccgt tactggagcc cgtgcccctc cctccccgtg cttcatgtga | | 1580 |
| ctcttggcct ctctgctgct cgttggcag aaccctgggt gggcaggcac ccggaggagg | | 1640 |
| agcagcagct gtgtcatcct gtgcccccca tgtgctgtgt gctgtttgca tggcagggct | | 1700 |
| ccagctgcct tcagccctgt gacgtctcct cagggcagct ggacaggctt ggcacggccc | | 1760 |
| gggaagtgca gcaggcagct tttctttggg gtgggacttg ccctgagctt ggagctgcca | | 1820 |
| cctggaggac ttgcctgttc cgactccacc tgtgcagccg gggccacccc aggagaaagt | | 1880 |
| gtccaggtgg gggctggcag tccctggctg cagacccga gctggccctc ggaccgcacc | | 1940 |
| tctgaaggtt ttctgtgtgc tgcacggtgc aggcctcatc cctgactgca gcttgactct | | 2000 |
| gggcccaacc cccatttccc ttcaggagac cagcgagagg ccctggccat ccctccagcg | | 2060 |
| gtgcaatgaa ctatatgctg tggaccgtca cccagccct gcttctcagt gtggggcagg | | 2120 |
| tgtctcagga cgaaggcgcc gcgtgaccac atgggcagct ctgttcacaa agtggaggcc | | 2180 |
| tcgtttcct ggtcttgact gctctgtttg ggtgggagaa gattctctgg gggtccccac | | 2240 |
| atcctcccaa ggctcccctc acagcctctc ctttgcttga agccagaggt cagtggccgt | | 2300 |
| gctgtgttgc ggggaagctg tgtggaagga gaagctggtg gccacagcag agtcctgctc | | 2360 |
| tggggacgcc tgcttcattt acaagcctca agatggctct gtgtagggcc tgagcttgct | | 2420 |

```
gcccaacggg aggatggctt cacagcagag ccagcatgag gggtgggggcc tggcagggct    2480 tgcttgagcc aaactgcaaa ggctgtggtg gctgtgagga cactgcgggg gttg           2534
```

<210> SEQ ID NO 32
<211> LENGTH: 370
<212> TYPE: PRT
<213> ORGANISM: Homo Sapiens

<400> SEQUENCE: 32

```
Met Glu Pro Leu Phe Pro Ala Pro Phe Trp Glu Val Ile Tyr Gly Ser
 1               5                  10                  15

His Leu Gln Gly Asn Leu Ser Leu Ser Pro Asn His Ser Leu Leu
            20                  25                  30

Pro Pro His Leu Leu Leu Asn Ala Ser His Gly Ala Phe Leu Pro Leu
            35                  40                  45

Gly Leu Lys Val Thr Ile Val Gly Leu Tyr Leu Ala Val Cys Val Gly
        50                  55                  60

Gly Leu Leu Gly Asn Cys Leu Val Met Tyr Val Ile Leu Arg His Thr
65                  70                  75                  80

Lys Met Lys Thr Ala Thr Asn Ile Tyr Ile Phe Asn Leu Ala Leu Ala
                85                  90                  95

Asp Thr Leu Val Leu Leu Thr Leu Pro Phe Gln Gly Thr Asp Ile Leu
            100                 105                 110

Leu Gly Phe Trp Pro Phe Gly Asn Ala Leu Cys Lys Thr Val Ile Ala
        115                 120                 125

Ile Asp Tyr Tyr Asn Met Phe Thr Ser Thr Phe Thr Leu Thr Ala Met
    130                 135                 140

Ser Val Asp Arg Tyr Val Ala Ile Cys His Pro Ile Arg Ala Leu Asp
145                 150                 155                 160

Val Arg Thr Ser Ser Lys Ala Gln Ala Val Asn Val Ala Ile Trp Ala
                165                 170                 175

Leu Ala Ser Val Val Gly Val Pro Val Ala Ile Met Gly Ser Ala Gln
            180                 185                 190

Val Glu Asp Glu Glu Ile Glu Cys Leu Val Glu Ile Pro Thr Pro Gln
        195                 200                 205

Asp Tyr Trp Gly Pro Val Phe Ala Ile Cys Ile Phe Leu Phe Ser Phe
    210                 215                 220

Ile Val Pro Val Leu Val Ile Ser Val Cys Tyr Ser Leu Met Ile Arg
225                 230                 235                 240

Arg Leu Arg Gly Val Arg Leu Leu Ser Gly Ser Arg Glu Lys Asp Arg
                245                 250                 255

Asn Leu Arg Arg Ile Thr Arg Leu Val Leu Val Val Val Ala Val Phe
            260                 265                 270

Val Gly Cys Trp Thr Pro Val Gln Val Phe Val Leu Ala Gln Gly Leu
        275                 280                 285

Gly Val Gln Pro Ser Ser Glu Thr Ala Val Ala Ile Leu Arg Phe Cys
    290                 295                 300

Thr Ala Leu Gly Tyr Val Asn Ser Cys Leu Asn Pro Ile Leu Tyr Ala
305                 310                 315                 320

Phe Leu Asp Glu Asn Phe Lys Ala Cys Phe Arg Lys Phe Cys Cys Ala
                325                 330                 335

Ser Ala Leu Arg Arg Asp Val Gln Val Ser Asp Arg Val Arg Ser Ile
            340                 345                 350

Ala Lys Asp Val Ala Leu Ala Cys Lys Thr Ser Glu Thr Val Pro Arg
```

```
                    355                 360                 365
Pro Ala
    370

<210> SEQ ID NO 33
<211> LENGTH: 2857
<212> TYPE: DNA
<213> ORGANISM: Homo Sapiens
<220> FEATURE:
<221> NAME/KEY: CDS
<222> LOCATION: (174)...(1175)

<400> SEQUENCE: 33
aacagtattt tccttttcaa cacatctatt gaaagtgttg gataaatgca ggatgttaat      60
atgctataaa cataaagtct gtttttaaaa aatagcattt gaaaatcatg aagggctttt     120
tgttttcttt tgtttgtata tatgtttatt ggtaacaggt gacactggaa gca atg       176
                                                           Met
                                                             1 aac acc aca gtg atg caa ggc ttc aac aga tct gag cgg tgc ccc aga      224
Asn Thr Thr Val Met Gln Gly Phe Asn Arg Ser Glu Arg Cys Pro Arg
            5                  10                  15 gac act cgg ata gta cag ctg gta ttc cca gcc ctc tac aca gtg gtt      272
Asp Thr Arg Ile Val Gln Leu Val Phe Pro Ala Leu Tyr Thr Val Val
         20                  25                  30 ttc ttg acc ggc atc ctg ctg aat act ttg gct ctg tgg gtg ttt gtt      320
Phe Leu Thr Gly Ile Leu Leu Asn Thr Leu Ala Leu Trp Val Phe Val
     35                  40                  45 cac atc ccc agc tcc tcc acc ttc atc atc tac ctc aaa aac act ttg      368
His Ile Pro Ser Ser Ser Thr Phe Ile Ile Tyr Leu Lys Asn Thr Leu
 50                  55                  60                  65 gtg gcc gac ttg ata atg aca ctc atg ctt cct ttc aaa atc ctc tct      416
Val Ala Asp Leu Ile Met Thr Leu Met Leu Pro Phe Lys Ile Leu Ser
                 70                  75                  80 gac tca cac ctg gca ccc tgg cag ctc aga gct ttt gtg tgt cgt ttt      464
Asp Ser His Leu Ala Pro Trp Gln Leu Arg Ala Phe Val Cys Arg Phe
             85                  90                  95 tct tcg gtg ata ttt tat gag acc atg tat gtg ggc atc gtg ctg tta      512
Ser Ser Val Ile Phe Tyr Glu Thr Met Tyr Val Gly Ile Val Leu Leu
        100                 105                 110 ggg ctc ata gcc ttt gac aga ttc ctc aag atc atc aga cct ttg aga      560
Gly Leu Ile Ala Phe Asp Arg Phe Leu Lys Ile Ile Arg Pro Leu Arg
    115                 120                 125 aat att ttt cta aaa aaa cct gtt ttt gca aaa acg gtc tca atc ttc      608
Asn Ile Phe Leu Lys Lys Pro Val Phe Ala Lys Thr Val Ser Ile Phe
130                 135                 140                 145 atc tgg ttc ttt ttg ttc ttc atc tcc ctg cca aat atg atc ttg agc      656
Ile Trp Phe Phe Leu Phe Phe Ile Ser Leu Pro Asn Met Ile Leu Ser
                150                 155                 160 aac aag gaa gca aca cca tcg tct gtg aaa aag tgt gct tcc tta aag      704
Asn Lys Glu Ala Thr Pro Ser Ser Val Lys Lys Cys Ala Ser Leu Lys
            165                 170                 175 ggg cct ctg ggg ctg aaa tgg cat caa atg gta aat aac ata tgc cag      752
Gly Pro Leu Gly Leu Lys Trp His Gln Met Val Asn Asn Ile Cys Gln
        180                 185                 190 ttt att ttc tgg act gtt ttt atc cta atg ctt gtg ttt tat gtg gtt      800
Phe Ile Phe Trp Thr Val Phe Ile Leu Met Leu Val Phe Tyr Val Val
    195                 200                 205 att gca aaa aaa gta tat gat tct tat aga aag tcc aaa agt aag gac      848
Ile Ala Lys Lys Val Tyr Asp Ser Tyr Arg Lys Ser Lys Ser Lys Asp
210                 215                 220                 225
```

|   |   |
|---|---|
| aga aaa aac aac aaa aag ctg gaa ggc aaa gta ttt gtt gtc gtg gct<br>Arg Lys Asn Asn Lys Lys Leu Glu Gly Lys Val Phe Val Val Val Ala<br>230                            235                         240 | 896 |
| gtc ttc ttt gtg tgt ttt gct cca ttt cat ttt gcc aga gtt cca tat<br>Val Phe Phe Val Cys Phe Ala Pro Phe His Phe Ala Arg Val Pro Tyr<br>245                            250                         255 | 944 |
| act cac agt caa acc aac aat aag act gac tgt aga ctg caa aat caa<br>Thr His Ser Gln Thr Asn Asn Lys Thr Asp Cys Arg Leu Gln Asn Gln<br>            260                         265                      270 | 992 |
| ctg ttt att gct aaa gaa aca act ctc ttt ttg gca gca act aac att<br>Leu Phe Ile Ala Lys Glu Thr Thr Leu Phe Leu Ala Ala Thr Asn Ile<br>275                            280                         285 | 1040 |
| tgt atg gat ccc tta ata tac ata ttc tta tgt aaa aaa ttc aca gaa<br>Cys Met Asp Pro Leu Ile Tyr Ile Phe Leu Cys Lys Lys Phe Thr Glu<br>290                            295                        300                        305 | 1088 |
| aag cta cca tgt atg caa ggg aga aag acc aca gca tca agc caa gaa<br>Lys Leu Pro Cys Met Gln Gly Arg Lys Thr Thr Ala Ser Ser Gln Glu<br>                            310                         315                        320 | 1136 |
| aat cat agc agt cag aca gac aac ata acc tta ggc tga caactgtaca<br>Asn His Ser Ser Gln Thr Asp Asn Ile Thr Leu Gly *<br>            325                         330 | 1185 |
| tagggttaac ttctatttat tgatgagact tccgtagata atgtggaaat caaatttaac | 1245 |
| caagaaaaaa agattggaac aaatgctctc ttacatttta ttatcctggt gtacagaaaa | 1305 |
| gattatataa aatttaaatc cacatagatc tattcataag ctgaatgaac cattactaag | 1365 |
| agaatgcaac aggatacaaa tggccactag aggtcattat ttctttcttt ctttttttt | 1425 |
| tttttaattt caagagcatt tcactttaac attttggaaa agactaagga gaaacgtata | 1485 |
| tccctacaaa cctcccctcc aaacaccttc tcacattctt ttccacaatt cacataacac | 1545 |
| tactgctttt gtgcccctta aatgtagata tgtgctgaaa gaaaaaaaaa acgcccaact | 1605 |
| cttgaagtcc attgctgaaa actgcagcca ggggttgaaa gggatgcaga cttgaagagt | 1665 |
| ctgaggaact gaagtgggtc agcaagacct ctgaaatcct gggtaaagga ttttctcctt | 1725 |
| acaattacaa acagcctctt tcacattaca ataatatacc ataggaggca caagcaccat | 1785 |
| tattaagcca ctttgcttac accttaagtg tgtacaattc aagtgtgaga atgctgtgtt | 1845 |
| aactattctt tggaattctc cttctgtcca gcaaatactc taatgatggt taaacatggc | 1905 |
| acctactcag caatgccttc ctggaccaca accctatcc ccctgcccca cctcctcat | 1965 |
| taaaaacaaa tacttctact gtttgggtgt gtgatagggt tctcaatgca gatctccctt | 2025 |
| ttctagttag ctatattctt gactgcatcc gctaaaaatg ttaaagcttc ttgagagaca | 2085 |
| gacatgccag attttcttgg tatctcccat aatacgacct acagtccatg gtctacagat | 2145 |
| gttttaaata gaattgctat tctcgataca tacaaagacg taattgctga cccacaatca | 2205 |
| gtaacatcca tattgggaga tttttcaaag gatggtgacc ctgcttgtat ttatttacct | 2265 |
| tggtatttt tcttgcatcc ttctgtgatt caaaaaagta aaatgtggct ttctgaaatg | 2325 |
| atggataaga gtctacatct tctagaaaaa atacataaag gagtagttaa gctctgtaaa | 2385 |
| tgtgccacga gctccaacac gaccatcgta gggtgaagcc cacgttttct tccatggcct | 2445 |
| caaaggccct agaacttgcc taccttttctg gccttacctc ctagctactt atccatctct | 2505 |
| tgaactttat actcttgtat aaatttctaa cttttcagaaa atgccatact ctgttttggc | 2565 |
| accacacatg tatatttccc cctggtacac ttggaagact cttatccatc tgtgaaaccc | 2625 |
| tatgttgtca tcacttggtc catgaaatat tacctggcca atatcccacc atcacctcaa | 2685 |

```
acccaatcac ccctcctct gtatgctgtc acacctatat tattaaactt atcacattgc    2745
attgtaatta cttcctgacc tttgtatcta ctctttagt aactgatgta tatatctgaa    2805
aggagagatt gtttcattgt gcaatcaata aatgtttgat aaaataaagc cc           2857
```

<210> SEQ ID NO 34
<211> LENGTH: 333
<212> TYPE: PRT
<213> ORGANISM: Homo Sapiens

<400> SEQUENCE: 34

```
Met Asn Thr Thr Val Met Gln Gly Phe Asn Arg Ser Glu Arg Cys Pro
  1               5                  10                  15

Arg Asp Thr Arg Ile Val Gln Leu Val Phe Pro Ala Leu Tyr Thr Val
                 20                  25                  30

Val Phe Leu Thr Gly Ile Leu Leu Asn Thr Leu Ala Leu Trp Val Phe
             35                  40                  45

Val His Ile Pro Ser Ser Thr Phe Ile Ile Tyr Leu Lys Asn Thr
         50                  55                  60

Leu Val Ala Asp Leu Ile Met Thr Leu Met Leu Pro Phe Lys Ile Leu
 65                  70                  75                  80

Ser Asp Ser His Leu Ala Pro Trp Gln Leu Arg Ala Phe Val Cys Arg
                 85                  90                  95

Phe Ser Ser Val Ile Phe Tyr Glu Thr Met Tyr Val Gly Ile Val Leu
            100                 105                 110

Leu Gly Leu Ile Ala Phe Asp Arg Phe Leu Lys Ile Ile Arg Pro Leu
        115                 120                 125

Arg Asn Ile Phe Leu Lys Lys Pro Val Phe Ala Lys Thr Val Ser Ile
130                 135                 140

Phe Ile Trp Phe Phe Leu Phe Phe Ile Ser Leu Pro Asn Met Ile Leu
145                 150                 155                 160

Ser Asn Lys Glu Ala Thr Pro Ser Ser Val Lys Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Val Tyr Asp Ser Tyr Arg Lys Ser Lys Ser Lys
    210                 215                 220

Asp Arg Lys Asn Asn Lys Lys Leu Glu Gly Lys Val Phe Val Val Val
225                 230                 235                 240

Ala Val Phe Phe Val Cys Phe Ala Pro Phe His Phe Ala Arg Val Pro
                245                 250                 255

Tyr Thr His Ser Gln Thr Asn Asn Lys Thr Asp Cys Arg Leu Gln Asn
            260                 265                 270

Gln Leu Phe Ile Ala Lys Glu Thr Thr Leu Phe Leu Ala Ala Thr Asn
        275                 280                 285

Ile Cys Met Asp Pro Leu Ile Tyr Ile Phe Leu Cys Lys Lys Phe Thr
    290                 295                 300

Glu Lys Leu Pro Cys Met Gln Gly Arg Lys Thr Thr Ala Ser Ser Gln
305                 310                 315                 320

Glu Asn His Ser Ser Gln Thr Asp Asn Ile Thr Leu Gly
                325                 330
```

<210> SEQ ID NO 35

```
<211> LENGTH: 2372
<212> TYPE: DNA
<213> ORGANISM: Homo Sapiens
<220> FEATURE:
<221> NAME/KEY: CDS
<222> LOCATION: (157)...(1233)

<400> SEQUENCE: 35
gggccgccgt cggcgcgctg ggtgcgggaa gggggctctg gatttcggtc cctcccttt         60 ttcctctgag tctcggaacg ctccagctct cagaccctct tcctcccagg taaaggccgg       120
gagaggaggg cgcatctctt ttccaggcac cccacc atg ggc aat gcc tcc aat         174
                                        Met Gly Asn Ala Ser Asn
                                        1               5 gac tcc cag tct gag gac tgc gag acg cga cag tgg ctt ccc cca ggc         222
Asp Ser Gln Ser Glu Asp Cys Glu Thr Arg Gln Trp Leu Pro Pro Gly
        10                  15                  20 gaa agc cca gcc atc agc tcc gtc atg ttc tcg gcc ggg gtg ctg ggg         270
Glu Ser Pro Ala Ile Ser Ser Val Met Phe Ser Ala Gly Val Leu Gly
            25                  30                  35 aac ctc ata gca ctg gcg ctg ctg gcg cgc cgc tgg cgg ggg gac gtg         318
Asn Leu Ile Ala Leu Ala Leu Leu Ala Arg Arg Trp Arg Gly Asp Val
        40                  45                  50 ggg tgc agc gcc ggc cgc agg agc tcc ctc tcc ttg ttc cac gtg ctg         366
Gly Cys Ser Ala Gly Arg Arg Ser Ser Leu Ser Leu Phe His Val Leu
55                  60                  65                  70 gtg acc gag ctg gtg ttc acc gac ctg ctc ggg acc tgc ctc atc agc         414
Val Thr Glu Leu Val Phe Thr Asp Leu Leu Gly Thr Cys Leu Ile Ser
                75                  80                  85 cca gtg gta ctg gct tcg tac gcg cgg aac cag acc ctg gtg gca ctg         462
Pro Val Val Leu Ala Ser Tyr Ala Arg Asn Gln Thr Leu Val Ala Leu
            90                  95                 100 gcg ccc gag agc cgc gcg tgc acc tac ttc gct ttc gcc atg acc ttc         510
Ala Pro Glu Ser Arg Ala Cys Thr Tyr Phe Ala Phe Ala Met Thr Phe
        105                 110                 115 ttc agc ctg gcc acg atg ctc atg ctc ttc gcc atg gcc ctg gag cgc         558
Phe Ser Leu Ala Thr Met Leu Met Leu Phe Ala Met Ala Leu Glu Arg
    120                 125                 130 tac ctc tcg atc ggg cac ccc tac ttc tac cag cgc cgc gtc tcg gcc         606
Tyr Leu Ser Ile Gly His Pro Tyr Phe Tyr Gln Arg Arg Val Ser Ala
135                 140                 145                 150 tcc ggg ggc ctg gcc gtg ctg cct gtc atc tat gca gtc tcc ctg ctc         654
Ser Gly Gly Leu Ala Val Leu Pro Val Ile Tyr Ala Val Ser Leu Leu
                155                 160                 165 ttc tgc tcg ctg ccg ctg ctg gac tat ggg cag tac gtc cag tac tgc         702
Phe Cys Ser Leu Pro Leu Leu Asp Tyr Gly Gln Tyr Val Gln Tyr Cys
            170                 175                 180 ccc ggg acc tgg tgc ttc atc cgg cac ggg cgg acc gct tac ctg cag         750
Pro Gly Thr Trp Cys Phe Ile Arg His Gly Arg Thr Ala Tyr Leu Gln
        185                 190                 195 ctg tac gcc acc ctg ctg ctg ctt ctc att gtc tcg gtg ctc gcc tgc         798
Leu Tyr Ala Thr Leu Leu Leu Leu Leu Ile Val Ser Val Leu Ala Cys
    200                 205                 210 aac ttc agt gtc att ctc aac ctc atc cgc atg cac cgc cga agc cgg         846
Asn Phe Ser Val Ile Leu Asn Leu Ile Arg Met His Arg Arg Ser Arg
215                 220                 225                 230 aga agc cgc tgc gga cct tcc ctg ggc agt ggc cgg ggc ggc ccc ggg         894
Arg Ser Arg Cys Gly Pro Ser Leu Gly Ser Gly Arg Gly Gly Pro Gly
                235                 240                 245 gcc cgc agg aga ggg gaa agg gtg tcc atg gcg gag gag acg gac cac         942
Ala Arg Arg Arg Gly Glu Arg Val Ser Met Ala Glu Glu Thr Asp His
```

|     |     |     |     |     |     |     |     |     |     |     |     |     |     |     |     |      |
|---|---|---|---|---|---|---|---|---|---|---|---|---|---|---|---|---|
|     |     |     | 250 |     |     |     |     | 255 |     |     |     |     | 260 |     |     |      |
| ctc | att | ctc | ctg | gct | atc | atg | acc | atc | acc | ttc | gcc | gtc | tgc | tcc | ttg | 990  |
| Leu | Ile | Leu | Leu | Ala | Ile | Met | Thr | Ile | Thr | Phe | Ala | Val | Cys | Ser | Leu |      |
|     |     | 265 |     |     |     |     | 270 |     |     |     |     | 275 |     |     |     |      |
| cct | ttc | acg | att | ttt | gca | tat | atg | aat | gaa | acc | tct | tcc | cga | aag | gaa | 1038 |
| Pro | Phe | Thr | Ile | Phe | Ala | Tyr | Met | Asn | Glu | Thr | Ser | Ser | Arg | Lys | Glu |      |
|     |     | 280 |     |     |     |     | 285 |     |     |     |     | 290 |     |     |     |      |
| aaa | tgg | gac | ctc | caa | gct | ctt | agg | ttt | tta | tca | att | aat | tca | ata | att | 1086 |
| Lys | Trp | Asp | Leu | Gln | Ala | Leu | Arg | Phe | Leu | Ser | Ile | Asn | Ser | Ile | Ile |      |
| 295 |     |     |     |     | 300 |     |     |     |     | 305 |     |     |     |     | 310 |      |
| gac | cct | tgg | gtc | ttt | gcc | atc | ctt | agg | cct | cct | gtt | ctg | aga | cta | atg | 1134 |
| Asp | Pro | Trp | Val | Phe | Ala | Ile | Leu | Arg | Pro | Pro | Val | Leu | Arg | Leu | Met |      |
|     |     |     |     | 315 |     |     |     |     | 320 |     |     |     |     | 325 |     |      |
| cgt | tca | gtc | ctc | tgt | tgt | cgg | att | tca | tta | aga | aca | caa | gat | gca | aca | 1182 |
| Arg | Ser | Val | Leu | Cys | Cys | Arg | Ile | Ser | Leu | Arg | Thr | Gln | Asp | Ala | Thr |      |
|     |     |     | 330 |     |     |     |     | 335 |     |     |     |     | 340 |     |     |      |
| caa | act | tcc | tgt | tct | aca | cag | tca | gat | gcc | agt | aaa | cag | gct | gac | ctt | 1230 |
| Gln | Thr | Ser | Cys | Ser | Thr | Gln | Ser | Asp | Ala | Ser | Lys | Gln | Ala | Asp | Leu |      |
|     |     | 345 |     |     |     |     | 350 |     |     |     |     | 355 |     |     |     |      |

```
tga ggtcagtagt ttaaaagttc ttagttatat agcatctgga agatcatttt    1283
 *
gaaattgttc cctggagaaa tgaaaacagt gtgtaaacaa atgaagctg ccctaataaa    1343
aaggagtata caaacattta agctgtggtc aaggctacag atgtgctgac aaggcacttc    1403
atgtaaagtg tcagaaggag ctacaaaacc taccctcaat gagcatggta cttggccttt    1463
ggaggaacaa tcggctgcat tgaagatcca gctgcctatt gatttaagct ttcctgttga    1523
atgacaaagt atgtggtttt gtaatttgtt tgaaacccca acagtgact gtactttcta    1583
ttttaatctt gctactaccg ttatacacat atagtgtaca gccagaccag attaaacttc    1643
atatgtaatc tctaggaagt caatatgtgg aagcaaccaa gcctgctgtc ttgtgatcac    1703
ttagcgaacc ctttatttga acaatgaagt tgaaaatcat aggcaccttt tactgtgatg    1763
tttgtgtatg tgggagtact ctcatcacta cagtattact cttacaagag tggactcagt    1823
gggttaacat cagttttgtt tactcatcct ccaggaactg caggtcaagt tgtcaggtta    1883
tttatttat aatgtccata tgctaatagt gatcaagaag actttaggaa tggttctctc    1943
aacaagaaat aatagaaatg tctcaaggca gttaattctc attaatactc ttattatcct    2003
atttctgggg gaggatgtac gtggccatgt atgaagccaa atattaggct taaaaactga    2063
aaaatctggt tcattcttca gatatactgg aacccttta aagttgatat tggggccatg    2123
agtaaaatag attttataag atgactgtgt tgtaccaaaa ttcatctgtc tatattttat    2183
ttaggggaac atggtttgac tcatcttata tgggaaacca tgtagcagtg agtcatatct    2243
taatatattt ctaaatgttt ggcatgtaaa tgtaaactca gcatcaaaat atttcagtga    2303
atttgcactg tttaatcata gttactgtgt aaactcatct gaaatgttac aaaaataaac    2363
tataaaaca                                                           2372

<210> SEQ ID NO 36
<211> LENGTH: 358
<212> TYPE: PRT
<213> ORGANISM: Homo Sapiens

<400> SEQUENCE: 36

Met Gly Asn Ala Ser Asn Asp Ser Gln Ser Glu Asp Cys Glu Thr Arg
 1               5                  10                  15

Gln Trp Leu Pro Pro Gly Glu Ser Pro Ala Ile Ser Ser Val Met Phe
```

```
                     20                  25                  30
Ser Ala Gly Val Leu Gly Asn Leu Ile Ala Leu Ala Leu Leu Ala Arg
        35                  40                  45

Arg Trp Arg Gly Asp Val Gly Cys Ser Ala Gly Arg Arg Ser Ser Leu
 50                  55                  60

Ser Leu Phe His Val Leu Val Thr Glu Leu Val Phe Thr Asp Leu Leu
 65                  70                  75                  80

Gly Thr Cys Leu Ile Ser Pro Val Val Leu Ala Ser Tyr Ala Arg Asn
                 85                  90                  95

Gln Thr Leu Val Ala Leu Ala Pro Glu Ser Arg Ala Cys Thr Tyr Phe
            100                 105                 110

Ala Phe Ala Met Thr Phe Phe Ser Leu Ala Thr Met Leu Met Leu Phe
        115                 120                 125

Ala Met Ala Leu Glu Arg Tyr Leu Ser Ile Gly His Pro Tyr Phe Tyr
130                 135                 140

Gln Arg Arg Val Ser Ala Ser Gly Gly Leu Ala Val Leu Pro Val Ile
145                 150                 155                 160

Tyr Ala Val Ser Leu Leu Phe Cys Ser Leu Pro Leu Leu Asp Tyr Gly
                165                 170                 175

Gln Tyr Val Gln Tyr Cys Pro Gly Thr Trp Cys Phe Ile Arg His Gly
            180                 185                 190

Arg Thr Ala Tyr Leu Gln Leu Tyr Ala Thr Leu Leu Leu Leu Leu Ile
        195                 200                 205

Val Ser Val Leu Ala Cys Asn Phe Ser Val Ile Leu Asn Leu Ile Arg
210                 215                 220

Met His Arg Arg Ser Arg Arg Ser Arg Cys Gly Pro Ser Leu Gly Ser
225                 230                 235                 240

Gly Arg Gly Gly Pro Gly Ala Arg Arg Gly Glu Arg Val Ser Met
                245                 250                 255

Ala Glu Glu Thr Asp His Leu Ile Leu Leu Ala Ile Met Thr Ile Thr
            260                 265                 270

Phe Ala Val Cys Ser Leu Pro Phe Thr Ile Phe Ala Tyr Met Asn Glu
        275                 280                 285

Thr Ser Ser Arg Lys Glu Lys Trp Asp Leu Gln Ala Leu Arg Phe Leu
290                 295                 300

Ser Ile Asn Ser Ile Ile Asp Pro Trp Val Phe Ala Ile Leu Arg Pro
305                 310                 315                 320

Pro Val Leu Arg Leu Met Arg Ser Val Leu Cys Cys Arg Ile Ser Leu
                325                 330                 335

Arg Thr Gln Asp Ala Thr Gln Thr Ser Cys Ser Thr Gln Ser Asp Ala
            340                 345                 350

Ser Lys Gln Ala Asp Leu
        355

<210> SEQ ID NO 37
<211> LENGTH: 5910
<212> TYPE: DNA
<213> ORGANISM: Homo Sapiens
<220> FEATURE:
<221> NAME/KEY: CDS
<222> LOCATION: (337)...(4632)

<400> SEQUENCE: 37
cggaggacag ccggaccgag ccaacgccgg ggactttgtt ccctccacgg aggggactcg    60
gcaactcgca gcggcagggt ctggggccgg cgcctgggag ggatctgcgc ccccccactca   120
```

-continued

```
ctccctagct gtgttcccgc cgccgccccg gctagtctcc ggcgctggcg cctatggtcg      180
gcctccgaca gcgctccgga gggaccgggg gagctcccag gcgcccggga ctggagactg      240
atgcatgagg ggcctacgga ggcgcaggag cggtggtgat ggtctgggaa gcggagctga      300
agtcccctgg gctttggtga ggcgtgacag tttatc atg acc gtg ttc agg cag        354
                                    Met Thr Val Phe Arg Gln
                                     1               5 gaa aac gtg gat gat tac tac gac acc ggc gag gaa ctt ggc agt gga        402
Glu Asn Val Asp Asp Tyr Tyr Asp Thr Gly Glu Glu Leu Gly Ser Gly
            10                  15                  20 cag ttt gcg gtt gtg aag aaa tgc cgt gag aaa agt acc ggc ctc cag        450
Gln Phe Ala Val Val Lys Lys Cys Arg Glu Lys Ser Thr Gly Leu Gln
        25                  30                  35 tat gcc gcc aaa ttc atc aag aaa agg agg act aag tcc agc cgg cgg        498
Tyr Ala Ala Lys Phe Ile Lys Lys Arg Arg Thr Lys Ser Ser Arg Arg
    40                  45                  50 ggt gtg agc cgc gag gac atc gag cgg gag gtc agc atc ctg aag gag        546
Gly Val Ser Arg Glu Asp Ile Glu Arg Glu Val Ser Ile Leu Lys Glu
55                  60                  65                  70 atc cag cac ccc aat gtc atc acc ctg cac gag gtc tat gag aac aag        594
Ile Gln His Pro Asn Val Ile Thr Leu His Glu Val Tyr Glu Asn Lys
                75                  80                  85 acg gac gtc atc ctg atc ttg gaa ctc gtt gca ggt ggc gag ctg ttt        642
Thr Asp Val Ile Leu Ile Leu Glu Leu Val Ala Gly Gly Glu Leu Phe
            90                  95                 100 gac ttc tta gct gaa aag gaa tct tta act gaa gag gaa gca act gaa        690
Asp Phe Leu Ala Glu Lys Glu Ser Leu Thr Glu Glu Glu Ala Thr Glu
        105                 110                 115 ttt ctc aaa caa att ctt aat ggt gtt tac tac ctg cac tcc ctt caa        738
Phe Leu Lys Gln Ile Leu Asn Gly Val Tyr Tyr Leu His Ser Leu Gln
    120                 125                 130 atc gcc cac ttt gat ctt aag cct gag aac ata atg ctt ttg gat aga        786
Ile Ala His Phe Asp Leu Lys Pro Glu Asn Ile Met Leu Leu Asp Arg
135                 140                 145                 150 aat gtc ccc aaa cct cgg atc aag atc att gac ttt ggg ttg gcc cat        834
Asn Val Pro Lys Pro Arg Ile Lys Ile Ile Asp Phe Gly Leu Ala His
                155                 160                 165 aaa att gac ttt gga aat gaa ttt aaa aac ata ttt ggg act cca gag        882
Lys Ile Asp Phe Gly Asn Glu Phe Lys Asn Ile Phe Gly Thr Pro Glu
            170                 175                 180 ttt gtc gct cct gag ata gtc aac tat gaa cct ctt ggt ctt gag gca        930
Phe Val Ala Pro Glu Ile Val Asn Tyr Glu Pro Leu Gly Leu Glu Ala
        185                 190                 195 gat atg tgg agt atc ggg gta ata acc tat atc ctc cta agt ggg gcc        978
Asp Met Trp Ser Ile Gly Val Ile Thr Tyr Ile Leu Leu Ser Gly Ala
    200                 205                 210 tcc cca ttt ctt gga gac act aag caa gaa acg tta gca aat gta tcc       1026
Ser Pro Phe Leu Gly Asp Thr Lys Gln Glu Thr Leu Ala Asn Val Ser
215                 220                 225                 230 gct gtc aac tac gaa ttt gag gat gaa tac ttc agt aat acc agt gcc       1074
Ala Val Asn Tyr Glu Phe Glu Asp Glu Tyr Phe Ser Asn Thr Ser Ala
                235                 240                 245 cta gcc aaa gat ttc ata aga aga ctt ctg gtc aag gat cca aag aag       1122
Leu Ala Lys Asp Phe Ile Arg Arg Leu Leu Val Lys Asp Pro Lys Lys
            250                 255                 260 aga atg aca att caa gat agt ttg cag cat ccc tgg atc aag cct aaa       1170
Arg Met Thr Ile Gln Asp Ser Leu Gln His Pro Trp Ile Lys Pro Lys
        265                 270                 275
```

```
gat aca caa cag gca ctt agt aga aaa gca tca gca gta aac atg gag      1218
Asp Thr Gln Gln Ala Leu Ser Arg Lys Ala Ser Ala Val Asn Met Glu
    280                 285                 290 aaa ttc aag aag ttt gca gcc cgg aaa aaa tgg aaa caa tcc gtt cgc      1266
Lys Phe Lys Lys Phe Ala Ala Arg Lys Lys Trp Lys Gln Ser Val Arg
295                 300                 305                 310 ttg ata tca ctg tgc caa aga tta tcc agg tca ttc ctg tcc aga agt      1314
Leu Ile Ser Leu Cys Gln Arg Leu Ser Arg Ser Phe Leu Ser Arg Ser
                315                 320                 325 aac atg agt gtt gcc aga agc gat gat act ctg gat gag gaa gac tcc      1362
Asn Met Ser Val Ala Arg Ser Asp Asp Thr Leu Asp Glu Glu Asp Ser
            330                 335                 340 ttt gtg atg aaa gcc atc atc cat gcc atc aac gat gac aat gtc cca      1410
Phe Val Met Lys Ala Ile Ile His Ala Ile Asn Asp Asp Asn Val Pro
        345                 350                 355 ggc ctg cag cac ctt ctg ggc tca tta tcc aac tat gat gtt aac caa      1458
Gly Leu Gln His Leu Leu Gly Ser Leu Ser Asn Tyr Asp Val Asn Gln
    360                 365                 370 ccc aac aag cac ggg aca cct cca tta ctc att gct gct ggc tgt ggg      1506
Pro Asn Lys His Gly Thr Pro Pro Leu Leu Ile Ala Ala Gly Cys Gly
375                 380                 385                 390 aat att caa ata cta cag ttg ctc att aaa aga ggc tcg aga atc gat      1554
Asn Ile Gln Ile Leu Gln Leu Leu Ile Lys Arg Gly Ser Arg Ile Asp
                395                 400                 405 gtc cag gat aag ggc ggg tcc aat gcc gtc tac tgg gct gct cgg cat      1602
Val Gln Asp Lys Gly Gly Ser Asn Ala Val Tyr Trp Ala Ala Arg His
            410                 415                 420 ggc cac gtc gat acc ttg aaa ttt ctc agt gag aac aaa tgc cct ttg      1650
Gly His Val Asp Thr Leu Lys Phe Leu Ser Glu Asn Lys Cys Pro Leu
        425                 430                 435 gat gtg aaa gac aag tct gga gag atg gcc ctc cac gtg gca gct cgc      1698
Asp Val Lys Asp Lys Ser Gly Glu Met Ala Leu His Val Ala Ala Arg
    440                 445                 450 tat ggc cat gct gac gtg gct caa gtt act tgt gca gct tcg gct caa      1746
Tyr Gly His Ala Asp Val Ala Gln Val Thr Cys Ala Ala Ser Ala Gln
455                 460                 465                 470 atc cca ata tcc agg aca aag gaa gaa gaa acc ccc ctg cac tgt gct      1794
Ile Pro Ile Ser Arg Thr Lys Glu Glu Glu Thr Pro Leu His Cys Ala
                475                 480                 485 gct tgg cac ggc tat tac tct gtg gcc aaa gcc ctt tgt gaa gcc ggc      1842
Ala Trp His Gly Tyr Tyr Ser Val Ala Lys Ala Leu Cys Glu Ala Gly
            490                 495                 500 tgt aac gtg aac atc aag aac cga gaa gga gag acg ccc ctc ctg aca      1890
Cys Asn Val Asn Ile Lys Asn Arg Glu Gly Glu Thr Pro Leu Leu Thr
        505                 510                 515 gcc tct gcc agg ggc tac cac gac atc gtg gag tgt ctg gcc gaa cat      1938
Ala Ser Ala Arg Gly Tyr His Asp Ile Val Glu Cys Leu Ala Glu His
    520                 525                 530 gga gcc gac ctt aat gct tgc gac aag gac gga cac att gcc ctt cat      1986
Gly Ala Asp Leu Asn Ala Cys Asp Lys Asp Gly His Ile Ala Leu His
535                 540                 545                 550 ctg gct gta aga cgg tgt cag atg gag gta atc aag act ctc ctc agc      2034
Leu Ala Val Arg Arg Cys Gln Met Glu Val Ile Lys Thr Leu Leu Ser
                555                 560                 565 caa ggg tgt ttc gtc gat tat caa gac agg cac ggc aat act ccc ctc      2082
Gln Gly Cys Phe Val Asp Tyr Gln Asp Arg His Gly Asn Thr Pro Leu
            570                 575                 580 cat gtg gca tgt aaa gat ggc aac atg cct atc gtg gtg gcc ctc tgt      2130
His Val Ala Cys Lys Asp Gly Asn Met Pro Ile Val Val Ala Leu Cys
        585                 590                 595
```

-continued

```
gaa gca aac tgc aat ttg gac atc tcc aac aag tat ggg cga acg cct      2178
Glu Ala Asn Cys Asn Leu Asp Ile Ser Asn Lys Tyr Gly Arg Thr Pro
    600                 605                 610 ctg cac ctt gcg gcc aac aac gga atc cta gac gtg gtc cgg tat ctc      2226
Leu His Leu Ala Ala Asn Asn Gly Ile Leu Asp Val Val Arg Tyr Leu
615                 620                 625                 630 tgt ctg atg gga gcc agc gtt gag gcg ctg acc acg gac gga aag acg      2274
Cys Leu Met Gly Ala Ser Val Glu Ala Leu Thr Thr Asp Gly Lys Thr
                635                 640                 645 gca gaa gat ctt gct aga tcg gaa cag cac gag cac gta gca ggt ctc      2322
Ala Glu Asp Leu Ala Arg Ser Glu Gln His Glu His Val Ala Gly Leu
        650                 655                 660 ctt gca aga ctt cga aag gat acg cac cga gga ctc ttc atc cag cag      2370
Leu Ala Arg Leu Arg Lys Asp Thr His Arg Gly Leu Phe Ile Gln Gln
    665                 670                 675 ctc cga ccc aca cag aac ctg cag cca aga att aag ctc aag ctg ttt      2418
Leu Arg Pro Thr Gln Asn Leu Gln Pro Arg Ile Lys Leu Lys Leu Phe
680                 685                 690 ggc cac tcg gga tcc ggg aaa acc acc ctt gta gaa tct ctc aag tgt      2466
Gly His Ser Gly Ser Gly Lys Thr Thr Leu Val Glu Ser Leu Lys Cys
695                 700                 705                 710 ggg ctg ctg agg agc ttt ttc aga agg cgt cgg ccc aga ctg tct tcc      2514
Gly Leu Leu Arg Ser Phe Phe Arg Arg Arg Pro Arg Leu Ser Ser
                715                 720                 725 acc aac tcc agc agg ttc cca cct tca ccc ctg gct tct aag ccc aca      2562
Thr Asn Ser Ser Arg Phe Pro Pro Ser Pro Leu Ala Ser Lys Pro Thr
        730                 735                 740 gtc tca gtg agc atc aac aac ctg tac cca ggc tgc gag aac gtg agt      2610
Val Ser Val Ser Ile Asn Asn Leu Tyr Pro Gly Cys Glu Asn Val Ser
    745                 750                 755 gtg agg agc cgc agc atg atg ttc gag ccg ggt ctt acc aaa ggg atg      2658
Val Arg Ser Arg Ser Met Met Phe Glu Pro Gly Leu Thr Lys Gly Met
760                 765                 770 ctg gag gtg ttt gtg gcc ccg acc cac cac ccg cac tgc tcg gcc gat      2706
Leu Glu Val Phe Val Ala Pro Thr His His Pro His Cys Ser Ala Asp
775                 780                 785                 790 gac cag tcc acc aag gcc atc gac atc cag aac gct tat ttg aat gga      2754
Asp Gln Ser Thr Lys Ala Ile Asp Ile Gln Asn Ala Tyr Leu Asn Gly
                795                 800                 805 gtt ggc gat ttc agc gtg tgg gag ttc tct gga aat cct gtg tat ttc      2802
Val Gly Asp Phe Ser Val Trp Glu Phe Ser Gly Asn Pro Val Tyr Phe
        810                 815                 820 tgc tgt tat gac tat ttt gct gca aat gat ccc acg tca atc cat gtt      2850
Cys Cys Tyr Asp Tyr Phe Ala Ala Asn Asp Pro Thr Ser Ile His Val
    825                 830                 835 gtt gtc ttt agt cta gaa gag ccc tat gag atc cag ctg aac cca gtg      2898
Val Val Phe Ser Leu Glu Glu Pro Tyr Glu Ile Gln Leu Asn Pro Val
840                 845                 850 att ttc tgg ctc agt ttc ctg aag tcc ctt gtc cca gtt gaa gaa ccc      2946
Ile Phe Trp Leu Ser Phe Leu Lys Ser Leu Val Pro Val Glu Glu Pro
855                 860                 865                 870 ata gcc ttc ggt ggc aag ctg aag aac cca ctc caa gtt gtc ctg gtg      2994
Ile Ala Phe Gly Gly Lys Leu Lys Asn Pro Leu Gln Val Val Leu Val
                875                 880                 885 gcc acc cac gct gac atc atg aat gtt cct cga ccg gct gga ggc gag      3042
Ala Thr His Ala Asp Ile Met Asn Val Pro Arg Pro Ala Gly Gly Glu
        890                 895                 900 ttt gga tat gac aaa gac aca tcg ttg ctg aaa gag att agg aac agg      3090
Phe Gly Tyr Asp Lys Asp Thr Ser Leu Leu Lys Glu Ile Arg Asn Arg
```

-continued

```
             905                 910                 915
ttt gga aat gat ctt cac att tca aat aag ctg ttt gtt ctg gat gct      3138
Phe Gly Asn Asp Leu His Ile Ser Asn Lys Leu Phe Val Leu Asp Ala
    920                 925                 930 ggg gct tct ggg tca aag gac atg aag gta ctt cga aat cat ctg caa      3186
Gly Ala Ser Gly Ser Lys Asp Met Lys Val Leu Arg Asn His Leu Gln
935                 940                 945                 950 gaa ata cga agc cag att gtt tcg gtc tgt cct ccc atg act cac ctg      3234
Glu Ile Arg Ser Gln Ile Val Ser Val Cys Pro Pro Met Thr His Leu
                955                 960                 965 tgt gag aaa atc atc tcc acg ctg cct tcc tgg agg aag ctc aat gga      3282
Cys Glu Lys Ile Ile Ser Thr Leu Pro Ser Trp Arg Lys Leu Asn Gly
            970                 975                 980 ccc aac cag ctg atg tcg ctg cag cag ttt gtg tac gac gtg cag gac      3330
Pro Asn Gln Leu Met Ser Leu Gln Gln Phe Val Tyr Asp Val Gln Asp
        985                 990                 995 cag ctg aac ccc ctg gcc agc gag gag gac ctc agg cgc att gct cag      3378
Gln Leu Asn Pro Leu Ala Ser Glu Glu Asp Leu Arg Arg Ile Ala Gln
    1000                1005                1010 cag ctc cac agc aca ggc gag atc aac atc atg caa agt gaa aca gtt      3426
Gln Leu His Ser Thr Gly Glu Ile Asn Ile Met Gln Ser Glu Thr Val
1015                1020                1025                1030 cag gac gtg ctc ctg ctg gac ccc cgc tgg ctc tgc aca aac gtc ctg      3474
Gln Asp Val Leu Leu Leu Asp Pro Arg Trp Leu Cys Thr Asn Val Leu
                1035                1040                1045 ggg aag ttg ctg tcc gtg gag acc cca cgg gcg ctg cac cac tac cgg      3522
Gly Lys Leu Leu Ser Val Glu Thr Pro Arg Ala Leu His His Tyr Arg
            1050                1055                1060 ggc cgc tac acc gtg gag gac atc cag cgc ctg gtg ccc gac agc gac      3570
Gly Arg Tyr Thr Val Glu Asp Ile Gln Arg Leu Val Pro Asp Ser Asp
        1065                1070                1075 gtg gag gag ctg ctg cag atc ctc gat gcc atg gac atc tgc gcc cgg      3618
Val Glu Glu Leu Leu Gln Ile Leu Asp Ala Met Asp Ile Cys Ala Arg
    1080                1085                1090 gac ctg agc agc ggg acc atg gtg gac gtc cca gcc ctg atc aag aca      3666
Asp Leu Ser Ser Gly Thr Met Val Asp Val Pro Ala Leu Ile Lys Thr
1095                1100                1105                1110 gac aac ctg cac cgc tcc tgg gct gat gag gag gac gag gtg atg gtg      3714
Asp Asn Leu His Arg Ser Trp Ala Asp Glu Glu Asp Glu Val Met Val
                1115                1120                1125 tat ggt ggc gtg cgc atc gtg ccc gtg gaa cac ctc acc ccc ttc cca      3762
Tyr Gly Gly Val Arg Ile Val Pro Val Glu His Leu Thr Pro Phe Pro
            1130                1135                1140 tgt ggc atc ttt cac aag gtc cag gtg aac ctg tgc cgg tgg atc cac      3810
Cys Gly Ile Phe His Lys Val Gln Val Asn Leu Cys Arg Trp Ile His
        1145                1150                1155 cag caa agc aca gag ggc gac gcg gac atc cgc ctg tgg gtg aat ggc      3858
Gln Gln Ser Thr Glu Gly Asp Ala Asp Ile Arg Leu Trp Val Asn Gly
    1160                1165                1170 tgc aag ctg gcc aac cgt ggg gcc gag ctg ctg gtg ctg ctg gtc aac      3906
Cys Lys Leu Ala Asn Arg Gly Ala Glu Leu Leu Val Leu Leu Val Asn
1175                1180                1185                1190 cac ggc cag ggc att gag gtc cag gtc cgt ggc ctg gag acg gag aag      3954
His Gly Gln Gly Ile Glu Val Gln Val Arg Gly Leu Glu Thr Glu Lys
                1195                1200                1205 atc aag tgc tgc ctg ctg ctg gac tcg gtg tgc agc acc att gag aac      4002
Ile Lys Cys Cys Leu Leu Leu Asp Ser Val Cys Ser Thr Ile Glu Asn
            1210                1215                1220 gtc atg gcc acc acg ctg cca ggg ctc ctg acc gtg aag cat tac ctg      4050
```

-continued

```
Val Met Ala Thr Thr Leu Pro Gly Leu Leu Thr Val Lys His Tyr Leu
    1225                1230                1235 agc ccc cag cag ctg cgg gag cac cat gag ccc gtc atg atc tac cag    4098
Ser Pro Gln Gln Leu Arg Glu His His Glu Pro Val Met Ile Tyr Gln
    1240                1245                1250 cca cgg gac ttc ttc cgg gca cag act ctg aag gaa acc tca ctg acc    4146
Pro Arg Asp Phe Phe Arg Ala Gln Thr Leu Lys Glu Thr Ser Leu Thr
1255                1260                1265                1270 aac acc atg ggg ggg tac aag gaa agc ttc agc agc atc atg tgc ttc    4194
Asn Thr Met Gly Gly Tyr Lys Glu Ser Phe Ser Ser Ile Met Cys Phe
            1275                1280                1285 ggg tgt cac gac gtc tac tca cag gcc agc ctc ggc atg gac atc cat    4242
Gly Cys His Asp Val Tyr Ser Gln Ala Ser Leu Gly Met Asp Ile His
                1290                1295                1300 gca tca gac ctg aac ctc ctc act cgg agg aaa ctg agt cgc ctg ctg    4290
Ala Ser Asp Leu Asn Leu Leu Thr Arg Arg Lys Leu Ser Arg Leu Leu
            1305                1310                1315 gac ccg ccc gac ccc ctg ggg aag gac tgg tgc ctt ctc gcc atg aac    4338
Asp Pro Pro Asp Pro Leu Gly Lys Asp Trp Cys Leu Leu Ala Met Asn
    1320                1325                1330 tta ggc ctc cct gac ctc gtg gca aag tac aac acc aat aac ggg gct    4386
Leu Gly Leu Pro Asp Leu Val Ala Lys Tyr Asn Thr Asn Asn Gly Ala
1335                1340                1345                1350 ccc aag gat ttc ctc ccc agc ccc ctc cac gcc ctg ctg cgg gaa tgg    4434
Pro Lys Asp Phe Leu Pro Ser Pro Leu His Ala Leu Leu Arg Glu Trp
            1355                1360                1365 acc acc tac cct gag agc aca gtg ggc acc ctc atg tcc aaa ctg agg    4482
Thr Thr Tyr Pro Glu Ser Thr Val Gly Thr Leu Met Ser Lys Leu Arg
                1370                1375                1380 gag ctg ggt cgc cgg gat gcc gca gac ctt ttg ctg aag gca tcc tct    4530
Glu Leu Gly Arg Arg Asp Ala Ala Asp Leu Leu Leu Lys Ala Ser Ser
            1385                1390                1395 gtg ttc aaa atc aac ctg gat ggc aat ggc cag gag gcc tat gcc tcg    4578
Val Phe Lys Ile Asn Leu Asp Gly Asn Gly Gln Glu Ala Tyr Ala Ser
    1400                1405                1410 agc tgc aac agc ggc acc tct tac aat tcc att agc tct gtt gta tcc    4626
Ser Cys Asn Ser Gly Thr Ser Tyr Asn Ser Ile Ser Ser Val Val Ser
1415                1420                1425                1430 cgg tga gggcagcctc tggcttggac agggtctgtt tggactgcag aaccaagggg    4682
Arg * gtgatgtagc ccatccttcc ctttggagat gctgagggtg tttcttcctg cacccacagc    4742 caggggatg ccactcctcc ctccggcttg acctgtttct ctgccgctac ctccctcccc    4802
gtctcattcc gttgtctgtg atggtcatt gcagtttaag agcagaacag atcttttact    4862
ttggccgctt gaaaagctag tgtacctcct ctcagtgttt tggactccat ctctcatcct    4922
ccagtacctt gcttcttact gataattttg ctggaattcc taacttttca atgacatttt    4982
ttttaactat catattgatt gtcctttaaa aagaaaagt gcatatttat ccaaaatgtg    5042
tatttcttat acgcttttct gtgttatacc atttcctcag cttatctctt ttatatttgt    5102
aggagaaact cccatgtatg gaatcccact gtatgattta taaacagaca atatgtgagt    5162
gccttttgca gaagagggtg tgtttgaaat catcggagtc agccaggagc tgtcaccaag    5222
gaaacgctac ctctctgtcc cttgctgtat gctgatcatc gccagaggtg cttcaccctg    5282
agttttgttt tgtattgttt tctgacagtt tttctgtttt gtttggcaag gaaaggggag    5342
aagggaatcc tcctccaggg tgattttatg atcagtgttg ttgctctagg aagacatttt    5402
tccgtttgct tttgttccaa tgtcaatgtg aacgtccaca tgaaacctac acactgtcat    5462
```

-continued

```
gcttcatcat tccctctcat ctcaggtaga aggttgacac agttgtaggg ttacagagac      5522
ctatgtaaga attcagaaga cccctgactc atcatttgtg gcagtccctt ataattggtg      5582
catagcagat ggtttccaca tttagatcct ggtttcataa cttcctgtac ttgaagtcta      5642
aaagcagaaa ataaaggaag caagttttct tccatgattt taaattgtga tcgagtttta      5702
aattgatagg agggaacatg tcctaattct tctgtcctga aagcatgta atgttaatgt       5762 tatatcatat gtatatatat atatgcacta tgtatataca tatatattaa tactggtatt      5822
tttacttaat ctataaaatg tcgttaaaaa gttgtttgtt tttttctttt tttataaata      5882
aactgttgct cgttaaaaaa aaaaaaaa                                         5910
```

<210> SEQ ID NO 38
<211> LENGTH: 1431
<212> TYPE: PRT
<213> ORGANISM: Homo Sapiens

<400> SEQUENCE: 38

```
Met Thr Val Phe Arg Gln Glu Asn Val Asp Asp Tyr Tyr Asp Thr Gly
1               5                   10                  15

Glu Glu Leu Gly Ser Gly Gln Phe Ala Val Val Lys Lys Cys Arg Glu
            20                  25                  30

Lys Ser Thr Gly Leu Gln Tyr Ala Ala Lys Phe Ile Lys Lys Arg Arg
        35                  40                  45

Thr Lys Ser Ser Arg Arg Gly Val Ser Arg Glu Asp Ile Glu Arg Glu
    50                  55                  60

Val Ser Ile Leu Lys Glu Ile Gln His Pro Asn Val Ile Thr Leu His
65                  70                  75                  80

Glu Val Tyr Glu Asn Lys Thr Asp Val Ile Leu Ile Leu Glu Leu Val
                85                  90                  95

Ala Gly Gly Glu Leu Phe Asp Phe Leu Ala Glu Lys Glu Ser Leu Thr
            100                 105                 110

Glu Glu Glu Ala Thr Glu Phe Leu Lys Gln Ile Leu Asn Gly Val Tyr
        115                 120                 125

Tyr Leu His Ser Leu Gln Ile Ala His Phe Asp Leu Lys Pro Glu Asn
    130                 135                 140

Ile Met Leu Leu Asp Arg Asn Val Pro Lys Pro Arg Ile Lys Ile Ile
145                 150                 155                 160

Asp Phe Gly Leu Ala His Lys Ile Asp Phe Gly Asn Glu Phe Lys Asn
                165                 170                 175

Ile Phe Gly Thr Pro Glu Phe Val Ala Pro Glu Ile Val Asn Tyr Glu
            180                 185                 190

Pro Leu Gly Leu Glu Ala Asp Met Trp Ser Ile Gly Val Ile Thr Tyr
        195                 200                 205

Ile Leu Leu Ser Gly Ala Ser Pro Phe Leu Gly Asp Thr Lys Gln Glu
    210                 215                 220

Thr Leu Ala Asn Val Ser Ala Val Asn Tyr Glu Phe Glu Asp Glu Tyr
225                 230                 235                 240

Phe Ser Asn Thr Ser Ala Leu Ala Lys Asp Phe Ile Arg Arg Leu Leu
                245                 250                 255

Val Lys Asp Pro Lys Lys Arg Met Thr Ile Gln Asp Ser Leu Gln His
            260                 265                 270

Pro Trp Ile Lys Pro Lys Asp Thr Gln Gln Ala Leu Ser Arg Lys Ala
        275                 280                 285
```

```
Ser Ala Val Asn Met Glu Lys Phe Lys Lys Phe Ala Ala Arg Lys Lys
    290                 295                 300
Trp Lys Gln Ser Val Arg Leu Ile Ser Leu Cys Gln Arg Leu Ser Arg
305                 310                 315                 320
Ser Phe Leu Ser Arg Ser Asn Met Ser Val Ala Arg Ser Asp Asp Thr
                325                 330                 335
Leu Asp Glu Glu Asp Ser Phe Val Met Lys Ala Ile Ile His Ala Ile
            340                 345                 350
Asn Asp Asp Asn Val Pro Gly Leu Gln His Leu Leu Gly Ser Leu Ser
        355                 360                 365
Asn Tyr Asp Val Asn Gln Pro Asn Lys His Gly Thr Pro Pro Leu Leu
    370                 375                 380
Ile Ala Ala Gly Cys Gly Asn Ile Gln Ile Leu Gln Leu Leu Ile Lys
385                 390                 395                 400
Arg Gly Ser Arg Ile Asp Val Gln Asp Lys Gly Gly Ser Asn Ala Val
                405                 410                 415
Tyr Trp Ala Ala Arg His Gly His Val Asp Thr Leu Lys Phe Leu Ser
            420                 425                 430
Glu Asn Lys Cys Pro Leu Asp Val Lys Asp Lys Ser Gly Glu Met Ala
        435                 440                 445
Leu His Val Ala Ala Arg Tyr Gly His Ala Asp Val Ala Gln Val Thr
    450                 455                 460
Cys Ala Ala Ser Ala Gln Ile Pro Ile Ser Arg Thr Lys Glu Glu Glu
465                 470                 475                 480
Thr Pro Leu His Cys Ala Ala Trp His Gly Tyr Tyr Ser Val Ala Lys
                485                 490                 495
Ala Leu Cys Glu Ala Gly Cys Asn Val Asn Ile Lys Asn Arg Glu Gly
            500                 505                 510
Glu Thr Pro Leu Leu Thr Ala Ser Ala Arg Gly Tyr His Asp Ile Val
        515                 520                 525
Glu Cys Leu Ala Glu His Gly Ala Asp Leu Asn Ala Cys Asp Lys Asp
    530                 535                 540
Gly His Ile Ala Leu His Leu Ala Val Arg Arg Cys Gln Met Glu Val
545                 550                 555                 560
Ile Lys Thr Leu Leu Ser Gln Gly Cys Phe Val Asp Tyr Gln Asp Arg
                565                 570                 575
His Gly Asn Thr Pro Leu His Val Ala Cys Lys Asp Gly Asn Met Pro
            580                 585                 590
Ile Val Val Ala Leu Cys Glu Ala Asn Cys Asn Leu Asp Ile Ser Asn
        595                 600                 605
Lys Tyr Gly Arg Thr Pro Leu His Leu Ala Ala Asn Asn Gly Ile Leu
    610                 615                 620
Asp Val Val Arg Tyr Leu Cys Leu Met Gly Ala Ser Val Glu Ala Leu
625                 630                 635                 640
Thr Thr Asp Gly Lys Thr Ala Glu Asp Leu Ala Arg Ser Glu Gln His
                645                 650                 655
Glu His Val Ala Gly Leu Leu Ala Arg Leu Arg Lys Asp Thr His Arg
            660                 665                 670
Gly Leu Phe Ile Gln Gln Leu Arg Pro Thr Gln Asn Leu Gln Pro Arg
        675                 680                 685
Ile Lys Leu Lys Leu Phe Gly His Ser Gly Ser Gly Lys Thr Thr Leu
    690                 695                 700
Val Glu Ser Leu Lys Cys Gly Leu Leu Arg Ser Phe Phe Arg Arg Arg
```

```
             705                 710                 715                 720
Arg Pro Arg Leu Ser Ser Thr Asn Ser Ser Arg Phe Pro Pro Ser Pro
                725                 730                 735
Leu Ala Ser Lys Pro Thr Val Ser Val Ser Ile Asn Asn Leu Tyr Pro
                740                 745                 750
Gly Cys Glu Asn Val Ser Val Arg Ser Arg Ser Met Met Phe Glu Pro
                755                 760                 765
Gly Leu Thr Lys Gly Met Leu Glu Val Phe Val Ala Pro Thr His His
                770                 775                 780
Pro His Cys Ser Ala Asp Asp Gln Ser Thr Lys Ala Ile Asp Ile Gln
785                 790                 795                 800
Asn Ala Tyr Leu Asn Gly Val Gly Asp Phe Ser Val Trp Glu Phe Ser
                805                 810                 815
Gly Asn Pro Val Tyr Phe Cys Cys Tyr Asp Tyr Phe Ala Ala Asn Asp
                820                 825                 830
Pro Thr Ser Ile His Val Val Phe Ser Leu Glu Glu Pro Tyr Glu
                835                 840                 845
Ile Gln Leu Asn Pro Val Ile Phe Trp Leu Ser Phe Leu Lys Ser Leu
                850                 855                 860
Val Pro Val Glu Glu Pro Ile Ala Phe Gly Gly Lys Leu Lys Asn Pro
865                 870                 875                 880
Leu Gln Val Val Leu Val Ala Thr His Ala Asp Ile Met Asn Val Pro
                885                 890                 895
Arg Pro Ala Gly Gly Glu Phe Gly Tyr Asp Lys Asp Thr Ser Leu Leu
                900                 905                 910
Lys Glu Ile Arg Asn Arg Phe Gly Asn Asp Leu His Ile Ser Asn Lys
                915                 920                 925
Leu Phe Val Leu Asp Ala Gly Ala Ser Gly Ser Lys Asp Met Lys Val
                930                 935                 940
Leu Arg Asn His Leu Gln Glu Ile Arg Ser Gln Ile Val Ser Val Cys
945                 950                 955                 960
Pro Pro Met Thr His Leu Cys Glu Lys Ile Ile Ser Thr Leu Pro Ser
                965                 970                 975
Trp Arg Lys Leu Asn Gly Pro Asn Gln Leu Met Ser Leu Gln Gln Phe
                980                 985                 990
Val Tyr Asp Val Gln Asp Gln Leu Asn Pro Leu Ala Ser Glu Glu Asp
                995                 1000                1005
Leu Arg Arg Ile Ala Gln Gln Leu His Ser Thr Gly Glu Ile Asn Ile
                1010                1015                1020
Met Gln Ser Glu Thr Val Gln Asp Val Leu Leu Leu Asp Pro Arg Trp
1025                1030                1035                1040
Leu Cys Thr Asn Val Leu Gly Lys Leu Leu Ser Val Glu Thr Pro Arg
                1045                1050                1055
Ala Leu His His Tyr Arg Gly Arg Tyr Thr Val Glu Asp Ile Gln Arg
                1060                1065                1070
Leu Val Pro Asp Ser Asp Val Glu Glu Leu Leu Gln Ile Leu Asp Ala
                1075                1080                1085
Met Asp Ile Cys Ala Arg Asp Leu Ser Ser Gly Thr Met Val Asp Val
                1090                1095                1100
Pro Ala Leu Ile Lys Thr Asp Asn Leu His Arg Ser Trp Ala Asp Glu
1105                1110                1115                1120
Glu Asp Glu Val Met Val Tyr Gly Gly Val Arg Ile Val Pro Val Glu
                1125                1130                1135
```

His Leu Thr Pro Phe Pro Cys Gly Ile Phe His Lys Val Gln Val Asn
        1140                1145                1150

Leu Cys Arg Trp Ile His Gln Gln Ser Thr Glu Gly Asp Ala Asp Ile
    1155                1160                1165

Arg Leu Trp Val Asn Gly Cys Lys Leu Ala Asn Arg Gly Ala Glu Leu
    1170                1175                1180

Leu Val Leu Val Asn His Gly Gln Gly Ile Glu Val Gln Val Arg
1185                1190                1195                1200

Gly Leu Glu Thr Glu Lys Ile Lys Cys Cys Leu Leu Leu Asp Ser Val
                1205                1210                1215

Cys Ser Thr Ile Glu Asn Val Met Ala Thr Thr Leu Pro Gly Leu Leu
            1220                1225                1230

Thr Val Lys His Tyr Leu Ser Pro Gln Gln Leu Arg Glu His His Glu
        1235                1240                1245

Pro Val Met Ile Tyr Gln Pro Arg Asp Phe Phe Arg Ala Gln Thr Leu
    1250                1255                1260

Lys Glu Thr Ser Leu Thr Asn Thr Met Gly Gly Tyr Lys Glu Ser Phe
1265                1270                1275                1280

Ser Ser Ile Met Cys Phe Gly Cys His Asp Val Tyr Ser Gln Ala Ser
                1285                1290                1295

Leu Gly Met Asp Ile His Ala Ser Asp Leu Asn Leu Leu Thr Arg Arg
            1300                1305                1310

Lys Leu Ser Arg Leu Leu Asp Pro Pro Asp Pro Leu Gly Lys Asp Trp
        1315                1320                1325

Cys Leu Leu Ala Met Asn Leu Gly Leu Pro Asp Leu Val Ala Lys Tyr
    1330                1335                1340

Asn Thr Asn Asn Gly Ala Pro Lys Asp Phe Leu Pro Ser Pro Leu His
1345                1350                1355                1360

Ala Leu Leu Arg Glu Trp Thr Thr Tyr Pro Glu Ser Thr Val Gly Thr
                1365                1370                1375

Leu Met Ser Lys Leu Arg Glu Leu Gly Arg Arg Asp Ala Ala Asp Leu
            1380                1385                1390

Leu Leu Lys Ala Ser Ser Val Phe Lys Ile Asn Leu Asp Gly Asn Gly
        1395                1400                1405

Gln Glu Ala Tyr Ala Ser Ser Cys Asn Ser Gly Thr Ser Tyr Asn Ser
    1410                1415                1420

Ile Ser Ser Val Val Ser Arg
1425                1430

<210> SEQ ID NO 39
<211> LENGTH: 3906
<212> TYPE: DNA
<213> ORGANISM: Homo Sapiens
<220> FEATURE:
<221> NAME/KEY: CDS
<222> LOCATION: (202)...(1974)

<400> SEQUENCE: 39
atcgatgtct gtctgcccta gactccactt atttaaaata agagaatgaa cttgatgttt      60
ggcttcatag agattcagca ccctgtaata ggccttccat gtcttttaac gtatgtaatg     120
caaagaacaa acaaataaag gcagaaattt ttctaactct gtctcttctc tctttccccc     180
agactatgtc agagagtcac a atg acc ttg cac aat aac agt aca acc tcg      231
                        Met Thr Leu His Asn Asn Ser Thr Thr Ser
                          1               5                  10

-continued

| | |
|---|---|
| cct ttg ttt cca aac atc agc tcc tcc tgg ata cac agc ccc tcc gat<br>Pro Leu Phe Pro Asn Ile Ser Ser Ser Trp Ile His Ser Pro Ser Asp<br>                   15                     20                25 | 279 |
| gca ggg ctg ccc ccg gga acc gtc act cat ttc ggc agc tac aat gtt<br>Ala Gly Leu Pro Pro Gly Thr Val Thr His Phe Gly Ser Tyr Asn Val<br>           30                    35                    40 | 327 |
| tct cga gca gct ggc aat ttc tcc tct cca gac ggt acc acc gat gac<br>Ser Arg Ala Ala Gly Asn Phe Ser Ser Pro Asp Gly Thr Thr Asp Asp<br>        45                    50                    55 | 375 |
| cct cta gga ggt cat acc gtc tgg caa gtg gtc ttc atc gct ttc tta<br>Pro Leu Gly Gly His Thr Val Trp Gln Val Val Phe Ile Ala Phe Leu<br>    60                    65                    70 | 423 |
| acg ggc atc ctg gcc ttg gtg acc atc atc ggc aac atc ctg gta att<br>Thr Gly Ile Leu Ala Leu Val Thr Ile Ile Gly Asn Ile Leu Val Ile<br>75                    80                    85                    90 | 471 |
| gtg tca ttt aag gtc aac aag cag ctg aag acg gtc aac aac tac ttc<br>Val Ser Phe Lys Val Asn Lys Gln Leu Lys Thr Val Asn Asn Tyr Phe<br>                   95                   100              105 | 519 |
| ctc tta agc ctg gcc tgt gcc gat ctg att atc ggg gtc att tca atg<br>Leu Leu Ser Leu Ala Cys Ala Asp Leu Ile Ile Gly Val Ile Ser Met<br>           110                   115              120 | 567 |
| aat ctg ttt acg acc tac atc atc atg aat cga tgg gcc tta ggg aac<br>Asn Leu Phe Thr Thr Tyr Ile Ile Met Asn Arg Trp Ala Leu Gly Asn<br>        125                  130                135 | 615 |
| ttg gcc tgt gac ctc tgg ctt gcc att gac tac gta gcc agc aat gcc<br>Leu Ala Cys Asp Leu Trp Leu Ala Ile Asp Tyr Val Ala Ser Asn Ala<br>   140                    145                150 | 663 |
| tct gtt atg aat ctt ctg gtc atc agc ttt gac aga tac ttt tcc atc<br>Ser Val Met Asn Leu Leu Val Ile Ser Phe Asp Arg Tyr Phe Ser Ile<br>155                 160                   165                170 | 711 |
| acg agg ccg ctc acg tac cga gcc aaa cga aca aca aag aga gcc ggt<br>Thr Arg Pro Leu Thr Tyr Arg Ala Lys Arg Thr Thr Lys Arg Ala Gly<br>               175                  180                185 | 759 |
| gtg atg atc ggt ctg gct tgg gtc atc tcc ttt gtc ctt tgg gct cct<br>Val Met Ile Gly Leu Ala Trp Val Ile Ser Phe Val Leu Trp Ala Pro<br>          190                  195              200 | 807 |
| gcc atc ttg ttc tgg caa tac ttt gtt gga aag aga act gtg cct ccg<br>Ala Ile Leu Phe Trp Gln Tyr Phe Val Gly Lys Arg Thr Val Pro Pro<br>        205                  210                215 | 855 |
| gga gag tgc ttc att cag ttc ctc agt gag ccc acc att act ttt ggc<br>Gly Glu Cys Phe Ile Gln Phe Leu Ser Glu Pro Thr Ile Thr Phe Gly<br>   220                    225                230 | 903 |
| aca gcc atc gct gct ttt tat atg cct gtc acc att atg act att tta<br>Thr Ala Ile Ala Ala Phe Tyr Met Pro Val Thr Ile Met Thr Ile Leu<br>235                 240                   245                250 | 951 |
| tac tgg agg atc tat aag gaa act gaa aag cgt acc aaa gag ctt gct<br>Tyr Trp Arg Ile Tyr Lys Glu Thr Glu Lys Arg Thr Lys Glu Leu Ala<br>               255                  260                265 | 999 |
| ggc ctg caa gcc tct ggg aca gag gca gag aca gaa aac ttt gtc cac<br>Gly Leu Gln Ala Ser Gly Thr Glu Ala Glu Thr Glu Asn Phe Val His<br>          270                   275              280 | 1047 |
| ccc acg ggc agt tct cga agc tgc agc agt tac gaa ctt caa cag caa<br>Pro Thr Gly Ser Ser Arg Ser Cys Ser Ser Tyr Glu Leu Gln Gln Gln<br>        285                  290                295 | 1095 |
| agc atg aaa cgc tcc aac agg agg aag tat ggc cgc tgc cac ttc tgg<br>Ser Met Lys Arg Ser Asn Arg Arg Lys Tyr Gly Arg Cys His Phe Trp<br>   300                    305                310 | 1143 |
| ttc aca acc aag agc tgg aaa ccc agc tcc gag cag atg gac caa gac<br>Phe Thr Thr Lys Ser Trp Lys Pro Ser Ser Glu Gln Met Asp Gln Asp<br>315                 320                   325                330 | 1191 |

| | | |
|---|---|---|
| cac agc agc agt gac agt tgg aac aac aat gat gct gct gcc tcc ctg<br>His Ser Ser Ser Asp Ser Trp Asn Asn Asn Asp Ala Ala Ala Ser Leu<br>335 340 345 | | 1239 |
| gag aac tcc gcc tcc tcc gac gag gag gac att ggc tcc gag acg aga<br>Glu Asn Ser Ala Ser Ser Asp Glu Glu Asp Ile Gly Ser Glu Thr Arg<br>350 355 360 | | 1287 |
| gcc atc tac tcc atc gtg ctc aag ctt ccg ggt cac agc acc atc ctc<br>Ala Ile Tyr Ser Ile Val Leu Lys Leu Pro Gly His Ser Thr Ile Leu<br>365 370 375 | | 1335 |
| aac tcc acc aag tta ccc tca tcg gac aac ctg cag gtg cct gag gag<br>Asn Ser Thr Lys Leu Pro Ser Ser Asp Asn Leu Gln Val Pro Glu Glu<br>380 385 390 | | 1383 |
| gag ctg ggg atg gtg gac ttg gag agg aaa gcc gac aag ctg cag gcc<br>Glu Leu Gly Met Val Asp Leu Glu Arg Lys Ala Asp Lys Leu Gln Ala<br>395 400 405 410 | | 1431 |
| cag aag agc gtg gac gat gga ggc agt ttt cca aaa agc ttc tcc aag<br>Gln Lys Ser Val Asp Asp Gly Gly Ser Phe Pro Lys Ser Phe Ser Lys<br>415 420 425 | | 1479 |
| ctt ccc atc cag cta gag tca gcc gtg gac aca gct aag act tct gac<br>Leu Pro Ile Gln Leu Glu Ser Ala Val Asp Thr Ala Lys Thr Ser Asp<br>430 435 440 | | 1527 |
| gtc aac tcc tca gtg ggt aag agc acg gcc act cta cct ctg tcc ttc<br>Val Asn Ser Ser Val Gly Lys Ser Thr Ala Thr Leu Pro Leu Ser Phe<br>445 450 455 | | 1575 |
| aag gaa gcc act ctg gcc aag agg ttt gct ctg aag acc aga agt cag<br>Lys Glu Ala Thr Leu Ala Lys Arg Phe Ala Leu Lys Thr Arg Ser Gln<br>460 465 470 | | 1623 |
| atc act aag cgg aaa agg atg tcc ctg gtc aag gag aag aaa gcg gcc<br>Ile Thr Lys Arg Lys Arg Met Ser Leu Val Lys Glu Lys Lys Ala Ala<br>475 480 485 490 | | 1671 |
| cag acc ctc agt gcg atc ttg ctt gcc ttc atc atc act tgg acc cca<br>Gln Thr Leu Ser Ala Ile Leu Leu Ala Phe Ile Ile Thr Trp Thr Pro<br>495 500 505 | | 1719 |
| tac aac atc atg gtt ctg gtg aac acc ttt tgt gac agc tgc ata ccc<br>Tyr Asn Ile Met Val Leu Val Asn Thr Phe Cys Asp Ser Cys Ile Pro<br>510 515 520 | | 1767 |
| aaa acc ttt tgg aat ctg ggc tac tgg ctg tgc tac atc aac agc acc<br>Lys Thr Phe Trp Asn Leu Gly Tyr Trp Leu Cys Tyr Ile Asn Ser Thr<br>525 530 535 | | 1815 |
| gtg aac ccc gtg tgc tat gct ctg tgc aac aaa aca ttc aga acc act<br>Val Asn Pro Val Cys Tyr Ala Leu Cys Asn Lys Thr Phe Arg Thr Thr<br>540 545 550 | | 1863 |
| ttc aag atg ctg ctg ctg tgc cag tgt gac aaa aaa agg cgc aag<br>Phe Lys Met Leu Leu Leu Cys Gln Cys Asp Lys Lys Arg Arg Lys<br>555 560 565 570 | | 1911 |
| cag cag tac cag cag aga cag tcg gtc att ttt cac aag cgc gca ccc<br>Gln Gln Tyr Gln Gln Arg Gln Ser Val Ile Phe His Lys Arg Ala Pro<br>575 580 585 | | 1959 |
| gag cag gcc ttg tag aatgaggttg tatcaatagc agtgacaaaa cgcacacatc<br>Glu Gln Ala Leu *<br>590 | | 2014 |
| aacccacaga ccttaggagg aggaaggcga gggcggggtg acttctggtg atgataaaaa | | 2074 |
| tggttttatc acccagatgt gaaagaagct gcctgtttac tgatccattg aataaaccca | | 2134 |
| ttttaataga aaaagtcaat accaattcag caaaaagaaa aaaaaaacat actactgaat | | 2194 |
| ataaagaaat ttattctgaa atagacttta cgtgtttttt tcttaaagag gagaaaaata | | 2254 |
| ttgcttgacg gcaattatat acccaaagtg atttgcctgg gtcctttaat tcccattagc | | 2314 |

-continued

```
tttggaatct cagatgagca tagctgaccc agttcccaca ttcttcccaa ggatccaaaa    2374
gtgggaatcc agaccccaag tggaacactg caggcttacg aatctgtggt tccaaaatta    2434
tttcatacgt tgcaaagctg aatcttcttg tcccaataga gcttcctgtc ttttctttgg    2494
tgtgttgtta aactctattt gtggacttga ttcttgattc ttgcaaagta ctgttttgtg    2554
cagttcaagt ttcgtacaaa taaaatactt aagtatatat atatgtgtga gttctgcacg    2614
cacacacata gtgtatataa tatcatggga aacactgaac tggcaaatta ttcctgcaac    2674
atacgctttc agtactttgg taactgaagt tctctaggat cctaatgcaa cattaacgtg    2734
aaataagccc agtgtaatgt ttttgcaaac cagggctgtt ttccacagag agcagccagg    2794
ccttcccagc aggtctgtgc agagcggaca ggctcgtgag tcagctgagc gccgtggctt    2854
cgccagactt ggtgttaagc aacctccttt gttgatgtct aacagagct aaatcggggc    2914
ccctctgagc tcaaagaatg aaccacatcc acacgtttga atttaatcat ctaaatctga    2974
atgtttcaga acaaaatttc tgctatctaa actgcttgaa actcaataat agtgtcacgt    3034
ttgaatgtca tacacagcaa tatatatata tgtgtatata tatatatatg gcaaagcaaa    3094
aaaaaaaaca tggtaagaga gaatgaagga gaacattgtg tttgattctt gctgaatggc    3154
accttctcaa agaaaatagg gcttgcacct ttgttaatca gctgtggcca gtgctttctg    3214
gtgttcattg tgtaaccttc acccaggaat aggtgaggtt ttaggaagtt acatgtcctc    3274
tgaagaaaga attacactct gaaagtaat gcttcaaatt gatttcctta ccttttggga    3334
aaaaaaaaaa attgtttttt tgcattctcc cttgaattga ccaaaatgtt aactgtttca    3394
tttggggagg ggatggggtg ctgccatcat tgtcgttgtt gttgctgctg tagctgttgg    3454
ggtttctttt cctgttgccg gggctgtttg gggagaggga ggggagggag gtgggagggc    3514
cgcggagata tcttcccctt tgtacagggc attctgtgtt gtgaacccag agctgggtag    3574
aagctgcttt tgtattcagt gtgaggtggt gtttacagac gactttgaca acagtagaag    3634
tgtactcagt ggtgtctgtg tatctgaact atttaatttc gtgttatgtt tatatgcaga    3694
aatatttatg gatactacac caagtgttta tttattgttg ataaatatga ctcttcagtc    3754
gtcagccatg gtgtcctttc aaatgattct ttaaggtcca cttgagcaat gaatagagta    3814
tattggagct ttcctgtggc taagaagaag aaacatgtca tcctgttgcc atcaccaagc    3874
acctaactct ttctaggtaa taaaaagtca ac                                  3906
```

<210> SEQ ID NO 40
<211> LENGTH: 590
<212> TYPE: PRT
<213> ORGANISM: Homo Sapiens

<400> SEQUENCE: 40

```
Met Thr Leu His Asn Asn Ser Thr Thr Ser Pro Leu Phe Pro Asn Ile
  1               5                  10                  15

Ser Ser Ser Trp Ile His Ser Pro Ser Asp Ala Gly Leu Pro Pro Gly
             20                  25                  30

Thr Val Thr His Phe Gly Ser Tyr Asn Val Ser Arg Ala Ala Gly Asn
         35                  40                  45

Phe Ser Ser Pro Asp Gly Thr Thr Asp Asp Pro Leu Gly Gly His Thr
     50                  55                  60

Val Trp Gln Val Val Phe Ile Ala Phe Leu Thr Gly Ile Leu Ala Leu
 65                  70                  75                  80

Val Thr Ile Ile Gly Asn Ile Leu Val Ile Val Ser Phe Lys Val Asn
                 85                  90                  95
```

```
Lys Gln Leu Lys Thr Val Asn Asn Tyr Phe Leu Leu Ser Leu Ala Cys
            100                 105                 110

Ala Asp Leu Ile Ile Gly Val Ile Ser Met Asn Leu Phe Thr Thr Tyr
            115                 120                 125

Ile Ile Met Asn Arg Trp Ala Leu Gly Asn Leu Ala Cys Asp Leu Trp
    130                 135                 140

Leu Ala Ile Asp Tyr Val Ala Ser Asn Ala Ser Val Met Asn Leu Leu
145                 150                 155                 160

Val Ile Ser Phe Asp Arg Tyr Phe Ser Ile Thr Arg Pro Leu Thr Tyr
                165                 170                 175

Arg Ala Lys Arg Thr Thr Lys Arg Ala Gly Val Met Ile Gly Leu Ala
                180                 185                 190

Trp Val Ile Ser Phe Val Leu Trp Ala Pro Ala Ile Leu Phe Trp Gln
            195                 200                 205

Tyr Phe Val Gly Lys Arg Thr Val Pro Pro Gly Glu Cys Phe Ile Gln
    210                 215                 220

Phe Leu Ser Glu Pro Thr Ile Thr Phe Gly Thr Ala Ile Ala Ala Phe
225                 230                 235                 240

Tyr Met Pro Val Thr Ile Met Thr Ile Leu Tyr Trp Arg Ile Tyr Lys
                245                 250                 255

Glu Thr Glu Lys Arg Thr Lys Glu Leu Ala Gly Leu Gln Ala Ser Gly
                260                 265                 270

Thr Glu Ala Glu Thr Glu Asn Phe Val His Pro Thr Gly Ser Ser Arg
            275                 280                 285

Ser Cys Ser Ser Tyr Glu Leu Gln Gln Gln Ser Met Lys Arg Ser Asn
    290                 295                 300

Arg Arg Lys Tyr Gly Arg Cys His Phe Trp Phe Thr Thr Lys Ser Trp
305                 310                 315                 320

Lys Pro Ser Ser Glu Gln Met Asp Gln Asp His Ser Ser Ser Asp Ser
                325                 330                 335

Trp Asn Asn Asn Asp Ala Ala Ala Ser Leu Glu Asn Ser Ala Ser Ser
            340                 345                 350

Asp Glu Glu Asp Ile Gly Ser Glu Thr Arg Ala Ile Tyr Ser Ile Val
    355                 360                 365

Leu Lys Leu Pro Gly His Ser Thr Ile Leu Asn Ser Thr Lys Leu Pro
    370                 375                 380

Ser Ser Asp Asn Leu Gln Val Pro Glu Glu Glu Leu Gly Met Val Asp
385                 390                 395                 400

Leu Glu Arg Lys Ala Asp Lys Leu Gln Ala Gln Lys Ser Val Asp Asp
                405                 410                 415

Gly Gly Ser Phe Pro Lys Ser Phe Ser Lys Leu Pro Ile Gln Leu Glu
            420                 425                 430

Ser Ala Val Asp Thr Ala Lys Thr Ser Asp Val Asn Ser Ser Val Gly
            435                 440                 445

Lys Ser Thr Ala Thr Leu Pro Leu Ser Phe Lys Glu Ala Thr Leu Ala
450                 455                 460

Lys Arg Phe Ala Leu Lys Thr Arg Ser Gln Ile Thr Lys Arg Lys Arg
465                 470                 475                 480

Met Ser Leu Val Lys Glu Lys Lys Ala Ala Gln Thr Leu Ser Ala Ile
                485                 490                 495

Leu Leu Ala Phe Ile Ile Thr Trp Thr Pro Tyr Asn Ile Met Val Leu
            500                 505                 510
```

```
Val Asn Thr Phe Cys Asp Ser Cys Ile Pro Lys Thr Phe Trp Asn Leu
        515                 520                 525

Gly Tyr Trp Leu Cys Tyr Ile Asn Ser Thr Val Asn Pro Val Cys Tyr
    530                 535                 540

Ala Leu Cys Asn Lys Thr Phe Arg Thr Thr Phe Lys Met Leu Leu Leu
545                 550                 555                 560

Cys Gln Cys Asp Lys Lys Arg Arg Lys Gln Gln Tyr Gln Gln Arg
                565                 570                 575

Gln Ser Val Ile Phe His Lys Arg Ala Pro Glu Gln Ala Leu
            580                 585                 590

<210> SEQ ID NO 41
<211> LENGTH: 2416
<212> TYPE: DNA
<213> ORGANISM: Homo Sapiens
<220> FEATURE:
<221> NAME/KEY: CDS
<222> LOCATION: (217)...(1233)

<400> SEQUENCE: 41
```

| | | |
|---|---|---|
| gaacagtgtt accttggagc ctacaatgag aggtatttca aaatgagtga agcatgactc | 60 |
| tcacagatga aggcctagac gcaggatctt taatggaaaa acacttgggc cacttcaaga | 120 |
| cgacaaacgc tcactgggca aaacaccttc actgaaaaga gacctcatat tatgcaaaaa | 180 |
| aaatcttaag aggcctctgc cttcagaagt tacaag atg atc aat tca acc tcc | 234 |
|  | Met Ile Asn Ser Thr Ser | |
|  | 1               5 | |
| aca cag cct cca gat gaa tcc tgc tct cag aac ctc ctg atc act cag | 282 |
| Thr Gln Pro Pro Asp Glu Ser Cys Ser Gln Asn Leu Leu Ile Thr Gln | |
|             10                 15                 20 | |
| cag atc att cct gtg ctg tac tgt atg gtc ttc att gcg gga atc cta | 330 |
| Gln Ile Ile Pro Val Leu Tyr Cys Met Val Phe Ile Ala Gly Ile Leu | |
|         25                 30                 35 | |
| ctc aat gga gtg tca gga tgg ata ttc ttt tac gtg ccc agc tct aag | 378 |
| Leu Asn Gly Val Ser Gly Trp Ile Phe Phe Tyr Val Pro Ser Ser Lys | |
|     40                 45                 50 | |
| agt ttc atc atc tat ctc aag aac att gtt att gct gac ttt gtg atg | 426 |
| Ser Phe Ile Ile Tyr Leu Lys Asn Ile Val Ile Ala Asp Phe Val Met | |
| 55                 60                 65                 70 | |
| agc ctg act ttt cct ttc aag atc ctt ggt gac tca ggc ctt ggt ccc | 474 |
| Ser Leu Thr Phe Pro Phe Lys Ile Leu Gly Asp Ser Gly Leu Gly Pro | |
|             75                 80                 85 | |
| tgg cag ctg aac gtg ttt gtg tgc agg gtc tct gcc gtg ctc ttc tac | 522 |
| Trp Gln Leu Asn Val Phe Val Cys Arg Val Ser Ala Val Leu Phe Tyr | |
|         90                 95                 100 | |
| gtc aac atg tac gtc agc att gtg ttc ttt ggg ctc atc agc ttt gac | 570 |
| Val Asn Met Tyr Val Ser Ile Val Phe Phe Gly Leu Ile Ser Phe Asp | |
|     105                 110                 115 | |
| agg tat tat aaa att gta aag cct ctt tgg act tct ttc atc cag tca | 618 |
| Arg Tyr Tyr Lys Ile Val Lys Pro Leu Trp Thr Ser Phe Ile Gln Ser | |
| 120                 125                 130 | |
| gtg agt tac agc aaa ctt ctg tca gtg ata gta tgg atg ctc atg ctc | 666 |
| Val Ser Tyr Ser Lys Leu Leu Ser Val Ile Val Trp Met Leu Met Leu | |
| 135                 140                 145                 150 | |
| ctc ctt gct gtt cca aat att att ctc acc aac cag agt gtt agg gag | 714 |
| Leu Leu Ala Val Pro Asn Ile Ile Leu Thr Asn Gln Ser Val Arg Glu | |
|             155                 160                 165 | |
| gtt aca caa ata aaa tgt ata gaa ctg aaa agt gaa ctg gga cgg aag | 762 |
| Val Thr Gln Ile Lys Cys Ile Glu Leu Lys Ser Glu Leu Gly Arg Lys | |
|         170                 175                 180 | |

```
tgg cac aaa gca tca aac tac atc ttc gtg gcc atc ttc tgg att gtg      810
Trp His Lys Ala Ser Asn Tyr Ile Phe Val Ala Ile Phe Trp Ile Val
        185                 190                 195 ttt ctt ttg tta atc gtt ttc tat act gct atc aca aag aaa atc ttt      858
Phe Leu Leu Leu Ile Val Phe Tyr Thr Ala Ile Thr Lys Lys Ile Phe
200                 205                 210 aag tcc cac ctt aag tca agt cgg aat tcc act tcg gtc aaa aag aaa      906
Lys Ser His Leu Lys Ser Ser Arg Asn Ser Thr Ser Val Lys Lys Lys
215                 220                 225                 230 tct agc cgc aac ata ttc agc atc gtg ttt gtg ttt ttt gtc tgt ttt      954
Ser Ser Arg Asn Ile Phe Ser Ile Val Phe Val Phe Phe Val Cys Phe
                235                 240                 245 gta cct tac cat att gcc aga atc ccc tac aca aag agt cag acc gaa      1002
Val Pro Tyr His Ile Ala Arg Ile Pro Tyr Thr Lys Ser Gln Thr Glu
        250                 255                 260 gct cat tac agc tgc cag tca aaa gaa atc ttg cgg tat atg aaa gaa      1050
Ala His Tyr Ser Cys Gln Ser Lys Glu Ile Leu Arg Tyr Met Lys Glu
265                 270                 275 ttc act ctg cta cta tct gct gca aat gta tgc ttg gac cct att att      1098
Phe Thr Leu Leu Leu Ser Ala Ala Asn Val Cys Leu Asp Pro Ile Ile
280                 285                 290 tat ttc ttt cta tgc cag ccg ttt agg gaa atc tta tgt aag aaa ttg      1146
Tyr Phe Phe Leu Cys Gln Pro Phe Arg Glu Ile Leu Cys Lys Lys Leu
295                 300                 305                 310 cac att cca tta aaa gct cag aat gac cta gac att tcc aga atc aaa      1194
His Ile Pro Leu Lys Ala Gln Asn Asp Leu Asp Ile Ser Arg Ile Lys
                315                 320                 325 aga gga aat aca aca ctt gaa agc aca gat act ttg tga gttcctaccc       1243
Arg Gly Asn Thr Thr Leu Glu Ser Thr Asp Thr Leu  *
                330                 335 tcttccaaag aaagaccacg tgtgcatgtt gtcatcttca attacataac agaaatcaat    1303
aagatatgtg ccctcatcat aaatatcatc tctagcactg ccatccaatt tagttcaata    1363
aaattcaaat ataagtttcc atgcttttt gtaacatcaa agaaaacata cccatcagta     1423
atttctctaa tactgacctt tctattctct attaataaaa aattaataca tacaattatt    1483
caattctatt atattaaaat aagttaaagt ttataaccac tagtctggtc agttaatgta    1543
gaaatttaaa tagtaaataa aacacaacat aatcaaagac aactcactca ggcatcttct    1603
ttctctaaat accagaatct agtatgtaat tgttttcaac actgtcctta aagactaact    1663
tgaaagcagg cacagtttga tgaagggcta gagagctgtt tgcaataaaa agtcaggttt    1723
ttttcctgat tgaagaagc aggaaaagct gacacccaga caatcactta agaaacccct     1783
tattgatgta tttcatggca ctgcaaagga agaggaatat taattgtata cttagcaaga    1843 aaatttttt tttctgatag cactttgagg atattagata catgctaaat atgttttcta     1903
caaagactta cgtcatttaa tgagcctggg gttctggtgt tagaatattt ttaagtaggc    1963
tttactgaga gaaactaaat attggcatac gttatcagca acttcccctg ttcaatagta    2023
tgggaaaaat aagatgactg ggaaaaagac acacccacac cgtagaacat atattaatct    2083
actggcgaat gggaaaggag accatttct tagaaagcaa ataaacttga ttttttttaaa    2143 tctaaaattt acattaatga gtgcaaaata acacataaaa tgaaaattca cacatcacat    2203
ttttctggaa aacagacgga ttttacttct ggagacatgg catacggtta ctgacttatg    2263
agctaccaaa actaaattct ttctctgcta ttaactggct agaagacatt catctatttt    2323
tcaaatgttc tttcaaaaca tttttataag taatgtttgt atctatttca tgctttactg    2383
```

-continued tctatatact aataaagaaa tgttttaata ctg 2416

<210> SEQ ID NO 42
<211> LENGTH: 338
<212> TYPE: PRT
<213> ORGANISM: Homo Sapiens

<400> SEQUENCE: 42

Met Ile Asn Ser Thr Ser Thr Gln Pro Pro Asp Glu Ser Cys Ser Gln
1               5                   10                  15

Asn Leu Leu Ile Thr Gln Gln Ile Ile Pro Val Leu Tyr Cys Met Val
            20                  25                  30

Phe Ile Ala Gly Ile Leu Leu Asn Gly Val Ser Gly Trp Ile Phe Phe
        35                  40                  45

Tyr Val Pro Ser Ser Lys Ser Phe Ile Ile Tyr Leu Lys Asn Ile Val
    50                  55                  60

Ile Ala Asp Phe Val Met Ser Leu Thr Phe Pro Phe Lys Ile Leu Gly
65                  70                  75                  80

Asp Ser Gly Leu Gly Pro Trp Gln Leu Asn Val Phe Val Cys Arg Val
                85                  90                  95

Ser Ala Val Leu Phe Tyr Val Asn Met Tyr Val Ser Ile Val Phe Phe
            100                 105                 110

Gly Leu Ile Ser Phe Asp Arg Tyr Tyr Lys Ile Val Lys Pro Leu Trp
        115                 120                 125

Thr Ser Phe Ile Gln Ser Val Ser Tyr Ser Lys Leu Leu Ser Val Ile
    130                 135                 140

Val Trp Met Leu Met Leu Leu Leu Ala Val Pro Asn Ile Ile Leu Thr
145                 150                 155                 160

Asn Gln Ser Val Arg Glu Val Thr Gln Ile Lys Cys Ile Glu Leu Lys
                165                 170                 175

Ser Glu Leu Gly Arg Lys Trp His Lys Ala Ser Asn Tyr Ile Phe Val
            180                 185                 190

Ala Ile Phe Trp Ile Val Phe Leu Leu Leu Ile Val Phe Tyr Thr Ala
        195                 200                 205

Ile Thr Lys Lys Ile Phe Lys Ser His Leu Lys Ser Ser Arg Asn Ser
    210                 215                 220

Thr Ser Val Lys Lys Lys Ser Ser Arg Asn Ile Phe Ser Ile Val Phe
225                 230                 235                 240

Val Phe Phe Val Cys Phe Val Pro Tyr His Ile Ala Arg Ile Pro Tyr
                245                 250                 255

Thr Lys Ser Gln Thr Glu Ala His Tyr Ser Cys Gln Ser Lys Glu Ile
            260                 265                 270

Leu Arg Tyr Met Lys Glu Phe Thr Leu Leu Leu Ser Ala Ala Asn Val
        275                 280                 285

Cys Leu Asp Pro Ile Ile Tyr Phe Phe Leu Cys Gln Pro Phe Arg Glu
    290                 295                 300

Ile Leu Cys Lys Lys Leu His Ile Pro Leu Lys Ala Gln Asn Asp Leu
305                 310                 315                 320

Asp Ile Ser Arg Ile Lys Arg Gly Asn Thr Thr Leu Glu Ser Thr Asp
                325                 330                 335

Thr Leu

<210> SEQ ID NO 43
<211> LENGTH: 2063
<212> TYPE: DNA

```
<213> ORGANISM: Homo Sapiens
<220> FEATURE:
<221> NAME/KEY: CDS
<222> LOCATION: (36)...(1775)

<400> SEQUENCE: 43
tgccgggcgg taggcagcag caggctgaag ggatc atg gtg cag tac gag ctg           53
                                       Met Val Gln Tyr Glu Leu
                                         1               5 tgg gcc gcg ctg cct ggc gcc tcc ggg gtc gcc ctg gcc tgc tgc ttc         101
Trp Ala Ala Leu Pro Gly Ala Ser Gly Val Ala Leu Ala Cys Cys Phe
             10                  15                  20 gtg gcg gcg gcc gtg gcc ctg cgc tgg tcc ggg cgc cgg acg gcg cgg         149
Val Ala Ala Ala Val Ala Leu Arg Trp Ser Gly Arg Arg Thr Ala Arg
     25                  30                  35 ggc gcg gtg gtc cgg gcg cga cag aag cag cga gcg ggc ctg gag aac         197
Gly Ala Val Val Arg Ala Arg Gln Lys Gln Arg Ala Gly Leu Glu Asn
 40                  45                  50 atg gac agg gcg gcg cag cgc ttc cgg ctc cag aac cca gac ctg gac         245
Met Asp Arg Ala Ala Gln Arg Phe Arg Leu Gln Asn Pro Asp Leu Asp
 55                  60                  65                  70 tca gag gcg ctg cta gcc ctg ccc ctg cct cag ctg gtg cag aag tta         293
Ser Glu Ala Leu Leu Ala Leu Pro Leu Pro Gln Leu Val Gln Lys Leu
                 75                  80                  85 cac agt aga gag ctg gcc cct gag gcc gtg ctc ttc acc tat gtg gga         341
His Ser Arg Glu Leu Ala Pro Glu Ala Val Leu Phe Thr Tyr Val Gly
             90                  95                 100 aag gcc tgg gaa gtg aac aaa ggg acc aac tgt gtg acc tcc tat ctg         389
Lys Ala Trp Glu Val Asn Lys Gly Thr Asn Cys Val Thr Ser Tyr Leu
        105                 110                 115 gct gac tgt gag act cag ctg tct cag gcc cca agg cag ggc ctg ctc         437
Ala Asp Cys Glu Thr Gln Leu Ser Gln Ala Pro Arg Gln Gly Leu Leu
    120                 125                 130 tat ggc gtc cct gtg agc ctc aag gag tgc ttc acc tac aag ggc cag         485
Tyr Gly Val Pro Val Ser Leu Lys Glu Cys Phe Thr Tyr Lys Gly Gln
135                 140                 145                 150 gac tcc acg ctg ggc ttg agc ctg aat gaa ggg gtg ccg gcg gag tgc         533
Asp Ser Thr Leu Gly Leu Ser Leu Asn Glu Gly Val Pro Ala Glu Cys
                155                 160                 165 gac agc gta gtg gtg cat gtg ctg aag ctg cag ggt gcc gtg ccc ttc         581
Asp Ser Val Val Val His Val Leu Lys Leu Gln Gly Ala Val Pro Phe
            170                 175                 180 gtg cac acc aat gtt cca cag tcc atg ttc agc tat gac tgc agt aac         629
Val His Thr Asn Val Pro Gln Ser Met Phe Ser Tyr Asp Cys Ser Asn
        185                 190                 195 ccc ctc ttt ggc cag acc gtg aac cca tgg aag tcc tcc aaa agc cca         677
Pro Leu Phe Gly Gln Thr Val Asn Pro Trp Lys Ser Ser Lys Ser Pro
    200                 205                 210 ggg ggc tcc tca ggg ggt gaa ggg gcc ctc atc ggg tct gga ggc tcc         725
Gly Gly Ser Ser Gly Gly Glu Gly Ala Leu Ile Gly Ser Gly Gly Ser
215                 220                 225                 230 ccc ctg ggc tta ggc act gat atc gga ggc agc atc cgc ttc ccc tcc         773
Pro Leu Gly Leu Gly Thr Asp Ile Gly Gly Ser Ile Arg Phe Pro Ser
                235                 240                 245 tcc ttc tgc ggc atc tgc ggc ctc aag ccc aca ggg aac cgc ctc agc         821
Ser Phe Cys Gly Ile Cys Gly Leu Lys Pro Thr Gly Asn Arg Leu Ser
            250                 255                 260 aag agt ggc ctg aag ggc tgt gtc tat gga cag gag gca gtg cgt ctc         869
Lys Ser Gly Leu Lys Gly Cys Val Tyr Gly Gln Glu Ala Val Arg Leu
        265                 270                 275
```

-continued

| | | |
|---|---|---|
| tcc gtg ggc ccc atg gcc cgg gac gtg gag agc ctg gca ctg tgc ctg<br>Ser Val Gly Pro Met Ala Arg Asp Val Glu Ser Leu Ala Leu Cys Leu<br>280                         285                    290 | 917 |
| cga gcc ctg ctg tgc gag gac atg ttc cgc ttg gac ccc act gtg cct<br>Arg Ala Leu Leu Cys Glu Asp Met Phe Arg Leu Asp Pro Thr Val Pro<br>295                       300                    305              310 | 965 |
| ccc ttg ccc ttc aga gaa gag gtc tac acc agc tct cag ccc ctg cgt<br>Pro Leu Pro Phe Arg Glu Glu Val Tyr Thr Ser Ser Gln Pro Leu Arg<br>                    315                    320                    325 | 1013 |
| gtg ggc tac tat gag act gac aac tat acc atg ccc tcc ccg gcc atg<br>Val Gly Tyr Tyr Glu Thr Asp Asn Tyr Thr Met Pro Ser Pro Ala Met<br>          330                    335                    340 | 1061 |
| agg cgg gcc gtg ctg gag acc aaa cag agc ctt gag gct gcg ggg cac<br>Arg Arg Ala Val Leu Glu Thr Lys Gln Ser Leu Glu Ala Ala Gly His<br>         345                    350                    355 | 1109 |
| acg ctg gtt ccc ttc ttg cca agc aac ata ccc cat gct ctg gag acc<br>Thr Leu Val Pro Phe Leu Pro Ser Asn Ile Pro His Ala Leu Glu Thr<br>360                       365                    370 | 1157 |
| ctg tca aca ggt ggg ctc ttc agt gat ggt ggc cac acc ttc cta cag<br>Leu Ser Thr Gly Gly Leu Phe Ser Asp Gly Gly His Thr Phe Leu Gln<br>375                       380                    385              390 | 1205 |
| aac ttc aaa ggt gat ttc gtg gac ccc tgc ctg ggg gac ctg gtc tca<br>Asn Phe Lys Gly Asp Phe Val Asp Pro Cys Leu Gly Asp Leu Val Ser<br>                    395                    400              405 | 1253 |
| att ctg aag ctt ccc caa tgg ctt aaa gga ctg ctg gcc ttc ctg gtg<br>Ile Leu Lys Leu Pro Gln Trp Leu Lys Gly Leu Leu Ala Phe Leu Val<br>         410                    415                    420 | 1301 |
| aag cct ctg ctg cca agg ctg tca gct ttc ctc agc aac atg aag tct<br>Lys Pro Leu Leu Pro Arg Leu Ser Ala Phe Leu Ser Asn Met Lys Ser<br>         425                    430                    435 | 1349 |
| cgt tcg gct gga aaa ctc tgg gaa ctg cag cac gag atc gag gtg tac<br>Arg Ser Ala Gly Lys Leu Trp Glu Leu Gln His Glu Ile Glu Val Tyr<br>440                       445                    450 | 1397 |
| cgc aaa acc gtg att gcc cag tgg agg gcg ctg gac ctg gat gtg gtg<br>Arg Lys Thr Val Ile Ala Gln Trp Arg Ala Leu Asp Leu Asp Val Val<br>455                       460                    465              470 | 1445 |
| ctg acc ccc atg ctg gcc cct gct ctg gac ttg aat gcc cca ggc agg<br>Leu Thr Pro Met Leu Ala Pro Ala Leu Asp Leu Asn Ala Pro Gly Arg<br>                    475                    480                    485 | 1493 |
| gcc aca ggg gcc gtc agc tac act atg ctg tac aac tgc ctg gac ttc<br>Ala Thr Gly Ala Val Ser Tyr Thr Met Leu Tyr Asn Cys Leu Asp Phe<br>         490                    495                    500 | 1541 |
| cct gca ggg gtg gtg cct gtc acc acg gtg act gct gag gac gag gcc<br>Pro Ala Gly Val Val Pro Val Thr Thr Val Thr Ala Glu Asp Glu Ala<br>         505                    510                    515 | 1589 |
| cag atg gaa cat tac agg ggc tac ttt ggg gat atc tgg gac aag atg<br>Gln Met Glu His Tyr Arg Gly Tyr Phe Gly Asp Ile Trp Asp Lys Met<br>520                       525                    530 | 1637 |
| ctg cag aag ggc atg aag aag agt gtg ggg ctg ccg gtg gcc gtg cag<br>Leu Gln Lys Gly Met Lys Lys Ser Val Gly Leu Pro Val Ala Val Gln<br>535                       540                    545              550 | 1685 |
| tgt gtg gct ctg ccc tgg caa gaa gag ttg tgt ctg cgg ttc atg cgg<br>Cys Val Ala Leu Pro Trp Gln Glu Glu Leu Cys Leu Arg Phe Met Arg<br>                    555                    560              565 | 1733 |
| gag gtg gag cga ctg atg acc cct gaa aag cag tca tcc tga<br>Glu Val Glu Arg Leu Met Thr Pro Glu Lys Gln Ser Ser *<br>         570                    575 | 1775 |
| tggctctggc tccagaggac ctgagactca cactctctgc agcccagcct agtcagggca | 1835 |
| cagctgccct gctgccacag caaggaaatg tcctgcatgg ggcagaggct tccgtgtcct | 1895 |

-continued

```
ctcccccaac ccctgcaag aagcgccgac tccctgagtc tggacctcca tccctgctct    1955
ggtcccctct cttcgtcctg atccctccac ccccatgtgg cagcccatgg gtatgacata    2015
ggccaaggcc caactaacag tcaagaaaca aaaaaaaaaa aaaaaaa                  2063
```

<210> SEQ ID NO 44
<211> LENGTH: 579
<212> TYPE: PRT
<213> ORGANISM: Homo Sapiens

<400> SEQUENCE: 44

```
Met Val Gln Tyr Glu Leu Trp Ala Ala Leu Pro Gly Ala Ser Gly Val
  1               5                  10                  15

Ala Leu Ala Cys Cys Phe Val Ala Ala Val Ala Leu Arg Trp Ser
             20                  25                  30

Gly Arg Arg Thr Ala Arg Gly Ala Val Val Arg Ala Gln Lys Gln
         35                  40                  45

Arg Ala Gly Leu Glu Asn Met Asp Arg Ala Ala Gln Arg Phe Arg Leu
 50                  55                  60

Gln Asn Pro Asp Leu Asp Ser Glu Ala Leu Leu Ala Leu Pro Leu Pro
 65                  70                  75                  80

Gln Leu Val Gln Lys Leu His Ser Arg Glu Leu Ala Pro Glu Ala Val
                 85                  90                  95

Leu Phe Thr Tyr Val Gly Lys Ala Trp Glu Val Asn Lys Gly Thr Asn
            100                 105                 110

Cys Val Thr Ser Tyr Leu Ala Asp Cys Glu Thr Gln Leu Ser Gln Ala
            115                 120                 125

Pro Arg Gln Gly Leu Leu Tyr Gly Val Pro Val Ser Leu Lys Glu Cys
        130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val His Val Leu Lys Leu
                165                 170                 175

Gln Gly Ala Val Pro Phe Val His Thr Asn Val Pro Gln Ser Met Phe
            180                 185                 190

Ser Tyr Asp Cys Ser Asn Pro Leu Phe Gly Gln Thr Val Asn Pro Trp
            195                 200                 205

Lys Ser Ser Lys Ser Pro Gly Gly Ser Ser Gly Glu Gly Ala Leu
        210                 215                 220

Ile Gly Ser Gly Gly Ser Pro Leu Gly Leu Gly Thr Asp Ile Gly Gly
225                 230                 235                 240

Ser Ile Arg Phe Pro Ser Ser Phe Cys Gly Ile Cys Gly Leu Lys Pro
                245                 250                 255

Thr Gly Asn Arg Leu Ser Lys Ser Gly Leu Lys Gly Cys Val Tyr Gly
            260                 265                 270

Gln Glu Ala Val Arg Leu Ser Val Gly Pro Met Ala Arg Asp Val Glu
        275                 280                 285

Ser Leu Ala Leu Cys Leu Arg Ala Leu Leu Cys Glu Asp Met Phe Arg
    290                 295                 300

Leu Asp Pro Thr Val Pro Pro Leu Pro Phe Arg Glu Glu Val Tyr Thr
305                 310                 315                 320

Ser Ser Gln Pro Leu Arg Val Gly Tyr Tyr Glu Thr Asp Asn Tyr Thr
                325                 330                 335

Met Pro Ser Pro Ala Met Arg Arg Ala Val Leu Glu Thr Lys Gln Ser
```

```
                340             345             350
Leu Glu Ala Ala Gly His Thr Leu Val Pro Phe Leu Pro Ser Asn Ile
            355                 360                 365
Pro His Ala Leu Glu Thr Leu Ser Thr Gly Gly Leu Phe Ser Asp Gly
        370                 375                 380
Gly His Thr Phe Leu Gln Asn Phe Lys Gly Asp Phe Val Asp Pro Cys
385                 390                 395                 400
Leu Gly Asp Leu Val Ser Ile Leu Lys Leu Pro Gln Trp Leu Lys Gly
                405                 410                 415
Leu Leu Ala Phe Leu Val Lys Pro Leu Leu Pro Arg Leu Ser Ala Phe
            420                 425                 430
Leu Ser Asn Met Lys Ser Arg Ser Ala Gly Lys Leu Trp Glu Leu Gln
        435                 440                 445
His Glu Ile Glu Val Tyr Arg Lys Thr Val Ile Ala Gln Trp Arg Ala
    450                 455                 460
Leu Asp Leu Asp Val Leu Thr Pro Met Leu Ala Pro Ala Leu Asp
465                 470                 475                 480
Leu Asn Ala Pro Gly Arg Ala Thr Gly Ala Val Ser Tyr Thr Met Leu
                485                 490                 495
Tyr Asn Cys Leu Asp Phe Pro Ala Gly Val Val Pro Val Thr Thr Val
            500                 505                 510
Thr Ala Glu Asp Glu Ala Gln Met Glu His Tyr Arg Gly Tyr Phe Gly
        515                 520                 525
Asp Ile Trp Asp Lys Met Leu Gln Lys Gly Met Lys Lys Ser Val Gly
    530                 535                 540
Leu Pro Val Ala Val Gln Cys Val Ala Leu Pro Trp Gln Glu Glu Leu
545                 550                 555                 560
Cys Leu Arg Phe Met Arg Glu Val Glu Arg Leu Met Thr Pro Glu Lys
                565                 570                 575
Gln Ser Ser

<210> SEQ ID NO 45
<211> LENGTH: 1154
<212> TYPE: DNA
<213> ORGANISM: Homo Sapiens
<220> FEATURE:
<221> NAME/KEY: CDS
<222> LOCATION: (18)...(845)

<400> SEQUENCE: 45
ggaattccgt ggccagg atg ctg agc ctg ctg ctg ctg gcg ctg ccc gtc         50
                   Met Leu Ser Leu Leu Leu Leu Ala Leu Pro Val
                    1               5                  10 ctg gcg agc cgc gcc tac gcg gcc cct gcc cca gtc cag gcc ctg cag        98
Leu Ala Ser Arg Ala Tyr Ala Ala Pro Ala Pro Val Gln Ala Leu Gln
                15                  20                  25 caa gcg ggt atc gtc ggg ggt cag gag gcc ccc agg agc aag tgg ccc       146
Gln Ala Gly Ile Val Gly Gly Gln Glu Ala Pro Arg Ser Lys Trp Pro
            30                  35                  40 tgg cag gtg agc ctg aga gtc cgc gac cga tac tgg atg cac ttc tgc       194
Trp Gln Val Ser Leu Arg Val Arg Asp Arg Tyr Trp Met His Phe Cys
        45                  50                  55 ggg ggc tcc ctc atc cac ccc cag tgg gtg ctg acc gcg gcg cac tgc       242
Gly Gly Ser Leu Ile His Pro Gln Trp Val Leu Thr Ala Ala His Cys
60                  65                  70                  75 ctg gga ccg gac gtc aag gat ctg gcc acc ctc agg gtg caa ctg cgg       290
Leu Gly Pro Asp Val Lys Asp Leu Ala Thr Leu Arg Val Gln Leu Arg
```

```
                    80                    85                    90
gag cag cac ctc tac tac cag gac cag ctg ctg cca gtc agc agg atc        338
Glu Gln His Leu Tyr Tyr Gln Asp Gln Leu Leu Pro Val Ser Arg Ile
                95                   100                  105 atc gtg cac cca cag ttc tac atc atc cag act gga gcg gat atc gcc        386
Ile Val His Pro Gln Phe Tyr Ile Ile Gln Thr Gly Ala Asp Ile Ala
            110                  115                  120 ctg ctg gag ctg gag gag ccc gtg aac atc tcc agc cgc gtc cac acg        434
Leu Leu Glu Leu Glu Glu Pro Val Asn Ile Ser Ser Arg Val His Thr
        125                  130                  135 gtc atg ctg ccc cct gcc tcg gag acc ttc ccc ccg ggg atg ccg tgc        482
Val Met Leu Pro Pro Ala Ser Glu Thr Phe Pro Pro Gly Met Pro Cys
140                  145                  150                  155 tgg gtc act ggc tgg ggc gat gtg gac aat gat gag ccc ctc cca ccg        530
Trp Val Thr Gly Trp Gly Asp Val Asp Asn Asp Glu Pro Leu Pro Pro
                160                  165                  170 cca ttt ccc ctg aag cag gtg aag gtc ccc ata atg gaa aac cac att        578
Pro Phe Pro Leu Lys Gln Val Lys Val Pro Ile Met Glu Asn His Ile
            175                  180                  185 tgt gac gca aaa tac cac ctt ggc gcc tac acg gga gac gac gtc cgc        626
Cys Asp Ala Lys Tyr His Leu Gly Ala Tyr Thr Gly Asp Asp Val Arg
        190                  195                  200 atc atc cgt gac gac atg ctg tgt gcc ggg aac agc cag agg gac tcc        674
Ile Ile Arg Asp Asp Met Leu Cys Ala Gly Asn Ser Gln Arg Asp Ser
    205                  210                  215 tgc aag ggc gac tct gga ggg ccc ctg gtg tgc aag gtg aat ggc acc        722
Cys Lys Gly Asp Ser Gly Gly Pro Leu Val Cys Lys Val Asn Gly Thr
220                  225                  230                  235 tgg cta cag gcg ggc gtg gtc agc tgg gac gag ggc tgt gcc cag ccc        770
Trp Leu Gln Ala Gly Val Val Ser Trp Asp Glu Gly Cys Ala Gln Pro
                240                  245                  250 aac cgg cct ggc atc tac acc cgt gtc acc tac tac ttg gac tgg atc        818
Asn Arg Pro Gly Ile Tyr Thr Arg Val Thr Tyr Tyr Leu Asp Trp Ile
            255                  260                  265 cac cac tat gtc ccc aaa aag ccg tga gtcaggcctg ggtgtgccac              865
His His Tyr Val Pro Lys Lys Pro *
        270                  275 ctgggtcact ggaggaccaa cccctgctgt ccaaaacacc actgcttcct acccaggtgg      925
cgactgcccc ccacaccttc cctgcccgt cctgagtgcc cttcctgtc ctaagccccc        985 tgctctcttc tgagccccttccctgtcct gaggacccttccccatcctg agccccttc         1045 cctgtcctaa gcctgacgcc tgcactgctc cggccctccc ctgcccaggc agctggtggt   1105
gggcgctaat cctcctgagt gctggacctc attaaagtgc atggaaatc               1154
```

<210> SEQ ID NO 46
<211> LENGTH: 275
<212> TYPE: PRT
<213> ORGANISM: Homo Sapiens

<400> SEQUENCE: 46

Met Leu Ser Leu Leu Leu Leu Ala Leu Pro Val Leu Ala Ser Arg Ala
 1               5                  10                  15

Tyr Ala Ala Pro Ala Pro Val Gln Ala Leu Gln Gln Ala Gly Ile Val
            20                  25                  30

Gly Gly Gln Glu Ala Pro Arg Ser Lys Trp Pro Trp Gln Val Ser Leu
        35                  40                  45

Arg Val Arg Asp Arg Tyr Trp Met His Phe Cys Gly Gly Ser Leu Ile
    50                  55                  60

-continued

```
His Pro Gln Trp Val Leu Thr Ala Ala His Cys Leu Gly Pro Asp Val
 65                  70                  75                  80

Lys Asp Leu Ala Thr Leu Arg Val Gln Leu Arg Glu Gln His Leu Tyr
                 85                  90                  95

Tyr Gln Asp Gln Leu Leu Pro Val Ser Arg Ile Ile Val His Pro Gln
            100                 105                 110

Phe Tyr Ile Ile Gln Thr Gly Ala Asp Ile Ala Leu Leu Glu Leu Glu
        115                 120                 125

Glu Pro Val Asn Ile Ser Ser Arg Val His Thr Val Met Leu Pro Pro
    130                 135                 140

Ala Ser Glu Thr Phe Pro Pro Gly Met Pro Cys Trp Val Thr Gly Trp
145                 150                 155                 160

Gly Asp Val Asp Asn Asp Glu Pro Leu Pro Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Ile Arg Asp Asp
        195                 200                 205

Met Leu Cys Ala Gly Asn Ser Gln Arg Asp Ser Cys Lys Gly Asp Ser
    210                 215                 220

Gly Gly Pro Leu Val Cys Lys Val Asn Gly Thr Trp Leu Gln Ala Gly
225                 230                 235                 240

Val Val Ser Trp Asp Glu Gly Cys Ala Gln Pro Asn Arg Pro Gly Ile
                245                 250                 255

Tyr Thr Arg Val Thr Tyr Tyr Leu Asp Trp Ile His His Tyr Val Pro
            260                 265                 270

Lys Lys Pro
        275

<210> SEQ ID NO 47
<211> LENGTH: 1143
<212> TYPE: DNA
<213> ORGANISM: Homo Sapiens
<220> FEATURE:
<221> NAME/KEY: CDS
<222> LOCATION: (6)...(833)

<400> SEQUENCE: 47 ccagg atg ctg aat ctg ctg ctg ctg gcg ctg ccc gtc ctg gcg agc cgc      50
      Met Leu Asn Leu Leu Leu Leu Ala Leu Pro Val Leu Ala Ser Arg
      1               5                   10                  15 gcc tac gcg gcc cct gcc cca ggc cag gcc ctg cag cga gtg ggc atc       98
Ala Tyr Ala Ala Pro Ala Pro Gly Gln Ala Leu Gln Arg Val Gly Ile
            20                  25                  30 gtt ggg ggt cag gag gcc ccc agg agc aag tgg ccc tgg cag gtg agc      146
Val Gly Gly Gln Glu Ala Pro Arg Ser Lys Trp Pro Trp Gln Val Ser
        35                  40                  45 ctg aga gtc cac ggc cca tac tgg atg cac ttc tgc ggg ggc tcc ctc      194
Leu Arg Val His Gly Pro Tyr Trp Met His Phe Cys Gly Gly Ser Leu
    50                  55                  60 atc cac ccc cag tgg gtg ctg acc gca gcg cac tgc gtg gga ccg gac      242
Ile His Pro Gln Trp Val Leu Thr Ala Ala His Cys Val Gly Pro Asp
65                  70                  75 gtc aag gat ctg gcc gcc ctc agg gtg caa ctg cgg gag cag cac ctc      290
Val Lys Asp Leu Ala Ala Leu Arg Val Gln Leu Arg Glu Gln His Leu
            80                  85                  90                  95 tac tac cag gac cag ctg ctg ccg gtc agc agg atc atc gtg cac cca      338
```

```
                                                                              386
cag ttc tac acc gcc cag atc gga gcg gac atc gcc ctg ctg gag ctg
Gln Phe Tyr Thr Ala Gln Ile Gly Ala Asp Ile Ala Leu Leu Glu Leu
            115                 120                 125

434
gag gag ccg gtg aag gtc tcc agc cac gtc cac acg gtc acc ctg ccc
Glu Glu Pro Val Lys Val Ser Ser His Val His Thr Val Thr Leu Pro
        130                 135                 140

482
cct gcc tca gag acc ttc ccc ccg ggg atg ccg tgc tgg gtc act ggc
Pro Ala Ser Glu Thr Phe Pro Pro Gly Met Pro Cys Trp Val Thr Gly
    145                 150                 155

530
tgg ggc gat gtg gac aat gat gag cgc ctc cca ccg cca ttt cct ctg
Trp Gly Asp Val Asp Asn Asp Glu Arg Leu Pro Pro Pro Phe Pro Leu
160                 165                 170                 175

578
aag cag gtg aag gtc ccc ata atg gaa aac cac att tgt gac gca aaa
Lys Gln Val Lys Val Pro Ile Met Glu Asn His Ile Cys Asp Ala Lys
                180                 185                 190

626
tac cac ctt ggc gcc tac acg gga gac gac gtc cgc atc gtc cgt gac
Tyr His Leu Gly Ala Tyr Thr Gly Asp Asp Val Arg Ile Val Arg Asp
            195                 200                 205

674
gac atg ctg tgt gcc ggg aac acc cgg agg gac tca tgc cag ggc gac
Asp Met Leu Cys Ala Gly Asn Thr Arg Arg Asp Ser Cys Gln Gly Asp
        210                 215                 220

722
tcc gga ggg ccc ctg gtg tgc aag gtg aat ggc acc tgg ctg cag gcg
Ser Gly Gly Pro Leu Val Cys Lys Val Asn Gly Thr Trp Leu Gln Ala
    225                 230                 235

770
ggc gtg gtc agc tgg ggc gag ggc tgt gcc cag ccc aac cgg cct ggc
Gly Val Val Ser Trp Gly Glu Gly Cys Ala Gln Pro Asn Arg Pro Gly
240                 245                 250                 255

818
atc tac acc cgt gtc acc tac tac ttg gac tgg atc cac cac tat gtc
Ile Tyr Thr Arg Val Thr Tyr Tyr Leu Asp Trp Ile His His Tyr Val
                260                 265                 270

873
ccc aaa aag ccg tga gtcaggcctg ggtgtgccac ctgggtcact ggaggaccaa
Pro Lys Lys Pro *
            275 ccctgctgt ccaaaacacc actgcttcct acccaggtgg cgactgcccc ccacaccttc      933
cctgccccgt cctgagtgcc ccttcctgtc ctaagcccccc tgctctcttc tgagccccttt    993 ccctgtcct gaggacccttt ccccatcctg agccccttc cctgtcctaa gcctgacgcc      1053
tgcactgctc cggccctccc ctgcccaggc agctggtggt gggcgctaat cctcctgagt     1113
gctggacctc attaaagtgc atggaaatca                                      1143
```

<210> SEQ ID NO 48
<211> LENGTH: 275
<212> TYPE: PRT
<213> ORGANISM: Homo Sapiens

<400> SEQUENCE: 48

```
Met Leu Asn Leu Leu Leu Ala Leu Pro Val Leu Ala Ser Arg Ala
1               5                   10                  15

Tyr Ala Ala Pro Ala Pro Gly Gln Ala Leu Gln Arg Val Gly Ile Val
            20                  25                  30

Gly Gly Gln Glu Ala Pro Arg Ser Lys Trp Pro Trp Gln Val Ser Leu
        35                  40                  45

Arg Val His Gly Pro Tyr Trp Met His Phe Cys Gly Gly Ser Leu Ile
    50                  55                  60

His Pro Gln Trp Val Leu Thr Ala Ala His Cys Val Gly Pro Asp Val
65                  70                  75                  80
```

```
Lys Asp Leu Ala Ala Leu Arg Val Gln Leu Arg Glu Gln His Leu Tyr
                85                  90                  95
Tyr Gln Asp Gln Leu Leu Pro Val Ser Arg Ile Ile Val His Pro Gln
            100                 105                 110
Phe Tyr Thr Ala Gln Ile Gly Ala Asp Ile Ala Leu Leu Glu Leu Glu
        115                 120                 125
Glu Pro Val Lys Val Ser Ser His Val His Thr Val Thr Leu Pro Pro
    130                 135                 140
Ala Ser Glu Thr Phe Pro Pro Gly Met Pro Cys Trp Val Thr Gly Trp
145                 150                 155                 160
Gly Asp Val Asp Asn Asp Glu Arg Leu Pro Pro Pro Phe Pro Leu Lys
                165                 170                 175
Gln Val Lys Val Pro Ile Met Glu Asn His Ile Cys Asp Ala Lys Tyr
            180                 185                 190
His Leu Gly Ala Tyr Thr Gly Asp Asp Val Arg Ile Val Arg Asp Asp
        195                 200                 205
Met Leu Cys Ala Gly Asn Thr Arg Arg Asp Ser Cys Gln Gly Asp Ser
    210                 215                 220
Gly Gly Pro Leu Val Cys Lys Val Asn Gly Thr Trp Leu Gln Ala Gly
225                 230                 235                 240
Val Val Ser Trp Gly Glu Gly Cys Ala Gln Pro Asn Arg Pro Gly Ile
                245                 250                 255
Tyr Thr Arg Val Thr Tyr Tyr Leu Asp Trp Ile His His Tyr Val Pro
            260                 265                 270
Lys Lys Pro
        275

<210> SEQ ID NO 49
<211> LENGTH: 2877
<212> TYPE: DNA
<213> ORGANISM: Homo Sapiens
<220> FEATURE:
<221> NAME/KEY: CDS
<222> LOCATION: (387)...(1457)

<400> SEQUENCE: 49
cggccggata ggcgcgaggg ggccgcgtga ggcggtgccg gcgttctggc ccccaaagcc      60
ggtctagcgc gccgggcgtc ttccttactt ccgctgccgc cgccgccaca tcccgggacc     120
cgacgggccg cggcgcggag gcctcggggc aaggtggggc gggcctcccg agctcccagg     180
accccgcgcg cttcgcccac aggcccggcg aagcccgacc cgcgcggcgc ccccagggcc     240
aggggaggag cctaaggacc cggacgagcg ccgctccagt aggtgacaag aggaaacaag     300
aacctcagtt caggggaaac acagcaagga aatgtgagcc ccaggctgca gaaggaagag     360
tcagtgaatg gctgcggtgt gacaac atg cac cac cag tgg ctt ctg ctg gcc     413
                            Met His His Gln Trp Leu Leu Leu Ala
                              1               5 gca tgc ttt tgg gtg att ttc atg ttc atg gtg gct agc aag ttc atc     461
Ala Cys Phe Trp Val Ile Phe Met Phe Met Val Ala Ser Lys Phe Ile
 10                  15                  20                  25 acg ttg acc ttt aaa gac cca gat gtg tac agt gcc aaa cag gag ttt     509
Thr Leu Thr Phe Lys Asp Pro Asp Val Tyr Ser Ala Lys Gln Glu Phe
                 30                  35                  40 ctg ttc ctg aca acc atg ccg gaa gtg agg aag ttg cca gaa gag aag     557
Leu Phe Leu Thr Thr Met Pro Glu Val Arg Lys Leu Pro Glu Glu Lys
             45                  50                  55
```

```
cac att cct gag gaa ctg aag cca act ggg aag gag ctt cca gac agc    605
His Ile Pro Glu Glu Leu Lys Pro Thr Gly Lys Glu Leu Pro Asp Ser
        60                  65                  70 cag ctc gtt cag ccc ctg gtc tac atg gag cgc ctg gaa ctc atc aga    653
Gln Leu Val Gln Pro Leu Val Tyr Met Glu Arg Leu Glu Leu Ile Arg
 75                  80                  85 aac gtc tgc agg gat gat gcc ctg aag aat ctc tcg cac act cct gtc    701
Asn Val Cys Arg Asp Asp Ala Leu Lys Asn Leu Ser His Thr Pro Val
 90                  95                 100                 105 tcc aag ttt gtc ctg gac cga ata ttt gtc tgt gac aag cac aag att    749
Ser Lys Phe Val Leu Asp Arg Ile Phe Val Cys Asp Lys His Lys Ile
            110                 115                 120 ctt ttc tgc cag act ccc aaa gtg ggc aac acc cag tgg aag aaa gtg    797
Leu Phe Cys Gln Thr Pro Lys Val Gly Asn Thr Gln Trp Lys Lys Val
            125                 130                 135 ctg att gtt cta aat gga gca ttt tct tcc att gag gag atc ccc gaa    845
Leu Ile Val Leu Asn Gly Ala Phe Ser Ser Ile Glu Glu Ile Pro Glu
            140                 145                 150 aac gtg gtg cac gac cac gag aag aac ggc ctt cct cgg ctc tct tcc    893
Asn Val Val His Asp His Glu Lys Asn Gly Leu Pro Arg Leu Ser Ser
        155                 160                 165 ttc agt gat gca gaa att cag aag cga ttg aaa aca tac ttc aag ttt    941
Phe Ser Asp Ala Glu Ile Gln Lys Arg Leu Lys Thr Tyr Phe Lys Phe
170                 175                 180                 185 ttt att gta aga gat ccc ttc gaa aga ctt att tct gca ttt aag gat    989
Phe Ile Val Arg Asp Pro Phe Glu Arg Leu Ile Ser Ala Phe Lys Asp
                190                 195                 200 aaa ttt gtt cac aat ccc cgg ttt gag cct tgg tac agg cat gag att   1037
Lys Phe Val His Asn Pro Arg Phe Glu Pro Trp Tyr Arg His Glu Ile
            205                 210                 215 gct cct ggc atc atc aga aaa tac agg agg aac cgg aca gag acg cgg   1085
Ala Pro Gly Ile Ile Arg Lys Tyr Arg Arg Asn Arg Thr Glu Thr Arg
            220                 225                 230 ggg atc cag ttt gaa gat ttc gtg cgc tac ctc ggc gat ccg aac cac   1133
Gly Ile Gln Phe Glu Asp Phe Val Arg Tyr Leu Gly Asp Pro Asn His
        235                 240                 245 aga tgg cta gac ctt cag ttt ggg gac cac atc att cac tgg gtg acg   1181
Arg Trp Leu Asp Leu Gln Phe Gly Asp His Ile Ile His Trp Val Thr
250                 255                 260                 265 tat gta gag ctc tgt gct ccc tgt gag ata atg tac agt gtg att gga   1229
Tyr Val Glu Leu Cys Ala Pro Cys Glu Ile Met Tyr Ser Val Ile Gly
            270                 275                 280 cac cac gag acc ctg gag gac gat gcc cca tac atc tta aaa gag gct   1277
His His Glu Thr Leu Glu Asp Asp Ala Pro Tyr Ile Leu Lys Glu Ala
        285                 290                 295 ggc att gac cac ctg gtg tca tac ccg act atc cct ccg ggc att acc   1325
Gly Ile Asp His Leu Val Ser Tyr Pro Thr Ile Pro Pro Gly Ile Thr
            300                 305                 310 gtg tat aac aga acc aag gtg gag cac tat ttc ctg ggc atc agc aaa   1373
Val Tyr Asn Arg Thr Lys Val Glu His Tyr Phe Leu Gly Ile Ser Lys
            315                 320                 325 cga gac atc cga cgc ctg tat gcc cgt ttc gaa ggg gac ttt aag ctc   1421
Arg Asp Ile Arg Arg Leu Tyr Ala Arg Phe Glu Gly Asp Phe Lys Leu
330                 335                 340                 345 ttt ggg tac cag aaa cca gac ttt ttg cta aac taa tgcataagac        1467
Phe Gly Tyr Gln Lys Pro Asp Phe Leu Leu Asn  *
            350                 355 ctatgaattc aaaatatcttt attagacctg gggctaacca ggtgaagatc tgagcccaga 1527 aatgaccctt cctccaccac acccctcctt tgaggatgcc cggggtctcc cacaggcctg  1587
```

```
tgagttgcct cggcatatga cgcagaaccc caactgttac aacttagttt ggatgtaaga    1647
tgctctgagg accctgccca caccctgcg tgcattagga tgtcgctggc ctttgctcac    1707
ctcagagggg agaaaaggct aaagatttgc agtttgacag cccagcaggg aggaagcatc   1767
acacagcgtt aggagccgtt tccttcaggt gttaaggaag gggatgcccc tgaggttctc   1827
ctggctagtc ggggtggctt cacccatcac tggtgggttg caggaacagc acccaggact   1887
ctgaggaggg acagagaagc aagggggctg ctgaaatcgc agagactttt gcagcatcag   1947
atctgaggag taaaacggca cctctggcct tcatcttggt gctgcgacaa ttgtggaggc   2007
aaagcattct ttctgtgact attttgttcc tgtagacagt cagcgatggc cagagggtgg   2067
tgtggtgtcc aggggtccat ctttccagaa tccatgcctg tgtaatgctg gtccatgctt   2127
ctgaacctgt gtctgccaag cgcctatttc attcagcaca agacatacga ttttagaagg   2187
tgaggggagg ggaggctttt tctacctgag aaggggagtg tctttgaggg ccttaaaagg   2247
accatggccc aggaatgggg gcgctggttg ggcttggagc tcaggctgct gtggatcccg   2307
gcgcatcagt tctgacttgc cttacctggg tggacagcag tgaatctcca cctgtcttct   2367
ccagggagct cccatgttgg ggctgaagac gagcagggc aacctgccag catcacagaa    2427
ttcagtgtag tttatacatt tcgattcctt tcatctcagc aaaatgggca ctgccagagc   2487
catttctgat cacaccacca tcctggacca tgtgactgga aggtgggtaa ccaagttcac   2547
cagcaataaa acccagcgcc caggtagcct ccagcagtgc ggcttcctgg caacaaggta   2607
ggccctggtg cagggcaagc cgcagcgacc atttcagata ccgtccacag ccaggaccgc   2667
tgagaactgg gacagtttcc tgggatgagt gccagcctga gcctgcatgg tgccgccgag   2727
cccgggtgg aggagggagc caggcttcgc ttcaaggcgg cctctacctt ttctcagaat    2787
ggtttcctga ttgtgtcaat gtgaaagtta aataaatttt atgtgccaaa aaaaaaaaa    2847
aaaaaaaaa aaaaaaaaaa aaaaaaaaa                                     2877
```

<210> SEQ ID NO 50
<211> LENGTH: 356
<212> TYPE: PRT
<213> ORGANISM: Homo Sapiens

<400> SEQUENCE: 50

```
Met His His Gln Trp Leu Leu Leu Ala Ala Cys Phe Trp Val Ile Phe
 1               5                  10                  15

Met Phe Met Val Ala Ser Lys Phe Ile Thr Leu Thr Phe Lys Asp Pro
            20                  25                  30

Asp Val Tyr Ser Ala Lys Gln Glu Phe Leu Phe Leu Thr Thr Met Pro
        35                  40                  45

Glu Val Arg Lys Leu Pro Glu Glu Lys His Ile Pro Glu Glu Leu Lys
    50                  55                  60

Pro Thr Gly Lys Glu Leu Pro Asp Ser Gln Leu Val Gln Pro Leu Val
65                  70                  75                  80

Tyr Met Glu Arg Leu Glu Leu Ile Arg Asn Val Cys Arg Asp Asp Ala
                85                  90                  95

Leu Lys Asn Leu Ser His Thr Pro Val Ser Lys Phe Leu Asp Arg
            100                 105                 110

Ile Phe Val Cys Asp Lys His Lys Ile Leu Phe Cys Gln Thr Pro Lys
        115                 120                 125

Val Gly Asn Thr Gln Trp Lys Lys Val Leu Ile Val Leu Asn Gly Ala
    130                 135                 140
```

```
Phe Ser Ser Ile Glu Glu Ile Pro Glu Asn Val Val His Asp His Glu
145                 150                 155                 160

Lys Asn Gly Leu Pro Arg Leu Ser Ser Phe Ser Asp Ala Glu Ile Gln
            165                 170                 175

Lys Arg Leu Lys Thr Tyr Phe Lys Phe Ile Val Arg Asp Pro Phe
        180                 185                 190

Glu Arg Leu Ile Ser Ala Phe Lys Asp Lys Phe Val His Asn Pro Arg
            195                 200                 205

Phe Glu Pro Trp Tyr Arg His Glu Ile Ala Pro Gly Ile Ile Arg Lys
210                 215                 220

Tyr Arg Arg Asn Arg Thr Glu Thr Arg Gly Ile Gln Phe Glu Asp Phe
225                 230                 235                 240

Val Arg Tyr Leu Gly Asp Pro Asn His Arg Trp Leu Asp Leu Gln Phe
            245                 250                 255

Gly Asp His Ile Ile His Trp Val Thr Tyr Val Glu Leu Cys Ala Pro
            260                 265                 270

Cys Glu Ile Met Tyr Ser Val Ile Gly His His Glu Thr Leu Glu Asp
        275                 280                 285

Asp Ala Pro Tyr Ile Leu Lys Glu Ala Gly Ile Asp His Leu Val Ser
290                 295                 300

Tyr Pro Thr Ile Pro Pro Gly Ile Thr Val Tyr Asn Arg Thr Lys Val
305                 310                 315                 320

Glu His Tyr Phe Leu Gly Ile Ser Lys Arg Asp Ile Arg Arg Leu Tyr
            325                 330                 335

Ala Arg Phe Glu Gly Asp Phe Lys Leu Phe Gly Tyr Gln Lys Pro Asp
            340                 345                 350

Phe Leu Leu Asn
        355

<210> SEQ ID NO 51
<211> LENGTH: 1451
<212> TYPE: DNA
<213> ORGANISM: Homo Sapiens
<220> FEATURE:
<221> NAME/KEY: CDS
<222> LOCATION: (148)...(1341)

<400> SEQUENCE: 51
cggcccgccc tggggaggcg cgcagcagag gctccgattc ggggcaggtg agaggctgac      60
tttctctcgg tgcgtccagt ggagctctga gtttcgaatc ggtggcggcg gattccccgc     120
gcgcccggcg tcgggcttc aggagg atg cgg agc ccc agc gcg gcg tgg ctg       174
                             Met Arg Ser Pro Ser Ala Ala Trp Leu
                              1               5 ctg ggg gcc gcc atc ctg cta gca gcc tct ctc tcc tgc agt ggc acc       222
Leu Gly Ala Ala Ile Leu Leu Ala Ala Ser Leu Ser Cys Ser Gly Thr
 10              15                  20                  25 atc caa gga acc aat aga tcc tct aaa gga aga agc ctt att ggt aag       270
Ile Gln Gly Thr Asn Arg Ser Ser Lys Gly Arg Ser Leu Ile Gly Lys
             30                  35                  40 gtt gat ggc aca tcc cac gtc act gga aaa gga gtt aca gtt gaa aca       318
Val Asp Gly Thr Ser His Val Thr Gly Lys Gly Val Thr Val Glu Thr
         45                  50                  55 gtc ttt tct gtg gat gag ttt tct gca tct gtc ctc act gga aaa ctg       366
Val Phe Ser Val Asp Glu Phe Ser Ala Ser Val Leu Thr Gly Lys Leu
     60                  65                  70 acc acg gtc ttc ctt cca att gtc tac aca att gtg ttt gtg gtg ggt       414
```

```
                                                               -continued

Thr Thr Val Phe Leu Pro Ile Val Tyr Thr Ile Val Phe Val Val Gly
    75                  80                  85 ttg cca agt aac ggc atg gcc ctg tgg gtc ttt ctt ttc cga act aag      462
Leu Pro Ser Asn Gly Met Ala Leu Trp Val Phe Leu Phe Arg Thr Lys
 90                  95                 100                 105 aag aag cac cct gct gtg att tac atg gcc aat ctg gcc ttg gct gac      510
Lys Lys His Pro Ala Val Ile Tyr Met Ala Asn Leu Ala Leu Ala Asp
                    110                 115                 120 ctc ctc tct gtc atc tgg ttc ccc ttg aag att gcc tat cac ata cat      558
Leu Leu Ser Val Ile Trp Phe Pro Leu Lys Ile Ala Tyr His Ile His
                125                 130                 135 gcc aac aac tgg att tat ggg gaa gct ctt tgt aat gtg ctt att ggc      606
Ala Asn Asn Trp Ile Tyr Gly Glu Ala Leu Cys Asn Val Leu Ile Gly
            140                 145                 150 ttt ttc tat ggc aac atg tac tgt tcc att ctc ttc atg acc tgc ctc      654
Phe Phe Tyr Gly Asn Met Tyr Cys Ser Ile Leu Phe Met Thr Cys Leu
        155                 160                 165 agt gtg cag agg tat tgg gtc atc gtg aac ccc atg ggg cac tcc agg      702
Ser Val Gln Arg Tyr Trp Val Ile Val Asn Pro Met Gly His Ser Arg
170                 175                 180                 185 aag aag gca aac att gcc att ggc atc tcc ctg gca ata tgg ctg ctg      750
Lys Lys Ala Asn Ile Ala Ile Gly Ile Ser Leu Ala Ile Trp Leu Leu
                    190                 195                 200 att ctg ctg gtc acc atc cct ttg tat gtc gtg aag cag acc atc ttc      798
Ile Leu Leu Val Thr Ile Pro Leu Tyr Val Val Lys Gln Thr Ile Phe
                205                 210                 215 att cct gcc ctg aac atc acg acc tgt cat gat gtt ttg cct gag cag      846
Ile Pro Ala Leu Asn Ile Thr Thr Cys His Asp Val Leu Pro Glu Gln
            220                 225                 230 ctc ttg gtg gga gac atg ttc aat tac ttc ctc tct ctg gcc att ggg      894
Leu Leu Val Gly Asp Met Phe Asn Tyr Phe Leu Ser Leu Ala Ile Gly
        235                 240                 245 gtc ttt ctg ttc cca gcc ttc ctc aca gcc tct gcc tat gtg ctg atg      942
Val Phe Leu Phe Pro Ala Phe Leu Thr Ala Ser Ala Tyr Val Leu Met
250                 255                 260                 265 atc aga atg ctg cga tct tct gcc atg gat gaa aac tca gag aag aaa      990
Ile Arg Met Leu Arg Ser Ser Ala Met Asp Glu Asn Ser Glu Lys Lys
                    270                 275                 280 agg aag agg gcc atc aaa ctc att gtc act gtc ctg gcc atg tac ctg     1038
Arg Lys Arg Ala Ile Lys Leu Ile Val Thr Val Leu Ala Met Tyr Leu
                285                 290                 295 atc tgc ttc act cct agt aac ctt ctg ctt gtg gtg cat tat ttt ctg     1086
Ile Cys Phe Thr Pro Ser Asn Leu Leu Leu Val Val His Tyr Phe Leu
            300                 305                 310 att aag agc cag ggc cag agc cat gtc tat gcc ctg tac att gta gcc     1134
Ile Lys Ser Gln Gly Gln Ser His Val Tyr Ala Leu Tyr Ile Val Ala
        315                 320                 325 ctc tgc ctc tct acc ctt aac agc tgc atc gac ccc ttt gtc tat tac     1182
Leu Cys Leu Ser Thr Leu Asn Ser Cys Ile Asp Pro Phe Val Tyr Tyr
330                 335                 340                 345 ttt gtt tca cat gat ttc agg gat cat gca aag aac gct ctc ctt tgc     1230
Phe Val Ser His Asp Phe Arg Asp His Ala Lys Asn Ala Leu Leu Cys
                    350                 355                 360 cga agt gtc cgc act gta aag cag atg caa gta tcc ctc acc tca aag     1278
Arg Ser Val Arg Thr Val Lys Gln Met Gln Val Ser Leu Thr Ser Lys
                365                 370                 375 aaa cac tcc agg aaa tcc agc tct tac tct tca agt tca acc act gtt     1326
Lys His Ser Arg Lys Ser Ser Ser Tyr Ser Ser Ser Thr Thr Val
            380                 385                 390
```

```
aag acc tcc tat tga gttttccagg tcctcagatg ggaattgcac agtaggatgt      1381
Lys Thr Ser Tyr *
    395 ggaacctgtt taatgttatg aggacgtgtc tgttatttcc taatcaaaaa ggtctcacca    1441 cataccaccg                                                            1451

<210> SEQ ID NO 52
<211> LENGTH: 397
<212> TYPE: PRT
<213> ORGANISM: Homo Sapiens

<400> SEQUENCE: 52

Met Arg Ser Pro Ser Ala Ala Trp Leu Leu Gly Ala Ala Ile Leu Leu
  1               5                  10                  15

Ala Ala Ser Leu Ser Cys Ser Gly Thr Ile Gln Gly Thr Asn Arg Ser
                 20                  25                  30

Ser Lys Gly Arg Ser Leu Ile Gly Lys Val Asp Gly Thr Ser His Val
             35                  40                  45

Thr Gly Lys Gly Val Thr Val Glu Thr Val Phe Ser Val Asp Glu Phe
         50                  55                  60

Ser Ala Ser Val Leu Thr Gly Lys Leu Thr Thr Val Phe Leu Pro Ile
 65                  70                  75                  80

Val Tyr Thr Ile Val Phe Val Val Gly Leu Pro Ser Asn Gly Met Ala
                 85                  90                  95

Leu Trp Val Phe Leu Phe Arg Thr Lys Lys Lys His Pro Ala Val Ile
                100                 105                 110

Tyr Met Ala Asn Leu Ala Leu Ala Asp Leu Leu Ser Val Ile Trp Phe
            115                 120                 125

Pro Leu Lys Ile Ala Tyr His Ile His Ala Asn Asn Trp Ile Tyr Gly
        130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
                180                 185                 190

Gly Ile Ser Leu Ala Ile Trp Leu Leu Ile Leu Leu Val Thr Ile Pro
            195                 200                 205

Leu Tyr Val Val Lys Gln Thr Ile Phe Ile Pro Ala Leu Asn Ile Thr
        210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

Leu Thr Ala Ser Ala Tyr Val Leu Met Ile Arg Met Leu Arg Ser Ser
                260                 265                 270

Ala Met Asp Glu Asn Ser Glu Lys Lys Arg Lys Arg Ala Ile Lys Leu
            275                 280                 285

Ile Val Thr Val Leu Ala Met Tyr Leu Ile Cys Phe Thr Pro Ser Asn
        290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
                325                 330                 335
```

```
                    Ser Cys Ile Asp Pro Phe Val Tyr Tyr Phe Val Ser His Asp Phe Arg
                            340                 345                 350

Asp His Ala Lys Asn Ala Leu Leu Cys Arg Ser Val Arg Thr Val Lys
                            355                 360                 365

Gln Met Gln Val Ser Leu Thr Ser Lys Lys His Ser Arg Lys Ser Ser
                            370                 375                 380

Ser Tyr Ser Ser Ser Ser Thr Thr Val Lys Thr Ser Tyr
                    385                 390                 395

<210> SEQ ID NO 53
<211> LENGTH: 2643
<212> TYPE: DNA
<213> ORGANISM: Homo Sapiens
<220> FEATURE:
<221> NAME/KEY: CDS
<222> LOCATION: (174)...(1373)

<400> SEQUENCE: 53
gcctccagct gacctctggc tcctgtcctc tggctccacc tgcaccgccc tgctcttcct        60
aaggggccag gaagccccca gaagctctac catcgacgtg ggtggtggca cccggctcac       120
cctgagagca gagggcgtgc aggggctca gttctgagcc cagccggccc acc atg          176
                                                             Met
                                                             1 gca cgg cgg ttc cag gag gag ctg gcc gcc ttc ctc ttc gag tat gac          224
Ala Arg Arg Phe Gln Glu Glu Leu Ala Ala Phe Leu Phe Glu Tyr Asp
        5                  10                  15 acc ccc cgc atg gtg ctg gtg cgt aat aag aag gtg ggc gtt atc ttc          272
Thr Pro Arg Met Val Leu Val Arg Asn Lys Lys Val Gly Val Ile Phe
    20                  25                  30 cga ctg atc cag ctg gtg gtc ctg gtc tac gtc atc ggg tgg gtg ttt          320
Arg Leu Ile Gln Leu Val Val Leu Val Tyr Val Ile Gly Trp Val Phe
35                  40                  45 ctc tat gag aag ggc tac cag acc tcg agc ggc ctc atc agc agt gtc          368
Leu Tyr Glu Lys Gly Tyr Gln Thr Ser Ser Gly Leu Ile Ser Ser Val
50                  55                  60                  65 tct gtg aaa ctc aag ggc ctg gcc gtg acc cag ctc cct ggc ctc ggc          416
Ser Val Lys Leu Lys Gly Leu Ala Val Thr Gln Leu Pro Gly Leu Gly
                70                  75                  80 ccc cag gtc tgg gat gtg gct gac tac gtc ttc cca gcc cag ggg gac          464
Pro Gln Val Trp Asp Val Ala Asp Tyr Val Phe Pro Ala Gln Gly Asp
            85                  90                  95 aac tcc ttc gtg gtc atg acc aat ttc atc gtg acc ccg aag cag act          512
Asn Ser Phe Val Val Met Thr Asn Phe Ile Val Thr Pro Lys Gln Thr
        100                 105                 110 caa ggc tac tgc gca gag cac cca gaa ggg ggc ata tgc aag gaa gac          560
Gln Gly Tyr Cys Ala Glu His Pro Glu Gly Gly Ile Cys Lys Glu Asp
    115                 120                 125 agt ggc tgt acc cct ggg aag gcc aag agg aag gcc caa ggc atc cgc          608
Ser Gly Cys Thr Pro Gly Lys Ala Lys Arg Lys Ala Gln Gly Ile Arg
130                 135                 140                 145 acg ggc aag tgt gtg gcc ttc aac gac act gtg aag acg tgt gag atc          656
Thr Gly Lys Cys Val Ala Phe Asn Asp Thr Val Lys Thr Cys Glu Ile
                150                 155                 160 ttt ggc tgg tgc ccc gtg gag gtg gat gac gac atc ccg cgc cct gcc          704
Phe Gly Trp Cys Pro Val Glu Val Asp Asp Asp Ile Pro Arg Pro Ala
            165                 170                 175 ctt ctc cga gag gcc gag aac ttc act ctt ttc atc aag aac agc atc          752
Leu Leu Arg Glu Ala Glu Asn Phe Thr Leu Phe Ile Lys Asn Ser Ile
        180                 185                 190
```

-continued

| | | |
|---|---|---|
| agc ttt cca cgc ttc aag gtc aac agg cgc aac ctg gtg gag gag gtg<br>Ser Phe Pro Arg Phe Lys Val Asn Arg Arg Asn Leu Val Glu Glu Val<br>195                      200                    205 | 800 |
| aat gct gcc cac atg aag acc tgc ctc ttt cac aag acc ctg cac ccc<br>Asn Ala Ala His Met Lys Thr Cys Leu Phe His Lys Thr Leu His Pro<br>210                      215                    220              225 | 848 |
| ctg tgc cca gtc ttc cag ctt ggc tac gtg gtg caa gag tca ggc cag<br>Leu Cys Pro Val Phe Gln Leu Gly Tyr Val Val Gln Glu Ser Gly Gln<br>                    230                    235                    240 | 896 |
| aac ttc agc acc ctg gct gag aag ggt gga gtg gtt ggc atc acc atc<br>Asn Phe Ser Thr Leu Ala Glu Lys Gly Gly Val Val Gly Ile Thr Ile<br>                  245                    250                    255 | 944 |
| gac tgg cac tgt gac ctg gac tgg cac gta cgg cac tgc aga ccc atc<br>Asp Trp His Cys Asp Leu Asp Trp His Val Arg His Cys Arg Pro Ile<br>260                      265                    270 | 992 |
| tat gag ttc cat ggg ctg tac gaa gag aaa aat ctc tcc cca ggc ttc<br>Tyr Glu Phe His Gly Leu Tyr Glu Glu Lys Asn Leu Ser Pro Gly Phe<br>      275                    280                    285 | 1040 |
| aac ttc agg ttt gcc agg cac ttt gtg gag aac ggg acc aac tac cgt<br>Asn Phe Arg Phe Ala Arg His Phe Val Glu Asn Gly Thr Asn Tyr Arg<br>290                      295                    300              305 | 1088 |
| cac ctc ttc aag gtg ttt ggg att cgc ttt gac atc ctg gtg gac ggc<br>His Leu Phe Lys Val Phe Gly Ile Arg Phe Asp Ile Leu Val Asp Gly<br>                  310                    315                    320 | 1136 |
| aag gcc ggg aag ttt gac atc atc cct aca atg acc acc atc ggc tct<br>Lys Ala Gly Lys Phe Asp Ile Ile Pro Thr Met Thr Thr Ile Gly Ser<br>                  325                    330                    335 | 1184 |
| gga att ggc atc ttt ggg gtg gcc aca gtt ctc tgt gac ctg ctg ctg<br>Gly Ile Gly Ile Phe Gly Val Ala Thr Val Leu Cys Asp Leu Leu Leu<br>                340                    345                    350 | 1232 |
| ctt cac atc ctg cct aag agg cac tac tac aag cag aag aag ttc aaa<br>Leu His Ile Leu Pro Lys Arg His Tyr Tyr Lys Gln Lys Lys Phe Lys<br>355                      360                    365 | 1280 |
| tac gct gag gac atg ggg cca ggg gcg gct gag cgt gac ctc gca gct<br>Tyr Ala Glu Asp Met Gly Pro Gly Ala Ala Glu Arg Asp Leu Ala Ala<br>370                      375                    380              385 | 1328 |
| acc agc tcc acc ctg ggc ctg cag gag aac atg agg aca tcc tga<br>Thr Ser Ser Thr Leu Gly Leu Gln Glu Asn Met Arg Thr Ser  *<br>                  390                    395 | 1373 |
| tgctcgggcc ccaactcctg actgggtgca gcgtgaggct tcagcctgga gccctggtgg | 1433 |
| gtcccagcca gggcagaggg gcctccccag gaagtctcct accctctcag ccaggcagag | 1493 |
| agcagtttgc cagaagctca gggtgcatag taggagagac ctgtgcaaat ctgagctccg | 1553 |
| gctccgaccc cacacaccct gagggaggcc taccctagcc tcagccgctc ctggtggggg | 1613 |
| aatggctggg ggttgggcag gaccctccca cacacctgca ccctagcttc gtgcttctct | 1673 |
| ctccggactc tcattatcca acccgctgcc tccatttctc tagatctgtg ctctccgatg | 1733 |
| tggcagtcag taaccatagg tgactaaatt aaactaaaat aaaatagaat gaaacacaaa | 1793 |
| attcaattcc tcggctgaac tagccacatt tcaactgctc agtagatacg tgtggttagt | 1853 |
| ggctgccata ctggacagct cggggcattt tcactgtcaa agaaagttct attagacagc | 1913 |
| cctgcttgag ccctgtttct tcctggcttc ggtttccctg gggaacttat cgacaatgca | 1973 |
| agctcctggg cccaccccca gacctcctga accaaaagct ccagggctgg ccgtatgatc | 2033 |
| tgtgtggatg gcaaactccc caggccattc tgggacctaa gtttaagaag tgccgtcctc | 2093 |
| gaactttctg actctaagct cctgagcggg agtcagactt agccctgagc ctgcacttcc | 2153 |
| tgttcaggtg cagacactga acagggtctc aaacaccttc agcatgtgtg ttgtgtgctc | 2213 |

```
acgtgccaca cagtgtctca tgcacacaac ccagtgtaca caccacctac gtgcacacag    2273
catccttcca cactgtgtat gtgaacagct tgggccctgc aaacacaacc atctacacac    2333
atctacaccc ccaagcacac acacatggtc cgtgccatgt cacctccata gggaaaggct    2393
tctctccaag tgtgccaggc caggacagcc ctcccagcca tgaatcctta ctcagctacc    2453
tcgggttggg gtgggagccc cagccaaatc ctgggctccc tgcctgtggc tcagccccag    2513
ctcccaaggc ctgcctggct ctgtctgaac agaaggtctg ggggaagcga ggggtggagt    2573
acaataaagg gaatgaggac aaacaaaaaa aaaaaaaaa aaaaaaaaa aaaaaaaaa      2633 aaaaaaaaaa                                                         2643
```

<210> SEQ ID NO 54
<211> LENGTH: 399
<212> TYPE: PRT
<213> ORGANISM: Homo Sapiens

<400> SEQUENCE: 54

```
Met Ala Arg Arg Phe Gln Glu Glu Leu Ala Ala Phe Leu Phe Glu Tyr
  1               5                  10                  15

Asp Thr Pro Arg Met Val Leu Val Arg Asn Lys Lys Val Gly Val Ile
                 20                  25                  30

Phe Arg Leu Ile Gln Leu Val Val Leu Tyr Val Ile Gly Trp Val
             35                  40                  45

Phe Leu Tyr Glu Lys Gly Tyr Gln Thr Ser Ser Gly Leu Ile Ser Ser
         50                  55                  60

Val Ser Val Lys Leu Lys Gly Leu Ala Val Thr Gln Leu Pro Gly Leu
 65                  70                  75                  80

Gly Pro Gln Val Trp Asp Val Ala Asp Tyr Val Phe Pro Ala Gln Gly
                 85                  90                  95

Asp Asn Ser Phe Val Val Met Thr Asn Phe Ile Val Thr Pro Lys Gln
            100                 105                 110

Thr Gln Gly Tyr Cys Ala Glu His Pro Glu Gly Gly Ile Cys Lys Glu
        115                 120                 125

Asp Ser Gly Cys Thr Pro Gly Lys Ala Lys Arg Lys Ala Gln Gly Ile
    130                 135                 140

Arg Thr Gly Lys Cys Val Ala Phe Asn Asp Thr Val Lys Thr Cys Glu
145                 150                 155                 160

Ile Phe Gly Trp Cys Pro Val Glu Val Asp Asp Ile Pro Arg Pro
                165                 170                 175

Ala Leu Leu Arg Glu Ala Glu Asn Phe Thr Leu Phe Ile Lys Asn Ser
            180                 185                 190

Ile Ser Phe Pro Arg Phe Lys Val Asn Arg Arg Asn Leu Val Glu Glu
        195                 200                 205

Val Asn Ala Ala His Met Lys Thr Cys Leu Phe His Lys Thr Leu His
    210                 215                 220

Pro Leu Cys Pro Val Phe Gln Leu Gly Tyr Val Val Gln Glu Ser Gly
225                 230                 235                 240

Gln Asn Phe Ser Thr Leu Ala Glu Lys Gly Gly Val Val Gly Ile Thr
                245                 250                 255

Ile Asp Trp His Cys Asp Leu Asp Trp His Val Arg His Cys Arg Pro
            260                 265                 270

Ile Tyr Glu Phe His Gly Leu Tyr Glu Glu Lys Asn Leu Ser Pro Gly
        275                 280                 285
```

```
Phe Asn Phe Arg Phe Ala Arg His Phe Val Glu Asn Gly Thr Asn Tyr
    290                 295                 300

Arg His Leu Phe Lys Val Phe Gly Ile Arg Phe Asp Ile Leu Val Asp
305                 310                 315                 320

Gly Lys Ala Gly Lys Phe Asp Ile Ile Pro Thr Met Thr Thr Ile Gly
                325                 330                 335

Ser Gly Ile Gly Ile Phe Gly Val Ala Thr Val Leu Cys Asp Leu Leu
            340                 345                 350

Leu Leu His Ile Leu Pro Lys Arg His Tyr Tyr Lys Gln Lys Lys Phe
        355                 360                 365

Lys Tyr Ala Glu Asp Met Gly Pro Gly Ala Ala Glu Arg Asp Leu Ala
370                 375                 380

Ala Thr Ser Ser Thr Leu Gly Leu Gln Glu Asn Met Arg Thr Ser
385                 390                 395

<210> SEQ ID NO 55
<211> LENGTH: 2087
<212> TYPE: DNA
<213> ORGANISM: Homo Sapiens
<220> FEATURE:
<221> NAME/KEY: CDS
<222> LOCATION: (104)...(1612)

<400> SEQUENCE: 55
ggcacgagga gccgagcggc gaggtgcctc tgtggccgca cggcaggccc gggcgacacg      60
gagacgtgga gcgcgccggc tcgctgcagc tccgggactc aac atg cgc tgc tcg      115
                                                Met Arg Cys Ser
                                                    1 ccg gga ggc gtc tgg ctg ggc ctg gcc gcg tcg ctc ctg cac gtg tcc      163
Pro Gly Gly Val Trp Leu Gly Leu Ala Ala Ser Leu Leu His Val Ser
 5              10                  15                  20 ctg caa ggc gag ttc cag agg aag ctt tac aag gag ctg gtc aag aac      211
Leu Gln Gly Glu Phe Gln Arg Lys Leu Tyr Lys Glu Leu Val Lys Asn
            25                  30                  35 tac aat ccc ttg gag agg ccc gtg gcc aat gac tcg caa cca ctc acc      259
Tyr Asn Pro Leu Glu Arg Pro Val Ala Asn Asp Ser Gln Pro Leu Thr
        40                  45                  50 gtc tac ttc tcc ctg agc ctc ctg cag atc atg gac gtg gat gag aag      307
Val Tyr Phe Ser Leu Ser Leu Leu Gln Ile Met Asp Val Asp Glu Lys
    55                  60                  65 aac caa gtt tta acc acc aac att tgg ctg caa atg tct tgg aca gat      355
Asn Gln Val Leu Thr Thr Asn Ile Trp Leu Gln Met Ser Trp Thr Asp
70                  75                  80 cac tat tta cag tgg aat gtg tca gaa tat cca ggg gtg aag act gtt      403
His Tyr Leu Gln Trp Asn Val Ser Glu Tyr Pro Gly Val Lys Thr Val
85                  90                  95                 100 cgt ttc cca gat ggc cag att tgg aaa cca gac att ctt ctc tat aac      451
Arg Phe Pro Asp Gly Gln Ile Trp Lys Pro Asp Ile Leu Leu Tyr Asn
                105                 110                 115 agt gct gat gag cgc ttt gac gcc aca ttc cac act aac gtg ttg gtg      499
Ser Ala Asp Glu Arg Phe Asp Ala Thr Phe His Thr Asn Val Leu Val
            120                 125                 130 aat tct tct ggg cat tgc cag tac ctg cct cca ggc ata ttc aag agt      547
Asn Ser Ser Gly His Cys Gln Tyr Leu Pro Pro Gly Ile Phe Lys Ser
        135                 140                 145 tcc tgc tac atc gat gta cgc tgg ttt ccc ttt gat gtg cag cac tgc      595
Ser Cys Tyr Ile Asp Val Arg Trp Phe Pro Phe Asp Val Gln His Cys
    150                 155                 160 aaa ctg aag ttt ggg tcc tgg tct tac gga ggc tgg tcc ttg gat ctg      643
```

```
Lys Leu Lys Phe Gly Ser Trp Ser Tyr Gly Gly Trp Ser Leu Asp Leu
165                 170                 175                 180 cag atg cag gag gca gat atc agt ggc tat atc ccc aat gga gaa tgg      691
Gln Met Gln Glu Ala Asp Ile Ser Gly Tyr Ile Pro Asn Gly Glu Trp
                    185                 190                 195 gac cta gtg gga atc ccc ggc aag agg agt gaa agg ttc tat gag tgc      739
Asp Leu Val Gly Ile Pro Gly Lys Arg Ser Glu Arg Phe Tyr Glu Cys
                200                 205                 210 tgc aaa gag ccc tac ccc gat gtc acc ttc aca gtg acc atg cgc cgc      787
Cys Lys Glu Pro Tyr Pro Asp Val Thr Phe Thr Val Thr Met Arg Arg
            215                 220                 225 agg aca ctc tac tat ggc ctc aac ctg ctg atc ccc tgt gtg ctc atc      835
Arg Thr Leu Tyr Tyr Gly Leu Asn Leu Leu Ile Pro Cys Val Leu Ile
        230                 235                 240 tcc gcc ctc gcc ctg ctg gtg ttc ctg ctt cct gca gat tcc ggg gag      883
Ser Ala Leu Ala Leu Leu Val Phe Leu Leu Pro Ala Asp Ser Gly Glu
245                 250                 255                 260 aag att tcc ctg ggg ata aca gtc tta ctc tct ctt acc gtc ttc atg      931
Lys Ile Ser Leu Gly Ile Thr Val Leu Leu Ser Leu Thr Val Phe Met
                265                 270                 275 ctc ctc gtg gct gag atc atg ccc gca aca tcc gat tcg gta cca ttg      979
Leu Leu Val Ala Glu Ile Met Pro Ala Thr Ser Asp Ser Val Pro Leu
            280                 285                 290 ata gcc cag tac ttc gcc agc acc atg atc atc gtg ggc ctc tcg gtg     1027
Ile Ala Gln Tyr Phe Ala Ser Thr Met Ile Ile Val Gly Leu Ser Val
        295                 300                 305 gtg gtg aca gta atc gtg ctg cag tac cac cac cac gac ccc gac ggg     1075
Val Val Thr Val Ile Val Leu Gln Tyr His His His Asp Pro Asp Gly
310                 315                 320 ggc aag atg ccc aag tgg acc aga gtc atc ctt ctg aac tgg tgc gcg     1123
Gly Lys Met Pro Lys Trp Thr Arg Val Ile Leu Leu Asn Trp Cys Ala
325                 330                 335                 340 tgg ttc ctg cga atg aag agg ccc ggg gag gac aag gtg cgc ccg gcc     1171
Trp Phe Leu Arg Met Lys Arg Pro Gly Glu Asp Lys Val Arg Pro Ala
                345                 350                 355 tgc cag cac aag cag cgg cgc tgc agc ctg gcc agt gtg gag atg agc     1219
Cys Gln His Lys Gln Arg Arg Cys Ser Leu Ala Ser Val Glu Met Ser
            360                 365                 370 gcc gtg ggc ccg ccg ccc gcc agc aac ggg aac ctg cta tac atc ggc     1267
Ala Val Gly Pro Pro Pro Ala Ser Asn Gly Asn Leu Leu Tyr Ile Gly
        375                 380                 385 ttc cgc ggc ctg gac ggc gtg cac tgt gtc ccg acc ccc gac tct ggg     1315
Phe Arg Gly Leu Asp Gly Val His Cys Val Pro Thr Pro Asp Ser Gly
390                 395                 400 gta gtg tgt ggc cgc atg gcc tgc tcc ccc acg cac gat gag cac ctc     1363
Val Val Cys Gly Arg Met Ala Cys Ser Pro Thr His Asp Glu His Leu
405                 410                 415                 420 ctg cac ggc ggg caa ccc ccc gag ggg gac ccg gac ttg gcc aag atc     1411
Leu His Gly Gly Gln Pro Pro Glu Gly Asp Pro Asp Leu Ala Lys Ile
                425                 430                 435 ctg gag gag gtc cgc tac att gcc aac cgc ttc cgc tgc cag gac gaa     1459
Leu Glu Glu Val Arg Tyr Ile Ala Asn Arg Phe Arg Cys Gln Asp Glu
            440                 445                 450 agc gag gcg gtc tgc agc gag tgg aag ttc gcc gcc tgt gtg gtg gac     1507
Ser Glu Ala Val Cys Ser Glu Trp Lys Phe Ala Ala Cys Val Val Asp
        455                 460                 465 cgc ctg tgc ctc atg gcc ttc tcg gtc ttc acc atc atc tgc acc atc     1555
Arg Leu Cys Leu Met Ala Phe Ser Val Phe Thr Ile Ile Cys Thr Ile
470                 475                 480
```

```
ggc atc ctg atg tcg gct ccc aac ttc gtg gag gcc gtg tcc aaa gac    1603
Gly Ile Leu Met Ser Ala Pro Asn Phe Val Glu Ala Val Ser Lys Asp
485                 490                 495                 500 ttt gcg taa ccacactggt tctgtacatg tggaaaactc acagatggc              1652
Phe Ala * aaggcctttg gcttggcgag atttgggggt gctaatccag acagcatta cacgccacaa    1712 ctccagtgtt cccttctggc tgtcagtcgt gttgcttacg gtttctttgt tactttaggt   1772
agtagaatct cagcactttg tttcatattc tcagatgggc tgatagatac tccttggcac   1832
atccgtacca tcggtcagca gggccactga gtagtcattt tgccattagc cctcagcctg   1892
gaaagccctt cggagagctc cccatggctc ctcaccaccg agacagttgg ttttgcatgt   1952
ctgcatgaag gtctacctga aaattcaaca tttgcttttt gcttgtgtac aaacccagat   2012
tgaagctaaa ataaaccaga ctcactaaat cctttccaat aattgactgg tggaaggaaa   2072
acaaaaaaaa aaaaa                                                   2087

<210> SEQ ID NO 56
<211> LENGTH: 502
<212> TYPE: PRT
<213> ORGANISM: Homo Sapiens

<400> SEQUENCE: 56

Met Arg Cys Ser Pro Gly Gly Val Trp Leu Gly Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255
```

-continued

```
Asp Ser Gly Glu Lys Ile Ser Leu Gly Ile Thr Val Leu Leu Ser Leu
        260                 265                 270

Thr Val Phe Met Leu Leu Val Ala Glu Ile Met Pro Ala Thr Ser Asp
    275                 280                 285

Ser Val Pro Leu Ile Ala Gln Tyr Phe Ala Ser Thr Met Ile Ile Val
    290                 295                 300

Gly Leu Ser Val Val Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
            340                 345                 350

Val Arg Pro Ala Cys Gln His Lys Gln Arg Arg Cys Ser Leu Ala Ser
        355                 360                 365

Val Glu Met Ser Ala Val Gly Pro Pro Ala Ser Asn Gly Asn Leu
    370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
            420                 425                 430

Leu Ala Lys Ile Leu Glu Glu Val Arg Tyr Ile Ala Asn Arg Phe Arg
        435                 440                 445

Cys Gln Asp Glu Ser Glu Ala Val Cys Ser Glu Trp Lys Phe Ala Ala
    450                 455                 460

Cys Val Val Asp Arg Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                485                 490                 495

Val Ser Lys Asp Phe Ala
            500
```

<210> SEQ ID NO 57
<211> LENGTH: 857
<212> TYPE: DNA
<213> ORGANISM: Homo Sapiens
<220> FEATURE:
<221> NAME/KEY: CDS
<222> LOCATION: (9)...(776)

<400> SEQUENCE: 57

```
caggaaag atg cag cca ctc ctg ctt ctg ctg gcc ttt ctc cta ccc act      50
         Met Gln Pro Leu Leu Leu Leu Leu Ala Phe Leu Leu Pro Thr
         1               5                   10 ggg gct gag gca ggg gag atc atc gga ggc cgg gag agc agg ccc cac      98
Gly Ala Glu Ala Gly Glu Ile Ile Gly Gly Arg Glu Ser Arg Pro His
 15                  20                  25                  30 tcc cgc ccc tac atg gcg tat ctt cag atc cag agt cca gca ggt cag     146
Ser Arg Pro Tyr Met Ala Tyr Leu Gln Ile Gln Ser Pro Ala Gly Gln
                 35                  40                  45 agc aga tgt gga ggg ttc ctg gtg cga gaa gac ttt gtg ctg aca gca     194
Ser Arg Cys Gly Gly Phe Leu Val Arg Glu Asp Phe Val Leu Thr Ala
             50                  55                  60 gct cat tgc tgg gga agc aat ata aat gtc acc ctg ggc gcc cac aat     242
Ala His Cys Trp Gly Ser Asn Ile Asn Val Thr Leu Gly Ala His Asn
         65                  70                  75
```

```
atc cag aga cgg gaa aac acc cag caa cac atc act gcg cgc aga gcc    290
Ile Gln Arg Arg Glu Asn Thr Gln Gln His Ile Thr Ala Arg Arg Ala
 80                  85                  90 atc cgc cac cct caa tat aat cag cgg acc atc cag aat gac atc atg    338
Ile Arg His Pro Gln Tyr Asn Gln Arg Thr Ile Gln Asn Asp Ile Met
 95                 100                 105                 110 tta ttg cag ctg agc aga aga gtc aga cgg aat cga aac gtg aac cca    386
Leu Leu Gln Leu Ser Arg Arg Val Arg Arg Asn Arg Asn Val Asn Pro
                115                 120                 125 gtg gct ctg cct aga gcc cag gag gga ctg aga ccc ggg acg ctg tgc    434
Val Ala Leu Pro Arg Ala Gln Glu Gly Leu Arg Pro Gly Thr Leu Cys
            130                 135                 140 act gtg gcc ggc tgg ggc agg gtc agc atg agg agg gga aca gat aca    482
Thr Val Ala Gly Trp Gly Arg Val Ser Met Arg Arg Gly Thr Asp Thr
        145                 150                 155 ctc cga gag gtg cag ctg aga gtg cag agg gat agg cag tgc ctc cgc    530
Leu Arg Glu Val Gln Leu Arg Val Gln Arg Asp Arg Gln Cys Leu Arg
160                 165                 170 atc ttc ggt tcc tac gac ccc cga agg cag att tgt gtg ggg gac cgg    578
Ile Phe Gly Ser Tyr Asp Pro Arg Arg Gln Ile Cys Val Gly Asp Arg
175                 180                 185                 190 cgg gaa cgg aag gct gcc ttc aag ggg gat tcc gga ggc ccc ctg ctg    626
Arg Glu Arg Lys Ala Ala Phe Lys Gly Asp Ser Gly Gly Pro Leu Leu
                195                 200                 205 tgt aac aat gtg gcc cac ggc atc gtc tcc tat gga aag tcg tca ggg    674
Cys Asn Asn Val Ala His Gly Ile Val Ser Tyr Gly Lys Ser Ser Gly
            210                 215                 220 gtt cct cca gaa gtc ttc acc agg gtc tca agt ttc ctg ccc tgg ata    722
Val Pro Pro Glu Val Phe Thr Arg Val Ser Ser Phe Leu Pro Trp Ile
        225                 230                 235 agg aca aca atg aga agc ttc aaa ctg ctg gat cag atg gag acc ccc    770
Arg Thr Thr Met Arg Ser Phe Lys Leu Leu Asp Gln Met Glu Thr Pro
    240                 245                 250 ctg tga ctgactcttc ttctcgggga cacaggccag ctccacagtg ttgccagagc     826
Leu *
255 cttaataaac gtccacagag tataaataac c                                 857

<210> SEQ ID NO 58
<211> LENGTH: 255
<212> TYPE: PRT
<213> ORGANISM: Homo Sapiens

<400> SEQUENCE: 58

Met Gln Pro Leu Leu Leu Leu Ala Phe Leu Leu Pro Thr Gly Ala
 1               5                  10                  15

Glu Ala Gly Glu Ile Ile Gly Gly Arg Glu Ser Arg Pro His Ser Arg
                 20                  25                  30

Pro Tyr Met Ala Tyr Leu Gln Ile Gln Ser Pro Ala Gly Gln Ser Arg
             35                  40                  45

Cys Gly Gly Phe Leu Val Arg Glu Asp Phe Val Leu Thr Ala Ala His
     50                  55                  60

Cys Trp Gly Ser Asn Ile Asn Val Thr Leu Gly Ala His Asn Ile Gln
 65                  70                  75                  80

Arg Arg Glu Asn Thr Gln Gln His Ile Thr Ala Arg Arg Ala Ile Arg
                 85                  90                  95

His Pro Gln Tyr Asn Gln Arg Thr Ile Gln Asn Asp Ile Met Leu Leu
            100                 105                 110
```

```
Gln Leu Ser Arg Arg Val Arg Arg Asn Arg Asn Val Asn Pro Val Ala
        115                 120                 125
Leu Pro Arg Ala Gln Glu Gly Leu Arg Pro Gly Thr Leu Cys Thr Val
130                 135                 140
Ala Gly Trp Gly Arg Val Ser Met Arg Gly Thr Asp Thr Leu Arg
145                 150                 155                 160
Glu Val Gln Leu Arg Val Gln Arg Asp Arg Gln Cys Leu Arg Ile Phe
                165                 170                 175
Gly Ser Tyr Asp Pro Arg Arg Gln Ile Cys Val Gly Asp Arg Arg Glu
            180                 185                 190
Arg Lys Ala Ala Phe Lys Gly Asp Ser Gly Pro Leu Leu Cys Asn
        195                 200                 205
Asn Val Ala His Gly Ile Val Ser Tyr Gly Lys Ser Ser Gly Val Pro
210                 215                 220
Pro Glu Val Phe Thr Arg Val Ser Ser Phe Leu Pro Trp Ile Arg Thr
225                 230                 235                 240
Thr Met Arg Ser Phe Lys Leu Leu Asp Gln Met Glu Thr Pro Leu
                245                 250                 255

<210> SEQ ID NO 59
<211> LENGTH: 1354
<212> TYPE: DNA
<213> ORGANISM: Homo Sapiens
<220> FEATURE:
<221> NAME/KEY: CDS
<222> LOCATION: (21)...(1085)

<400> SEQUENCE: 59
gattctcagt gctgcggatc atg tcc cta agg ggc agc ctc tcg cgt ctc ctc      53
                     Met Ser Leu Arg Gly Ser Leu Ser Arg Leu Leu
                       1               5                  10 cag acg cga gtg cat tcc atc ctg aag aaa tcc gtc cac tcc gtg gct       101
Gln Thr Arg Val His Ser Ile Leu Lys Lys Ser Val His Ser Val Ala
             15                  20                  25 gtg ata gga gcc ccg ttc tca caa ggg cag aaa aga aaa gga gtg gag       149
Val Ile Gly Ala Pro Phe Ser Gln Gly Gln Lys Arg Lys Gly Val Glu
         30                  35                  40 cat ggt ccc gct gcc ata aga gaa gct ggc ttg atg aaa agg ctc tcc       197
His Gly Pro Ala Ala Ile Arg Glu Ala Gly Leu Met Lys Arg Leu Ser
     45                  50                  55 agt ttg ggc tgc cac cta aaa gac ttt gga gat ttg agt ttt act cca       245
Ser Leu Gly Cys His Leu Lys Asp Phe Gly Asp Leu Ser Phe Thr Pro
 60                  65                  70                  75 gtc ccc aaa gat gat ctc tac aac aac ctg ata gtg aat cca cgc tca       293
Val Pro Lys Asp Asp Leu Tyr Asn Asn Leu Ile Val Asn Pro Arg Ser
                 80                  85                  90 gtg ggt ctt gcc aac cag gaa ctg gct gag gtg gtt agc aga gct gtg       341
Val Gly Leu Ala Asn Gln Glu Leu Ala Glu Val Val Ser Arg Ala Val
             95                 100                 105 tca gat ggc tac agc tgt gtc aca ctg gga gga gac cac agc ctg gca       389
Ser Asp Gly Tyr Ser Cys Val Thr Leu Gly Gly Asp His Ser Leu Ala
        110                 115                 120 atc ggt acc att agt ggc cat gcc cga cac tgc cca gac ctt tgt gtt       437
Ile Gly Thr Ile Ser Gly His Ala Arg His Cys Pro Asp Leu Cys Val
    125                 130                 135 gtc tgg gtt gat gcc cat gct gac atc aac aca ccc ctt acc act tca       485
Val Trp Val Asp Ala His Ala Asp Ile Asn Thr Pro Leu Thr Thr Ser
140                 145                 150                 155 tca gga aat ctc cat gga cag cca gtt tca ttt ctc ctc aga gaa cta       533
```

```
                Ser Gly Asn Leu His Gly Gln Pro Val Ser Phe Leu Arg Glu Leu
                                160                 165                 170 cag gat aag gta cca caa ctc cca gga ttt tcc tgg atc aaa cct tgt        581
Gln Asp Lys Val Pro Gln Leu Pro Gly Phe Ser Trp Ile Lys Pro Cys
            175                 180                 185 atc tct tct gca agt att gtg tat att ggt ctg aga gac gtg gac cct        629
Ile Ser Ser Ala Ser Ile Val Tyr Ile Gly Leu Arg Asp Val Asp Pro
190                 195                 200 cct gaa cat ttt att tta aag aac tat gat atc cag tat ttt tcc atg        677
Pro Glu His Phe Ile Leu Lys Asn Tyr Asp Ile Gln Tyr Phe Ser Met
    205                 210                 215 aga gat att gat cga ctt ggt atc cag aag gtc atg gaa cga aca ttt        725
Arg Asp Ile Asp Arg Leu Gly Ile Gln Lys Val Met Glu Arg Thr Phe
220                 225                 230                 235 gat ctg ctg att ggc aag aga caa aga cca atc cat ttg agt ttt gat        773
Asp Leu Leu Ile Gly Lys Arg Gln Arg Pro Ile His Leu Ser Phe Asp
            240                 245                 250 att gat gca ttt gac cct aca ctg gct cca gcc aca gga act cct gtt        821
Ile Asp Ala Phe Asp Pro Thr Leu Ala Pro Ala Thr Gly Thr Pro Val
                255                 260                 265 gtc ggg gga cta acc tat cga gaa ggc atg tat att gct gag gaa ata        869
Val Gly Gly Leu Thr Tyr Arg Glu Gly Met Tyr Ile Ala Glu Glu Ile
            270                 275                 280 cac aat aca ggg ttg cta tca gca ctg gat ctt gtt gaa gtc aat cct        917
His Asn Thr Gly Leu Leu Ser Ala Leu Asp Leu Val Glu Val Asn Pro
    285                 290                 295 cag ttg gcc acc tca gag gaa gag gcg aag act aca gct aac ctg gca        965
Gln Leu Ala Thr Ser Glu Glu Glu Ala Lys Thr Thr Ala Asn Leu Ala
300                 305                 310                 315 gta gat gtg att gct tca agc ttt ggt cag aca aga gaa gga ggg cat       1013
Val Asp Val Ile Ala Ser Ser Phe Gly Gln Thr Arg Glu Gly Gly His
            320                 325                 330 att gtc tat gac caa ctt cct act ccc agt tca cca gat gaa tca gaa       1061
Ile Val Tyr Asp Gln Leu Pro Thr Pro Ser Ser Pro Asp Glu Ser Glu
                335                 340                 345 aat caa gca cgt gtg aga att tag gagacactgt gcactgacat gtttcacaac      1115
Asn Gln Ala Arg Val Arg Ile  *
            350 aggcattcca gaattatgag gcattgaggg gatagatgaa tactaaatgg ttgtctgggt     1175 caatactgcc ttaatgagaa catttacaca ttctcacaat tgtaaagttt ccctctatt      1235 ttggtgacca atactactgt aaatgtattt ggttttttgc agttcacagg gtattaatat     1295 gctatagtac tatgtaaatt taagaagtc ataaacagca tttattacct tggtatatc      1354

<210> SEQ ID NO 60
<211> LENGTH: 354
<212> TYPE: PRT
<213> ORGANISM: Homo Sapiens

<400> SEQUENCE: 60

Met Ser Leu Arg Gly Ser Leu Ser Arg Leu Leu Gln Thr Arg Val His
1               5                   10                  15

Ser Ile Leu Lys Lys Ser Val His Ser Val Ala Val Ile Gly Ala Pro
            20                  25                  30

Phe Ser Gln Gly Gln Lys Arg Lys Gly Val Glu His Gly Pro Ala Ala
        35                  40                  45

Ile Arg Glu Ala Gly Leu Met Lys Arg Leu Ser Ser Leu Gly Cys His
    50                  55                  60
```

```
Leu Lys Asp Phe Gly Asp Leu Ser Phe Thr Pro Val Pro Lys Asp Asp
 65                  70                  75                  80

Leu Tyr Asn Asn Leu Ile Val Asn Pro Arg Ser Val Gly Leu Ala Asn
                 85                  90                  95

Gln Glu Leu Ala Glu Val Val Ser Arg Ala Val Ser Asp Gly Tyr Ser
            100                 105                 110

Cys Val Thr Leu Gly Gly Asp His Ser Leu Ala Ile Gly Thr Ile Ser
            115                 120                 125

Gly His Ala Arg His Cys Pro Asp Leu Cys Val Val Trp Val Asp Ala
130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Ala Ser
            180                 185                 190

Ile Val Tyr Ile Gly Leu Arg Asp Val Asp Pro Glu His Phe Ile
            195                 200                 205

Leu Lys Asn Tyr Asp Ile Gln Tyr Phe Ser Met Arg Asp Ile Asp Arg
210                 215                 220

Leu Gly Ile Gln Lys Val Met Glu Arg Thr Phe Asp Leu Leu Ile Gly
225                 230                 235                 240

Lys Arg Gln Arg Pro Ile His Leu Ser Phe Asp Ile Asp Ala Phe Asp
                245                 250                 255

Pro Thr Leu Ala Pro Ala Thr Gly Thr Pro Val Val Gly Gly Leu Thr
            260                 265                 270

Tyr Arg Glu Gly Met Tyr Ile Ala Glu Glu Ile His Asn Thr Gly Leu
            275                 280                 285

Leu Ser Ala Leu Asp Leu Val Glu Val Asn Pro Gln Leu Ala Thr Ser
290                 295                 300

Glu Glu Glu Ala Lys Thr Thr Ala Asn Leu Ala Val Asp Val Ile Ala
305                 310                 315                 320

Ser Ser Phe Gly Gln Thr Arg Glu Gly Gly His Ile Val Tyr Asp Gln
                325                 330                 335

Leu Pro Thr Pro Ser Ser Pro Asp Glu Ser Glu Asn Gln Ala Arg Val
            340                 345                 350

Arg Ile

<210> SEQ ID NO 61
<211> LENGTH: 3032
<212> TYPE: DNA
<213> ORGANISM: Homo Sapiens
<220> FEATURE:
<221> NAME/KEY: CDS
<222> LOCATION: (296)...(2992)

<400> SEQUENCE: 61
tttaaataca taagtttaaa agagaattaa ctttcaattt gcaaattaaa atgagaatgg      60
ttgccttttc ttcattatca agagatggtg agttgtcctc ctgttgcatc ataaatacaa     120
aggactgaag ttataaaaga gaaagagaa gtttgctgct aaaatgaatc tgagcaatat      180
ggaatatttt gtgccacaca caaaaaggta ctgaagattt accccccaaa aaaaattgtc    240
aatgagaaat aaagctaact gatatcaaaa agcagagcct gctctactgg ccatc atg     298
                                                                    Met
                                                                     1
```

-continued

| | |
|---|---|
| cgt aaa ggg gtg ctg aag gac cca gag att gcc gat cta ttc tac aaa<br>Arg Lys Gly Val Leu Lys Asp Pro Glu Ile Ala Asp Leu Phe Tyr Lys<br>5                        10                       15 | 346 |
| gat gat cct gag gaa ctt ttt att ggt ttg cat gaa att gga cat gga<br>Asp Asp Pro Glu Glu Leu Phe Ile Gly Leu His Glu Ile Gly His Gly<br>20                     25                     30 | 394 |
| agt ttt gga gca gtt tat ttt gct aca aat gct cac acc agt gag gtg<br>Ser Phe Gly Ala Val Tyr Phe Ala Thr Asn Ala His Thr Ser Glu Val<br>35                    40                   45 | 442 |
| gtg gca att aag aag atg tcc tat agt ggg aag cag acc cat gag aaa<br>Val Ala Ile Lys Lys Met Ser Tyr Ser Gly Lys Gln Thr His Glu Lys<br>50                    55                   60                 65 | 490 |
| tgg caa gat att ctt aag gaa gtt aaa ttt tta cga caa ttg aag cat<br>Trp Gln Asp Ile Leu Lys Glu Val Lys Phe Leu Arg Gln Leu Lys His<br>70                    75                   80 | 538 |
| cct aat act att gag tac aaa ggc tgt tac ttg aaa gaa cac act gct<br>Pro Asn Thr Ile Glu Tyr Lys Gly Cys Tyr Leu Lys Glu His Thr Ala<br>85                    90                   95 | 586 |
| tgg ttg gtg atg gaa tat tgc tta ggc tca gcc tct gat tta tta gaa<br>Trp Leu Val Met Glu Tyr Cys Leu Gly Ser Ala Ser Asp Leu Leu Glu<br>100                  105                 110 | 634 |
| gtt cat aaa aaa cca ctt cag gaa gtg gag atc gct gcc att act cat<br>Val His Lys Lys Pro Leu Gln Glu Val Glu Ile Ala Ala Ile Thr His<br>115                  120                 125 | 682 |
| gga gcc ttg cat gga cta gcc tac cta cat tct cat gca ttg att cat<br>Gly Ala Leu His Gly Leu Ala Tyr Leu His Ser His Ala Leu Ile His<br>130                  135                 140                 145 | 730 |
| agg gat att aaa gca gga aat att ctt cta aca gag cca ggt cag gta<br>Arg Asp Ile Lys Ala Gly Asn Ile Leu Leu Thr Glu Pro Gly Gln Val<br>150                  155                 160 | 778 |
| aaa cta gct gat ttt gga tct gct tca atg gct tct cct gcc aac tcc<br>Lys Leu Ala Asp Phe Gly Ser Ala Ser Met Ala Ser Pro Ala Asn Ser<br>165                  170                 175 | 826 |
| ttc gtg ggc aca cct tac tgg atg gct cca gag gtg atc tta gct atg<br>Phe Val Gly Thr Pro Tyr Trp Met Ala Pro Glu Val Ile Leu Ala Met<br>180                  185                 190 | 874 |
| gat gaa gga cag tat gat ggg aaa gtt gat att tgg tca ctt ggc atc<br>Asp Glu Gly Gln Tyr Asp Gly Lys Val Asp Ile Trp Ser Leu Gly Ile<br>195                  200                 205 | 922 |
| act tgt att gaa ttg gcg gaa cgg aag ccg ccc ctt ttc aac atg aat<br>Thr Cys Ile Glu Leu Ala Glu Arg Lys Pro Pro Leu Phe Asn Met Asn<br>210                  215                 220                 225 | 970 |
| gca atg agt gcc tta tat cac att gcc cag aat gac tcc cca acg tta<br>Ala Met Ser Ala Leu Tyr His Ile Ala Gln Asn Asp Ser Pro Thr Leu<br>230                  235                 240 | 1018 |
| cag tct aat gaa tgg aca gac tcc ttt agg aga ttt gtt gat tac tgc<br>Gln Ser Asn Glu Trp Thr Asp Ser Phe Arg Arg Phe Val Asp Tyr Cys<br>245                  250                 255 | 1066 |
| ttg cag aaa ata cct cag gaa agg cca aca tca gca gaa cta tta agg<br>Leu Gln Lys Ile Pro Gln Glu Arg Pro Thr Ser Ala Glu Leu Leu Arg<br>260                  265                 270 | 1114 |
| cat gac ttt gtt cga cga gac cgg cca cta cgt gtc ctc att gac ctc<br>His Asp Phe Val Arg Arg Asp Arg Pro Leu Arg Val Leu Ile Asp Leu<br>275                  280                 285 | 1162 |
| ata cag agg aca aaa gat gca gtt cgt gag cta gat aac cta cag tac<br>Ile Gln Arg Thr Lys Asp Ala Val Arg Glu Leu Asp Asn Leu Gln Tyr<br>290                  295                 300                 305 | 1210 |
| cga aaa atg aaa aaa ata ctt ttc caa gag aca cgg aat gga ccc ttg<br>Arg Lys Met Lys Lys Ile Leu Phe Gln Glu Thr Arg Asn Gly Pro Leu<br>310                  315                 320 | 1258 |

```
                                                                          -continued aat gag tca cag gag gat gag gaa gac agt gaa cat gga acc agc ctg          1306
Asn Glu Ser Gln Glu Asp Glu Glu Asp Ser Glu His Gly Thr Ser Leu
            325                 330                 335 aac agg gaa atg gac agc ctg ggc agc aac cat tcc att cca agc atg          1354
Asn Arg Glu Met Asp Ser Leu Gly Ser Asn His Ser Ile Pro Ser Met
        340                 345                 350 tcc gtg agc aca ggc agc cag agc agc agt gtg aac agc atg cag gaa          1402
Ser Val Ser Thr Gly Ser Gln Ser Ser Ser Val Asn Ser Met Gln Glu
    355                 360                 365 gtc atg gac gag agc agt tcc gaa ctt gtc atg atg cac gat gac gaa          1450
Val Met Asp Glu Ser Ser Ser Glu Leu Val Met Met His Asp Asp Glu
370                 375                 380                 385 agc aca atc aat tcc agc tcc tcc gtc gtg cat aag aaa gat cat gta          1498
Ser Thr Ile Asn Ser Ser Ser Ser Val Val His Lys Lys Asp His Val
                390                 395                 400 ttc ata agg gat gag gcg ggc cac ggc gat ccc agg cct gag ccg cgg          1546
Phe Ile Arg Asp Glu Ala Gly His Gly Asp Pro Arg Pro Glu Pro Arg
            405                 410                 415 cct acc cag tca gtt cag agc cag gcc ctc cac tac cgg aac aga gag          1594
Pro Thr Gln Ser Val Gln Ser Gln Ala Leu His Tyr Arg Asn Arg Glu
        420                 425                 430 cgc ttt gcc acg atc aaa tca gca tct ttg gtt aca cga cag atc cat          1642
Arg Phe Ala Thr Ile Lys Ser Ala Ser Leu Val Thr Arg Gln Ile His
    435                 440                 445 gag cat gag cag gag aac gag ttg cgg gaa cag atg tca ggt tat aag          1690
Glu His Glu Gln Glu Asn Glu Leu Arg Glu Gln Met Ser Gly Tyr Lys
450                 455                 460                 465 cgg atg cgg cgc cag cac cag aag cag ctg atc gcc ctg gag aac aag          1738
Arg Met Arg Arg Gln His Gln Lys Gln Leu Ile Ala Leu Glu Asn Lys
                470                 475                 480 ctg aag gct gag atg gac gag cac cgc ctc aag cta cag aag gag gtg          1786
Leu Lys Ala Glu Met Asp Glu His Arg Leu Lys Leu Gln Lys Glu Val
            485                 490                 495 gag acg cat gcc aac aac tcg tcc atc gag ctg gag aag ctg gcc aag          1834
Glu Thr His Ala Asn Asn Ser Ser Ile Glu Leu Glu Lys Leu Ala Lys
        500                 505                 510 aag caa gtg gct atc ata gaa aag gag gca aag gta gct gca gca gat          1882
Lys Gln Val Ala Ile Ile Glu Lys Glu Ala Lys Val Ala Ala Ala Asp
    515                 520                 525 gag aag aag ttc cag caa cag atc ttg gcc cag cag aag aaa gat ttg          1930
Glu Lys Lys Phe Gln Gln Gln Ile Leu Ala Gln Gln Lys Lys Asp Leu
530                 535                 540                 545 aca act ttc tta gaa agt cag aag aag cag tat aag att tgt aag gaa          1978
Thr Thr Phe Leu Glu Ser Gln Lys Lys Gln Tyr Lys Ile Cys Lys Glu
                550                 555                 560 aaa ata aaa gag gaa atg aat gag gac cat agc aca ccc aag aaa gag          2026
Lys Ile Lys Glu Glu Met Asn Glu Asp His Ser Thr Pro Lys Lys Glu
            565                 570                 575 aag caa gag cgg atc tcc aaa cat aaa gag aac ttg cag cac aca cag          2074
Lys Gln Glu Arg Ile Ser Lys His Lys Glu Asn Leu Gln His Thr Gln
        580                 585                 590 gct gaa gag gaa gcc cac ctt ctc act caa cag aga ctg tac tac gac          2122
Ala Glu Glu Glu Ala His Leu Leu Thr Gln Gln Arg Leu Tyr Tyr Asp
    595                 600                 605 aaa aat tgt cgt ttc ttc aag cgg aaa ata atg atc aag cgg cac gag          2170
Lys Asn Cys Arg Phe Phe Lys Arg Lys Ile Met Ile Lys Arg His Glu
610                 615                 620                 625 gtg gag cag cag aac att cgg gag gaa cta aat aaa aag agg acc cag          2218
Val Glu Gln Gln Asn Ile Arg Glu Glu Leu Asn Lys Lys Arg Thr Gln
```

```
                     630                 635                 640
aag gag atg gag cat gcc atg cta atc cgg cac gac gag tcc acc cga      2266
Lys Glu Met Glu His Ala Met Leu Ile Arg His Asp Glu Ser Thr Arg
                645                 650                 655 gag cta gag tac agg cag ctg cac acg tta cag aag cta cgc atg gat      2314
Glu Leu Glu Tyr Arg Gln Leu His Thr Leu Gln Lys Leu Arg Met Asp
            660                 665                 670 ctg atc cgt tta cag cac cag acg gaa ctg gaa aac cag ctg gag tac      2362
Leu Ile Arg Leu Gln His Gln Thr Glu Leu Glu Asn Gln Leu Glu Tyr
        675                 680                 685 aat aag agg cga gaa aga gaa ctg cac aga aag cat gtc atg gaa ctt      2410
Asn Lys Arg Arg Glu Arg Glu Leu His Arg Lys His Val Met Glu Leu
690                 695                 700                 705 cgg caa cag cca aaa aac tta aag gcc atg gaa atg caa att aaa aaa      2458
Arg Gln Gln Pro Lys Asn Leu Lys Ala Met Glu Met Gln Ile Lys Lys
                710                 715                 720 cag ttt cag gac act tgc aaa gta cag acc aaa cag tat aaa gca ctc      2506
Gln Phe Gln Asp Thr Cys Lys Val Gln Thr Lys Gln Tyr Lys Ala Leu
            725                 730                 735 aag aat cac cag ttg gaa gtt act cca aag aat gag cac aaa aca atc      2554
Lys Asn His Gln Leu Glu Val Thr Pro Lys Asn Glu His Lys Thr Ile
        740                 745                 750 tta aag aca ctg aaa gat gag cag aca aga aaa ctt gcc att ttg gca      2602
Leu Lys Thr Leu Lys Asp Glu Gln Thr Arg Lys Leu Ala Ile Leu Ala
755                 760                 765 gag cag tat gaa cag agt ata aat gaa atg atg gcc tct caa gcg tta      2650
Glu Gln Tyr Glu Gln Ser Ile Asn Glu Met Met Ala Ser Gln Ala Leu
770                 775                 780                 785 cgg cta gat gag gct caa gaa gca gaa tgc cag gcc ttg agg cta cag      2698
Arg Leu Asp Glu Ala Gln Glu Ala Glu Cys Gln Ala Leu Arg Leu Gln
                790                 795                 800 ctc cag cag gaa atg gag ctg ctc aac gcc tac cag agc aaa atc aag      2746
Leu Gln Gln Glu Met Glu Leu Leu Asn Ala Tyr Gln Ser Lys Ile Lys
            805                 810                 815 atg caa aca gag gca caa cat gaa cgt gag ctc cag aag cta gag cag      2794
Met Gln Thr Glu Ala Gln His Glu Arg Glu Leu Gln Lys Leu Glu Gln
        820                 825                 830 aga gtg tct ctg cgc aga gca cac ctt gag cag aag att gaa gag gag      2842
Arg Val Ser Leu Arg Arg Ala His Leu Glu Gln Lys Ile Glu Glu Glu
835                 840                 845 ctg gct gcc ctt cag aag gaa cgc agc gag aga ata aag aac cta ttg      2890
Leu Ala Ala Leu Gln Lys Glu Arg Ser Glu Arg Ile Lys Asn Leu Leu
850                 855                 860                 865 gaa agg caa gag cga gag att gaa act ttt gac atg gag agc ctc aga      2938
Glu Arg Gln Glu Arg Glu Ile Glu Thr Phe Asp Met Glu Ser Leu Arg
                870                 875                 880 atg gga ttt ggg aat ttg gtt aca tta gat ttt cct aag gag gac tac      2986
Met Gly Phe Gly Asn Leu Val Thr Leu Asp Phe Pro Lys Glu Asp Tyr
            885                 890                 895 aga tga gattaaattt tttgccattt acaaaaaaaa aaaaaaaaa                   3032
Arg *

<210> SEQ ID NO 62
<211> LENGTH: 898
<212> TYPE: PRT
<213> ORGANISM: Homo Sapiens

<400> SEQUENCE: 62

Met Arg Lys Gly Val Leu Lys Asp Pro Glu Ile Ala Asp Leu Phe Tyr
1               5                   10                  15
```

```
Lys Asp Asp Pro Glu Glu Leu Phe Ile Gly Leu His Glu Ile Gly His
             20                  25                  30

Gly Ser Phe Gly Ala Val Tyr Phe Ala Thr Asn Ala His Thr Ser Glu
             35                  40                  45

Val Val Ala Ile Lys Lys Met Ser Tyr Ser Gly Lys Gln Thr His Glu
             50                  55                  60

Lys Trp Gln Asp Ile Leu Lys Glu Val Lys Phe Leu Arg Gln Leu Lys
 65                  70                  75                  80

His Pro Asn Thr Ile Glu Tyr Lys Gly Cys Tyr Leu Lys Glu His Thr
                     85                  90                  95

Ala Trp Leu Val Met Glu Tyr Cys Leu Gly Ser Ala Ser Asp Leu Leu
                    100                 105                 110

Glu Val His Lys Lys Pro Leu Gln Glu Val Glu Ile Ala Ala Ile Thr
            115                 120                 125

His Gly Ala Leu His Gly Leu Ala Tyr Leu His Ser His Ala Leu Ile
            130                 135                 140

His Arg Asp Ile Lys Ala Gly Asn Ile Leu Leu Thr Glu Pro Gly Gln
145                 150                 155                 160

Val Lys Leu Ala Asp Phe Gly Ser Ala Ser Met Ala Ser Pro Ala Asn
                    165                 170                 175

Ser Phe Val Gly Thr Pro Tyr Trp Met Ala Pro Glu Val Ile Leu Ala
            180                 185                 190

Met Asp Glu Gly Gln Tyr Asp Gly Lys Val Asp Ile Trp Ser Leu Gly
            195                 200                 205

Ile Thr Cys Ile Glu Leu Ala Glu Arg Lys Pro Pro Leu Phe Asn Met
210                 215                 220

Asn Ala Met Ser Ala Leu Tyr His Ile Ala Gln Asn Asp Ser Pro Thr
225                 230                 235                 240

Leu Gln Ser Asn Glu Trp Thr Asp Ser Phe Arg Arg Phe Val Asp Tyr
                    245                 250                 255

Cys Leu Gln Lys Ile Pro Gln Glu Arg Pro Thr Ser Ala Glu Leu Leu
                    260                 265                 270

Arg His Asp Phe Val Arg Arg Asp Arg Pro Leu Arg Val Leu Ile Asp
            275                 280                 285

Leu Ile Gln Arg Thr Lys Asp Ala Val Arg Glu Leu Asp Asn Leu Gln
            290                 295                 300

Tyr Arg Lys Met Lys Lys Ile Leu Phe Gln Glu Thr Arg Asn Gly Pro
305                 310                 315                 320

Leu Asn Glu Ser Gln Glu Asp Glu Asp Ser Glu His Gly Thr Ser
                    325                 330                 335

Leu Asn Arg Glu Met Asp Ser Leu Gly Ser Asn His Ser Ile Pro Ser
            340                 345                 350

Met Ser Val Ser Thr Gly Ser Gln Ser Ser Val Asn Ser Met Gln
            355                 360                 365

Glu Val Met Asp Glu Ser Ser Glu Leu Val Met Met His Asp Asp
370                 375                 380

Glu Ser Thr Ile Asn Ser Ser Ser Val Val His Lys Lys Asp His
385                 390                 395                 400

Val Phe Ile Arg Asp Glu Ala Gly His Gly Asp Pro Arg Pro Glu Pro
                    405                 410                 415

Arg Pro Thr Gln Ser Val Gln Ser Gln Ala Leu His Tyr Arg Asn Arg
            420                 425                 430
```

```
Glu Arg Phe Ala Thr Ile Lys Ser Ala Ser Leu Val Thr Arg Gln Ile
            435                 440                 445

His Glu His Glu Gln Glu Asn Glu Leu Arg Glu Gln Met Ser Gly Tyr
        450                 455                 460

Lys Arg Met Arg Arg Gln His Gln Lys Gln Leu Ile Ala Leu Glu Asn
465                 470                 475                 480

Lys Leu Lys Ala Glu Met Asp Glu His Arg Leu Lys Leu Gln Lys Glu
            485                 490                 495

Val Glu Thr His Ala Asn Asn Ser Ser Ile Glu Leu Glu Lys Leu Ala
        500                 505                 510

Lys Lys Gln Val Ala Ile Ile Glu Lys Glu Ala Lys Val Ala Ala Ala
            515                 520                 525

Asp Glu Lys Lys Phe Gln Gln Ile Leu Ala Gln Gln Lys Lys Asp
        530                 535                 540

Leu Thr Thr Phe Leu Glu Ser Gln Lys Lys Gln Tyr Lys Ile Cys Lys
545                 550                 555                 560

Glu Lys Ile Lys Glu Glu Met Asn Glu Asp His Ser Thr Pro Lys Lys
            565                 570                 575

Glu Lys Gln Glu Arg Ile Ser Lys His Lys Glu Asn Leu Gln His Thr
        580                 585                 590

Gln Ala Glu Glu Glu Ala His Leu Leu Thr Gln Gln Arg Leu Tyr Tyr
        595                 600                 605

Asp Lys Asn Cys Arg Phe Phe Lys Arg Lys Ile Met Ile Lys Arg His
        610                 615                 620

Glu Val Glu Gln Gln Asn Ile Arg Glu Glu Leu Asn Lys Lys Arg Thr
625                 630                 635                 640

Gln Lys Glu Met Glu His Ala Met Leu Ile Arg His Asp Glu Ser Thr
            645                 650                 655

Arg Glu Leu Glu Tyr Arg Gln Leu His Thr Leu Gln Lys Leu Arg Met
        660                 665                 670

Asp Leu Ile Arg Leu Gln His Gln Thr Glu Leu Glu Asn Gln Leu Glu
            675                 680                 685

Tyr Asn Lys Arg Arg Glu Arg Glu Leu His Arg Lys His Val Met Glu
        690                 695                 700

Leu Arg Gln Gln Pro Lys Asn Leu Lys Ala Met Glu Met Gln Ile Lys
705                 710                 715                 720

Lys Gln Phe Gln Asp Thr Cys Lys Val Gln Thr Lys Gln Tyr Lys Ala
            725                 730                 735

Leu Lys Asn His Gln Leu Glu Val Thr Pro Lys Asn Glu His Lys Thr
            740                 745                 750

Ile Leu Lys Thr Leu Lys Asp Glu Gln Thr Arg Lys Leu Ala Ile Leu
        755                 760                 765

Ala Glu Gln Tyr Glu Gln Ser Ile Asn Glu Met Met Ala Ser Gln Ala
        770                 775                 780

Leu Arg Leu Asp Glu Ala Gln Glu Ala Glu Cys Gln Ala Leu Arg Leu
785                 790                 795                 800

Gln Leu Gln Gln Glu Met Glu Leu Leu Asn Ala Tyr Gln Ser Lys Ile
                805                 810                 815

Lys Met Gln Thr Glu Ala Gln His Glu Arg Glu Leu Gln Lys Leu Glu
            820                 825                 830

Gln Arg Val Ser Leu Arg Arg Ala His Leu Glu Gln Lys Ile Glu Glu
            835                 840                 845

Glu Leu Ala Ala Leu Gln Lys Glu Arg Ser Glu Arg Ile Lys Asn Leu
```

-continued

```
              850                 855                 860
Leu Glu Arg Gln Glu Arg Glu Ile Glu Thr Phe Asp Met Glu Ser Leu
865                 870                 875                 880

Arg Met Gly Phe Gly Asn Leu Val Thr Leu Asp Phe Pro Lys Glu Asp
                885                 890                 895

Tyr Arg
```

METHODS FOR IDENTIFYING COMPOUNDS WHICH MODULATE HEMATOPOIESTS

RELATED APPLICATIONS

The present application claims the benefit of U.S. Provisional Application Ser. No. 60/354,333, filed on Feb. 4, 2002, of U.S. Provisional Application Ser. No. 60/360,258, filed on Feb. 28, 2002, of U.S. Provisional Application Ser. No. 60/364,476, filed on Mar. 15, 2002, of U.S. Provisional Application Ser. No. 60/375,626, filed on Apr. 26, 2002, of U.S. Provisional Application Ser. No. 60/386,494, filed on Jun. 6, 2002, of U.S. Provisional Application Ser. No. 60/390,965, filed on Jun. 24, 2002, of U.S. Provisional Application Ser. No. 60/392,480, filed on Jun. 28, 2002, of U.S. Provisional Application Ser. No. 60/394,128, filed on Jul. 3, 2002, of U.S. Provisional Application Ser. No. 60/399,783, filed on Jul. 31, 2002, of U.S. Provisional Application Ser. No. 60/403,221, filed on Aug. 13, 2002, of U.S. Provisional Application Ser. No. 60/407,045, filed on Aug. 30, 2002, and of U.S. Provisional Application Ser. No. 60/429,048, filed on Nov. 25, 2002. The entire contents of these provisional patent applications are hereby incorporated by this reference.

BACKGROUND OF THE INVENTION

Targets involved in the regulation of bone marrow development provide novel therapeutic approaches to the treatment of primary bone marrow failure and bone marrow dysfunction secondary to toxic insults, most notably chemotherapy-induced cytopenias. There is a severe unmet medical need in this arena as the few therapies currently available are recombinant proteins and all act at a relatively late stage of lineage differentiation.

Marrow populations of human and murine origin enriched for hematopoetic stem cells as well as bone marrow stromal cell populations provide useful sources of material for gene discovery and annotation of targets involved in proliferation and maturation of precursor populations. Hematopoietic cells cultured under various circumstances, isolated from humans in vivo, or from animal models in vivo provide a rich source of raw material for gene expression analysis leading to the identification of novel therapeutics useful for hematological disorders.

DETAILED DESCRIPTION OF THE INVENTION

The present invention provides methods and compositions for the diagnosis and treatment of patients with hematological disorders.

"Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, at least one symptom of disease or disorder or the predisposition toward a disease or disorder. A therapeutic agent includes, but is not limited to, small molecules, peptides, antibodies, ribozymes and antisense oligonucleotides. As used herein, therapeutic agents are also known as modulators. Representative molecules are described herein.

A hematological disorder as used herein includes, but is not limited to erythroid-associated disorders. As used herein, the term "erythroid associated disorders" include disorders involving aberrant (increased or deficient) erythroblast proliferation, e.g., an erythroleukemia, and aberrant (increased or deficient) erythroblast differentiation, e.g., an anemia. Erythrocyte-associated disorders include anemias such as, for example, drug-(chemotherapy-) induced anemias, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in non-hematolic disorders, for example, as a result of chemotherapy, alcoholism, or liver disease; anemia of chronic disease, such as chronic renal failure; and endocrine deficiency diseases.

Agents that modulate the polypeptides of the present invention or nucleic acid activity or expression can be used to treat anemias, in particular, drug-induced anemias or anemias associated with cancer chemotherapy, chronic renal failure, malignancies, adult and juvenile rheumatoid arthritis, disorders of hemoglobin synthesis, prematurity, and zidovudine treatment of HIV infection. A subject receiving the treatment can be additionally treated with a second agent, e.g., erythropoietin, to further at least one symptom of the condition. The order of the treatments can be reversed. The two treatments can be administered simultaneously. The timing between treatments can be varied.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, *Ann. Rev. Med.* 29:51 (1978); Eschbach and Adamson, *Kidney Intl.* 28:1 (1985). Recombinant human erythropoietin (rHuEpo or epoietin alpha) is commercially available as EPOGEN.RTM. (epoietin alpha, recombinant human erythropoietin) (Amgen Inc., Thousand Oaks, Calif.) and as PROCRIT.RTM. (epoietin alpha, recombinant human erythropoietin) (Ortho Biotech Inc., Raritan, N.J.).

Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

A hematological disorder as used herein includes disorders involving B-cells which include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

A hematological disorder as used herein includes disorders of the bone marrow which include but are not limited to: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

A hematological disorder as used herein can include platelet disorders including but not limited to disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

A hematological disorder can also include thrombosis. Thrombosis can result from platelet dysfunction, e.g. seen in myocardial infarction, angina, hypertension, lipid disorders, diabetes mellitus; myelodysplastic syndromes; myeloproliferative yndromes (including polycythemia vera and thombocythemia); thrombotic thrombocytopenic purpuras; HIV-induced platelet disorders (AIDS-Thrombocytopenia); heparin induced thrombocytopenia; mural cell alterations/interactions leading to platelet aggregation/degranulation, vascular endothelial cell activation/injury, monocyte/macrophage extravasation and smooth muscle cell proliferation; autoimmune disorders such as, but not limited to vasculitis, antiphospholipid syndromes, systemic lupus erythromatosis; inflammatory diseases, such as, but not limited to immune activation; graft vs. host disease; radiation induced hypercoagulation; clotting factor dysregulation either hereditary (autosomal dominant or recessive) such as, but not limited to clotting factor pathways including protein C/S, Antithrombin III deficiency, and the Factor V Leiden mutation or acquired such as but not limited to autoimmune, cancer-associated and drug-induced dysregulation of clotting factors.

A hematological disorder as used herein can include red cell disorders including but not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

A hematological disorder as used herein can include disease of T cells including but not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sé zary syndrome, and Hodgkin disease.

One aspect of the invention features 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptides and biologically active or antigenic fragments thereof that are useful, e.g., as reagents or targets in assays applicable to treatment and diagnosis of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mediated or related disorders, e.g., hematopoietic disorders (e.g., erythroid associated disorders). In another embodiment, the invention provides 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptides having a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. Preferred polypeptides are 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins including at least one dual specificity phosphatase catalytic domain, and, preferably, having a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity, e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity as described herein.

In a related aspect, the invention provides 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptides orfragments operatively linked to non-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptides to form fusion proteins.

In another aspect, the invention features antibodies and antigen-binding fragments thereof, that react with, or more preferably, specifically bind 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptides.

In another aspect, the invention provides methods of screening for compounds that modulate the expression or activity of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptides or nucleic acids.

In still another aspect, the invention provides a process for modulating 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide or nucleic acid expression or activity, e.g. using the screened compounds. In certain embodiments, the methods involve treatment of conditions related to decreased activity or expression of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptides or nucleic acids, such as conditions involving aberrant cellular proliferation of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, e.g., a hematopocitic cell (e.g., a myeloid (neutrophil) cell, a monocyte, an erythroid cell, a bone marrow cell, a CD34-expressing cell, a megakaryocyte). The condition may involve increased hematopoeitic cell activity or proliferation as in the case of leukemia, e.g., an erythroleukemia; or decreased hematopoietic cell differentiation as in the case of, e.g., an anemia.

In still another aspect, the invention features a method of modulating (e.g., enhancing or inhibiting) the proliferation, survival, and/or differentiation of a cell, e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, e.g., a hematopoietic cell (e.g., a myeloid (neutrophil) cell, a monocyte, an erythroid cell, a bone marrow cell, a CD34-expressing cell, a megakaryocyte). The method includes contacting the cell with an agent that modulates the activity or expression of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide or nucleic acid, in an amount effective to modulate the proliferation and/or differentiation of the cell.

In a preferred embodiment, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide has an amino acid sequence identical to, or substantially identical to, SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60. In other embodiments, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide is a fragment of at least 15, 20, 50, 100, 150, 180, 200, or more contiguous amino acids of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60.

In a preferred embodiment, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid has a nucleotide sequence identical to, or substantially identical to, SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61. In other embodiments, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid is a fragment of at least 50, 100, 150, 200, 250, 300, 350, 400, 450, 500, 550, 600, or more contiguous nucleotides of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59or61.

In a preferred embodiment, an agent modulates (e.g., increases or decreases) expression of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or an 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid, or any combination thereof.

In a preferred embodiment, the agent is administered in combination with a cytotoxic agent.

In a preferred embodiment, the cell, e.g., the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, is a hematopoietic cell, e.g., a myeloid, lymphoid or erythroid cell, or a precursor cell thereof. Examples of such cells include myelocytic cells (polymorphoneuclear cells), erythrocytic cells, lymphocytes, monocytes, reticular cells, plasma cells and megakaryocytes, as well as stem cells for the different lineages, and precursors for the committed progenitor cells, for example, precursors of red blood cells (erythroblasts), macrophages (monoblasts), platelets (megakaryocytes), polymorphoneuclear leucocytes (myeloblasts), and lymphocytes (lymphoblasts).

In a preferred embodiment, the cell, e.g., the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, is a bone marrow cell, e.g., a bone marrow CD34-expressing cell. Examples of CD34-expressing cells include immature haematopoietic precursor cells, haematopoietic colony-forming cells in bone marrow, including unipotent (CFU-GM, BFU-E) and pluripotent progenitors (CFU-GEMM, CFU-Mix and CFU-blast); as well as stromal cell precursors, terminal deoxynucleotidyl transferase (TdT) expressing B- and T-lymphoid precursors, early myeloid cells and early erythroid cells.

In a preferred embodiment, the cell, e.g., the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, is a bone marrow erythroid cell, e.g., an erythroid progenitor (e.g., a GPA(low)CD71+ cell) or a differentiated cell, e.g., an erythrocyte or a megakaryocyte.

In a preferred embodiment, the cell, e.g., the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, is further contacted with a protein, e.g., a cytokine. Preferably, the protein is selected from the group consisting of G-CSF, GM-CSF, stem cell factor, and preferably erythropoietin. The protein contacting step can occur before, at the same time, or after the agent is contacted. The protein contacting step can be effected in vitro or ex vivo. For example, the cell, e.g., the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell is obtained from a subject, e.g., a patient, and contacted with the protein ex vivo. The treated cell can be re-introduced into the subject. Alternatively, the protein contacting step can occur in vivo.

In a preferred embodiment, the agent and the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-polypeptide or nucleic acid are contacted in vitro or ex vivo.

In a preferred embodiment, the contacting step is effected in vivo in a subject, e.g., as part of a therapeutic or prophylactic protocol. Preferably, the subject is a human, e.g., a patient with a hematopoietic disorder, e.g., a leukemia or an erythroid-associated disorder. For example, the subject can be a patient with an anemia, e.g., hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Alternatively, the subject can be a cancer patient, e.g., a patient with leukemic cancer, e.g., an erythroid leukemia, or a carcinoma, e.g., a renal carcinoma. In other embodiments, the subject is a non-human animal, e.g., an experimental animal.

The contacting step(s) can be repeated.

In a preferred embodiment, the agent decreases the proliferation and/or enhances the differentiation of the cell, e.g., the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, e.g., the hematopoietic cell (e.g., the myeloid (neutrophil) cell, the monocyte, the erythroid cell, the bone marrow cell, the CD34-expressing cell, the megakaryocyte). Such agents can be used to treat or prevent cancers, e.g., leukemic cancers.

In a preferred embodiment, the agent increases the number of hematopoietic cells (e.g., myeloid (neutrophil) cells, monocytes, erythroid cells, bone marrow cells, CD34-expressing cells, megakaryocytes), by e.g., increasing the proliferation, survival, and/or stimulating the differentiation, of progenitor cells. Such agents can be used to treat or prevent hematopoietic disorders, e.g., anemias (e.g., hemolytic anemias, aberrant erythropoiesis, secondary anemias in nonhematolic disorders, anemias of chronic diseases such as chronic renal failure; endocrine deficiency diseases; and/or erythrocytosis, e.g., polycythemias).

In another aspect, the invention features a method of modulating hematopoiesis, e.g., erythropoiesis, comprising contacting a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-expressing cell, e.g., a hematopoietic cell, (e.g., a myeloid (neutrophil) cell, a monocyte, an erythroid cell, a bone marrow cell, a CD34-expressing cell, a megakaryocyte), with a agent that increases or decreases the activity or expression of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide or nucleic acid, thereby modulating the differentiation of the hematopoietic cell.

In yet another aspect, the invention features a method of treating or preventing a hematopoietic disorder, e.g., an erythroid-associated disorder, in a subject. The method includes administering to the subject an effective amount of a agent that modulates the activity or expression of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide or nucleic acid such that the hematopoietic disorder is ameliorated or at least one symptom of the hematological disorder is decreased.

Molecules of the Present Invention

Gene ID 131

The human 131 sequence (SEQ ID NO: 1), (GI:181828), known also as human dopamine 2 receptor (DRD2), is approximately 1332 nucleotides long including untranslated regions. The coding sequence, located at about nucleic acids 1 to 1332 of SEQ ID NO: 1, encodes a 443 amino acid protein (SEQ ID NO: 2) (GI:181829).

As assessed by TAQMAN® analysis, 131 mRNA was expressed very specifically in human brain, kidney and GPA+ erythroid cells. By additional TaqMan analyses, expression was also seen in cultured neutrophils, erythroid cells and megakaryocytes. Expression was very low in all other tissues and cell types tested.

131 is the dopamine D2 receptor. It is known to be important in dopamine-mediated neuronal survival. 131 is known to be involved in schizophrenia and other brain diseases.

Dopamine is also known to inhibit proliferation and inducing apoptosis in some cell types. Inhibiting dopamine-mediated signal transduction by modulating the activity of 131 will serve to expand the erythroid lineage. Modulators of 131 activity would be useful in treating hematological disorders, including but not limited to anemia. 131 polypeptides would be useful in screening for modulators of 131 activity.

Gene ID 148

The human 148 sequence (SEQ ID NO: 3), (GI:32048), known also as human D5 dopamine receptor (HD5DR), is approximately 1434 nucleotides long including untranslated regions. The coding sequence, located at about nucleic acids 1 to 1434 of SEQ ID NO: 3, encodes a 477 amino acid protein (SEQ ID NO: 4) (GI:32049).

As assessed by TAQMAN® analysis, 148 mRNA was expressed very specifically in human brain, kidney and GPA+ erythroid cells. By additional TaqMan analyses, expression was also seen in cultured neutrophils, erythroid cells and megakaryocytes. Expression was very low in all other tissues and cell types tested.

148 is the dopamine D5 receptor. It is known to be important in dopamine-mediated neuronal survival. 148 is known to be involved in schizophrenia and other brain diseases.

Dopamine is also known to inhibit proliferation and inducing apoptosis in some cell types. Inhibiting dopamine-mediated signal transduction by modulating the activity of 148 will serve to expand the erythroid lineage. Modulators of 148 activity would be useful in treating hematological disorders, including but not limited to anemia. 148 polypeptides would be useful in screening for modulators of 148 activity.

Gene ID 199

The human 199 sequence (SEQ ID NO: 5), (GI:307419), known also as a human serotonin receptor, is approximately 1141 nucleotides long including untranslated regions. The coding sequence, located at about nucleic acids 27 to 1127 of SEQ ID NO: 5, encodes a 366 amino acid protein (SEQ ID NO: 6) (GI:307420).

As assessed by TAQMAN® analysis, 199 mRNA exhibited a very restricted pattern of expression. High levels of expression were seen in CD34+ progenitor cells. Low levels of expression were seen in brain. Very low levels of expression were seen in placenta and lung.

199 is one of the serotonin receptors, known to be important in neuronal function. More specifically, agonists have been shown to inhibit neurogenic dural inflammation. A role for serotonin receptors in vasoconstriction of arteries has also been postulated. Signaling through 199 and other serotonin receptors is known to be mitogenic.

By modulating the activity of 199, proliferation of CD34+ progenitor cells would increase. This would result in an increase in the number of cells of all lineages of the the hematopoeitic system. Modulators of 199 activity would be useful in treating hematological disorders, including but not limited to cytopenias.

Gene ID 12303

The human 12303 sequence (SEQ ID NO: 7), (GI: 7576934), known also as two pore potassium channel (KT4.1b), is approximately 1408 nucleotides long including untranslated regions. The coding sequence, located at about nucleic acids 84 to 1343 of SEQ ID NO: 7, encodes a 419 amino acid protein (SEQ ID NO: 8) (GI:7576935).

As assessed by TAQMAN® analysis, 12303 mRNA exhibited a very restricted pattern of expression. It was only expressed in human brain and in GPA hi cells, with lower levels of expression in neutrophils, megakaryocytes, and erythroid cell cultures. Additional TAQMAN® analyses performed on a wide range of human organs showed a low level of 12303 mRNA expression in prostate.

12303 is a TWIK receptor. TWIK receptors are known to facilitate signaling via intracellular potassium exchange. Blockade of the 12303 transporter has been shown to lead to neuronal cell cytoprotection. Agonizing 12303 leads to cell death.

In vivo, 12303 is expressed very specifically in mature erythrocytes. By modulating 12303 activity, erythropoiesis will be stimulated and the net result will be larger numbers of red blood cells via induction of cytoprotective pathways. Modulators of 12303 activity would thus be useful in treating hematological disorders, including but not limited to anemia.

Gene ID 13906

The human 13906 sequence (SEQ ID NO: 9), known also as a serine protease(Omi/Htra2 protease), is approximately 1597 nucleotides long including untranslated regions. The coding sequence, located at about nucleic acids 18 to 1394 of SEQ ID NO: 9, encodes a 458 amino acid protein (SEQ ID NO: 10).

As assessed by TAQMAN® analyses, 13906 mRNA was specifically up-regulated in erythroid cells both in vitro and in vivo. High level of expression of 13906 mRNA was seen in GPA hi and lo expressing cells from bone marrow as well as differentiating erythroid cells in vitro (increasing at Day 6). Additional TAQMAN® analyses showed high levels of expression in the erythropoietic organ, fetal liver, in vivo.

13906 is the Omi/Htra2 protease. This protease is known to interact with and degrade the Inhibitor of Apoptosis (IAP) proteins, which are known to inhibit apoptosis. 13906 protein translocates from the mitochondria to the cytosol upon activation.

Due to its expression pattern and functional role, modulators of 13906 would result in higher levels of IAPs in erythroid cells in vivo, which will inhibit apoptosis in erythroid cells. This would effectively increase the number of erythrocytes in the periphery. Modulators of 13906 activity would be useful in treating hematological disorders, including but not limited to anemia.

Gene ID 15513

The human 15513 sequence (SEQ ID NO: 11), (GI: 1794206), known also as human kinase (Myt1), is approximately 1881 nucleotides long including untranslated regions. The coding sequence, located at about nucleic acids 214 to 1713 of SEQ ID NO: 11, encodes a 499 amino acid protein (SEQ ID NO: 12) (GI:1794207).

As assessed by TAQMAN® analysis, 15513 mRNA was expressed very specifically in erythroid cells in vitro and in vivo. Additional TAQMAN® analyses showed high levels of 15513 mRNA in GPA high erythrocytes in vivo and differentiating erythroid cells in vitro.

15513 is Myt1 kinase. It is known to phosphorylate Cdc2 and prevent its complexing with cyclin B1. Overproduction of 15513 protein induces a cell cycle delay in phase G2 of the cell cycle.

Modulating 15513 activity would result in increased activation of Cdc2 and therefore lead to increased cell proliferation. Increasing proliferation of differentiating erythroid cells would result in more erythrocytes. Due to 15513's mRNA expression pattern in differentiating erythrocytes and its role in affecting proliferation, modulators of 15513 activity would be useful in treating hematological disorders, including but not limited to anemia. 15513 polypeptides would be useful in screening for modulators of 15513 activity.

Gene ID 17822

The human 17822 sequence (SEQ ID NO: 13), (GI: 10334989), known also as a human dipeptidase, is approximately 1700 nucleotides long including untranslated regions. The coding sequence, located at about nucleic acids 125 to 1585 of SEQ ID NO: 13, encodes a 486 amino acid protein (SEQ ID NO: 14) (GI:14717396).

As assessed by TAQMAN® analysis, 17822 mRNA was shown to be broadly expressed in all hematopoietic lineages in vivo. Expression was high in CD34+ cells as well as erythroid cells (GPA+), neutrophils (CD15+) and megakaryocyte (CD61+) cell lineages. In vitro, expression in erthroid cells was maintained at high levels. Expression was low in most other tissues, except lymph organs (spleen, lymph node) and resting T-cells.

This gene is a dipeptidase and related to renal dipeptidase. Renal dipeptidase and members of this family are known to specifically convert Leukotriene D4 to E4. Leukotriene D4 is a known stimulator of CD34+ cell proliferation and migration in the bone marrow.

Modulating the activity of 17822 would result in higher levels of leukotriene D4 in the bone marrow, which will have a positive effect on increasing bone marrow CD34+ progenitor cells. Due to the expression pattern of 17822 mRNA and its ability to stimulate leukotriene D4, modulators of 17822 activity would be useful in treating hematological disorders, including but not limited to cytopenia. 17822 polypeptides would be useful in screening for modulators of 17822 activity.

Gene ID 302

The human 302 sequence (SEQ ID NO: 15), (GI: 13236496), known also as human 5-hydroxytryptamine (serotonin) receptor 5A (HTR5A), is approximately 1159 nucleotides long including untranslated regions. The coding sequence, located at about nucleic acids 64 to 1137 of SEQ ID NO: 15, encodes a 357 amino acid protein (SEQ ID NO: 16) (GI:13236497).

As assessed by TAQMAN® analysis, 302 mRNA was expressed specifically in cells of the erythroid lineage in vivo. High levels of expression were seen in brain, spinal cord, dorsal root ganglion (DRG) and GPA high cells.

302 is one of the serotonin receptors. Serotonin receptors are known to be important in neuronal function. More specifically, agonists have been shown to inhibit neurogenic dural inflammation. A role for serotonin receptors in vasoconstriction of arteries has also been postulated. In addtion, signalling through 302 is known to be mitogenic. Modulators of 302 activity would increase proliferation of erythroid progenitor cells. This would result in larger numbers of all blood lineage cells, and would be an effective treatment for hematological disorders including but not limited to anemia. Therefore, due to its expression pattern and its functional role in vivo, modulators of 302 activity would be useful in treating hematological disorders, including but not limited to anemia. 302 polypeptides of the present invention would be useful in screening for modulators of 302 activity.

Gene ID 5677

The human 5677 sequence (SEQ ID NO: 17), (GI: 8919627), known also as human leukotriene B4 receptor 2 (BLTR2), is approximately 1077 nucleotides long including untranslated regions. The coding sequence, located at about nucleic acids 1 to 1077 of SEQ ID NO: 17, encodes a 358 amino acid protein (SEQ ID NO: 18) (GI:8919628).

As assessed by TAGMAN® analysis, expression of 5677 mRNA was restricted to cells of the erythroid and mycloid lineages. High levels of 5677 mRNA expression was also seen in human nerve and skin. Further TAQMAN® studies showed that levels of 5677 mRNA increased during erythroid development. High levels of 5677 mRNA expression was seen in GPA+ cells in vivo.

5677 is the alternative receptor for leukotriene B4. 5677 mRNA has been shown to be expressed in T-cells and it functions to modulate chemotaxis/adhesion in those cells. Leukotriene B4 has been shown to inhibit erythroid colony formation in vitro. Inhibiting leukotriene signaling will increase the rate of erythropoiesis. Modulators of 5677 activity would be useful to increase the rate of erythropoiesis, thus being an effective treatment for hematological disorders, including but not limited to anemia. 5677 polypeptides of the present invention would be useful to screen for modulators of 5677 activity.

Gene ID 194

The human 194 sequence (SEQ ID NO: 19), (known also as human somatostatin receptor type I (SSIR)), is approximately 1634 nucleotides long including untranslated regions. The coding sequence, located at about nucleic acids 100 to 1275 of SEQ ID NO: 19, encodes a 391 amino acid protein (SEQ ID NO: 20).

194 is the somatostatin SSR-1. As assessed by TAQMAN® analysis 194 mRNA was detected in human tissues with highest levels in brain cortex and hypothalamus. It was also detected in dorsal root ganglion and small intestine, but at lower levels. Additional TAQMAN® analyses indicated that 194 mRNA was expressed in megakaryocytes grown in vitro.

Somatostatins are known effectors of neuronal activity. In addition, somatastatins have been implicated to act in several different organs through at least two specific G-protein coupled receptors, SSR-1 and SSR-2 [PNAS. 1992. 89(1): 251-255]. The mRNA expression of 194 indicates that 194 has a functional role in megakaryocytes and platelets. 194 has been linked to the regulation of adenylyl cyclase, an important mediator of platelet aggregation. Due to its functional role and expression pattern, 194 can play a role in regulating platelet aggregation. Therefor, modulators of 194 activity would be useful in treating hematological disorders including but not limited to thrombosis and those conditions characterized by aberrant blood clotting. 194 polypeptides of the current invention would be useful to screen for modulators of 194 activity.

Gene ID 14393

The human 14393 sequence (SEQ ID NO: 21), (known also as human orexin receptor type I (OXIR)), is approximately 1564 nucleotides long including untranslated regions. The coding sequence, located at about nucleic acids 154 to 1431 of SEQ ID NO: 21, encodes a 425 amino acid protein (SEQ ID NO: 22).

14393 is the human orexin 1 receptor OR-i. As assessed by TAQMAN® analysis, 14393 mRNA was most highly expressed in the brain cortex and placenta. 14393 mRNA was also expressed in megakaryocytes generated by in vitro differentiation, in bone marrow megakaryocytes and in normal platelets. Additional TAQMAN® analyses detected decreased levels of 14393 in the platelets of patients diagnosed with both coronary artery disease and diabetes mellitus as compared with patients with coronary artery disease alone or in normal platelets.

Diabetes is a risk factor for the acute coronary syndromes, myocardial infarction and unstable angina. The expression of 14393 mRNA in platelets is linked to the heightened platelet reactivity in diabetics. The orexins are known neuropeptides that regulate feeding behavior. There is evidence that the orexin receptors are oppositely regulated in the hypothalamus of a diabetic animal model, the obese Zucker rat [BBRC. 2001. 24;286(3):518-523]. Due to its functional role and expression pattern, 14393 can be shown to have a role in platelet aggregation. Therefore, modulators of 14393 activity would be useful in treating hematological disorders including but not limited to thrombosis and those conditions characterized by aberrant blood clotting. 14393 polypeptides of the current invention would be useful to screen for modulators of 14393 activity.

Gene ID 28059

The human 28059 sequence (SEQ ID NO: 23), a human ion channel, is approximately 4632 nucleotides long including untranslated regions. The coding sequence, located at about nucleic acids 225 to 3581 of SEQ ID NO: 23, encodes a 1118 amino acid protein (SEQ ID NO: 24).

28059 is a novel SLACK channel, a calcium-activated potassium channel. As assessed by TAQMAN® analysis, 28059 mRNA was expressed at relatively high levels in brain and fetal liver. 28059 mRNA was also detected in megakaryocytes generated in vitro and in normal platelets. 28059 was expressed in patients with coronary artery disease including myocardial infarction, unstable and stable angina.

SLACK channels have an identified role in neuronal cell excitation and secretion. SLACK channels are regulated by intracellular calcium in neuronal cells [Nature Neuroscience. 1998. (6):462-469]. The 28059 expression data indicate that SLACK plays an important role in calcium mobilization in platelets. Calcium mobilization is a critical regulator of platelet secretion and aggregation, therefore 28059 is a component of the calcium signaling pathway that regulates platelet activation.

Therefore, modulators of 28059 activity would be useful in treating hematological disorders including but not limited to thrombosis and those conditions characterized by aberrant blood clotting. 28059 polypeptides of the current invention would be useful to screen for modulators of 28059 activity.

Gene ID 7366

The human 7366 sequence (SEQ ID NO: 25), (known also as human chloride channel protein 4 (CLC-4)), is approximately 4454 nucleotides long including untranslated regions. The coding sequence, located at about nucleic acids 276 to 2558 of SEQ TD NO: 25, encodes a 760 amino acid protein (SEQ ID NO: 26).

As assessed by TAQMAN® analysis, expression of 7366 mRNA was restricted to brain, skeletal muscle and hematopoietic cells of the erythroid lineage. Expression of 7366 mRNA in vitro increased with megakaryocyte and erythroid lineage differentiation. Expression of 7366 mRNA in vivo was high in GPA low cells, which are erythroid cells that are actively proliferating. Expression of 7366 mRNA was also seen in BFU-E cells in vitro.

7366 is the chloride channel CLC-4. Chloride channels are known to play key roles in controlling membrane polarization as well as cell volume. Blockade of chloride channels is known to inhibit cell proliferation. Therefore agonizing 7366 would lead to increased proliferation of erythroid progenitor cells. Because 7366 mRNA was also expressed at a low level in CD34+ cells, increases in multiple lineages would result. Modulators of 7366 activity would be useful in treating hematological disorders including but not limited to pancytopenia. 7366 polypeptides of the present invention would be useful in screening for modulators of 7366 activity.

Gene ID 12212

The human 12212 sequence (SEQ ID NO: 27), (known also as human potassium intermediate/small conductance calcium-activated channel, subfamily member 4), is approximately 1284 nucleotides long including untranslated regions. The coding sequence, located at about nucleic acids 1 to 1284 of SEQ ID NO: 27, encodes a 427 amino acid protein (SEQ ID NO: 28).

As assessed by TAQMAN® analysis expression of 12212 mRNA was restricted to human breast, colon tumor, and hematopoietic cells of the erythroid lineage. 12212 mRNA expression is high in both GPA lo and GPA high cells in vivo and mRNA expression is increased with erythroid differentiation in vitro.

12212 is a calcium-activated K+ channel. A generalized inhibitor of this channel, clotrimazole, inhibits erythroid differentiation in mouse in vitro systems. Though implicated generally in its impact on membrane potential, mutations in this gene have also been associated with a rare genetic form of anemia (Diamond Blackfan Anemia). This form of anemia is known to result from perturbed erythropoiesis, specifically a block in erythroid progenitor proliferation/commitment.

Agonizing this channel increases proliferation of erythroid progenitor cells. Therefore, modulators of 12212 activity are useful in treating hematological disorders including but not limited anemia. 12212 polypeptides of the present invention are useful in screening for modulators of 12212 activity.

Gene ID 1981

The human 1981 sequence (SEQ ID NO: 29), (known also human glutamate receptor (KA-1), is approximately 2871 nucleotides long including untranslated regions. The coding sequence, located at about nucleic acids ito 2871 of SEQ ID NO: 29, encodes a 956 amino acid protein (SEQ ID NO: 30).

1981 is the human kainate receptor KA-1, which forms a ligand-gated ion channel. As assessed by TAQMAN® analysis, 1981 mRNA was almost exclusively expressed in brain, in vitro generated megakaryocytes and in normal platelets. Expression in brain and megakaryocytes was over ten-fold higher than expression in other organs and tissues examined. In additional TAQMAN® analyses, 1981 mRNA was also detected in platelets of patients with coronary artery disease and 1981 mRNA levels decreased in most patients following myocardial infarction.

The glutamate receptors have a known role in neuronal synapse excitation. In addition, glutamate has been shown to antagonize arachidonic acid-induced platelet aggregation [Thrombosis and Hemostasis. 1996. 76(1):84-87]. Due to its function and expression pattern, 1981 is involved in the regulation of platelet aggregation during the acute coronary syndrome, myocardial infarction. Modulators of 1981 activity would be useful in treating hematological disorders, including by not limited to thrombosis or those conditions characterized by aberrant thrombosis. 1981 polypeptides of the present invention would be useful in screening for modulators of 1981 activity.

Gene ID 261

The human 261 sequence (SEQ ID NO: 31), a human G protein-coupled receptor, is approximately 2534 nucleotides long including untranslated regions. The coding sequence, located at about nucleic acids 118 to 1230 of SEQ ID NO: 31, encodes a 370 amino acid protein (SEQ ID NO: 32).

As assessed by TAQMAN® analysis expression of 261 mRNA was restricted to brain and cells of the hematopoietic lineages. Expression of 261 mRNA was high in CD34+ cells of the bone marrow, in blood and in neutrophils, both in vivo and in vitro.

261 is a calcium-activated K+ channel. Though implicated generally in its impact on membrane potential, mutations in this gene have also been associated with a rare genetic form of anemia (Diamond Blackfan Anemia). This form of anemia is known to result from perturbed erythropoiesis, specifically a blockage in erythroid progenitor proliferation/commitment. Agonizing this channel would lead to an increase in proliferation of erythroid progenitor cells. Due to its function and expression pattern, 261 is involved in the regulation of platelet aggregation during the acute coronary syndrome, myocardial infarction. Modulators of 261 activity would be useful in treating hematological disorders, including by not limited to anemia and thrombosis. 261 polypeptides of the present invention would be useful in screening for modulators of 261 activity.

Gene ID 12416

The human 12416 sequence (SEQ ID NO: 33), known also ADP Receptor P2Y$_{13}$ (GPR86), is approximately 2857 nucleotides long including untranslated regions. The coding sequence, located at about nucleic acids 174 to 1175 of SEQ ID NO: 33, encodes a 333 amino acid protein (SEQ ID NO: 34).

As assessed by TAQMAN®, 12416 mRNA was expressed in the brain, spleen, granulocytes and GPA high erythrocytes. Further analysis showed that 12416 was expressed at high levels in varying cells of neutrophilic lineage (both in vivo and in vitro) and in mouse bone marrow mononuclear cells (mBM MNC). 12416 is expressed in CD15+11b+ and CD15+11b-cells as well as CD34+ cells and is increased during in vitro differentiation of neutrophil but not megakaryocyte or erythroid lineages.

12416 is a new member of the P2Y receptor family. P2Y receptors are coupled to either the phosphoinositide pathway or adenylate cyclase. Published literature indicates that cells transfected with 12416 when exposed to ADP results in an accumulation of IP$_3$ and has a biphasic effect on adenylate cyclase activity. Stimulation of 12416 with ADP also leads to the phosphorylation of the MAP kinases Erk1 and Erk2. ADP binding to P2Y$_1$ receptors also leads to the phosphorylation of MAP kinases and induction of apoptosis. Therefore, 12416 has a functional role in preventing the induction of apoptosis. Due to its functional role and expression pattern in the brain and spleen, 12416 plays a role in regulating diseases associated with hematological disorders. Therefore, modulators of 12416 activity would be useful in treating hematological disorders including but not limited to diseases characterized by neutropenia and/or an increase in the number of neutrophils. 12416 polypeptides of the current invention would be useful to screen for modulators of 12416 activity.

Gene ID 270

The human 270 sequence (SEQ ID NO: 35), known also as prostaglandin E2 receptor, EP2 subtype, is approximately 2372 nucleotides long including untranslated regions. The coding sequence, located at about nucleic acids 157 to 1233 of SEQ ID NO: 35, encodes a 358 amino acid protein (SEQ ID NO: 36).

As assessed by TAQMAN® analysis, 270 mRNA expression was shown in the heart, spleen, ovary and prostate. Further analysis showed an upregulation of 270 expression in hematopoietic progenitor cell populations of the bone marrow with highest levels of expression in the neutrophil lineage progenitors.

270 is a receptor for Prostaglandin E which is a molecule shown to have inhibitory effects on cytokine-induced proliferation of hematopoietic progenitor cells. Inhibiting the function of the prostaglandin E2 receptor (EP2 subtype) gene in hematopoietic progenitor cell populations blocks the inhibitory effects of its ligand, Prostaglandin E, and stimulates proliferation of these cells to give rise to increased numbers of cells of all lineages, in particular the neurophil lineage. Therefore, due to 270 mRNA expression in heart, spleen, ovary, prostate and hematopoietic progenitor cell populations of the bone marrow, along with its functional role, modulators of 270 activity would be useful in treating hematological disorders including but not limited to neutropenia and/or an increase in the number of neutrophils. 270 polypeptides of the current invention would be useful to screen for modulators of 270 activity.

Gene ID 1410

The human 1410 sequence (SEQ ID NO: 37), known also as death-associated protein kinase 1 (DAP kinase 1), is approximately 5910 nucleotides long including untranslated regions. The coding sequence, located at about nucleic acids 337 to 4632 of SEQ iD NO: 37, encodes a 1431 amino acid protein (SEQ ID NO: 38).

As assessed by TAQMAN® analysis, 1410 mRNA was expressed at high levels in hematopoietic progenitor CD34+ cells of the bone marrow and cord blood, and in the fetal liver. Further analysis indicated 1410 was also expressed in in vitro differentiated erythroid cells.

Death-associated protein kinase 1 (DAP kinase 1) or 1410 is a pro-apoptotic gene involved in interferon gamma induced HeLa cell death. Over-expression of 1410 in vitro causes apoptosis in PC12 cells. 1410 is a pro-apoptotic gene whose promoter is activated by TGF-beta in cells undergoing TGF-mediated apoptosis. Inhibition of 1410 activity protects hepatoma cells from TGF-beta induced apoptosis. Inhibition of 1410 in hematopoietic progenitor cells potentially leads to decreased apoptosis in these cells. With apoptosis blocked, hematopoietic cells can then continue to proliferate and give rise to increased numbers of new hematopoietic cells. Therefore, 1410 potentially has a functional role in preventing the induction of apoptosis. Due to its functional role and expression pattern in the bone marrow, cord blood and fetal liver, 1410 can play a role in regulating diseases associated with hematological disorders. Therefore, modulators of 1410 activity would be useful in treating hematological disorders including but not limited to anemia. 1410 polypeptides of the current invention would be useful to screen for modulators of 1410 activity.

Gene ID 137

The human 137 sequence (SEQ ID NO: 39), known also as muscarinic acetycholine receptor M3, is approximately 3906 nucleotides long including untranslated regions. The coding sequence, located at about nucleic acids 202 to 1974 of SEQ ID NO: 39, encodes a 590 amino acid protein (SEQ ID NO:40).

As assessed by TAQMAN® analysis, 137 mRNA was expressed in hematopoietic progenitor cells of the bone marrow and cord and peripheral blood and in brain. Levels of expression of this gene decreased upon in vitro differentiation of hematopoietic progenitor cells to the neutrophil, megakaryocyte and erythroid lineages.

The muscarinic acetylcholine receptor M3 or 137 mediates various cellular responses including inhibition of adenylate cyclases, breakdown of phosphoinositides and modulation of potassium ion channels. An agonist of 137 causes proliferation of neural stem cells and oligodendrocyte precursor cells in vitro, which suggests that stimulating this receptor will increase proliferation of CD34+ hematopoietic stem cells giving rise to increased numbers of cells of all hematopoietic lineages. Therefore, due to 137 mRNA expression in the bone marrow, cord blood and brain, along with its functional role, modulators of 137 activity would be useful in treating hematological disorders including but not limited to neutropenia, thrombocytopenia and anemia and/or conditions characterized by an increased number or aberrant neutrophils, platelets or red blood cells. 137 polypeptides of the current invention would be useful to screen for modulators of 137 activity.

Gene ID 1871

The human 1871 sequence (SEQ ID NO: 41), known also as an G-Protein Coupled Receptor, is approximately 2416 nucleotides long including untranslated regions. The coding sequence, located at about nucleic acids 217 to 1233 of SEQ ID NO: 41, encodes a 338 amino acid protein (SEQ ID NO: 42).

As assessed by TAQMAN® analysis, 1871 mRNA was expressed at significant levels in brain, placenta and in CD34 progenitor cells. Additional TAQMAN® analyses indicated that 1871 mRNA was expressed in erythroid, megakaryocyte, and neutrophil cultures grown in vitro.

The ligand for 1871, a G protein-coupled receptor, is UDP-glucose which is involved in restoring lipocyte proliferation in the regenerating livers of ethanol-treated rats. (Funaki et al., J Hepatol 192 15 (3):367-71). The ligand for 1871 induces cellular proliferation. Therefore, agonizing this receptor leads to increased proliferation of hematopoietic progenitor cells, resulting in increased numbers of erythroid neutrophil and megakaryocyte cells. Due to 1871 mRNA expression in the brain, placenta and in CD34+ progenitor cells, along with its functional role, modulators of 1871 would be useful in the treatment of hematological disorders including but not limited to neutropenia, thrombocytopenia and anemia and/or conditions characterized by an increased number or aberrant neutrophils, platelets or red blood cells. Modulators of 1871 activity would be useful in treating hematological disorders. 1871 polypeptides of the present invention would be useful in screening for modulators of 1871 activity.

Gene ID 13051

The human 13051 sequence (SEQ ID NO: 43), known also as fatty acid amide hydrolase, is approximately 2063 nucleotides long including untranslated regions. The coding sequence, located at about nucleic acids 36 to 1775 of SEQ ID NO: 43, encodes a 579 amino acid protein (SEQ ID NO: 44).

As assessed by TAQMAN®, 13051 mRNA was expressed in the hematiopoietic progenitor CD34+ cells and was downregulated during in vitro differentiation of erythroid, megakaryocyte and neutrophil cultures. 13051 mRNA was expressed at significantly higher levels in 11b-neutrophil progenitors than in the 11b+ neutrophil progenitorsin.

13051 is a fatty acid amide hydrolase. Fatty acid amide hydrolase is the major enzyme catalyzing the degradation of arachidonoylethanolamide (AEA) which has anti-proliferative effects on human breast cancer cells. Inhibition of fatty acid amide hydrolase enhances the anti-proliferative effect of AEA. Therefore, inhibiting 13051 will lead to an increased proliferation of hematopoietic progenitor cells leading to expansion of erythroid, megakaryocyte and neutrophil lineages. Due to its functional role and expression pattern in the hematiopoietic progenitor CD34+ cells, 13051 plays a role in regulating diseases associated with hematological disorders. Therefore, modulators of 13051 activity would be useful in treating hematological disorders including but not limited to diseases characterized by neutropenia and/or an increase in the number of neutrophils. 13051 polypeptides of the current invention would be useful to screen for modulators of 13051 activity.

Gene ID 1847

The human 1847 sequence (SEQ ID NO: 45), known also as tryptase 1, is approximately 1154 nucleotides long including untranslated regions. The coding sequence, located at about nucleic acids 18 to 845 of SEQ ID NO: 45, encodes a 275 amino acid protein (SEQ ID NO: 46).

As assessed by TAQMAN®, 1847 mRNA was expressed at highest levels in hematopoietic progenitor cells, non-irradiated stromal cells, mast cells and in vitro generated erythroid and megakaryocytic cells.

1847 or Tryptase 1 (alpha tryptase) is a major neutral protease present in mast cells. 1847 is secreted upon mast cell activation. Given the marked expression in hematopoietic progenitor and stromal cells, 1847's functional role is in degrading hormones which stimulate hematopoiesis. Therefore, inhibiting 1847, would stimulate hematopoietic progenitor proliferation in vivo. Due to its functional role and expression pattern in the hematopoietic progenitor cells, non-irradiated stromal cells, mast cells and in vitro generated erythroid and megakaryocytic cells, 1847 plays a role in regulating diseases associated with hematological disorders. Therefore, modulators of 1847 activity would be useful in treating hematological disorders. 1847 polypeptides of the current invention would be useful to screen for modulators of 1847 activity.

Gene ID 1849

The human 1849 sequence (SEQ ID NO: 47), known also as tryptase 2, is approximately 1143 nucleotides long including untranslated regions. The coding sequence, located at about nucleic acids 6 to 833 of SEQ ID NO: 47, encodes a 275 amino acid protein (SEQ ID NO: 48).

As assessed by TAQMAN® analysis, 1849 mRNA was expressed at highest levels in hematopoietic progenitor cells, non-irradiated stromal cells, mast cells and in vitro generated erythroid and megakaryocytic cells and lung tissue.

1849 or tryptase 2 (beta tryptase) gene is a major neutral protease present in mast cells. 1849 is secreted upon mast cell activation. Given the marked expression in hematopoietic progenitor and stromal cells, 1849's functional role is in degrading hormones which stimulate hematopoiesis. Therefore, inhibiting 1849 would stimulate hematopoietic progenitor proliferation in vivo. Due to its functional role and expression pattern in hematopoietic progenitor cells, non-irradiated stromal cells, mast cells and in vitro generated erythroid and megakaryocytic cells and lung tissue, 1849 plays a role in regulating diseases associated with hematological disorders. Therefore, modulators of 1849 activity would be useful in treating hematological disorders. 1849 polypeptides of the current invention would be useful to screen for modulators of 1849 activity.

Gene ID 15402

The human 15402 sequence (SEQ ID NO: 49), known also as sulfotransferase (HNK-1), is approximately 2877 nucleotides long including untranslated regions. The coding sequence, located at about nucleic acids 387 to 1457 of SEQ ID NO: 49, encodes a 356 amino acid protein (SEQ ID NO: 50).

As assessed by TAQMAN® analysis, 15402 mRNA was expressed in the brain, hematopoietic progenitor cells, in vitro generated erythroid cells and the erythroid cell line K562. Further TAQMAN® analysis showed that 15402 mRNA expression was higher in Glycophorin A (GPA) low cells compared to GPA high cells. In addition, 15402 mRNA was upregulated during in vitro generation of erythroid cells, while 15402 mRNA expression was downregulated during in vitro generation of neutrophils and megakaryocytes.

As assessed by TAQMAN® analysis, 137 mRNA was expressed in the kidney as well as in hematopoietic progenitor cells of the bone marrow and cord and peripheral blood and in brain. Levels of expression of this gene decreased upon in vitro differentiation of hematopoietic progenitor cells to the neutrophil, megakaryocyte and erythroid lineages.

As assessed by TaqMan analysis, 15402 mRNA was expressed in the brain, hematopoietic progenitor cells, in vitro generated erythroid cells and the erythroid cell line K562. Further TaqMan analysis showed that 15402 mRNA expression was higher in Glycophorin A (GPA) low cells compared to GPA high cells. In addition, 15402 mRNA was upregulated during in vitro generation of erythroid cells, while 15402 mRNA expression was downregulated during in vitro generation of neutrophils and megakaryocytes.

15402 or HNK-1 directs the synthesisof the HNK-1 carbohydrate epitope on call adhesion molecules. The HNK-1 carbohydrate epitope is involved in cell interactions (Bakker et al., JBC 272: 29942-29946). Cell-cell interactions via CAMs are known to serve as "potent negative regulators of hematopoiesis." (Zannettino et al., Blood 8:2613-2628). 15402 acts to inhibit hematopoietic proliferation by directing the synthesis of the HNK-1 carbohydrate epitope on cel adhesion molecules found on the hematopoietic progenitors. Therefore, inhibiting the action of 15402 would lead to increased numbers of hematopoietic cells. Due to 15402 mRNA expression in the brain, hematopoietic progenitor cells, in vitro generated erythroid cells and the erythroid cell line K562, along with its functional role, modulators of 15402 would be useful in the treatment of hematological disorders. Modulators of 15402 activity would be useful in treating hematological disorders. 15402 polypeptides of the present invention would be useful in screening for modulators of 15402 activity.

Gene ID 340

The human 340 sequence (SEQ ID NO: 51), known also as a G Protein Coupled Receptor (proteinase activated receptor-2, PAR-2), is approximately 1451 nucleotides long including untranslated regions. The coding sequence, located at about nucleic acids 148 to 1341 of SEQ ID NO: 51, encodes a 397 amino acid protein (SEQ ID NO: 52).

As assessed by TAQMAN® analysis, 340 mRNA was expressed in the kidney as well as in hematopoietic progenitor cells. 340 is the de-orphaned G Protein Coupled Receptor PAR-2 (proteinase activated receptor-2). Cleavage of the 340 gene by known proteases activates this gene and causes cellular proliferation. Therefore, agonizing 340 or PAR-2 activates this receptor and causes proliferation of hematopoietic progenitor cells resulting in an increased numbers of hematopoietic cells. Due to 340 mRNA expression in the kidney and hematopoietic progenitor cells, along with its functional role, modulators of 340 would be useful in the treatment of hematological disorders. 340 polypeptides of the present invention would be useful in screening for modulators of 340 activity.

Gene ID 10217

The human 10217 sequence (SEQ ID NO: 53), known also as P2X1 ATP receptor, is approximately 2643 nucleotides long including untranslated regions. The coding sequence, located at about nucleic acids 174 to 1373 of SEQ ID NO: 53, encodes a 399 amino acid protein (SEQ ID NO: 54).

As assessed by TAQMAN®, 10217 mRNA was expressed in hematopoietic progenitor cells, in vitro generated megakaryocytes and in vivo neutrophils. Further TAQMAN® analysis indicated that 10217 mRNA expression was downregulated from high levels in the CD34+ progenitors during in vitro differentiation to erythroid lineages.

Blocking the activity of 10217 or P2X1 ATP receptor has shown to inhibit ATP-induced apoptosis in thymocytes. (Nagy et al., Immunol Lett 72:23-30, 2000). Therefore, antagonizing the action of 10217 in hematopoieitic progenitor cells inhibits ATP-induced apoptosis leading to increased numbers of hematopoietic progenitor cells. Due to its functional role and expression pattern in the hematopoietic progenitor cells, megakaryocytes and neutrophils, 10217 plays a role in regulating diseases associated with hematological disorders. Therefore, modulators of 10217 activity would be useful in treating hematological disorders including but not limited to diseases characterized by neutropenia and/or an increase in the number of neutrophils. 10217 polypeptides of the current invention would be useful to screen for modulators of 10217 activity.

Gene ID 837

The human 837 sequence (SEQ ID NO: 55), known also Nicotinic acetylcholine receptor alpha 7, is approximately 2087 nucleotides long including untranslated regions. The coding sequence, located at about nucleic acids 104 to 1612 of SEQ ID NO: 55, encodes a 502 amino acid protein (SEQ ID NO: 56).

As assessed by TAQMAN®, 837 mRNA was expressed at high levels in the brain, hematopoietic progenitor cells and CD11b–15+ neutrophils. Further TAQMAN® analysis indicated that 837 mRNA expression was downregulated in vivo in CD11b+15+ cells when compared to the earlier CD11b–15+ cells. This expression was maintained throughout in vitro differentiation to the neutrophil lineage. In addition, 837 mRNA expression was downregulated during in vitro generation to the megakaryocyte and erythroid lineages.

837 is the nicotinic acetylcholine receptor alpha 7. Antagonists of 837 have been shown to inhibit cell proliferation (Codignola et al FEBS Lett 342:286-290). 837 is also important for proliferation of different cell types, with antagonists inhibiting proliferation. Therefore, agonizing 837 will increase proliferation of hematopoietic progenitor cells, particularly neutrophils. Due to its functional role, and expression pattern in the brain, hematopoietic progenitor cells and CD11b-15+ neutrophils, 837 plays a role in regulating diseases associated with hematological disorders. Therefore, modulators of 837 activity would be useful in treating hematological disorders including but not limited to diseases characterized by neutropenia and/or an increase in the number of neutrophils. 837 polypeptides of the current invention would be useful to screen for modulators of 837 activity.

Gene ID 1761

The human 1761 sequence (SEQ ID NO: 57), known also as Cathepsin G, is approximately 857 nucleotides long including untranslated regions. The coding sequence, located at about nucleic acids 9 to 776 of SEQ ID NO: 57, encodes a 255 amino acid protein (SEQ ID NO: 58).

As assessed by TAQMAN analysis, 1761 mRNA was expressed at high levels in hematopoietic progenitor cells, CD11b–15+ neutrophils, glycophorin A+ cells and in vitro differentiated neutrophils. Further TAQMAN® analysis indicated that 1761 mRNA was expressed higher in earlier CD11b−15+ neutrophils than in later CD11b+15b+ cells. In addition, 1761 mRNA was upregulated in in vitro generated megakaryocyte and erythroid cells then downregulated by day 12 in these cultures. 1761 mRNA remained upregulated in vitro neutrophil cultures.

1761 is a protease known to be expressed in neutrophils. 1761 cleaves and inactivates stromal-cell derived factor SDF-1 (Eur J Immunol (3):699-707, 2001). SDF-1 is a growth factor known to be an important regulator of hematopoiesis, suppressing apoptosis of hematopoietic progenitor cells (Lataillade et al., Blood 4: 1117-29, 2002). Therefore, inhibiting the function of the 1761 protease in hematopoietic progenitor cells will lead to increased activity of SDF-1, which positively regulates primitive hematopoiesis leading to increased numbers of hematopoietic cells. Due to 1761 mRNA expression in hematopoietic progenitor cells, CD11b-15+ neutrophils, glycophorin A+ cells and in vitro differentiated neutrophils, along with its functional role, modulators of 1761 activity would be useful in treating hematological disorders including but not limited to neutropenia and/or an increase in the number of neutrophils. 1761 polypeptides of the current invention would be useful to screen for modulators of 1761 activity.

Gene ID 8990

The human 8990 sequence (SEQ ID NO: 59), known also as Arginase II, is approximately 1354 nucleotides long including untranslated regions. The coding sequence, located at about nucleic acids 21 to 1085 of SEQ ID NO: 59, encodes a 354 amino acid protein (SEQ ID NO: 60).

As assessed by TAQMAN®, 8990 mRNA was upregulated with maturation of erythroid and megakaryocytic cells. 8990 mRNA was rapidly upregulated in in vitro differentiating erythroid cells, being low in pooled erythroid cell cultures at days 0, 1, 2, 6 and being very high in pooled erythroid cell cultures at days 10/12. 8990 mRNA was also upregulated in CFU-E cells in response to EPO stimulation.

Inhibition of Arginase II potentially prevents apoptosis in erythroid cells. Arginase II upregulation is related to differentiation of the erythroid lineage and the ability to keep the cells in the earlier, cycling phase, for a longer period would lead to expansion of the pool of erythroid cells. Due to its functional role and expression pattern in erythroid and megakaryocytic cells, 8990 plays a role in regulating diseases associated with hematological disorders. Therefore, modulators of 8990 activity would be useful in treating hematological disorders. 8990 polypeptides of the current invention would be useful to screen for modulators of 8990 activity.

Gene ID 13249

The human 13249 sequence (SEQ ID NO: 61), known also as a serine threonine kinase (JIK), is approximately 3032 nucleotides long including untranslated regions. The coding sequence, located at about nucleic acids 296 to 2992 of SEQ ID NO: 61, encodes a 898 amino acid protein (SEQ ID NO: 62).

As assessed by TAQMAN®, 13249 mRNA was expressed in CD34 progenitor cells, in vitro differentiated erythroid and megakaryocytic cells and neutrophils. Further TAQMAN® analysis indicated that 13249 mRNA levels were also high in fresh (GPA high and low expressing populations) and in vitro cultured erybroid cells at all stages of differentiation, rising slightly in the most mature erythroid cells.

13249 is also known as JNK inhibitory kinase (JIK) as it inhibits JNK. JNK acts downstream of the EPO receptor. The EPO receptor is crucial for erythroid cell proliferation and differentiation. 13249 or JIK also inhibits basal JNK activity and diminishes response to EGF activation whereas it doesn't inhibit ERK2, 5, 6 or p38 MAP kinase (Tassi, E et al. JBC, 274, 1999, 33287-95). Therefore, inhibition of 13249 or JIK will lead to increased activity of JNK and increased signaling through the EPO receptor, leading to an increased proliferation of erythroid cells. Due to its functional role and expression pattern in the CD34 progenitor cells, in vitro differentiated erythroid and megakaryocytic cells and neutrophils, 13249 plays a role in regulating diseases associated with hematological disorders. Therefore, modulators of 13249 activity would be useful in treating hematological disorders including but not limited to diseases characterized by neutropenia and/or an increase in the number of neutrophils. 13249 polypeptides of the current invention would be useful to screen for modulators of 13249 activity Various aspects of the invention are described in further detail in the following subsections:

Screening Assays:

The invention provides a method (also referred to herein as a "screening assay") for identifying modulators, i.e., candidate or test compounds or agents (e.g., peptides, peptidomimetics, small molecules (organic or inorganic) or other drugs) which bind to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins, have a stimulatory or inhibitory effect on, for example, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity, or have a stimulatory or inhibitory effect on, for example, the expression or activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate. Compounds identified using the assays described herein may be useful for treating hematological disorders.

These assays are designed to identify compounds that bind to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, bind to other intracellular or extracellular proteins that interact with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, and interfere with the interaction of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein with other intercellular or extracellular proteins. For example, in the case of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, which is a transmembrane receptor-type protein, such techniques can identify ligands for such a receptor. A 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein ligand or substrate can, for example, be used to at least one syptom of a hematological disorder. Such compounds may include, but are not limited to peptides, antibodies, or small organic or inorganic compounds. Such compounds may also include other cellular proteins.

Compounds identified via assays such as those described herein may be useful, for example, for treating hematological disorders. In instances whereby a hematological disorder condition results from an overall lower level of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression and/or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein in a cell or tissue, compounds that interact with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein may include compounds which accentuate or amplify the activity of the bound 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Such compounds would bring about an effective increase in the level of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein activity, thus ameliorating symptoms.

In other instances, mutations within the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene may cause aberrant types or excessive amounts of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins to be made which have a deleterious effect that leads to a hematological disorder. Similarly, physiological conditions may cause an excessive increase in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression leading hematological disorders. In such cases, compounds that bind to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein may be identified that inhibit the activity of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Assays for testing the effectiveness of compounds identified by techniques such as those described in this section are discussed herein.

In one embodiment, the invention provides assays for screening candidate or test compounds which are substrates of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or polypeptide or biologically active portion thereof. In another embodiment, the invention provides assays for screening candidate or test compounds which bind to or modulate the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223, 409), spores (Ladner U.S. Pat. No. '409), plasmids (Cull et al. (1992) *Proc Natl Acad Sci USA* 89: 1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or biologically active portion thereof is contacted with a test compound and the ability of the test compound to modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is determined. Determining the ability of the test compound to modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity can be accomplished by monitoring, for example, intracellular calcium, $IP_3$, cAMP, or diacylglycerol concentration, the phosphorylation profile of intracellular proteins, cell proliferation and/or migration, gene expression of, for example, cell surface adhesion molecules or genes associated with hematopoeisis, or the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-regulated transcription factor. The cell can be of mammalian origin, e.g., a neural cell. In one embodiment, compounds that interact with a receptor domain can be screened for their ability to function as ligands, i.e., to bind to the receptor and modulate a signal transduction pathway.

Identification of ligands, and measuring the activity of the ligand-receptor complex, leads to the identification of modulators (e.g., antagonists) of this interaction. Such modulators may be useful in the treatment of hematological disorders.

The ability of the test compound to modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 binding to a substrate or to bind to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can also be determined. Determining the ability of the test compound to modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 binding to a substrate can be accomplished, for example, by coupling the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate with a radioisotope or enzymatic label such that binding of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be determined by detecting the labeled 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate in a complex. 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 could also be coupled with a radioisotope or enzymatic label to monitor the ability of a test compound to modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 binding to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate in a complex. Determining the ability of the test compound to bind 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be accomplished, for example, by coupling the compound with a radioisotope or enzymatic label such that binding of the compound to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be determined by detecting the labeled 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 compound in a complex. For example, compounds (e.g., 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 ligands or substrates) can be labeled with $^{125}I$, $^{35}S$, $^{14}C$, or $^{3}H$, either directly or indirectly, and the radioisotope detected by direct counting of radioemission or by scintillation counting. Compounds can further be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 ligand or substrate) to interact with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 without the labeling of any of the interactants. For example, a microphysiometer can be used to detect the interaction of a compound with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 without the labeling of either the compound or the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 (McConnell, H. M. et al. (1992) Science 257:1906-1912. As used herein, a "microphysiometer" (e.g., CYTOSENSOR®) is an analytical instrument that measures the rate at which a cell acidifies its environment using a light-addressable potentiometric sensor (LAPS). Changes in this acidification rate can be used as an indicator of the interaction between a compound and 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249.

In another embodiment, an assay is a cell-based assay comprising contacting a cell expressing a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule (e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate) with a test compound and determining the ability of the test compound to modulate (e.g., stimulate or inhibit) the activity of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule. Determining the ability of the test compound to modulate the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule can be accomplished, for example, by determining the ability of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to bind to or interact with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule.

Determining the ability of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or a biologically active fragment thereof, to bind to or interact with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule can be accomplished by one of the methods described above for determining direct binding. In a preferred embodiment, determining the ability of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to bind to or interact with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, cAMP), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response (e.g., gene expression).

In yet another embodiment, an assay of the present invention is a cell-free assay in which a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or biologically active portion thereof, is contacted with a test compound and the ability of the test compound to bind to the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or biologically active portion thereof is determined. Preferred biologically active portions of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins to be used in assays of the present invention include fragments which participate in interactions with non-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 molecules, e.g., fragments with high surface probability scores. Binding of the test compound to the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be determined either directly or indirectly as described above. In a preferred embodiment, the assay includes contacting the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or biologically active portion thereof with a known compound which binds 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 to form an assay mixture, contacting the assay mixture with a test compound, and determining the ability of the test compound to interact with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, wherein determining the ability of the test compound to interact with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein comprises determining the ability of the test compound to preferentially bind to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 or biologically active portion thereof as compared to the known compound. Compounds that modulate the interaction of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 with a known target protein may be useful in regulating the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, especially a mutant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein.

In another embodiment, the assay is a cell-free assay in which a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or biologically active portion thereof is contacted with a test compound and the ability of the test compound to modulate (e.g., stimulate or inhibit) the activity of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or biologically active portion thereof is determined. Detennining the ability of the test compound to modulate the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be accomplished, for example, by determining the ability of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to bind to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule by one of the methods described above for determining direct binding. Determining the ability of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to bind to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule can also be accomplished using a technology such as real-time Biomolecular Interaction Analysis (BIA) (Sjolander, S. and Urbaniczky, C. (1991) Anal. Chem. 63:2338-2345 and Szabo et al. (1995) Curr. Opin. Struct. Biol. 5:699-705). As used herein, "BIA" is a technology for studying biospecific interactions in real time, without labeling any of the interactants (e.g., BIACORE®). Changes in the optical phenomenon of surface plasmon resonance (SPR) can be used as an indication of real-time reactions between biological molecules.

In another embodiment, determining the ability of the test compound to modulate the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be accomplished by determining the ability of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to further modulate the activity of a downstream effector of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule. For example, the activity of the effector molecule on an appropriate target can be determined or the binding of the effector to an appropriate target can be determined as previously described.

In yet another embodiment, the cell-free assay involves contacting a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or biologically active portion thereof with a known compound which binds the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to form an assay mixture, contacting the assay mixture with a test compound, and determining the ability of the test compound to interact with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, wherein determining the ability of the test compound to interact with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein comprises determining the ability of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to preferentially bind to or modulate the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule.

In more than one embodiment of the above assay methods of the present invention, it may be desirable to immobilize either 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 or its target molecule to facilitate separation of complexed from uncomplexed forms of one or both of the proteins, as well as to accommodate automation of the assay, Binding of a test compound to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, or interaction of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 binding or activity determined using standard techniques.

Other techniques for immobilizing proteins on matrices can also be used in the screening assays of the invention. For example, either a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 target molecule can be immobilized utilizing conjugation of biotin and streptavidin. Biotinylated 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or target molecules but which do not interfere with binding of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to its target molecule can be derivatized to the wells of the plate, and unbound target or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein trapped in the wells by antibody conjugation. Methods for detecting such complexes, in addition to those described above for the GST-immobilized complexes, include immunodetection of complexes using antibodies reactive with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or target molecule, as well as enzyme-linked assays which rely on detecting an enzymatic activity associated with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or target molecule.

In another embodiment, modulators of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression are identified in a method wherein a cell is contacted with a candidate compound and the expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein in the cell is determined. The level of expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein in the presence of the candidate compound is compared to the level of expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein in the absence of the candidate compound. The candidate compound can then be identified as a modulator of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression based on this comparison. For example, when expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein is greater (statistically significantly greater) in the presence of the candidate compound than in its absence, the candidate compound is identified as a stimulator of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein expression. Alternatively, when expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein is less (statistically significantly less) in the presence of the candidate compound than in its absence, the candidate compound is identified as an inhibitor of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein expression in the cells can be determined by methods described herein for detecting 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or protein.

In yet another aspect of the invention, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins can be used as "bait proteins" in a two-hybrid assay or three-hybrid assay (see, e.g., U.S. Pat. No. 5,283, 317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 ("131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-binding proteins" or "131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-bp") and are involved in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. Such 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-binding proteins are also likely to be involved in the propagation of signals by the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 targets as, for example, downstream elements of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-mediated signaling pathway. Alternatively, such 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-binding proteins are likely to be 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 inhibitors.

The two-hybrid system is based on the modular nature of most transcription factors, which consist of separable DNA-binding and activation domains. Briefly, the assay utilizes two different DNA constructs. In one construct, the gene that codes for a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein.

In another aspect, the invention pertains to a combination of two or more of the assays described herein. For example, a modulating agent can be identified using a cell-based or a cell free assay, and the ability of the agent to modulate the activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be confirmed in vivo, e.g., in an animal such as an animal model for hematological disorders, as described herein.

This invention further pertains to novel agents identified by the above-described screening assays. Accordingly, it is within the scope of this invention to further use an agent identified as described herein in an appropriate animal model. For example, an agent identified as described herein (e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulating agent, an antisense 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecule, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-specific antibody, or a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to treat hematological disorders. Cell-based and animal model-based assays for the identification of compounds exhibiting such an ability to at least one symptom of hematological disorders are described herein.

In addition, animal-based models of hematological disorders, such as those described herein, may be used to identify compounds capable of treating hematological disorders. Such animal models may be used as test substrates for the identification of drugs, pharmaceuticals, therapies, and interventions which may be effective in treating hematological disorders. For example, animal models may be exposed to a compound, suspected of exhibiting an ability to treat hematological disorders, at a sufficient concentration and for a time sufficient to elicit such an amelioration of hematological disorders in the exposed animals. The response of the animals to the exposure may be monitored by assessing the reversal of the symptoms of hematological disorders before and after treatment.

With regard to intervention, any treatments which reverse any aspect of hematological disorders should be considered as candidates for human hematological disorders therapeutic intervention. Dosages of test agents may be determined by deriving dose-response curves.

Additionally, gene expression patterns may be utilized to assess the ability of a compound to at least one symptom of hematological disorders. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Gene expression profiles may be generated, for example, by utilizing a differential display procedure, Northern analysis and/or RT-PCR. In one embodiment, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences may be used as probes and/or PCR primers for the generation and corroboration of such gene expression profiles.

Gene expression profiles may be characterized for known states, either cardiovascular disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a hematological disorder disease model system to more closely resemble the control system. Administration of a compound may, alternatively, cause the gene expression profile of a control system to begin to mimic hematological disorders or a hematological disorder disease state. Such a compound may, for example, be used in further characterizing the compound of interest, or may be used in the generation of additional animal models.

Cell- and Animal-Based Model Systems

Described herein are cell- and animal-based systems which act as models for hematological disorders. These systems may be used in a variety of applications. For example, the cell- and animal-based model systems may be used to further characterize differentially expressed genes associated with cardiovascular disease, e.g., 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249. In addition, animal- and cell-based assays may be used as part of screening strategies designed to identify compounds which are capable of ameliorating hematological disorders, as described, below. Thus, the animal- and cell-based models may be used to identify drugs, pharmaceuticals, therapies and interventions which may be effective in treating a hematological disorder. Furthermore, such animal models may be used to determine the LD50 and the ED50 in animal subjects, and such data can be used to determine the in vivo efficacy of potential hematological disorders treatments.

Animal-Based Systems

Animal-based model systems of hematological disorders may include, but are not limited to, non-recombinant and engineered transgenic animals.

Non-recombinant animal models for hematological disorders may include, for example, genetic models.

Additionally, animal models exhibiting hematological disorders may be engineered by using, for example, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences described above, in conjunction with techniques for producing transgenic animals that are well known to those of skill in the art. For example, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences may be introduced into, and overexpressed in, the genome of the animal of interest, or, if endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences are present, they may either be overexpressed or, alternatively, be disrupted in order to underexpress or inactivate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression.

The host cells of the invention can also be used to produce non-human transgenic animals. For example, in one embodiment, a host cell of the invention is a fertilized oocyte or an embryonic stem cell into which 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-coding sequences have been introduced. Such host cells can then be used to create non-human transgenic animals in which exogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequences have been introduced into their genome or homologous recombinant animals in which endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequences have been altered. Such animals are useful for studying the function and/or activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 and for identifying and/or evaluating modulators of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene has been altered by homologous recombination between the endogenous gene and an exogenous DNA molecule introduced into a cell of the animal, e.g., an embryonic cell of the animal, prior to development of the animal.

A transgenic animal used in the methods of the invention can be created by introducing a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-encoding nucleic acid into the male pronuclei of a fertilized oocyte, e.g., by microinjection, retroviral infection, and allowing the oocyte to develop in a pseudopregnant female foster animal. The 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 cDNA sequence can be introduced as a transgene into the genome of a non-human animal. Alternatively, a nonhuman homologue of a human 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, such as a mouse or rat 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, can be used as a transgene. Alternatively, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene homologue, such as another 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 family member, can be isolated based on hybridization to the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 cDNA sequences and used as a transgene. Intronic sequences and polyadenylation signals can also be included in the transgene to increase the efficiency of expression of the transgene. A tissue-specific regulatory sequence(s) can be operably linked to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 transgene to direct expression of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 transgene in its genome and/or expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA in tissues or cells of the animals. A transgenic founder animal can then be used to breed additional animals carrying the transgene. Moreover, transgenic animals carrying a transgene encoding a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can further be bred to other transgenic animals carrying other transgenes.

To create a homologous recombinant animal, a vector is prepared which contains at least a portion of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene into which a deletion, addition or substitution has been introduced to thereby alter, e.g., functionally disrupt, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene. The 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene can be a human gene but more preferably, is a non-human homologue of a human 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene. For example, a rat 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene can be used to construct a homologous recombination nucleic acid molecule, e.g., a vector, suitable for altering an endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene in the mouse genome. In a preferred embodiment, the homologous recombination nucleic acid molecule is designed such that, upon homologous recombination, the endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene is functionally disrupted (i.e., no longer encodes a functional protein; also referred to as a "knock out" vector). Alternatively, the homologous recombination nucleic acid molecule can be designed such that, upon homologous recombination, the endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene is mutated or otherwise altered but still encodes functional protein (e.g., the upstream regulatory region can be altered to thereby alter the expression of the endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein). In the homologous recombination nucleic acid molecule, the altered portion of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene is flanked at its 5' and 3' ends by additional nucleic acid sequence of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene to allow for homologous recombination to occur between the exogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene carried by the homologous recombination nucleic acid molecule and an endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene in a cell, e.g., an embryonic stem cell. The additional flanking 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene has homologously recombined with the endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinonias and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals for use in the methods of the invention can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

The 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 transgenic animals that express 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 peptide (detected immunocytochemically, using antibodies directed against 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 epitopes) at easily detectable levels should then be further evaluated to identify those animals which display characteristic hematological disorders.

Cell-Based Systems

Cells that contain and express 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences which encode a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, and, further, exhibit cellular phenotypes associated with e.g. hematopoeisis, may be used to identify compounds that exhibit an effect. Such cells may include non-recombinant monocyte cell lines, such as U937 (ATCC# CRL-1593), THP-1 (ATCC#TIB-202), and P388D1 (ATCC# TIB-63); endothelial cells such as human umbilical vein endothelial cells (HUVECs), human microvascular endothelial cells (HMVEC), and bovine aortic endothelial cells (BAECs); as well as generic mammalian cell lines such as HeLa cells and COS cells, e.g., COS-7 (ATCC# CRL-1651), cells described supra which constitute those cells relevant to hematology. Further, such cells may include recombinant, transgenic cell lines. For example, the hematological disorders animal models of the invention, discussed above, may be used to generate cell lines, containing one or more cell types involved in e.g. hematopoeisis, that can be used as cell culture models for this disorder. While primary cultures derived from the hematological disorders model transgenic animals of the invention may be utilized, the generation of continuous cell lines is preferred. For examples of techniques which may be used to derive a continuous cell line from the transgenic animals, see Small et al., (1985) *Mol. Cell Biol.* 5:642-648.

Alternatively, cells of a cell type known to be involved in e.g. hematopoeisis may be transfected with sequences capable of increasing or decreasing the amount of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression within the cell. For example, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences may be introduced into, and overexpressed in, the genome of the cell of interest, or, if endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences are present, they may be either overexpressed or, alternatively disrupted in order to underexpress or inactivate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression.

In order to overexpress a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, the coding portion of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene may be ligated to a regulatory sequence which is capable of driving gene expression in the cell type of interest, e.g., an endothelial cell. Such regulatory regions will be well known to those of skill in the art, and may be utilized in the absence of undue experimentation. Recombinant methods for expressing target genes are described above.

For underexpression of an endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequence, such a sequence may be isolated and engineered such that when reintroduced into the genome of the cell type of interest, the endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 alleles will be inactivated. Preferably, the engineered 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequence is introduced via gene targeting such that the endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequence is disrupted upon integration of the engineered 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequence into the cell's genome. Transfection of host cells with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 genes is discussed, above.

Cells treated with compounds or transfected with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 genes can be examined for phenotypes associated with e.g. hematopoeisis.

Transfection of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid may be accomplished by using standard techniques (described in, for example, Ausubel (1989) supra). Transfected cells should be evaluated for the presence of the recombinant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences, for expression and accumulation of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA, and for the presence of recombinant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein production. In instances wherein a decrease in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression is desired, standard techniques may be used to demonstrate whether a decrease in endogenous 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression and/or in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein production is achieved.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein and/or nucleic acid expression as well as 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity, in the context of a biological sample (e.g., blood, serum, cells, e.g., endothelial cells, or tissue, e.g., vascular tissue) to thereby determine whether an individual is afflicted with a predisposition or is experiencing hematological disorders. The invention also provides for prognostic (or predictive) assays for determining whether an individual is at risk of developing a hematological disorder. For example, mutations in a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene can be assayed for in a biological sample. Such assays can be used for prognostic or predictive purpose to thereby phophylactically treat an individual prior to the onset of a hematological disorder.

Another aspect of the invention pertains to monitoring the influence of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulators (e.g., anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 ribozymes) on the expression or activity of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 in clinical trials.

These and other agents are described in further detail in the following sections.

Diagnostic Assays

To determine whether a subject is afflicted with a disease, a biological sample may be obtained from a subject and the biological sample may be contacted with a compound or an agent capable of detecting a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or nucleic acid (e.g., mRNA or genomic DNA) that encodes a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, in the biological sample. A preferred agent for detecting 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or genomic DNA is a labeled nucleic acid probe capable of hybridizing to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or genomic DNA. The nucleic acid probe can be, for example, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, or a portion thereof, such as an oligonucleotide of at least 15, 20, 25, 30, 25, 40, 45, 50, 100, 250 or 500 nucleotides in length and sufficient to specifically hybridize under stringent conditions to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA or genomic DNA. Other suitable probes for use in the diagnostic assays of the invention are described herein.

A preferred agent for detecting 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein in a sample is an antibody capable of binding to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA, protein, or genomic DNA in a biological sample in vitro as well as in vivo. For example, in vitro techniques for detection of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA include Northern hybridizations and in situ hybridizations. In vitro techniques for detection of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein include enzyme linked immunosorbent assays (ELISAs), Western blots, immunoprecipitations and immunofluorescence. In vitro techniques for detection of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 genomic DNA include Southern hybridizations. Furthermore, in vivo techniques for detection of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein include introducing into a subject a labeled anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA, or genomic DNA, such that the presence of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA or genomic DNA is detected in the biological sample, and comparing the presence of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA or genomic DNA in the control sample with the presence of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA or genomic DNA in the test sample.

Prognostic Assays

The present invention further pertains to methods for identifying subjects having or at risk of developing a disease associated with aberrant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity.

As used herein, the term "aberrant" includes a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity which deviates from the wild type 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity. Aberrant expression or activity includes increased or decreased expression or activity, as well as expression or activity which does not follow the wild type developmental pattern of expression or the subcellular pattern of expression. For example, aberrant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity is intended to include the cases in which a mutation in the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene causes the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene to be under-expressed or over-expressed and situations in which such mutations result in a non-functional 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or a protein which does not function in a wild-type fashion, e.g., a protein which does not interact with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate, or one which interacts with a non-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate.

The assays described herein, such as the preceding diagnostic assays or the following assays, can be used to identify a subject having or at risk of developing a disease. A biological sample may be obtained from a subject and tested for the presence or absence of a genetic alteration. For example, such genetic alterations can be detected by ascertaining the existence of at least one of 1) a deletion of one or more nucleotides from a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, 2) an addition of one or more nucleotides to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, 3) a substitution of one or more nucleotides of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, 4) a chromosomal rearrangement of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, 5) an alteration in the level of a messenger RNA transcript of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, 6) aberrant modification of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, such as of the methylation pattern of the genomic DNA, 7) the presence of a non-wild type splicing pattern of a messenger RNA transcript of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, 8) a non-wild type level of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-protein, 9) allelic loss of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, and 10) inappropriate post-translational modification of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-protein.

As described herein, there are a large number of assays known in the art which can be used for detecting genetic alterations in a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene. For example, a genetic alteration in a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene (see Abravaya et al. (1995) *Nucleic Acids Res.* 23:675-682). This method includes collecting a biological sample from a subject, isolating nucleic acid (e.g., genomic DNA, mRNA or both) from the sample, contacting the nucleic acid sample with one or more primers which specifically hybridize to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene under conditions such that hybridization and amplification of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874-1878), transcriptional amplification system (Kwoh, D. Y. et al. (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be identified by hybridizing biological sample derived and control nucleic acids, e.g., DNA or RNA, to high density arrays containing hundreds or thousands of oligonucleotide probes (Cronin, M. T. et al. (1996) *Human Mutation* 7:244-255; Kozal, M. J. et al. (1996) *Nature Medicine* 2:753-759). For example, genetic mutations in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene in a biological sample and detect mutations by comparing the sequence of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 in the biological sample with the corresponding wild-type (control) sequence. Examples of sequencing reactions include those based on techniques developed by Maxam and Gilbert (1977) *Proc. Natl. Acad. Sci. USA* 74:560) or Sanger (1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type 131, 148, 199, 12303, 13906, 15513, 17822, 302, 5677, 194, 14393, 28059, 7366, 12212, 1981, 261, 12416, 270, 1410, 137, 1871, 13051, 1847, 1849, 340, 10217, 837, 1761, 8990 or 13249 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397 and Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequence, e.g., a wild-type 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766; see also Cotton (1993) *Mutat. Res.* 285:125-144 and Hayashi (1992) *Genet. Anal. Tech. Appl.* 9:73-79). Single-stranded DNA fragments of sample and control 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acids will be denatured and allowed to renature. The secondary structure of single-stranded, nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulator (e.g., an agonist, antagonist, peptidomimetic, protein, peptide, nucleic acid, or small molecule) to effectively treat a disease.

Monitoring of Effects During Clinical Trials

The present invention further provides methods for determining the effectiveness of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulator (e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulator identified herein) in treating a disease. For example, the effectiveness of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulator in increasing 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression, protein levels, or in upregulating 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity, can be monitored in clinical trials of subjects exhibiting decreased 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression, protein levels, or downregulated 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. Alternatively, the effectiveness of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulator in decreasing 131, 148, 199, 12303, 13906, 15513, 17822, 302, 5677, 194, 14393, 28059, 7366, 12212, 1981, 261, 12416, 270, 276, 1410, 137, 1871, 13051, 1847, 1849, 15402, 340, 10217, 837, 1761, 8990 or 13249 gene expression, protein levels, or in downregulating 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity, can be monitored in clinical trials of subjects exhibiting increased 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression, protein levels, or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. In such clinical trials, the expression or activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, and preferably, other genes that have been implicated in e.g. hematopoeisis can be used as a "read out" or marker of the phenotype of a particular cell.

For example, and not by way of limitation, genes, including 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249, that are modulated in cells by treatment with an agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity (e.g., identified in a screening assay as described herein) can be identified. Thus, to study the effect of agents which modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity on subjects suffering from a hematological disorder in, for example, a clinical trial, cells can be isolated and RNA prepared and analyzed for the levels of expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 and other genes implicated in the hematological disorders disorder. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 or other genes. In this way, the gene expression pattern can serve as a marker, indicative of the physiological response of the cells to the agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. This response state may be determined before, and at various points during treatment of the individual with the agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity.

In a preferred embodiment, the present invention provides a method for monitoring the effectiveness of treatment of a subject with an agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA, or genomic DNA in the pre-administration sample; (iii) obtaining one or more post-administration samples from the subject; (iv) detecting the level of expression or activity of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA, or genomic DNA in the post-administration samples; (v) comparing the level of expression or activity of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA, or genomic DNA in the pre-administration sample with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, mRNA, or genomic DNA in the post administration sample or samples; and (vi) altering the administration of the agent to the subject accordingly. For example, increased administration of the agent may be desirable to increase the expression or activity of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 to higher levels than detected, i.e., to increase the effectiveness of the agent. Alternatively, decreased administration of the agent may be desirable to decrease expression or activity of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 to lower levels than detected, i.e. to decrease the effectiveness of the agent. According to such an embodiment, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity may be used as an indicator of the effectiveness of an agent, even in the absence of an observable phenotypic response.

Methods of Treatment

The present invention provides for both prophylactic and therapeutic methods of treating a subject, e.g., a human, at risk of (or susceptible to) a disease. With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring an subject's prophylactic or therapeutic treatment with either the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 molecules of the present invention or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Prophylactic Methods

In one aspect, the invention provides a method for preventing in a subject, a disease by administering to the subject an agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. Subjects at risk for a hematological disorder, can be identified by, for example, any or a combination of the diagnostic or prognostic assays described herein. Administration of a prophylactic agent can occur prior to the manifestation of symptoms characteristic of aberrant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity, such that a disease is prevented or, alternatively, delayed in its progression. Depending on the type of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 aberrancy, for example, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 agonist or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antagonist agent can be used for treating the subject. The appropriate agent can be determined based on screening assays described herein.

Therapeutic Methods

Described herein are methods and compositions whereby hematological disorders may be ameliorated. Certain hematological disorders disorders are brought about, at least in part, by an excessive level of a gene product, or by the presence of a gene product exhibiting an abnormal or excessive activity. As such, the reduction in the level and/or activity of such gene products would bring about the amelioration of hematological disorders. Techniques for the reduction of gene expression levels or the activity of a protein are discussed below.

Alternatively, certain other hematological disorders disorders are brought about, at least in part, by the absence or reduction of the level of gene expression, or a reduction in the level of a protein's activity. As such, an increase in the level of gene expression and/or the activity of such proteins would bring about the amelioration of hematological disorders.

In some cases, the up-regulation of a gene in a disease state reflects a protective role for that gene product in responding to the disease condition. Enhancement of such a gene's expression, or the activity of the gene product, will reinforce the protective effect it exerts. Some hematological disorders states may result from an abnormally low level of activity of such a protective gene. In these cases also, an increase in the level of gene expression and/or the activity of such gene products would bring about the amelioration of hematological disorders. Techniques for increasing target gene expression levels or target gene product activity levels are discussed herein.

Accordingly, another aspect of the invention pertains to methods of modulating 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity for therapeutic purposes. Accordingly, in an exemplary embodiment, the modulatory method of the invention involves contacting a cell with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 or agent that modulates one or more of the activities of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein activity associated with the cell (e.g., an endothelial cell or an ovarian cell). An agent that modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein activity can be an agent as described herein, such as a nucleic acid or a protein, a naturally-occurring target molecule of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 ligand or substrate), a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 agonist or antagonist, a peptidomimetic of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 agonist or antagonist, or other small molecule. In one embodiment, the agent stimulates one or more 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activities. Examples of such stimulatory agents include active 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein and a nucleic acid molecule encoding 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 that has been introduced into the cell. In another embodiment, the agent inhibits one or more 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activities. Examples of such inhibitory agents include antisense 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecules, anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies, and 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or nucleic acid molecule. In one embodiment, the method involves administering an agent (e.g., an agent identified by a screening assay described herein), or combination of agents that modulates (e.g., upregulates or downregulates) 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity. In another embodiment, the method involves administering a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or nucleic acid molecule as therapy to compensate for reduced, aberrant, or unwanted 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity.

Stimulation of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is desirable in situations in which 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 is abnormally downregulated and/or in which increased 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is likely to have a beneficial effect. Likewise, inhibition of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is desirable in situations in which 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 is abnormally upregulated and/or in which decreased 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is likely to have a beneficial effect.

Methods for Inhibiting Target Gene Expression, Synthesis, or Activity

As discussed above, genes involved in cardiovascular disorders may cause such disorders via an increased level of gene activity. In some cases, such up-regulation may have a causative or exacerbating effect on the disease state. A variety of techniques may be used to inhibit the expression, synthesis, or activity of such genes and/or proteins.

For example, compounds such as those identified through assays described above, which exhibit inhibitory activity, may be used in accordance with the invention to at least one symptom of hematological disorders. Such molecules may include, but are not limited to, small organic molecules, peptides, antibodies, and the like.

For example, compounds can be administered that compete with endogenous ligand for the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. The resulting reduction in the amount of ligand-bound 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein will modulate endothelial cell physiology. Compounds that can be particularly useful for this purpose include, for example, soluble proteins or peptides, such as peptides comprising one or more of the extracellular domains, or portions and/or analogs thereof, of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the 131, 148,.199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 receptor site, but do not activate the protein, (e.g., receptor-ligand antagonists) can be effective in inhibiting 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein activity.

Further, antisense and ribozyme molecules which inhibit expression of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene may also be used in accordance with the invention to inhibit aberrant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene activity. Still further, triple helix molecules may be utilized in inhibiting aberrant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene activity.

The antisense nucleic acid molecules used in the methods of the invention are typically administered to a subject or generated in situ such that they hybridize with or bind to cellular mRNA and/or genomic DNA encoding a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pot III promoter are preferred.

In yet another embodiment, an antisense nucleic acid molecule used in the methods of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA transcripts to thereby inhibit translation of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA. A ribozyme having specificity for a 577, 20739 or 57145-encoding nucleic acid can be designed based upon the nucleotide sequence of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 cDNA disclosed herein (i.e., SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61). For example, a derivative of a Tetrahymena L-19 IVS RNA can be constructed in which the nucleotide sequence of the active site is complementary to the nucleotide sequence to be cleaved in a 577, 20739 or 57145-encoding mRNA (see, for example, Cech et al. U.S. Pat. No. 4,987,071; and Cech et al. U.S. Pat. No. 5,116,742). Alternatively, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA can be used to select a catalytic RNA having a specific ribonuclease activity from a pool of RNA molecules (see, for example, Bartel, D. and Szostak, J. W. (1993) Science 261:1411-1418).

131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression can also be inhibited by targeting nucleotide sequences complementary to the regulatory region of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 (e.g., the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 promoter and/or enhancers) to form triple helical structures that prevent transcription of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene in target cells (see, for example, Helene, C. (1991) Anticancer Drug Des. 6(6):569-84; Helene, C. et al. (1992) Ann. N.Y. Acad. Sci. 660:27-36; and Maher, L. J. (1992) Bioassays 14(12):807-15).

Antibodies that are both specific for the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein and interfere with its activity may also be used to modulate or inhibit 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein function. Such antibodies may be generated using standard techniques described herein, against the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. LIPOFECTIN® liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) Proc. Natl. Acad. Sci. USA 90:7889-7893).

In some instances, the target gene protein is extracellular, or is a transmembrane protein, such as the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Antibodies that are specific for one or more extracellular domains of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, for example, and that interfere with its activity, are particularly useful in treating hematological disorders or a hematological disorder. Such antibodies are especially efficient because they can access the target domains directly from the bloodstream. Any of the administration techniques described below which are appropriate for peptide administration may be utilized to effectively administer inhibitory target gene antibodies to their site of action.

Methods for Restoring or Enhancing Target Gene Activity

Genes that cause hematological disorders may be underexpressed within disease situations. Alternatively, the activity of the protein products of such genes may be decreased, leading to the development of hematological disorders. Such down-regulation of gene expression or decrease of protein activity might have a causative or exacerbating effect on the disease state.

In some cases, genes that are up-regulated in the disease state might be exerting a protective effect. A variety of techniques may be used to increase the expression, synthesis, or activity of genes and/or proteins that exert a protective effect in response to hematological disorders conditions.

Described in this section are methods whereby the level 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity may be increased to levels wherein hematological disorders are ameliorated. The level of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity may be increased, for example, by either increasing the level of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene expression or by increasing the level of active 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein which is present.

For example, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, at a level sufficient to at least one symptom of hematological disorders may be administered to a patient exhibiting such symptoms. Any of the techniques discussed below may be used for such administration. One of skill in the art will readily know how to determine the concentration of effective, non-toxic doses of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, utilizing techniques such as those described below.

Additionally, RNA sequences encoding a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein may be directly administered to a patient exhibiting hematological disorders, at a concentration sufficient to produce a level of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein such that hematological disorders are ameliorated. Any of the techniques discussed below, which achieve intracellular administration of compounds, such as, for example, liposome administration, may be used for the administration of such RNA molecules. The RNA molecules may be produced, for example, by recombinant techniques such as those described herein.

Further, subjects may be treated by gene replacement therapy. One or more copies of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene, or a portion thereof, that directs the production of a normal 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene sequences into human cells.

Cells, preferably, autologous cells, containing 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expressing gene sequences may then be introduced or reintroduced into the subject at positions which allow for the amelioration of hematological disorders. Such cell replacement techniques may be preferred, for example, when the gene product is a secreted, extracellular gene product.

Pharmaceutical Compositions

Another aspect of the invention pertains to methods for treating a subject suffering from a disease. These methods involve administering to a subject an agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity (e.g., an agent identified by a screening assay described herein), or a combination of such agents. In another embodiment, the method involves administering to a subject a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or nucleic acid molecule as therapy to compensate for reduced, aberrant, or unwanted 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 expression or activity.

Stimulation of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is desirable in situations in which 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 is abnormally downregulated and/or in which increased 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is likely to have a beneficial effect. Likewise, inhibition of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is desirable in situations in which 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 is abnormally upregulated and/or in which decreased 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity is likely to have a beneficial effect.

The agents which modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL® (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity (e.g., a fragment of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or an anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, andlor adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL®, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity can also be prepared in the form of suppositories (e.g., with conventional suppository bases such as cocoa butter and other glycerides) or retention enemas for rectal delivery.

In one embodiment, the agents that modulate 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, and 15402, 340, 10217, 837, 1761, 8990 or 13249 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity, as well as tailoring the dosage and/or therapeutic regimen of treatment with an agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once in every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein used in the methods of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 molecule or 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 modulator used in the methods of the present invention) can give an indication whether gene pathways related to toxicity have been turned on.

Information generated from more than one of the above pharmacogenomics approaches can be used to determine appropriate dosage and treatment regimens for prophylactic or therapeutic treatment of a subject. This knowledge, when applied to dosing or drug selection, can avoid adverse reactions or therapeutic failure and, thus, enhance therapeutic or prophylactic efficiency when treating a subject suffering from a cardiovascular disease, e.g., atherosclerosis, with an agent which modulates 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity.

Recombinant Expression Vectors and Host Cells Used in the Methods of the Invention The methods of the invention (e.g., the screening assays described herein) include the use of vectors, preferably expression vectors, containing a nucleic acid encoding a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins, mutant forms of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins, fusion proteins, and the like).

The recombinant expression vectors to be used in the methods of the invention can be designed for expression of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins in prokaryotic or eukaryotic cells. For example, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity assays, (e.g., direct assays or competitive assays described in detail below), or to generate antibodies specific for 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins. In a preferred embodiment, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to the use of host cells into which a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecule of the invention is introduced, e.g., a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecule within a recombinant expression vector or a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Accordingly, the invention further provides methods for producing a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein using the host cells of the invention. In one embodiment, the method comprises culturing the host cell of the invention (into which a recombinant expression vector encoding a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein has been introduced) in a suitable medium such that a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein is produced. In another embodiment, the method further comprises isolating a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein from the medium or the host cell.

Isolated Nucleic Acid Molecules Used in the Methods of the Invention

The methods of the invention include the use of isolated nucleic acid molecules that encode 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins or biologically active portions thereof, as well as nucleic acid fragments sufficient for use as hybridization probes to identify 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-encoding nucleic acid molecules (e.g., 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA) and fragments for use as PCR primers for the amplification or mutation of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, or a portion thereof, can be isolated using standard molecular biology techniques and the sequence information provided herein. Using all or portion of the nucleic acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, as a hybridization probe, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61 can be isolated by the polymerase chain reaction (PCR) using synthetic oligonucleotide primers designed based upon the sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59or61.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, a complement of the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, or a portion of any of these nucleotide sequences. A nucleic acid molecule which is complementary to the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, is one which is sufficiently complementary to the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61 such that it can hybridize to the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, or a portion of any of this nucleotide sequence.

Moreover, the nucleic acid molecules used in the methods of the invention can comprise only a portion of the nucleic acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, for example, a fragment which can be used as a probe or primer or a fragment encoding a portion of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, e.g., a biologically active portion of a 131, 148, 199, 12303, 13906, 15513, 17822, 302, 5677, 194, 14393, 28059, 7366, 12212, 1981, 261., 12416, 270, 1410, 137, 1871, 13051, 1847, 1849, 15402, 340, 10217, 837, 1761, 8990 or 13249 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61 of an anti-sense sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61 or of a naturally occurring allelic variant or mutant of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61. In one embodiment, a nucleic acid molecule used in the methods of the present invention comprises a nucleotide sequence which is greater than 100, 100-200, 200-300, 300-400, 400-500, 500-600, 600-700, 700-800, 800-900, 900-1000, 1000-1100, 1100-1200, 1200-1300, or more nucleotides in length and hybridizes under stringent hybridization conditions to a nucleic acid molecule of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% G+C)-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, such as by measuring a level of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-encoding nucleic acid in a sample of cells from a subject e.g., detecting 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA levels or determining whether a genomic 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene has been mutated or deleted.

The methods of the invention further encompass the use of nucleic acid molecules that differ from the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, due to degeneracy of the genetic code and thus encode the same 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins as those encoded by the nucleotide sequence shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61. In another embodiment, an isolated nucleic acid molecule included in the methods of the invention has a nucleotide sequence encoding a protein having an amino acid sequence shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60.

The methods of the invention further include the use of allelic variants of human 131, 148, 199, 12303, 13906, 15513, 17822, 302, 5677, 194, 14393, 28059, 7366, 12212, 1981, 261, 12416, 270, 1410,137, 1871, 13051, 1847, 1849, 15402, 340, 10217, 837, 1761, 8990 or 13249, e.g., functional and non-functional allelic variants. Functional allelic variants are naturally occurring amino acid sequence variants of the human 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein that maintain a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. Functional allelic variants will typically contain only conservative substitution of one or more amino acids of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60, or substitution, deletion or insertion of non-critical residues in non-critical regions of the protein.

Non-functional allelic variants are naturally occurring amino acid sequence variants of the human 131, 148, 199, 12303, 13906, 15513, 17822, 302, 5677, 194, 14393, 28059, 7366, 12212, 1981, 261, 12416, 270, 1410, 137,1871, 13051, 1847, 1849, 15402, 340, 10217, 837, 1761, 8990 or 13249 protein that do not have a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. Non-functional allelic variants will typically contain a non-conservative substitution, deletion, or insertion or premature truncation of the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60, or a substitution, insertion or deletion in critical residues or critical regions of the protein.

The methods of the present invention may further use non-human orthologues of the human 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Orthologues of the human 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein are proteins that are isolated from non-human organisms and possess the same 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity.

The methods of the present invention further include the use of nucleic acid molecules comprising the nucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 (e.g., the sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60) without altering the biological activity, whereas an "essential" amino acid residue is required for biological activity. For example, amino acid residues that are conserved among the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins of the present invention are not likely to be amenable to alteration.

Mutations can be introduced into SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or61 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein is preferably replaced with another amino acid residue from the same side chain family. Alternatively, in another embodiment, mutations can be introduced randomly along all or part of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 coding sequence, such as by saturation mutagenesis, and the resultant mutants can be screened for 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 biological activity to identify mutants that retain activity. Following mutagenesis of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, the encoded protein can be expressed recombinantly and the activity of the protein can be determined using the assay described herein.

Another aspect of the invention pertains to the use of isolated nucleic acid molecules which are antisense to the nucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 coding strand, or to only a portion thereof. In one embodiment, an antisense nucleic acid molecule is antisense to a "coding region" of the coding strand of a nucleotide sequence encoding a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249. The term "noncoding region" refers to 5' and 3' sequences which flank the coding region that are not translated into amino acids (also referred to as 5' and 3' untranslated regions).

Given the coding strand sequences encoding 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 disclosed herein, antisense nucleic acids of the invention can be designed according to the rules of Watson and Crick base pairing. The antisense nucleic acid molecule can be complementary to the entire coding region of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA, but more preferably is an oligonucleotide which is antisense to only a portion of the coding or noncoding region of 131, 148, 199, 12303, 13906, 15513, 17822, 302, 5677, 194, 14393, 28059, 7366, 12212, 1981,261, 12416, 270, 1410, 137, 1871, 13051, 1847, 1849, 15402, 340, 10217, 837, 1761, 8990 or 13249 mRNA. For example, the antisense oligonucleotide can be complementary to the region surrounding the translation start site of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). Antisense nucleic acid molecules used in the methods of the invention are further described above, in section IV.

In yet another embodiment, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci.* 93:14670-675.

PNAs of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5'PNA segment and a 3'DNA segment (Finn P. J. et al. (1996) supra). Alternatively, chimeric molecules can be synthesized with a 5'DNA segment and a 3'PNA segment (Peterser, K. H. et al. (1975) *Bioorganic Med. Chem. Lett.* 5: 1119-11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Isolated 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 Proteins and Anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 Antibodies Used in the Methods of the Invention The methods of the invention include the use of isolated 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins, and biologically active portions thereof, as well as polypeptide fragments suitable for use as immunogens to raise anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies. In one embodiment, native 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins can be isolated from cells or tissue sources by an appropriate purification scheme using standard protein purification techniques. In another embodiment, 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins are produced by recombinant DNA techniques. Alternative to recombinant expression, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or polypeptide can be synthesized chemically using standard peptide synthesis techniques.

As used herein, a "biologically active portion" of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein includes a fragment of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein having a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity. Biologically active portions of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein include peptides comprising amino acid sequences sufficiently identical to or derived from the amino acid sequence of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, e.g., the amino acid sequence shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60, which include fewer amino acids than the full length 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins, and exhibit at least one activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Typically, biologically active portions comprise a domain or motif with at least one activity of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein (e.g., the N-terminal region of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein that is believed to be involved in the regulation of apoptotic activity). A biologically active portion of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be a polypeptide which is, for example, 25, 50, 75, 100, 125, 150, 175, 200, 250, 300 or more amino acids in length. Biologically active portions of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be used as targets for developing agents which modulate a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 activity.

In a preferred embodiment, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein used in the methods of the invention has an amino acid sequence shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60. In other embodiments, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein is substantially identical to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60, and retains the functional activity of the protein of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60, yet differs in amino acid sequence due to natural allelic variation or mutagenesis, as described in detail in subsection V above. Accordingly, in another embodiment, the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970)) algorithm which has been incorporated into the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11-17 (1988)) which has been incorporated into the ALIGN program (version 2.0 or 2.0U), using a PAM120 weight residue table, a gap length penalty of 12 and a gap penalty of 4.

The methods of the invention may also use 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 chimeric or fusion proteins. As used herein, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 "chimeric protein" or "fusion protein" comprises a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide operatively linked to a non-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide. An "131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide" refers to a polypeptide having an amino acid sequence corresponding to a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 molecule, whereas a "non-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide" refers to a polypeptide having an amino acid sequence corresponding to a protein which is not substantially homologous to the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, e.g., a protein which is different from the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein and which is derived from the same or a different organism. Within a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion protein the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide can correspond to all or a portion of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 176 1, 8990 or 13249 protein. In a preferred embodiment, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion protein comprises at least one biologically active portion of a 131, 148, 199, 12303, 13906, 15513, 17822, 302, 5677, 194, 14393, 28059, 7366, 12212, 1981, 261, 12416, 270, 1410, 137, 1871, 13051, 1847,1849, 15402, 340, 10217, 837, 1761, 8990 or 13249 protein. In another preferred embodiment, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion protein comprises at least two biologically active portions of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Within the fusion protein, the term "operatively linked" is intended to indicate that the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide and the non-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide are fused in-frame to each other. The non-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide can be fused to the N-terminus or C-terminus of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide.

For example, in one embodiment, the fusion protein is a GST-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion protein in which the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequences are fused to the C-terminus of the GST sequences. Such fusion proteins can facilitate the purification of recombinant 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249.

In another embodiment, this fusion protein is a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein containing a heterologous signal sequence at its N-terminus. In certain host cells (e.g., mammalian host cells), expression and/or secretion of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be increased through use of a heterologous signal sequence.

The 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion proteins used in the methods of the invention can be incorporated into pharmaceutical compositions and administered to a subject in vivo. The 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion proteins can be used to affect the bioavailability of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate. Use of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fusion proteins may be useful therapeutically for the treatment of disorders caused by, for example, (i) aberrant modification or mutation of a gene encoding a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein; (ii) mis-regulation of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 gene; and (iii) aberrant post-translational modification of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein.

Moreover, the 131, 148, 199, 12303, 13906, 15513, 17822, 302, 5677, 194, 14393, 28059, 7366, 12212, 1981, 261, 12416, 270, 1410,137, 1871, 13051, 1847, 1849, 15402, 340, 10217, 837, 1761, 8990 or 13249-fusion proteins used in the methods of the invention can be used as immunogens to produce anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies in a subject, to purify 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 ligands and in screening assays to identify molecules which inhibit the interaction of 131, 148, 199, 12303, 13906, 15513, 17822, 302, 5677, 194, 14393, 28059, 7366, 12212, 1981, 261, 12416, 270, 1410, 137, 1871, 13051,1847, 1849, 15402, 340, 10217, 837, 1761, 8990 or 13249 with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 substrate.

Preferably, a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-encoding nucleic acid can be cloned into such an expression vector such that the fusion moiety is linked in-frame to the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein.

The present invention also pertains to the use of variants of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins which function as either 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 agonists (mimetics) or as 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antagonists. Variants of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins can be generated by mutagenesis, e.g., discrete point mutation or truncation of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. An agonist of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins can retain substantially the same, or a subset, of the biological activities of the naturally occurring form of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. An antagonist of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can inhibit one or more of the activities of the naturally occurring form of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249, protein by, for example, competitively modulating a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249-mediated activity of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein.

In one embodiment, variants of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein which function as either 131, 148, 199, 12303, 13906, 15513, 17822, 302, 5677, 194, 14393, 28059, 7366, 12212, 1981, 261, 12416, 270, 1410, 137, 1871, 13051, 1847,1849, 15402, 340, 10217, 837, 1761, 8990 or 13249 agonists (mimetics) or as 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antagonists can be identified by screening combinatorial libraries of mutants, e.g., truncation mutants, of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein for 131, 148, 199, 12303, 13906, 15513, 17822, 302, 5677, 194, 14393, 28059, 7366, 12212, 1981, 261, 12416, 270, 1410,137, 1871, 13051, 1847, 1849, 15402, 340, 10217, 837, 1761, 8990 or 13249 protein agonist or antagonist activity. In one embodiment, a variegated library of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 variants is generated by combinatorial mutagenesis at the nucleic acid level and is encoded by a variegated gene library. A variegated library of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 variants can be produced by, for example, enzymatically ligating a mixture of synthetic oligonucleotides into gene sequences such that a degenerate set of potential 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequences is expressible as individual polypeptides, or alternatively, as a set of larger fusion proteins (e.g., for phage display) containing the set of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 sequences therein. There are a variety of methods which can be used to produce libraries of potential 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 252, 304, 1980, 14717, 9941, 19310 OR 17832 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein coding sequence can be used to generate a variegated population of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 fragments for screening and subsequent selection of variants of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. In one embodiment, a library of coding sequence fragments can be generated by treating a double stranded PCR fragment of a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 proteins. The most widely used techniques, which are amenable to high throughput put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 variants (Arkin and Yourvan (1992) *Proc. Natl. Acad. Sci. USA* 89:7811-7815; Delgrave et al. (1993) *Protein Engineering* 6(3):327-331).

The methods of the present invention further include the use of anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies. An isolated 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein, or a portion or fragment thereof, can be used as an immunogen to generate antibodies that bind 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 using standard techniques for polyclonal and monoclonal antibody preparation. A full-length 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein can be used or, alternatively, antigenic peptide fragments of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be used as immunogens. The antigenic peptide of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 comprises at least 8 amino acid residues of the amino acid sequence shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 and encompasses an epitope of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 such that an antibody raised against the peptide forms a specific immune complex with the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 that are located on the surface of the protein, e.g., hydrophilic regions, as well as regions with high antigenicity.

A 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 immunogen is typically used to prepare antibodies by immunizing a suitable subject, (e.g., rabbit, goat, mouse, or other mammal) with the immunogen. An appropriate immunogenic preparation can contain, for example, recombinantly expressed 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein or a chemically synthesized 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 polypeptide. The preparation can further include an adjuvant, such as Freund's complete or incomplete adjuvant, or similar immunostimulatory agent. Immunization of a suitable subject with an immunogenic 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 preparation induces a polyclonal anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind 131, 148, 199, 12303, 13906, 15513, 17822, 302, 5677, 194, 14393, 28059, 7366, 12212, 1981, 261, 12416, 270, 1410, 137,1871, 13051, 1847, 1849, 15402, 340, 10217, 837, 1761, 8990 or 13249 molecules. The term "monoclonal antibody" or "monoclonal antibody composition", as used herein, refers to a population of antibody molecules that contain only one species of an antigen binding site capable of immunoreacting with a particular epitope of 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249. A monoclonal antibody composition thus typically displays a single binding affinity for a particular 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein with which it immunoreacts.

Polyclonal anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies can be prepared as described above by immunizing a suitable subject with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 immunogen. The anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody titer in the immunized subject can be monitored over time by standard techniques, such as with an enzyme linked immunosorbent assay (ELISA) using immobilized 131, 148, 199, 12303, 13906, 15513, 17822, 302, 5677, 194, 14393, 28059, 7366, 12212, 1981, 261, 12416, 270, 1410, 137, 1871,13051, 1847, 1849, 15402, 340, 10217, 837, 1761, 8990 or 13249. If desired, the antibody molecules directed against 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 can be isolated from the mammal (e.g., from the blood) and further purified by well known techniques, such as protein A chromatography to obtain the IgG fraction. At an appropriate time after immunization, e.g., when the anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with a 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 immunogen as described above, and the culture supernatants of the resulting hybridoma cells are screened to identify a hybridoma producing a monoclonal antibody that binds 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249.

Any of the many well known protocols used for fusing lymphocytes and immortalized cell lines can be applied for the purpose of generating an anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 monoclonal antibody (see, e.g., G. Galfre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249, e.g., using a standard ELISA assay.

Alternative to preparing monoclonal antibody-secreting hybridomas, a monoclonal anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody can be identified and isolated by screening a recombinant combinatorial immunoglobulin library (e.g., an antibody phage display library) with 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 to thereby isolate immunoglobulin library members that bind 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies; such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240: 1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; Shaw et al. (1988) *J. Natl. Cancer Inst.* 80:1553-1559; Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibody can be used to detect 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein (e.g., in a cellular lysate or cell supernatant) in order to evaluate the abundance and pattern of expression of the 131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 protein. Anti-131, 148, 199, 12303, 13906, 15513, 17822, 302, 5677, 194, 14393, 28059, 7366, 12212, 1981, 261, 12416, 270, 1410, 137, 1871, 13051, 1847, 1849, 15402, 340, 10217, 837, 1761, 8990 or 13249 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

This invention is further illustrated by the following examples which should not be construed as limiting. The contents of all references, patents and published patent applications cited throughout this application, as well as the Figure and the Sequence Listing is incorporated herein by reference.

EXAMPLES

Example 1

Tissue Distribution of Using TAQMAN® Analysis

This example describes the TAQMAN® procedure. The TAQMAN® procedure is a quantitative, reverse transcription PCR-based approach for detecting mRNA. The RT-PCR reaction exploits the 5' nuclease activity of AmpliTaq Gold.TM. DNA Polymerase to cleave a TAQMAN® probe during PCR. Briefly, cDNA was generated from the samples of interest, e.g., heart, kidney, liver, skeletal muscle, and various vessels, and used as the starting material for PCR amplification. In addition to the 5' and 3' gene-specific primers, a gene-specific oligonucleotide probe (complementary to the region being amplified) was included in the reaction (i.e., the TAQMAN® probe). The TAQMAN® probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AMPLITAQ GOLD® DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Equivalents

Those skilled in the art will recognize, or be able to ascertain using no more than routine experimentation, many equivalents to the specific embodiments of the invention described herein. Such equivalents are intended to be encompassed by the following claims.

---

What claimed is:

1. A method for identifying a candidate compound that modulates hematopoiesis, comprising:
  i) combining a compound to be tested with hematopoietic cells expressing a polypeptide selected from the group consisting of:
    a) a polypeptide comprising the amino acid sequence of SEQ ID NO:26, wherein the polypeptide has chloride channel protein activity; and
    b) a polypeptide encoded by the nucleotide sequence set forth in SEQ ID NO:25, wherein the polypeptide has chloride channel protein activity; under conditions suitable for binding of the test compound to the polypeptide;
  ii) detecting binding of the test compound to the polypeptide to thereby identify a compound which binds to the polypeptide; and
  iii) determining if the hematopoietic cells differentiate into mature cells; thereby identifying a compound that modulates hematopolesis.

2. The method of claim 1, wherein the compound is selected from the group consisting of a small molecule, a peptide an and antibody.

3. The method of claim 1, wherein the polypeptide further comprises a heterologous signal sequence.

4. The method of claim 1, wherein the binding of the test compound to the polypeptide is detected by an assay selected from the group consisting of:
  a) a competition binding assay;
  b) an immunoassay; and
  c) a yeast two-hybrid assay.

5. The method of claim 1, wherein the binding of the test compound to the polypeptide is detected by assaying for chloride channel activity of the polypeptide.

6. The method of claim 1, wherein the polypeptide further comprises glutathione-S-transferase.

* * * * *

UNITED STATES PATENT AND TRADEMARK OFFICE
CERTIFICATE OF CORRECTION

PATENT NO. : 7,250,262 B2 Page 1 of 1
APPLICATION NO. : 10/352684
DATED : July 31, 2007
INVENTOR(S) : Joseph M. Carroll et al.

It is certified that error appears in the above-identified patent and that said Letters Patent is hereby corrected as shown below:

On the Title Page, in the Title, section (54) and Col. 1:
 Please replace "Hematopiests" and insert --Hematopoiesis--

In Claim 1, Column 303, Line 16:
 Please replace "hematopoletic" and insert -- hematopoietic--

In Claim 1, Column 303, Line 32:
 Please delete "hematopolesis" and insert --hematopoiesis--

In Claim 2, Column 304, Line 16:
 Please delete "an and" and insert --and an--

Signed and Sealed this

Eighth Day of April, 2008

JON W. DUDAS
*Director of the United States Patent and Trademark Office*